(12) United States Patent
Alper

(10) Patent No.: US 9,448,239 B2
(45) Date of Patent: *Sep. 20, 2016

(54) MONOCLONAL ANTIBODIES AGAINST PCBP-1 ANTIGENS, AND USES THEREFOR

(71) Applicant: ALPER BIOTECH, LLC, Rockville, MD (US)

(72) Inventor: •gze Alper, Bethesda, MD (US)

(73) Assignee: ALPER BIOTECH LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,236

(22) Filed: Oct. 11, 2013

(65) Prior Publication Data

US 2014/0147858 A1 May 29, 2014

Related U.S. Application Data

(63) Continuation of application No. 13/739,931, filed on Jan. 11, 2013, now Pat. No. 8,703,441.

(51) Int. Cl.
| | |
|---|---|
| *G01N 33/53* | (2006.01) |
| *G01N 33/574* | (2006.01) |
| *C07K 16/30* | (2006.01) |
| *C12Q 1/68* | (2006.01) |
| *G01N 33/68* | (2006.01) |

(52) U.S. Cl.
CPC ..... *G01N 33/57415* (2013.01); *C07K 16/3015* (2013.01); *C12Q 1/6886* (2013.01); *G01N 33/6872* (2013.01); *C12Q 2600/118* (2013.01); *G01N 2800/52* (2013.01)

(58) Field of Classification Search
CPC .. G01N 33/53; G01N 33/574; G01N 33/577; C07K 16/18; C07K 16/30; C07K 16/3015
USPC ............ 435/7.1, 7.2, 7.21, 7.23, 7.9, 40.5, 435/40.52, 960, 967; 436/501, 503, 504; 530/387.3
See application file for complete search history.

(56) References Cited

U.S. PATENT DOCUMENTS

| | | | |
|---|---|---|---|
| 8,540,991 B2 * | 9/2013 | Alper | 424/138.1 |
| 8,609,096 B2 * | 12/2013 | Alper | 424/138.1 |
| 2004/0137513 A1 | 7/2004 | Devaux et al. | |
| 2006/0121022 A1 | 6/2006 | Koga et al. | |
| 2010/0272640 A1 | 10/2010 | Alper | |
| 2012/0301395 A1 | 11/2012 | Alper | |
| 2013/0190204 A1 | 7/2013 | Özge | |

FOREIGN PATENT DOCUMENTS

| | | |
|---|---|---|
| EP | 1 775 590 | 4/2007 |
| JP | 2008-164517 | 7/2008 |
| WO | WO 03/035848 A1 | 5/2003 |
| WO | WO 2010/080935 | 1/2010 |
| WO | WO 2012/154957 A2 | 11/2012 |

OTHER PUBLICATIONS

European Patent Application No. 11807538.1: Extended Search Report, including Supplementary Search Report and Search Opinion, dated Nov. 14, 2013.
Acs et al., "Differential Expression of E-Cadherin in Lobular and Ductal Neoplasms of the Breast and its Biologic and Diagnostic Implications," *Am. J. Clin. Pathol.* 115:85-98 (2001).
Balint et al., "Antibody Engineering by Parsimonious Mutagenesis," *Gene* 137:109-118 (1993).
Bedolla et al., "Nuclear Versus Cytoplasmic Localization of Filamin A in Prostate Cancer: Immunohistochemical Correlation with Metastases," Clin. Cancer Res. 15(3):788-786 (2009).
Chkheidze et al., "A Novel Set of Nuclear Localization Signals Determine Distributions of the αCP RNA-Binding Proteins," *Mol. Cell. Biol.* 23(23):8405-8415 (2003).
Dobbyn et al., "Regulation of BAG-1 IRES-Mediated Translation Following Chemotoxic Stress," *Oncogene* 27:1167-1174 (2008).
Gamarnik et al., "Two Functional Complexes Formed by KH Domain Containing Proteins with the 5' Noncoding Region of Poliovirus RNA," *RNA* 3:882-892 (1997).
Giretti et al., "Extra-Nuclear Signalling of Estrogen Receptor to Breast Cancer Cytoskeletal Remodelling, Migration and Invasion," PLos One 3(5):E2238 (2008).
O'Malley et al., "Nuclear Receptor Coregulators in Cancer Biology," *Cancer Res.* 69(21):8217-8222 (2009).
Pestalozzi, B.C., "Brain Metastases and Subtypes of Breast Cancer,"*Ann. Oncol.* 20(5):803-805 (2009).
Pillai et al., "Expression of Folate Receptors and Heterogeneous Nuclear Ribonucleoprotein E1 in Women with Human Papillomavirus Mediated Transformation of Cervical Tissue to Cancer," *Journal of Clinical Pathology* 56:569-574 (2003).
Thakur et al., "Regulation of BRCA1 Transcription by Specific Single-Stranded DNA Binding Factors," *Mol. Cell. Biol.* 23(11):3774-3787 (2003).
Wang et al., "PCBP1 Suppresses the Translation of Metastasis-Associated PRL-3 Phosphatase," *Cancer Cell* 18:52-62 (2010).
WPI Thomson English Abstract of Japanese Publication No. JP 2008-164517, Database WPI/Thomson AN 2008-J01538 [51] retrieved on Mar. 24, 2010.
Zhang, et al., "PCBP-1 Regulates Alternative Splicing of the CD44 Gene and Inhibits Invasion in Human Hepatoma Cell Line HepG2 Cells," *Mol. Cancer* 9(72):1-10 (2010).

* cited by examiner

*Primary Examiner* — Misook Yu
*Assistant Examiner* — Anne Holleran
(74) *Attorney, Agent, or Firm* — Kenealy Vaidya LLP

(57) ABSTRACT

The present invention provides and includes monoclonal antibodies specific or preferentially selective for PCBP-1 antigens, as well as methods utilizing these antibodies to determine the severity of breast cancer in a patient.

5 Claims, 37 Drawing Sheets

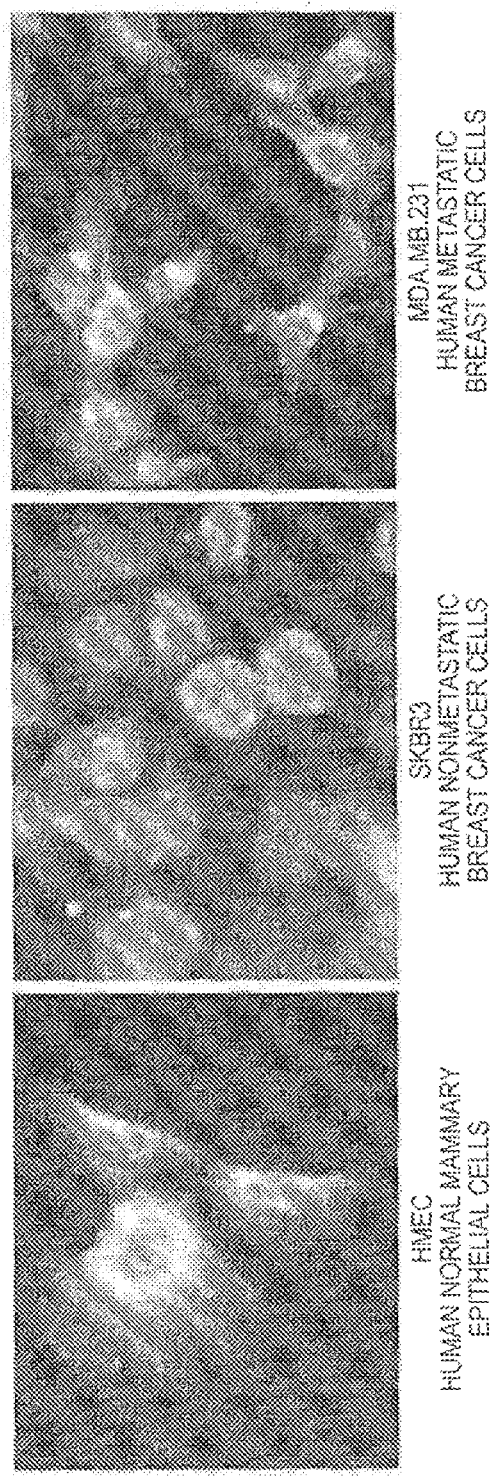

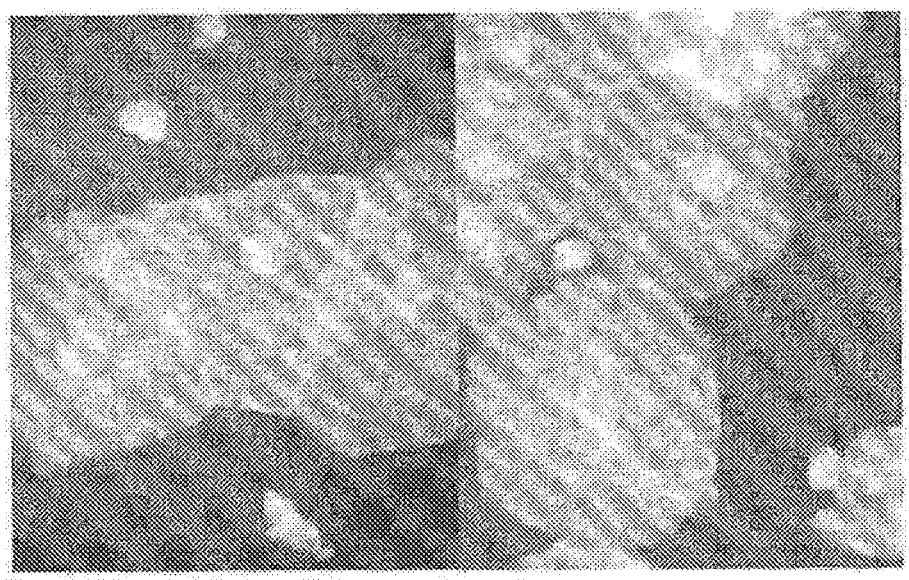
FIG. 4B
FIG. 4A

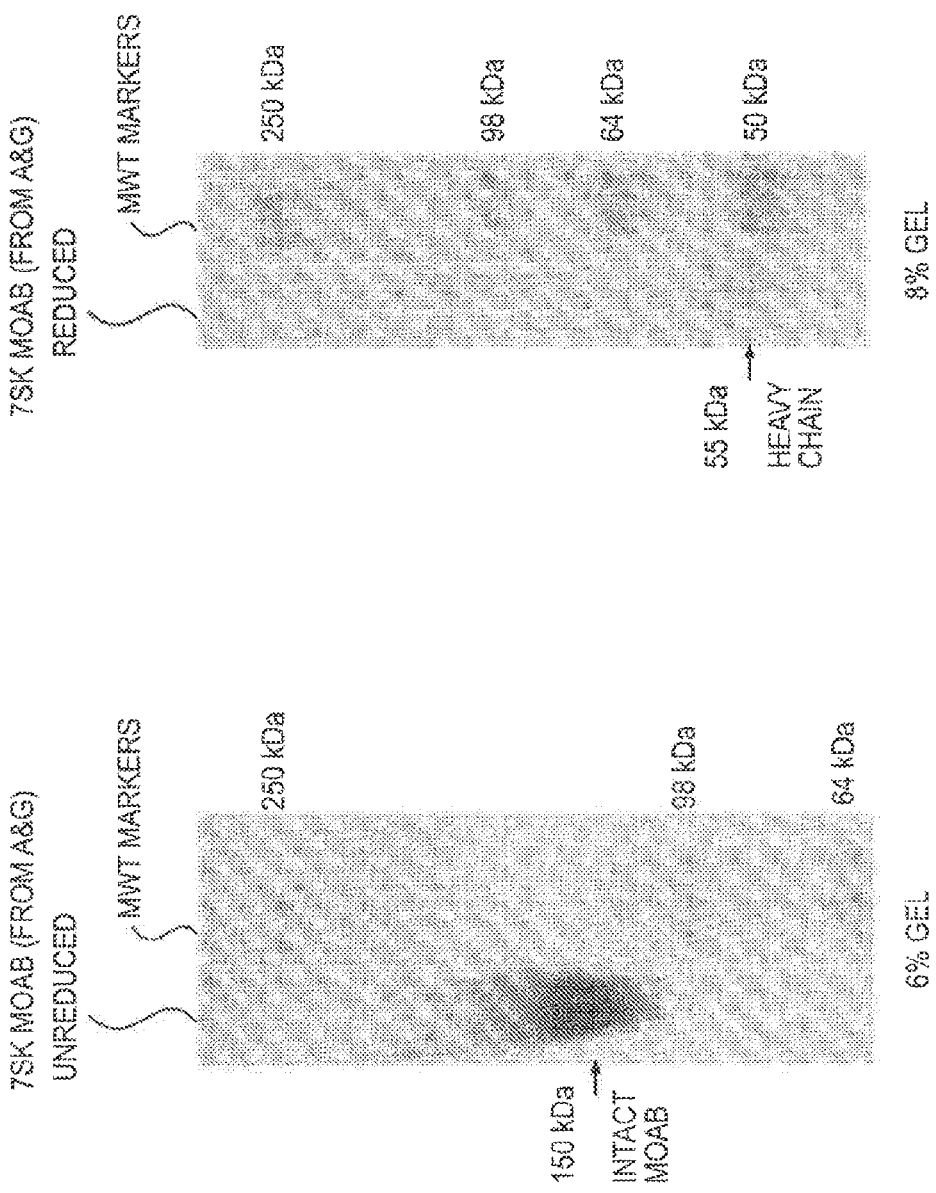

| M | M | NM | NM | C | C |
|---|---|---|---|---|---|
| 212 | 196 | 436 | 518 | 324 | 286 |
| 299 | 247 | 628 | 796 | 410 | 365 |
| 259 | 358 | 632 | 653 | 590 | 483 |
| 301 | 342 | 534 | 598 | 459 | 531 |
| 349 | 333 | 413 | 534 | 432 | 541 |
| 322 | 293 | 514 | 571 | 416 | 520 |
| 336 | 350 | 435 | 456 | 452 | 518 |
| 285 | 306 | 460 | 464 | 474 | 511 |
| 268 | 323 | 493 | 553 | 510 | 546 |
| 246 | 307 | 483 | 491 | 527 | 540 |
| 329 | 317 | 484 | 489 | 371 | 325 |
| 281 | 338 | 577 | 516 | 611 | 517 |
| 290.5833 | 309.1667 | 507.4167 | 553.25 | 464.6667 | 473.5833 |
| 299.875 | | 530.3333 | | 469.125 | |
| M | M | NM | NM | C | C |
| 291.9323 | 321.4524 | 496.2188 | 503.1786 | 487.0952 | 487.4635 |

1:10 DILUTED THEN 10ul IS TAKEN FROM 1:10 DILUTION AND ADDED ON TO 90ul PBS

FIG. 9A

BLASTN 2.2.17 [AUG-26-2007]

DATABASE: MGALLNCSEQ    630 SEQUENCES; 184,796 TOTAL LETTERS

QUERY= TMPSEQ_0    (1324 LETTERS)

| SEQUENCES PRODUCING SIGNIFICANT ALIGNMENTS: | SCORE (BITS) | E VALUE |
|---|---|---|
| J558.18 | 433 | e-123 |
| VMU-3.2 | 411 | e-116 |
| J558.85.191 | 411 | e-116 |
| J558.83.189 | 402 | e-113 |
| J558.29 | 361 | e-101 |
| J558.27 | 353 | 6e-99 |
| J558.87.193 | 350 | 5e-98 |
| VHA1 | 349 | 2e-97 |
| J558.30 | 349 | 2e-97 |
| J558.18A | 347 | 4e-97 |

DOMAIN CLASSIFICATION REQUESTED: KABAT SYSTEM

BLASTN 2.2.17 [Aug-26-2007]

Database: nrgalhuseq 630 sequences; 184,796 total letters

Query: tmpseq_0 (1055 letters)

SEQUENCES PRODUCING SIGNIFICANT ALIGNMENTS:

| | Score (bits) | E Value |
|---|---|---|
| 21-12 | 428 | e-121 |
| 21-7 | 384 | e-111 |
| 21-4 | 336 | 7e-94 |
| 21-10 | 333 | 8e-93 |
| 21-8 | 329 | 2e-91 |
| 21-3 | 327 | 4e-91 |
| 21-5 | 324 | 4e-90 |
| 21-2 | 319 | 1e-88 |
| 21-9 | 307 | 6e-85 |
| 21-1 | 307 | 6e-85 |
| 21-12 | 428 | e-121 |

DOMAIN CLASSIFICATION: KABAT SYSTEM

| SEQ ID NO. | MEASURED MASS, AMU (AVERAGE) | CALCULATED MASS, AMU (AVERAGE) | ERROR AMU | SEQUENCE POSITION START | SEQUENCE POSITION END | SEQUENCE |
|---|---|---|---|---|---|---|
| 1 | 917.06 | 916.98 | 0.08 | 39 | 46 | IREESGAR |
| 2 | 1302.39 | 1302.41 | -0.02 | 47 | 57 | INSEGNCPER Propionamide (C) |
| 3 | 1388.69 | 1388.65 | 0.04 | 58 | 70 | IITLTCPTNAIFK |
| 4 | 3379.88 | 3379.82 | 0.07 | 71 | 101 | AFAMIDKLEEDINSSMTNSTAASRPPVTLR |
| 4 | 3396.03 | 3395.81 | 0.22 | 71 | 101 | AFAMIDKLEEDINSSMTNSTAASRPPVTLR Oxidation (M) |
| 5 | 1456.86 | 1456.75 | 0.11 | 102 | 115 | LVVPATCCGSLICK Propionamide (C) |
| 6 | 2090.24 | 2090.23 | 0.01 | 125 | 144 | ESTGAQVQVAGDMLPNSTER |
| 6 | 2106.35 | 2106.23 | 0.12 | 125 | 144 | ESTGAQVQVAGDMLPNSTER Oxidation (M) |
| 7 | 1687.19 | 1686.97 | 0.22 | 145 | 160 | AITIAGVPQSVTECVK Propionamide (C) |
| 8 | 1974.30 | 1974.31 | 0.00 | 161 | 177 | QICLVMLETLSQSPQGR Propionamide (C) |
| 8 | 1990.42 | 1990.31 | 0.12 | 161 | 177 | QICLVMLETLSQSPQGR Oxidation (M), Propionamide (C) |
| 9 | 2489.80 | 2489.89 | -0.09 | 178 | 200 | VMITPYQPMPASSPVICAGGQDR Propionamide (C) |
| 9 | 2505.93 | 2505.89 | 0.05 | 178 | 200 | VMITPYQPMPASSPVICAGGQDR Oxidation (M), Propionamide (C) |
| 9 | 2522.04 | 2521.89 | 0.15 | 178 | 200 | VMITPYQPMPASSPVICAGGQDR 2 Oxidation (M), Propionamide (C) |
| 10 | 2606.86 | 2606.84 | 0.02 | 244 | 268 | QQSHFAMMHGGTGFAGIDSSSPEVK |
| 10 | 2622.79 | 2622.84 | -0.05 | 244 | 268 | QQSHFAMMHGGTGFAGIDSSSPEVK Oxidation (M) |
| 10 | 2638.91 | 2638.84 | 0.07 | 244 | 268 | QQSHFAMMHGGTGFAGIDSSSPEVK 2 Oxidation (M) |
| 11 | 3216.38 | 3216.58 | -0.20 | 269 | 297 | GYWASLDASTQTTHELTIPNNLIGCHGR Propionamide (C) |
| 12 | 1086.29 | 1086.16 | 0.14 | 315 | 325 | IANPYEGSSGR |
| 13 | 2177.46 | 2177.46 | 0.01 | 326 | 346 | QVTITGSAASISLAQYLINAR |
| 14 | 1014.19 | 1014.13 | 0.06 | 347 | 356 | LSSEKGMGCS Oxidation (M) |

FIG. 12

PCBP-1 EXPRESSION IN HUMAN
NORMAL AND CANCER TISSUES

| TISSUE | INTENSITY | TISSUE | INTENSITY |
|---|---|---|---|
| NORMAL COLON | + | COLON CANCER | +++ |
| NORMAL SKIN | + | MELANOMA | ++ |
| NORMAL BREAST | + | SQUAMOUS CARCINOMA | +++/++++ |
| NORMAL BRAIN | - | GLIOBLASTOMA MULTIFORME | + |
| NORMAL OVARY | +++ | OVARIAN CANCER | +/- |
| NORMAL ENDOMETRIUM | +/- | ENDOMETRIAL CANCER | +++ |
| NORMAL MUSCLE | + | SARCOMA | ++ |
| NORMAL BLADDER | + | BLADDER CANCER | ++ |

FIG. 13

Ductal Carcinoma

Metastatic MDA 231 cell line

Metastatic C2T2 cell line

Nonmetastatic SK-BR 3 cell line

MONOCLONAL ANTIBODIES AGAINST PCBP-1 ANTIGENS, AND USES THEREFOR

CROSS-REFERENCE TO RELATED APPLICATIONS

This application, filed under 35 U.S.C. §111(a), is a continuation of U.S. application Ser. No. 13/739,931, filed Jan. 11, 2013, which is a national stage entry under 35 U.S.C. §371 based on PCT of International Application PCT/US2011/044080, filed Jul. 14, 2011, which claims priority to U.S. Provisional Application No. 61/364,362, filed on Jul. 14, 2010, all of which are incorporated herein by reference in their entirety.

BACKGROUND OF THE INVENTION

1. Field of the Invention

The present invention provides and includes monoclonal antibodies (MoAbs or mAbs) specific or preferentially selective for a PCBP-1 antigen, hybridoma lines that secrete these PCBP-1 antibodies or antibody fragments, and the use of such antibodies and antibody fragments to detect PCBP-1 antigens, particularly those expressed by cancer cells. The present invention also includes antibodies that are specific for or show preferential binding to a soluble form of PCBP-1 (sPCBP-1). The present invention further includes chimeric and humanized antibodies, processes for producing monoclonal, chimeric, and humanized antibodies using recombinant DNA technology, and therapeutic uses of these antibodies, particularly in the treatment of cancer. The present invention further includes methods and kits for the immunodetection and immunotherapy of cells for samples which express a PCBP-1 antigen of the present invention.

2. Background

One human carcinoma tumor antigen is PCBP-1 (poly(rC) binding protein-1). Pcbp-1 is an intronless human gene reported to have been generated by retrotransposition of a fully processed PCBP-2 mRNA. It is also reported to be located on chromosome 2 (70.17-70.17 Mb). The protein encoded by the Pcbp-1 gene is a reported multifunctional protein. PCBP-1, along with PCBP-2 and hnRNPK, are reported to form the major cellular poly(rC)-binding proteins. Pcbp-1 has been sequenced. See UniProt Q15365, Q53SS8, Q14975; OMIM 601209; NCBI Gene 5093; NCBI RefSeq NP_006187; NCBI RefSeq NM_006196, NP_006187; NCBI UniGene 5093; and NCBI Accession AK130439, AAA91317. Homologues of Pcbp-1 are also reported, including, but not limited to, homologues of Pcbp-1 in the mouse (see NCBI UniGene 23983; UniProt P60335; and NCBI RefSeq NM_011865, NP_035995), dog, and rat.

PCBP-1 has also been reported to regulate transcription for a few individual promoters, to be important for the metabolism and gene expression of HIV-1 and poliovirus, and to stimulate IRES-mediated translation initiation in vitro and in vivo (Mitchell et al., 2003). It has also been reported to be modestly increased in the epidermis of elderly individuals (Gromov et al., *Mol Cell Proteomics* 2(2):70-84, 2003).

The breast cancer-specific survival rates of women with one or two positive nodes were found to have similar likelihoods of long-term survival; however, women with three positive nodes experienced significantly reduced survival compared to those with one or two involved nodes. (Tai, P., et al., Prognostic Significance of Number of Positive Nodes: A Long-Term Study of One to Two Nodes Versus Three Nodes in Breast Cancer Patients, *International Journal of Radiation Oncology;* 77 (1) p. 180-187 (May 2010)). Accordingly, there is a need for an additional molecular marker, more than just lymph node status, of overall survival, particularly for women with three or more positive nodes. There is also a need for a molecular marker to determine metastatic status of a ductal breast cancer in women with any lymph node involvement.

SUMMARY OF THE INVENTION

The present invention includes a method of determining a metastatic status of a breast cell or tissue in a sample comprising contacting the sample from a patient in need thereof with an antibody capable of detecting nuclear and cytoplasmic PCBP-1 and determining the subcellular location of said PCBP-1, where localization of said PCBP-1 in a cell cytoplasm of the sample is indicative of cellular metastasis.

In another aspect, the present invention includes a method of determining a metastatic status of a breast cell or tissue in a sample comprising contacting the sample from a patient in need thereof with an antibody capable of detecting nuclear and cytoplasmic PCBP-1 and determining the subcellular location of said PCBP-1, where the absence of subcellular co-localization of PCBP-1 and estrogen receptor (ER), progesterone receptor (PR), or ER and PR, is inversely correlated with overall survival. In this aspect, the absence of co-localization can include a lack of ER or PR staining where PCBP-1 staining is present in a ductal breast cancer cell cytoplasm.

The present invention includes a method of determining a likelihood of survival for a patient of breast cancer comprising contacting the sample from the patient in need thereof with an antibody capable of detecting nuclear and cytoplasmic PCBP-1; and determining the expression level of PCBP-1, where greater expression of said PCBP-1 in the sample is inversely correlated with overall survival.

The present invention includes a method of determining likelihood of survival for a patient of breast cancer comprising contacting the sample from the patient in need thereof with an DNA probe capable of detecting pcbp-1; and determining the chromosome localization of pcbp-1, wherein detection of more than two copies of said pcbp-1 in the sample is correlated with overall survival.

The present invention also provides a method for determining the likelihood of survival of a patient suffering from a disease characterized by the expression of gene products of Pcbp-1 and homologues thereof, comprising the steps of contacting a tissue specimen from a subject in need thereof with a PCBP-1 antibody of the present invention or an antibody fragment thereof, and staining said tissue specimens with an immunohistochemical staining.

The present invention also provides a method of determining the status of a cell in a sample comprising: (a) contacting a sample from a patient in need thereof with an antibody capable of preferentially detecting a soluble form of PCBP-1 antigen; and (b) determining the quantity of said antigen.

The present invention also provides a method of determining the status of a cell in a sample comprising: (a) contacting a sample from a patient in need thereof with an antibody or a fragment thereof capable of preferentially detecting a soluble form of PCBP-1 antigen; and (b) determining the localization of said antigen.

The present invention also provides a method for diagnosing breast cancer in a patient in need thereof, comprising:

(a) determining the level, localization, or both of PCBP-1 in a sample obtained from said patient; (b) determining whether said breast cancer is ductal carcinoma or lobular carcinoma; (c) determining whether said breast cancer is HER2-positive or HER2-negative; (d) determining whether said breast cancer is estrogen receptor-positive or estrogen receptor-negative; and (e) determining whether said breast cancer is progesterone receptor-positive or progesterone receptor-negative.

The present invention also provides a method for determining the cytopathology of a breast cancer in a patient in need thereof comprising: (a) contacting a specimen from said patient with a monoclonal antibody having one or more of the heavy chain CDR antigen binding site sequences selected from the group consisting of SEQ ID NO: 45, SEQ ID NO: 46 and SEQ ID NO: 47, and one or more of the light chain CDR antigen binding site sequences selected from the group consisting of SEQ ID NO: 48, SEQ ID NO: 49 and SEQ ID NO: 50, thereby forming antigen-antibody complexes in said specimen; labeling the specimen with a label specific for the antigen-antibody complex; and (d) detecting the level, localization, or both of the antigen-antibody complex.

The present invention also provides a method for determining whether a breast cancer specimen is from a ductal breast carcinoma or a lobular breast carcinoma comprising: (a) contacting the specimen with a monoclonal antibody having one or more of the heavy chain CDR antigen binding site sequences selected from the group consisting of SEQ ID NO: 45, SEQ ID NO: 46 and SEQ ID NO: 47, and one or more of the light chain CDR antigen binding site sequences selected from the group consisting of SEQ ID NO: 48, SEQ ID NO: 49 and SEQ ID NO: 50, thereby forming antigen-antibody complexes in said specimen; labeling the specimen with a label specific for the antigen-antibody complex; (b) detecting the level, localization or both of the antigen-antibody complex; and (c) correlating the level, localization, or both of the antigen-antibody complex with the type of breast cancer present in said patient.

The present invention also provides an immunoassay for determining whether a breast cancer specimen is from a ductal breast carcinoma or a lobular breast carcinoma comprising: (a) contacting the specimen with a monoclonal antibody having one or more of the heavy chain CDR antigen binding site sequences selected from the group consisting of SEQ ID NO: 45, SEQ ID NO: 46 and SEQ ID NO: 47, and one or more of the light chain CDR antigen binding site sequences selected from the group consisting of SEQ ID NO: 48, SEQ ID NO: 49 and SEQ ID NO: 50, thereby forming antigen-antibody complexes in said specimen; labeling the specimen with a label specific for the antigen-antibody complex; and (b) detecting the level, localization, or both of the antigen-antibody complex.

The present invention also provides a method of determining whether a breast cancer sample is a ductal breast carcinoma or a lobular breast carcinoma, comprising: (a) contacting said sample with an antibody capable of preferentially detecting a soluble form of PCBP-1 antigen; (b) determining the localization of said antigen; and (c) correlating the localization of said antigen with ductal breast carcinoma or lobular breast carcinoma.

The present invention also provides a method of determining whether a breast cancer sample is a ductal breast carcinoma or a lobular breast carcinoma, comprising: (a) contacting said sample with an antibody capable of preferentially detecting a soluble form of PCBP-1 antigen; (b) determining the level of said antigen; and (c) correlating the level of said antigen with ductal breast carcinoma or lobular breast carcinoma.

The present invention also provides a method for treating breast cancer in a patient in need thereof, comprising: (a) determining the level, localization, or both of PCBP-1 in a sample obtained from said patient; (b) determining whether said breast cancer is ductal carcinoma or lobular carcinoma; (c) determining whether said breast cancer is HER2-positive or HER2-negative; (d) determining whether said breast cancer is estrogen receptor-positive or estrogen receptor-negative; (e) determining whether said breast cancer is progesterone receptor-positive or progesterone receptor-negative; and (f) administering one or more chemotherapeutic agents to said patient.

The present invention also provides a method of selecting a treatment for a patient in need thereof, comprising: (a) determining whether a breast cancer is ductal or lobular; and (b) selecting an appropriate treatment based on whether said breast cancer is ductal or lobular.

The present invention also provides a method of identifying pre-metastic tumor cells in a tissue sample comprising: a) contacting said sample from a patient in need thereof with an antibody capable of detecting nuclear and cytoplasmic PCBP-1; and b) determining the subcellular location of said PCBP-1 in cells of said sample, wherein localization of said PCBP-1 in a cell cytoplasm of said cells is indicative of the presence of pre-metastic tumor cells.

BRIEF DESCRIPTION OF THE DRAWINGS

FIG. 2A is a bar graph of duplicate ELISA results. FIG. 2B is a box plot of averaged ELISA results.

FIGS. 3A, 3B, and 3C. Human normal mammary epithelial cells (HMECs), SKBR3 cells (human non-metastatic breast cancer cells) and MDA-MB-231 cells (human metastatic breast cancer cells) are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm of HMECs (FIG. 3A). SKBR3 cells exhibit cytoplasmic and nuclear staining (FIG. 3B). MDA-MB-231 cells exhibit cytoplasmic staining (FIG. 3C).

FIGS. 4A and 4B. Cervical cells obtained from pap smears of healthy and cervical cancer patients are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm and nucleus of normal cervical cells (FIG. 4A). Cervical cancer cells (CIN III) display cytoplasmic staining only (FIG. 4B).

FIGS. 5A and 5B. Approximately 2 µg of purified Alper PCBP-1 mouse mAb (identified as 7SK) is suspended in PBS, and is applied under reducing (boiled 3 minutes in sample buffer with beta-mercaptoethanol and 10% SDS) and non-reducing (not boiled, and without beta-mercaptoethanol) conditions to 8 and 6% Tris-glycine gels, respectively, and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the right. The 6% Tris-glycine gel shows the Alper PCBP-1 mouse IgG1 antibody (7SK) at ~150 kDa under non-reduced conditions (FIG. 5A). The 8% Tris-glycine gel shows the heavy chain of the Alper PCBP-1 mouse IgG1 antibody (7SK) at ~50 kDa (FIG. 5B).

FIG. 7A shows PCBP-1 staining only, and FIG. 7B shows both PCBP-1 and nuclei staining.

FIG. 8A represents the measured optical density (OD) values of plasma readings for PCBP-1 levels for each patient; FIG. 8B is the bar chart of the OD values of plasma readings for PCBP-1 levels; FIG. 8C is the bar chart of the average OD values of plasma readings for PCBP-1 levels for the controls and each patient group.

FIGS. 9A, 9B, 9C, and 9D. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The plasma samples are analyzed in a blinded fashion. The wells are washed with PBS and incubated at room temperature for one hour with blocking buffer (5% BSA in PBS). After washing with PBS, the primary antibody, Alper PCBP-1 mouse mAB (7SK) (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N H2SO4 and the analysis is performed with an ELISA Reader. FIG. 9A represents the measured OD values for PCBP-1 levels in the plasma of controls (C) and patients suffering from non-metastatic cancer (NM) and patients suffering from metastatic cancer (M). FIG. 9B is the vertical bar chart of the OD values for PCBP-1 plasma levels, in which series 1-2 represent control plasma samples, series 3-4 represent nonmetastatic plasma samples and series 5-6 represent metastatic plasma samples. FIG. 9C represents the horizontal bar chart (top) of the average OD values for the controls and patient groups. FIG. 9D shows the vertical bar chart of the overall average OD values of the controls and patient groups, in which 1 represents metastatic plasma samples, 3 represents nonmetastatic plasma samples, and 6 represents control plasma samples.

Figure 10B:
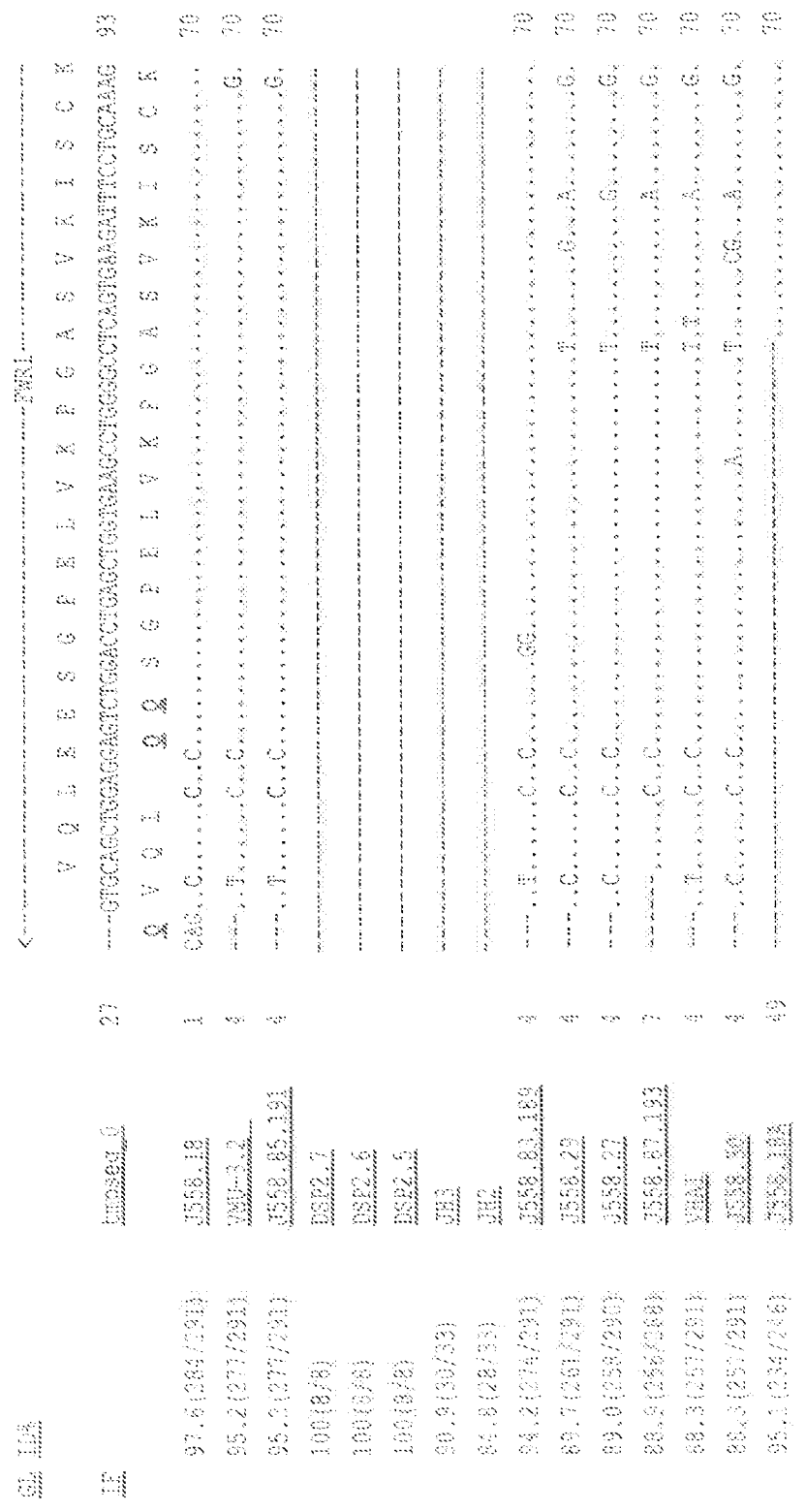
Figure 10C:
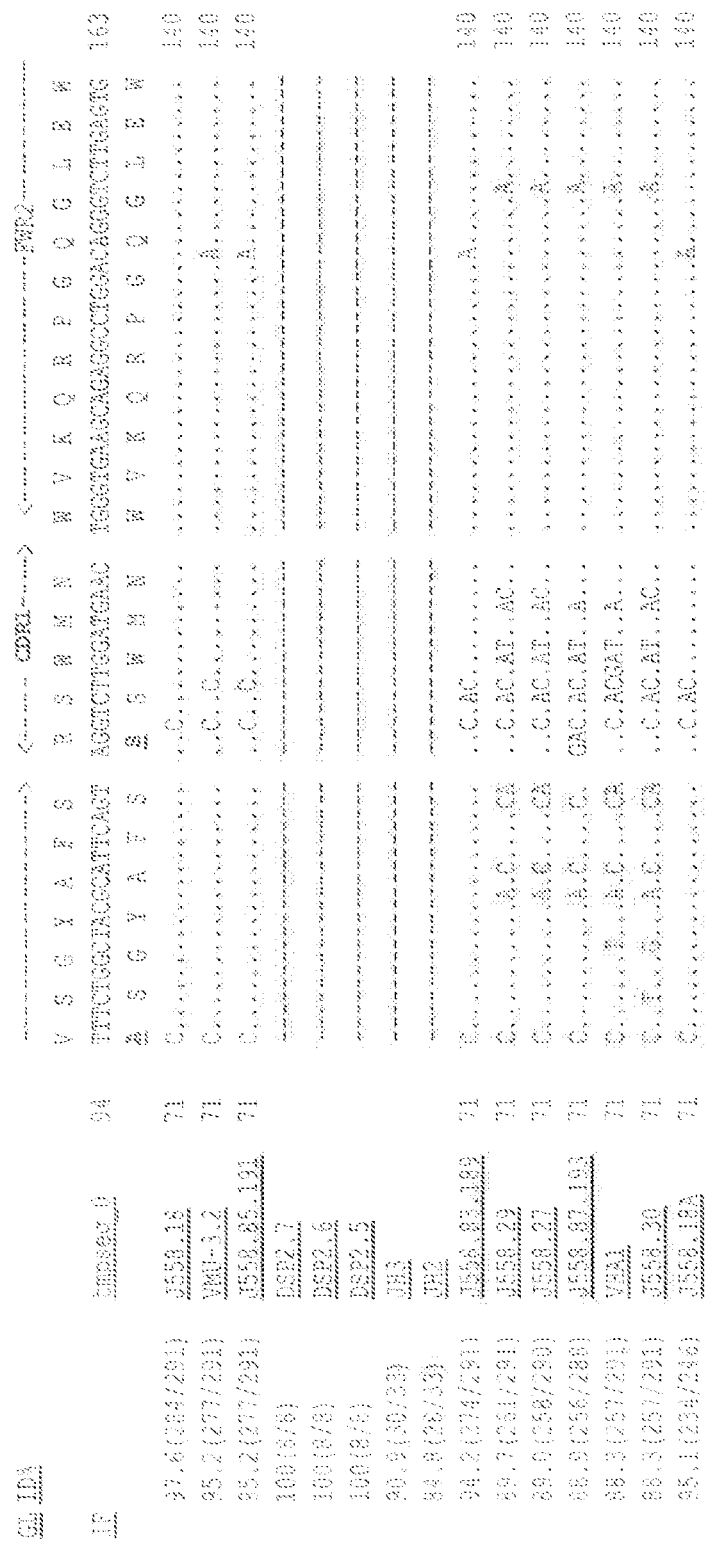
Figure 10D:
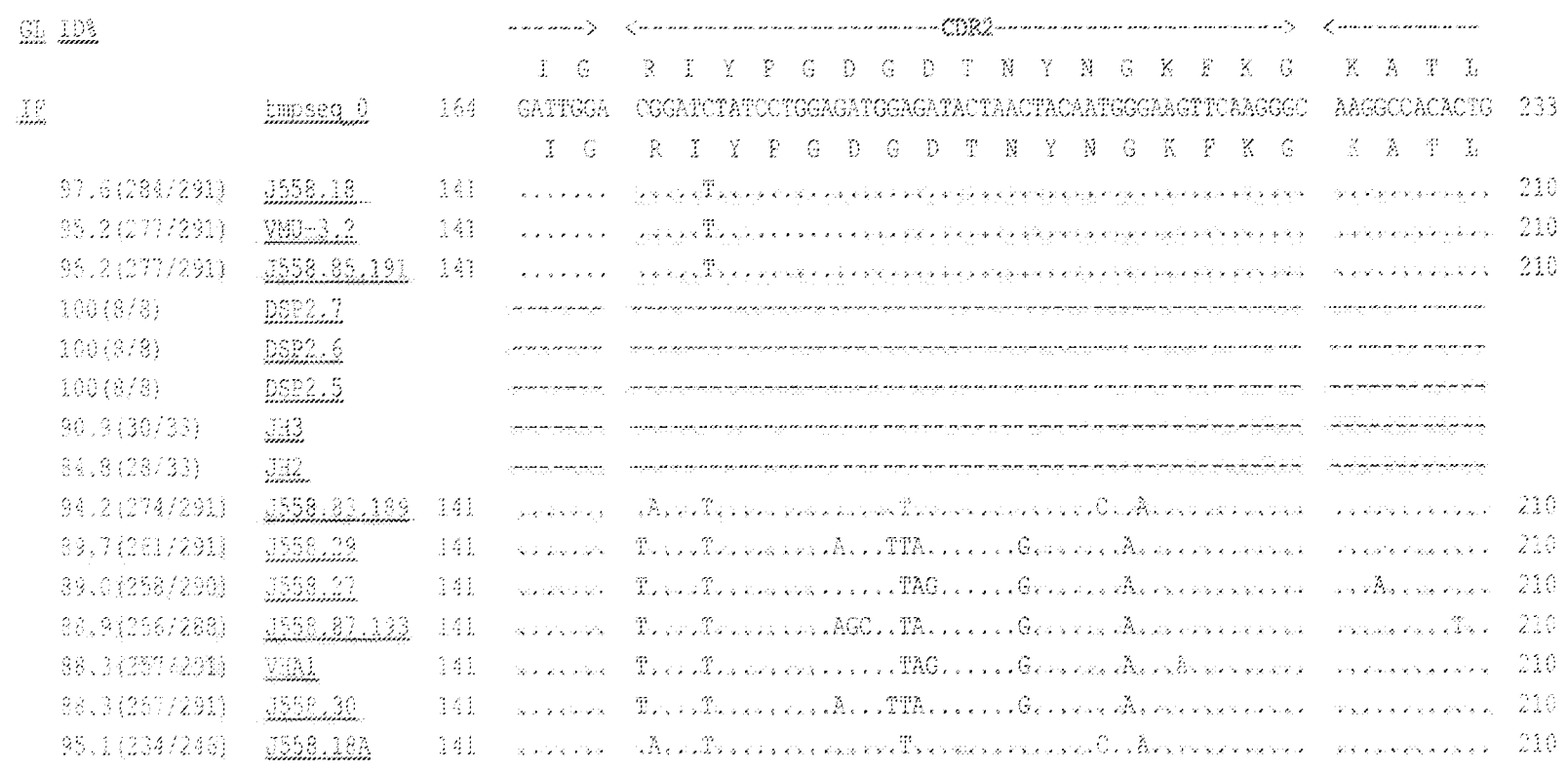
Figure 10E:
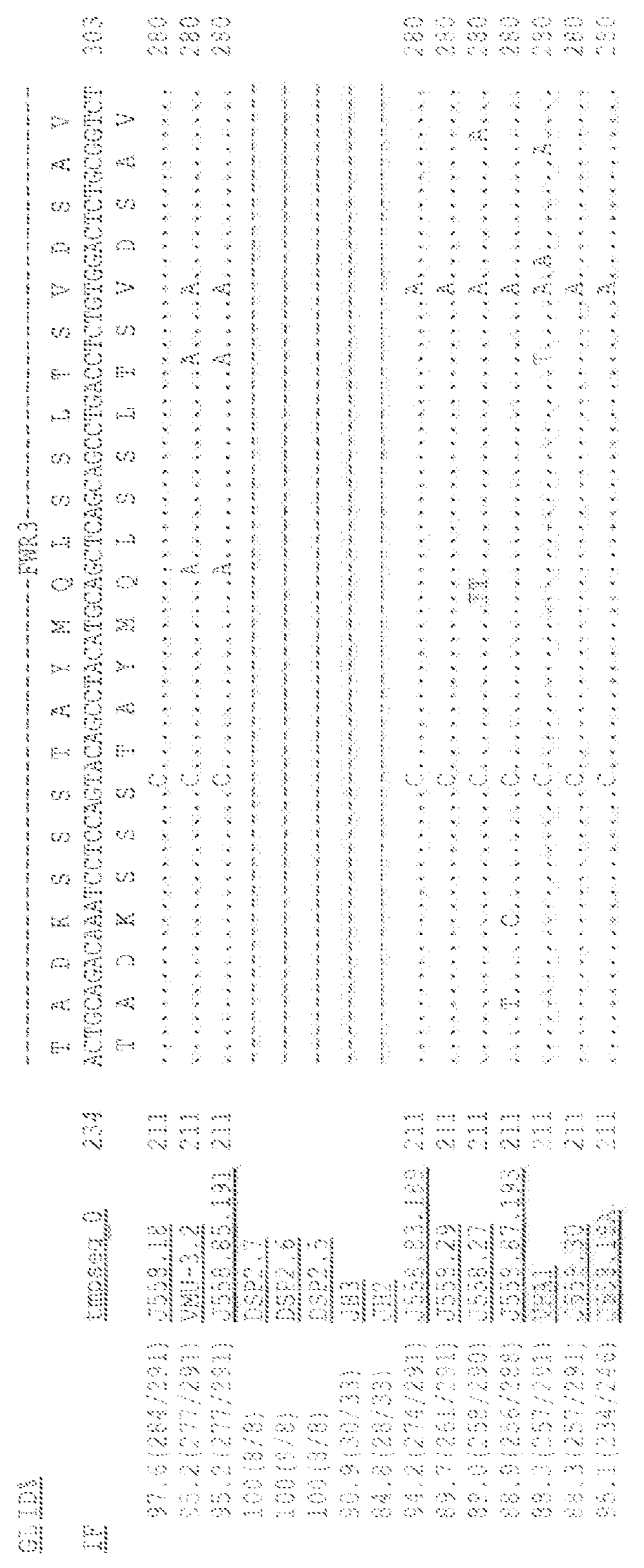
Figure 10F:
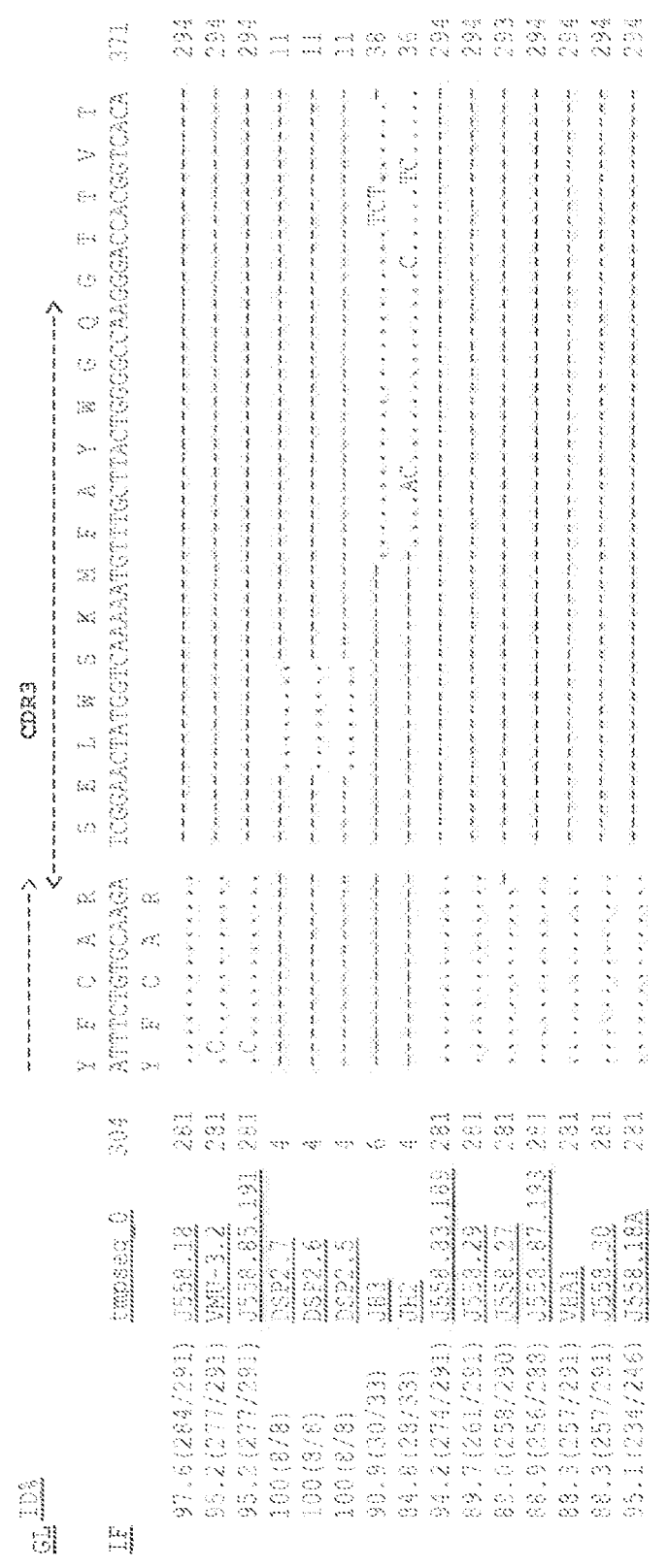

FIGS. 10A, 10B, 10C, 10D, 10E, and 10F. Multiple Sequence Alignment. FIG. 10A summarizes the BLAST search results of the heavy chain sequence of a PCBP-1 mAb (7SK). FIGS. 10B, 10C, 10D, 10E, and 10F show the FWRs and CDRs of the heavy chain of a PCBP-1 mAb (7SK), in which the polypeptide sequence provided in the top line (SEQ ID NO: 16) corresponds to the sequence of a PCBP-1 mAb (SEQ ID NO:15). The figures also disclose the following sequences, in order of appearance: J558.18 (SEQ ID NO: 17); VMU-3.2 (SEQ ID NO: 19); J558.85.191 (SEQ ID NO: 20); JH3 (SEQ ID NO: 21); JE2 (SEQ ID NO: 22); J558.83.189 (SEQ ID NO: 23); J558.29 (SEQ ID NO: 24); J558.27 (SEQ ID NO: 25); J558.87.193 (SEQ ID NO: 26); VEA1 (SEQ ID NO: 27); J558.30 (SEQ ID NO: 28); and J558.18A (SEQ ID NO: 29). Amino acid residues are numbered using the convention of Kabat et al., (1991) Sequences of Proteins of Immunological Interest, 5th Edition, Department of Health and Human Services, Public Health Service, National Institutes of Health, Bethesda (NIH Publication No. 91-3242). Bold residues set forth in underlined text indicate specificity determining residues (SDRs) (SEQ ID NO: 18).

FIGS. 11A, 11B, 11C, 11D, and 11F. Multiple Sequence Alignment. FIG. 11A summarizes the BLAST search results of the light heavy chain sequence of a PCBP-1 mAb (7SK). FIGS. 11B, 11C, 11D, 11E, and 11F show the FWRs and CDRs of the light chain of a PCBP-1 mAb (7SK), in which the polypeptide sequence provided in the top line (SEQ ID NO: 31) corresponds to the nucleotide sequence of a PCBP-1 mAb (SEQ ID NO: 30). The figures also disclose the following sequences, in order of appearance: 21-12 SEQ ID NO: 32); 21-7 (SEQ ID NO: 34); 21-4 (SEQ ID NO: 35); JK2 (SEQ ID NO: 36); JK1 (SEQ ID NO: 37); 21-10 (SEQ ID NO: 38); 21-8 (SEQ ID NO: 39); 21-3 (SEQ ID NO: 40); 21-5 (SEQ ID NO: 41); 21-2 (SEQ ID NO: 42); 21-9 (SEQ ID NO: 43); 21-1 (SEQ ID NO: 44). Amino acid residues are numbered using the convention of Kabat et al. Bold residues set forth in underlined text indicate the specificity determining residues (SDRs) (SEQ ID NO: 33).

FIG. 12. Experimental mass, calculated mass and sequence of PCBP-1 regions (SEQ ID NOs. 1-14).

FIG. 13. Chart of PCBP-1 expression as detected by immunohistochemistry using Alper PCBP-1 mouse monoclonal antibody in normal vs. cancer tissues.

FIG. 14A shows the staining of a sample from a lobular carcinoma patient, and FIG. 14B shows the staining of a sample from a ductal carcinoma patient.

FIGS. 17A, 17B, and 17C are examples of lobular carcinoma samples displaying low (1+) (FIG. 17A) and high (2+ or 3+) (FIGS. 17B and 17C, respectively) immunohistochemical staining with Alper anti-PCBP-1 mouse monoclonal antibody.

FIGS. 18A, 18B, and 18C are examples of ductal carcinoma samples displaying low (1+) (FIG. 18A) and high (2+ or 3+) (FIGS. 18B and 18C, respectfully) immunohistochemical staining with Alper anti-PCBP-1 mouse monoclonal antibody.

FIGS. 19A, 19B, and 19C are FISH analyses for PCBP-1 in the human breast cancer cell lines: metastatic MDA 231 cell line (FIG. 19A), metastatic C2T2 cell line (FIG. 19B), and nonmetastatic SK-BR 3 cell line (FIG. 19C).

FIGS. 22A, 22B, 22C, and 22D show nuclear subcellular localization of ER and PCBP-1 from whole tissues samples from ductal invasive breast carcinoma patients. White bars are 50 µm (20×) and 10 µm (60×). FIGS. 22A and 22C show PCBP-1 expression at 20× and 63× magnification, respectively. FIGS. 22B and 22D show ER expression at 20× and 63× magnification, respectively.

DETAILED DESCRIPTION

1. Definitions

Figure 1:
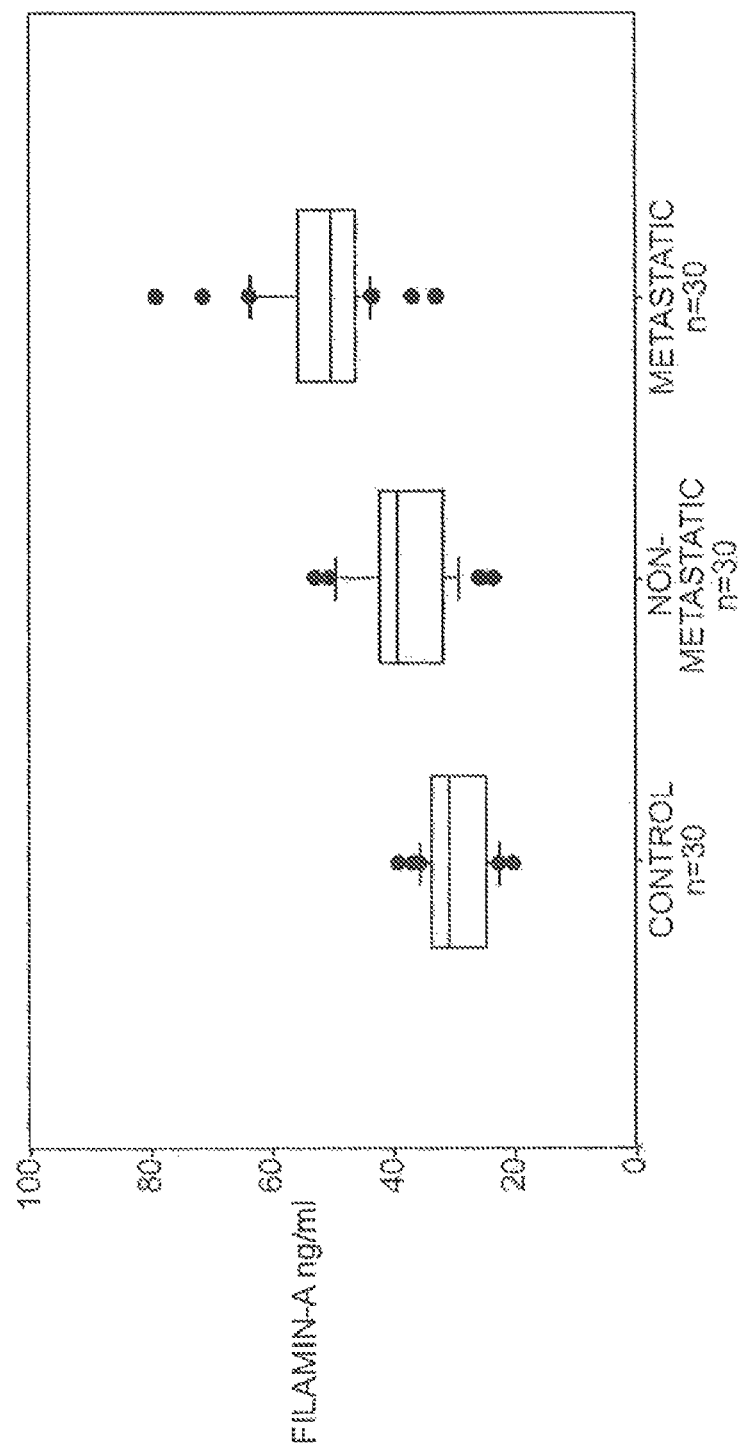
FIG. 1. Plasma filamin-A levels are measured with an enzyme-linked immunosorbent enzyme assay. The figures represent optical density (OD) values of plasma readings for filamin-A levels. P-values are derived using the Mann Whitney Test and show a significant difference between the control and non-metastatic groups, and between the control and metastatic groups ($p<0.001$). P values are determined by comparison with controls by ANOVA. Data are representative of four independent experiments performed in triplicate.

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes.

Monoclonal Antibody: This refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a VH-VL pair where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions.

Humanized Antibody: This refers to an antibody derived from a non-human antibody, and a human antibody which retains or substantially retains the antigen-binding properties of the parent antibody but which is less immunogenic in humans.

Antibody Conjugates, Fusion Proteins, and Bispecific Antibodies: These refer to monoclonal antibodies conjugated by chemical methods with radionuclides, drugs, macromolecules, or other agents.

Antigen: This refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

Epitope: This refers to that portion of any molecule capable of being recognized by, and bound by, an antibody.

In general, epitopes consist of chemically active surface groupings of molecules, for example, amino acids or sugar side chains, and have specific three-dimensional structural characteristics as well as specific charge characteristics. The present invention includes epitopes that are comprising amino acids.

Complementarity Determining Region, or CDR: This refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions 30 and 34 (CDR1), 49 and 65 (CDR2), 75 and 88 (CDR3); the CDRs of the heavy chain are bounded by the residues at positions 22 and 36 (CDR1), 52 and 58 (CDR2), and 70 and 77 (CDR3), using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242).

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues of an immunoglobulin that are directly involved in antigen contact.

Constant Region: This refers to the portion of the antibody molecule which confers effector functions. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to PCBP-1.

Immunoreactivity: A measure of the ability of an immunoglobulin to recognize and bind to a specific antigen.

PCBP-1 Antibodies or PCBP-1 mAbs: This refers to antibodies specific to expression products of the PCBP-1 gene and homologues of the PCBP-1 gene, which can include antibodies specific to modified forms of the expression product that are produced by cancer cells. Antibodies of the present invention can include variants, such as chimeric, humanized, and other variants known to those skilled in the art. PCBP-1 antibodies are said to be specific for the PCBP-1 antigen if they exhibit preferential binding to the PCBP-1 antigen at least 85% of the time, at least 90% of the time, or, in a preferred aspect, at least 95% of the time. An example of such an antibody is Alper PCBP-1 mouse monoclonal antibody (7SK).

Figure 11B:
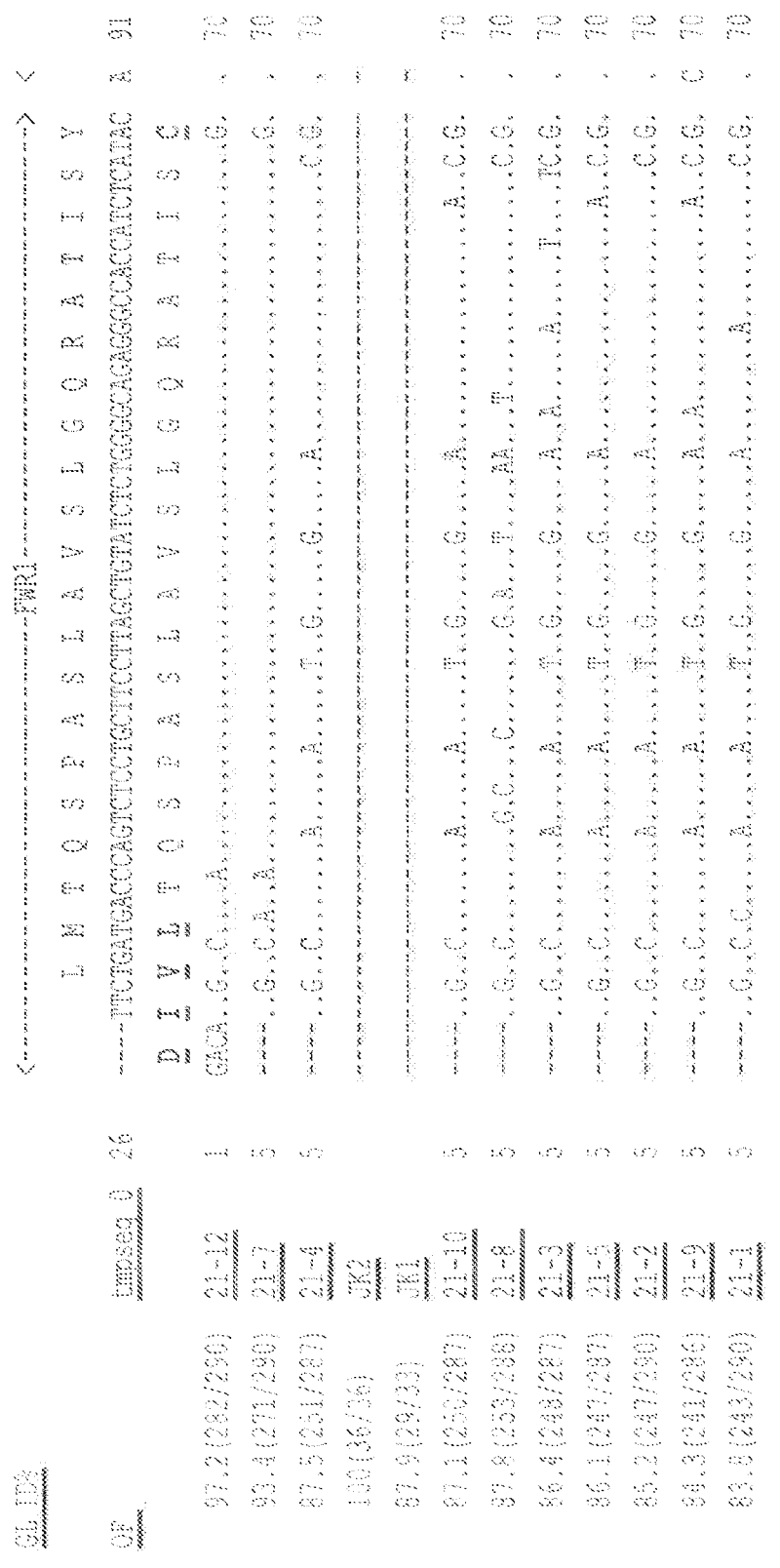
Figure 11C:
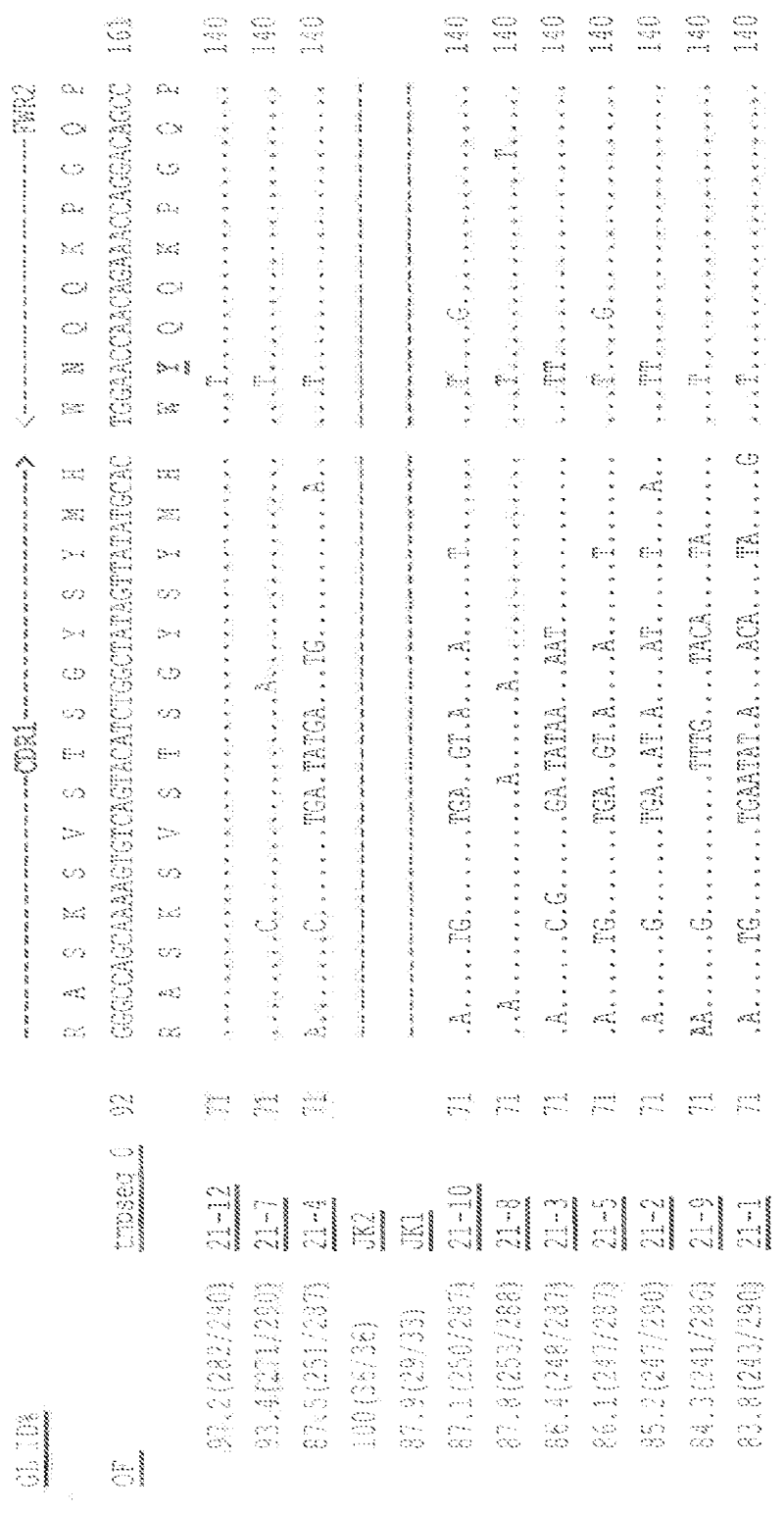
Figure 11D:
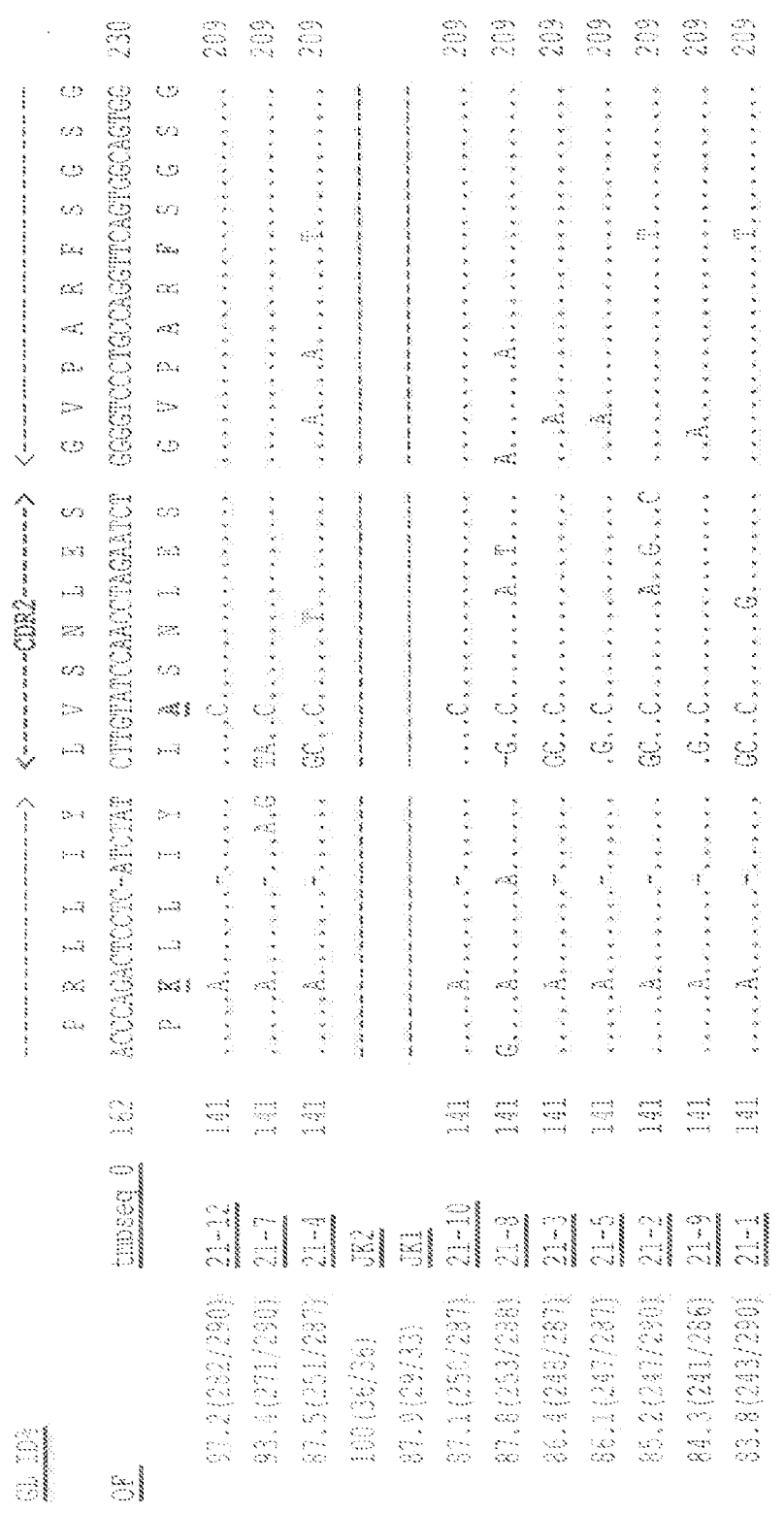
Figure 11E:
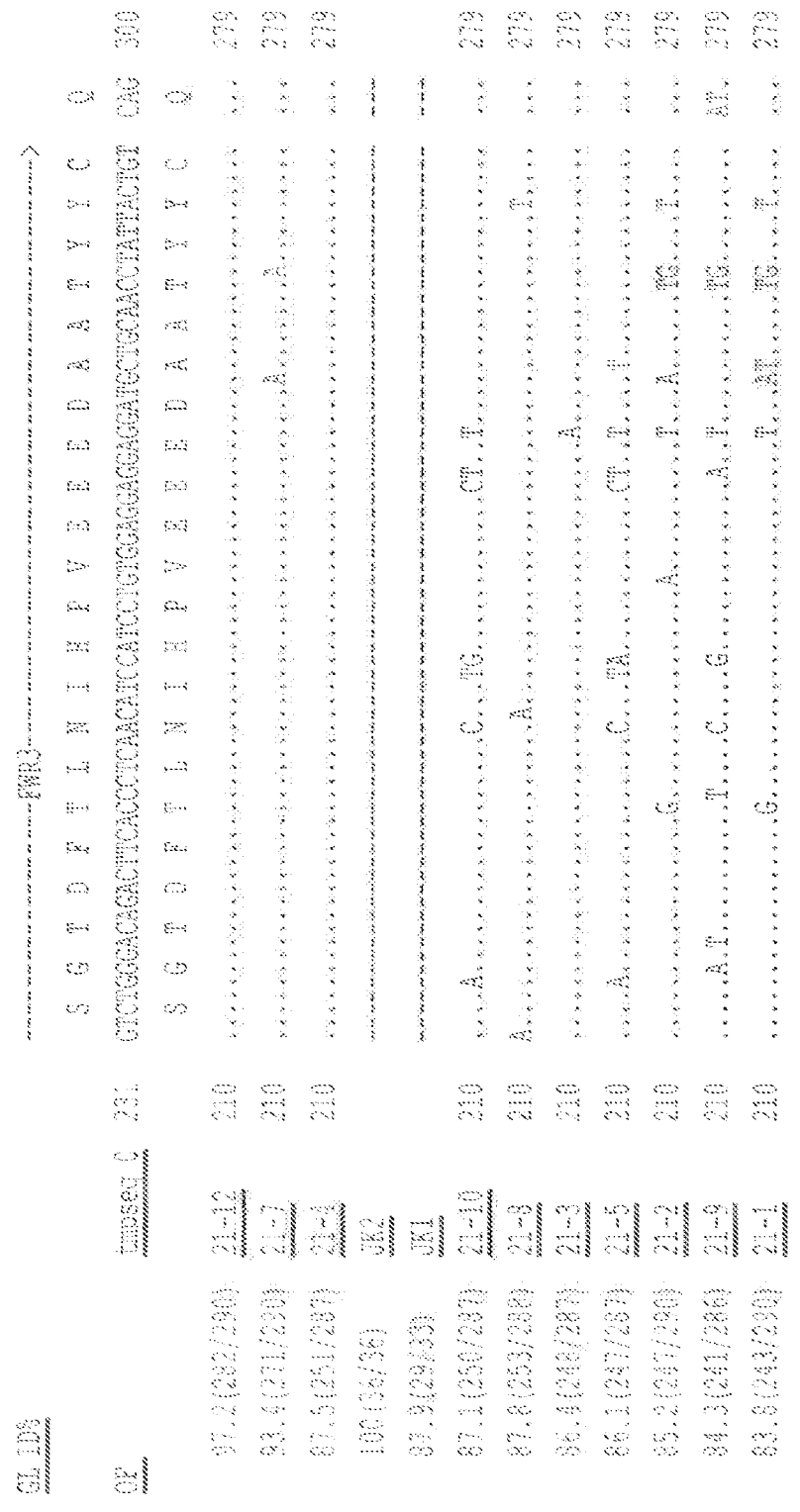
Figure 11F:
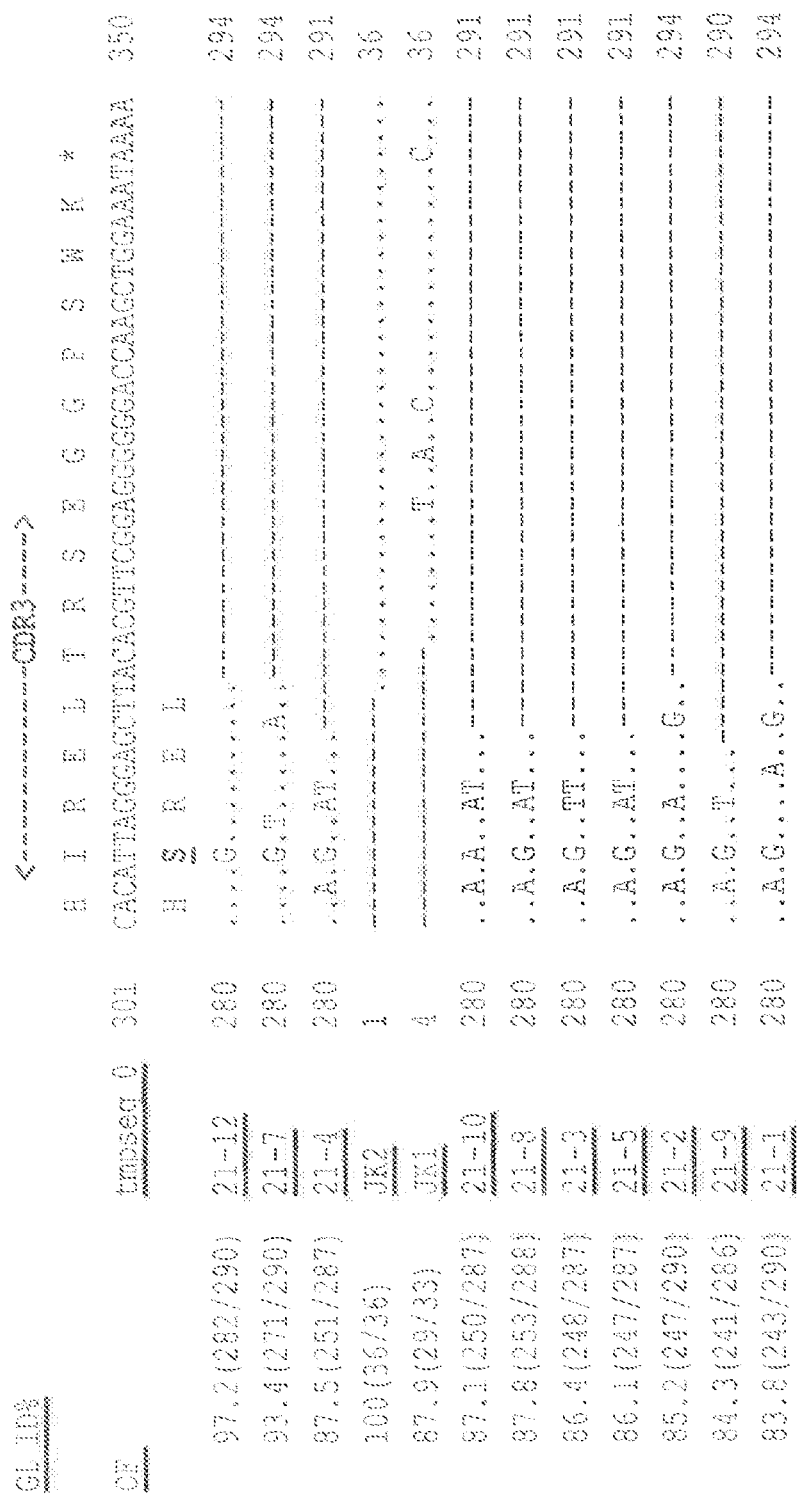

PCBP-1 antibodies of the present invention are specific for a PCBP-1 antigen and can comprise the heavy chain CDR antigen binding site sequences CDR1 (SEQ ID NO: 45), CDR2 (SEQ ID NO: 46), and CDR3 (SEQ ID NO: 47) as set forth in FIG. 10, and the light chain CDR antigen binding site sequences CDR1 (SEQ ID NO: 48), CDR2 (SEQ ID NO: 49), and CDR3 (SEQ ID NO: 50) as set forth in FIG. 11.

PCBP-1 antibodies of the present invention can also comprise one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50).

The present invention also includes nucleic acid molecules that may comprise an isolated DNA sequence which encodes the heavy chain of an antibody molecule, wherein said antibody molecule has specificity for PCBP-1 and wherein the variable domain of said heavy chain comprises a CDR having the antigen binding site sequences CDR1 (SEQ ID NO: 45), CDR2 (SEQ ID NO: 46), and CDR3 (SEQ ID NO: 47) set forth in FIG. 10.

The present invention also includes nucleic acid molecules that may also comprise an isolated DNA sequence which encodes the light chain of an antibody molecule, wherein said antibody molecule has specificity for PCBP-1 and further wherein the variable domain of said light chain comprises a CDR having the antigen binding site sequences CDR1 (SEQ ID NO: 48), CDR2 (SEQ ID NO: 49), and CDR3 (SEQ ID NO: 50) set forth in FIG. 11.

PCBP-1 Antigens: This refers to expression products generated by PCBP-1, which can be used as antigens, target molecules, biomarkers, or any combination thereof, for a PCBP-1 antibody. The PCBP-1 antigens can be produced by the PCBP-1 gene or homologues of the PCBP-1 gene, and can include various modifications introduced by the cells expressing the PCBP-1 antigens, such as cancer cells.

Substantially Similar Binding Properties: This refers to a chimeric or humanized antibody or antibody fragment which retains the ability to specifically bind the antigen recognized by the parent PCBP-1 antibody used to produce the chimeric antibody, humanized antibody, or antibody fragment. Preferably, the affinity of a chimeric antibody, humanized antibody, or antibody fragment is at least about 10% of the affinity of the parent PCBP-1 antibody, more preferably at least about 25%, even more preferably at least about 50%. Most preferably, the chimeric antibody, humanized antibody, or antibody fragment exhibits antigen-binding affinity that is at least about 75% of the affinity of the parent PCBP-1 antibody. Methods for assaying antigen-binding affinity are known in the art and include half-maximal binding assays, competition assays, and Scatchard analysis. In a preferred aspect, antigen-binding affinity is assayed using a competition assay. Such a comparison can be relative to Alper PCBP-1 mouse monoclonal antibody (7SK).

Substantially Homologous Refers to immunoglobulin sequences that exhibit at least about 85% identity, more preferably about 90% identity, most preferably about 95% identity with a reference immunoglobulin, wherein % identity is determined by comparing the number identical of amino acid residues between the two immunoglobulins, wherein the positions of the amino acid residues are indicated using the Kabat numbering scheme.

Sameness for Monoclonal Antibody Products: For the purpose of determining sameness of monoclonal antibodies, and products thereof, the complementarity determining regions of the heavy and light chain variable regions are the principal molecular structural feature of a monoclonal antibody product. Two monoclonal antibodies can be considered the same if the amino acid sequences of the CDRs are the same, or if there are only minor amino acid differences between them. Whether differences in the amino acid sequences are minor can be determined by factors that include (but are not limited to) whether any particular residues have been established to be important for antigen binding. Amino acid differences outside the CDRs, or differences due to glycosylation patterns or post translational modifications do not result in different monoclonal antibodies. Changes in antibody structure that do not constitute differences between two monoclonal antibody products with the same CDRs include changes in the FWRs (i.e., humanizing a non-human derived monoclonal antibody or engineering certain framework residues that are important for antigen contact or for stabilizing the binding site, or changes in the constant region (i.e., changing the class or subclass of the constant region, changing specific amino acid residues which might alter an effector function, or changing the species from which the constant region is derived).

Substantially pure: For the purpose of the present invention, substantially pure refers to a homogeneous preparation preferably of PCBP-1 antibody or antibody fragment, or other chemical or biological agents. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

2. Antibodies and Antibody Fragments

The present invention provides antibodies and antibody fragments specific for PCBP-1 antigens, including an antibody or antibody fragment capable of binding to a soluble form of PCBP-1 with a specific affinity of between $10^{-8}$ M and $10^{-11}$ M; an antibody or antibody fragment capable of binding to a soluble form of PCBP-1 in a cell; an antibody or antibody fragment capable of selectively reducing the activity of a soluble PCBP-1 in a cell; and an antibody or antibody fragment capable of preferentially binding to a soluble form of a PCBP-1.

A soluble form of PCBP-1 can be found in the cytoplasm of a ductal cancer cell with a PCBP-1 antibody of the present invention. PCBP-1 can be localized and expressed in high amounts in the nucleus in healthy breast tissue epithelial cells. As a cell undergoes transformation, PCBP-1 expression can become more cytoplasmic with some nuclear expression as well, and overall increased expression than in the healthy cells. As the ductal carcinoma cells become metastatic, PCBP-1 expression is entirely in the cytoplasm of the cells with no staining in the nucleus. While not limited to any particular mechanism, PCBP-1 protein moves from the nucleus in normal ductal epithelial cells, and as the cells are transformed, PCBP-1 becomes more cytoplasmic with some nuclear expression. As the ductal epithelial cancer cells become metastatic, the PCBP-1 can localize entirely in the cytoplasm of the cells.

The present invention includes a method of determining a likelihood of survival for a patient of breast cancer comprising contacting the sample from the patient in need thereof with an antibody capable of detecting nuclear and cytoplasmic PCBP-1; and determining the expression level of PCBP-1, where greater expression of said PCBP-1 in the sample is inversely correlated with overall survival. In an aspect, normal, non-metastatic and metastatic breast cancer ductal epithelial cellular sample images be scored 0 to 3+ according to normal pathological methods. In a particular aspect, a PCBP-1 stained assay is sent to an independent pathology laboratory to blindly score samples.

In one aspect, a score of "0" can be directed to no staining observed in invasive tumor cells. A score of "1+" can be directed to Weak, nuclear staining observed in any proportion of invasive tumor cells, or weak, cytoplasmic staining observed in less than 30% of cells in the sample. A score of "2+" can be weak cytoplasmic observed in 50% or more cells or strong cytoplasmic staining of more than 30% is observed in invasive tumor cells. A score of "3+" can be strong cytoplasmic staining observed that is in more than 50% of tumor cells. In a preferred aspect, the difference between 0/+1 and +2/+3 in ductal breast cancer samples can be particularly apparent in the higher amount of cytoplasmic staining of arrayed tissue samples scored +2 or +3. In a preferred aspect, intense staining can be easily visualized with a 10× objective, and weak staining can require 40× objective for visualization.

In an aspect of the present invention, higher levels of PCBP-1 expression (PCBP-1 score of +2 or +3) can be correlated with a decrease in a ductal breast cancer patient's overall prognosis or survival relative to ductal breast cancer patients with a lower level of PCBP-1 expression (PCBP-1 score of 0 or +1). Correspondingly, low levels of PCBP-1 expression indicate a better prognosis for a ductal breast cancer patient than high levels of PCBP-1 expression in ductal breast cancer samples.

In another aspect, higher levels of PCBP-1 expression can be correlated with a decrease in the overall prognosis of a ductal breast cancer patient with three or more positive lymph nodes. The breast cancer-specific survival rates of women with one or two positive nodes were found to have similar long-term survival; however, women with three positive nodes experienced significantly reduced survival compared to those with one or two involved nodes. (Tai, P., et al., supra). Accordingly, detection of PCBP-1 expression levels can be used to estimate overall survival of a ductal breast cancer patient.

The present invention includes a method of determining metastatic status of a breast cell or tissue in a sample comprising contacting the sample from a patient in need thereof with an antibody capable of detecting nuclear and cytoplasmic PCBP-1 and determining the subcellular location of said PCBP-1, where localization of said PCBP-1 in a cell cytoplasm of the sample is indicative of cellular metastasis. In an aspect, an antibody capable of detecting nuclear and cytoplasmic PCBP-1 is a monoclonal antibody having one or more of the heavy chain CDR antigen binding site sequences selected from the group consisting of SEQ ID NO: 45, SEQ ID NO: 46 and SEQ ID NO: 47, and one or more of the light chain CDR antigen binding site sequences selected from the group consisting of SEQ ID NO: 48, SEQ ID NO: 49 and SEQ ID NO: 50.

In another aspect, the present invention includes a method of determining a metastatic status of a breast cell or tissue in a sample comprising contacting the sample from a patient in need thereof with an antibody capable of detecting nuclear and cytoplasmic PCBP-1 and determining the subcellular location of said PCBP-1 and estrogen receptor (ER), progesterone receptor (PR), or ER and PR, where greater expression of said PCBP-1 in the sample is inversely correlated with overall survival.

In another aspect, the present invention includes a method of determining a metastatic status of a breast cell or tissue in a sample comprising contacting the sample from a patient in need thereof with an antibody capable of detecting nuclear and cytoplasmic PCBP-1 and determining the subcellular location of said PCBP-1 and estrogen receptor (ER), progesterone receptor (PR), or ER and PR, where similar subcellular localization of PCBP-1 and estrogen receptor (ER), progesterone receptor (PR), or ER and PR, is positively correlated with overall survival, non-metastasis, or overall survival and non-metastasis. In these aspects, the absence of similar localization pattern, i.e. co-localization, can include a lack of ER or PR staining where PCBP-1 staining is present in a ductal breast cancer cell cytoplasm.

An antibody or antibody fragment can be any antibody or antibody fragment of a PCBP-1 antibody of the present invention and, without limitation, can be a monoclonal antibody, a chimeric antibody, a humanized antibody, or an antibody conjugate thereof.

In an aspect, an antibody or antibody fragment can be any gamma globulin protein found in blood or other bodily fluids of vertebrates, and used by the host immune system to identify and neutralize foreign objects, such as bacteria and viruses. In one aspect, the antibody or antibody fragment can be selected from an antibody, a monoclonal antibody, a chimeric antibody, a humanized antibody, or an antibody conjugate. In an aspect, an antibody or antibody fragment can be any type of immunoglobulin protein, such as IgA, IgD, IgE, IgG or IgM.

In one aspect, an antibody or antibody fragment is capable of reducing the activity of PCBP-1. PCBP-1 activity is determined by measuring the poly(rC) binding of a sample. In an aspect, the poly(rC)-binding assay is carried out using a gel-shift assay as described in Ausubel F M, (1994). *Current Protocols in Molecular Biology*. Chichester: John Wiley and Sons ("Ausubel").

Antibodies or antibody fragments include those that are specific or preferentially selective for PCBP-1, and can be used to detect a soluble form of the PCBP-1 protein. A soluble PCBP-1 protein has a molecular weight of about 35-40 kDa, as measured by gradient polyacrylamide gel electrophoresis.

In one aspect of the present invention, an antibody or antibody fragment is capable of preferentially binding to a soluble form of PCBP-1 protein. In this aspect, such preferential binding PCBP-1 can be relative to any protein. In a particular aspect, such preferential binding to PCBP-1 is relative to PCBP-1 that is membrane bound or associated. In another particular aspect, such preferential binding to PCBP-1 is relative to PCBP-1 that is nuclear membrane bound or associated.

As used herein, a membrane associated protein is a protein that can be found localized with a membrane upon examination of cell. A membrane bound protein is one that interfaces at least in part with the lipid bilayer. In one aspect, it is bound to the membrane via ionic interactions. In another aspect, a membrane bound protein is bound to the membrane via covalent interactions. In a preferred aspect, a membrane bound protein is bound to the membrane via hydrogen bonds.

In an aspect of the present invention, the preferential binding is at least 2-fold, 3-fold, 4-fold, 5-fold, 10-fold, 100-fold, 1,000-fold, 10,000-fold or 1,000,000-fold. In another aspect, an antibody of the present invention preferentially binds a soluble form of PCBP-1 compared to a membrane form of PCBP-1. In a particular aspect, an antibody of the present invention preferentially binds a soluble form of PCBP-1 compared to a nuclear membrane form of PCBP-1, or the reverse, in another aspect. A binding of the antibody can be measured in any way, and a preferred methodology is a gel-shift assay, set forth in Ausubel.

In an aspect, an antibody or antibody fragment binds PCBP-1 or a particular form of PCBP-1 such as a soluble form or a membrane bound form with a specific affinity of greater than $10^{-7}$ M, $10^{-8}$ M, $10^{-9}$ M, $10^{-10}$ M, or $10^{-11}$ M, between $10^{-8}$ M-$10^{-11}$ M, $10^{-9}$ M-$10^{-10}$ M, and $10^{-10}$ M-$10^{-11}$ M. In a preferred aspect, specific activity is measured using a competitive binding assay as set forth in Ausubel.

Antibodies and antibody fragments can optionally be immobilized on a solid phase, detectably labeled, or conjugated to a cytotoxic radionuclide, a cytotoxic drug, or a cytotoxic protein and the like.

Antibodies and antibody fragments of the present invention can target expression of soluble PCBP-1 antigen by cells, preferably human cells, more preferably human cancer cells, and most preferably human breast, ovary, cervix, prostate, colon, stomach, kidney, liver, head, neck, lung, blood, pancreas, skin, testicle, thyroid and brain cancer cells. In one aspect of the present invention, the human breast cells can be lobular breast carcinoma cells. In another aspect of the present invention, the human breast cells can be ductal breast carcinoma cells. Expressed PCBP-1 antigens can include any form of the gene product, although particularly preferred aspects relate to the detection of the soluble or secreted form of PCBP-1. Such antigens can also include gene produced homologues of the Pcbp-1 gene and modified PCBP-1 antigens expressed by cancer cells.

In one aspect, antibodies or antibody fragments of the present invention may be used to correlate PCBP-1 expression or localization status with prognosis of survival or to determine an appropriate treatment of a patient in need thereof. In one aspect, high cytoplasmic staining of PCBP-1 relative to healthy controls using the antibodies or antibody fragments of the present invention may indicate a low likelihood of patient survival. In another aspect, nuclear PCBP-1 staining that is normal (similar to that seen in healthy controls) using the antibodies or antibody fragments of the present invention may indicate a higher likelihood of patient survival.

In another aspect of the present invention, PCBP-1 antibodies or antibody fragments of the present invention may be used to correlate PCBP-1 expression or localization status with type of disease or to determine an appropriate treatment of a patient in need thereof. In one aspect, high (2+ or 3+) cytoplasmic immunohistochemical staining of breast cancer tissues with an antibodies or antibody fragment of the present invention may be indicative of ductal breast carcinoma, while negative (0) or low (1+) cytoplasmic staining of breast cancer tissues with the antibodies or antibody fragments of the present invention may be indicative of lobular breast carcinoma.

In one aspect of the present invention, immunohistochemical staining may be high or increased relative to a suitable control. In one aspect, high or increased immunohistochemical staining is assigned a value of 2+ or 3+ for purposes of quantitation of staining. In an aspect, the suitable control may be a cell line of the same tissue type, a sample from a healthy individual or a patient having a different cytopathology, or a healthy sample from a patient having a disease, where the healthy sample is unstained on the same sample slide. In one aspect, the disease may be cancer. In another aspect, the disease may be breast cancer. In yet another aspect, the disease may be lobular or ductal breast cancer. In one aspect, the increase relative to a suitable control is two-, four-, ten- or twenty-fold or more. In another aspect, the increase relative to a suitable control is greater than 10, 20, 30, 40, 50, 60, 70, 80, 90, 95 or 99%. In another aspect, the increase is in cytoplasmic levels of the PCBP-1 antigen-antibody complex. In an aspect, an increase in the cytoplasmic levels of the PCBP-1 antigen-antibody complex is associated with ductal breast carcinoma.

In one aspect of the present invention, immunohistochemical staining may be low or reduced relative to a suitable control. In one aspect, low or reduced immunohistochemical staining is assigned a value of 0 or 1+ for purposes of quantitation of staining. In one aspect, low or reduced immunohistochemical staining means that the cytoplasm of less than 10% of cells is stained. In a preferred aspect, a score of 2+ means that the cytoplasm of greater than 50% of cancer cells in a tissue sample is not stained, while the cytoplasm of less than 50% of cancer cells in the tissue sample is stained. In another aspect, a score of 2+ is associated with ductal breast cancer.

In a preferred aspect, a score of 3+ means that the cytoplasm of greater than 90% of cancer cells in a tissue sample is stained, while the cytoplasm of less than 10% of cancer cells in the tissue sample is not stained. In another aspect, a score of 3+ is associated with ductal breast cancer. In another aspect, tissue samples assigned a score of 3+ will have a higher number of stained cells, and the cells will be stained at a higher intensity than that seen in a tissue sample assigned a score of 2+.

In an aspect, the suitable control may be a normal commercial cell line of the same type (such as SKBR3 cells or MDA-MB-231 cells), a sample from a healthy individual, or a healthy sample from a patient having a disease. In one aspect, the disease may be cancer. In another aspect, the disease may be breast cancer. In yet another aspect, the disease may be lobular or ductal breast cancer. In one aspect, the reduction relative to a suitable control is two-, four-, ten- or twenty-fold or more. In another aspect, the reduction relative to a suitable control is greater than 10, 20, 30, 40, 50, 60, 70, 80, 90, 95 or 99%. In another aspect, the reduction is in cytoplasmic levels of the PCBP-1 antigen-antibody complex. In an aspect, a reduction in the cytoplasmic levels of the PCBP-1 antigen-antibody complex is associated with lobular breast carcinoma. In an aspect, the present invention provides an antibody or antibody fragment specific for a PCBP-1 antigen, including the heavy chain CDR antigen binding site amino acid sequences CDR1 (SEQ ID NO: 45), CDR2 (SEQ ID NO: 46), and CDR3 (SEQ ID NO: 47) as set forth in FIG. 10, and the light chain CDR antigen binding site amino acid sequences CDR1 (SEQ ID NO: 48), CDR2 (SEQ ID NO: 49), and CDR3 (SEQ ID NO: 50) as set forth in FIG. 11. The present invention also provides an antibody specific for a PCBP-1 antigen, comprising one or more of the heavy chain CDR antigen binding site amino acid sequences set forth in FIG. 10 (SEQ ID NOs: 45-47), and one or more of the light chain CDR antigen binding site amino acid sequences set forth in FIG. 11 (SEQ ID NOs: 48-50).

The present invention includes PCBP-1 antibodies or antibody fragments having antigen binding sites CDR1 (SEQ ID NO: 45), CDR2 (SEQ ID NO: 46), and CDR3 (SEQ ID NO: 47), both heavy and light chains, as described in FIGS. 10 and 11. The invention also includes antibodies and antibody fragments specific to PCBP-1 expression products that contain antigen binding sites that are substantially homologous to these, or that result in substantially similar binding properties. The present invention also includes new hybridoma lines, and the monoclonal antibody molecules that they secrete, which are specific to PCBP-1 antigen expressed by normal or cancer cells. The present invention also includes chimeric and humanized antibodies and antibody fragments and also includes other modified antibodies and antibody fragments.

In addition to the specific amino acid sequences of the antigen binding sites of the heavy and light chains set forth in FIGS. 10 and 11, the present invention also encompasses antibodies and antibody fragments that are specific to PCBP-1 but which have FWR and/or CDR antigen binding site nucleotide sequences that are not identical to those set forth in FIGS. 10 and 11 (SEQ ID NOs: 19-29 and 34-44). Such antibodies and antibody fragments are preferred if they are specific or preferentially selective for the PCBP-1 antigen, preferably at least 85% as specific, more preferably at least 90% as specific, and most preferably at least 95% as specific for the PCBP-1 antigen as the antibody or antibody fragment of the present invention. According to a preferred aspect, a variant of an antibody or antibody fragment of the present invention can be as specific for the PCBP-1 antigen as a non-variant antibody or antibody fragment of the present invention, or can be more specific.

Antibodies and antibody fragments that are specific to PCBP-1 but which have FWR and/or CDR antigen binding site amino acid sequences that are not identical to those set forth in FIGS. 10 and 11 can possess the same or different specificity determining regions (SDRs) as the FWRs and/or CDRs of FIGS. 10 and 11 (SEQ ID NOs: 17 and 32) are included (set forth in bold, underlined text in these figures).

Modifications to the amino acid sequences of the antigen binding sites CDR1 (SEQ ID NO: 45 and 48, respectively), CDR2 (SEQ ID NO: 46 and 49, respectively), and CDR3 (SEQ ID NO: 47 and 50, respectively) set forth in FIG. 10 (heavy chain) and FIG. 11 (light chain) can occur in either or both of the FWR and CDR sequences. According to certain aspects of the invention, variations in antibodies or antibody fragments can occur where they have substantially homologous amino acid sequences, antibodies having substantially similar binding properties, or both.

Humanized variants of the antibodies or antibody fragments of the invention can contain a reduced murine content, and potentially, reduced immunogenicity, when compared to the murine antibodies or antibody fragments. Humanized variants include those that retain a binding affinity that is substantially similar to that of the original antibody or antibody fragment. An aspect of the invention provides CDR variants of humanized PCBP-1 antibodies or antibody fragments in which 1, 2, 3, 4, 5, or 6 (three heavy chain and three light chain) CDRs are humanized. A second aspect of the invention provides SDR variants of humanized PCBP-1 antibodies and antibody fragments in which only Specificity Determining Regions (SDRs) of at least one CDR from the PCBP-1 antibodies and antibody fragments are present in the humanized antibodies. The SDRs are selected from Table 1 or Table 2.

TABLE 1

Specificity-Determining Residues in Alper PCBP-1 Mouse Monoclonal Antibody Heavy Chain (SEQ ID NO: 17)

| Position | Residue |
| --- | --- |
| −1 | Q |
| 4 | Q |
| 5 | Q |
| 23 | A |
| 30 | S |

TABLE 2

Specificity-Determining Residues in Alper PCBP-1 Mouse Monoclonal Antibody Light Chain (SEQ ID NO: 32)

| Position | Residue |
| --- | --- |
| −2 | D |
| −1 | I |
| 1 | V |

TABLE 2-continued

Specificity-Determining Residues in Alper PCBP-1 Mouse
Monoclonal Antibody Light Chain (SEQ ID NO: 32)

| Position | Residue |
|---|---|
| 2 | L |
| 21 | C |
| 38 | Y |
| 47 | K |
| 53 | A |
| 93 | S |

CDR variants can be formed by replacing at least one CDR of humanized PCBP-1 antibodies and antibody fragments with a corresponding CDR from a human antibody. CDR variants in which one, two, three, four, five, or six CDRs are replaced by a corresponding CDR from a human antibody and retain biological activity that is substantially similar to the binding affinity of the parental PCBP-1 mAb. CDR variants of the invention can have a binding affinity that is at least 25% of the binding affinity of the parental PCBP-1 antibody or antibody fragment, more preferably at least 50%, most preferably at least 75% or 90%.

CDR variants that have altered immunogenicity when compared to PCBP-1 antibodies and antibody fragments can be formed by grafting all six (three heavy chain and three light chain) CDRs from the PCBP-1 antibodies and antibody fragments of the present invention onto the variable light (VL) and variable heavy (VH) frameworks of human antibodies and antibody fragments. However, less than all six of the CDRs of the PCBP-1 antibodies and antibody fragments of the present invention can be present, while still permitting the humanized antibody to retain activity. Residues that are directly involved in antigen contact, the Specificity Determining Residues (SDRs), can be refined. SDR variants are formed by replacing at least one SDR of the PCBP-1 antibody or antibody fragment with a residue at a corresponding position from a human antibody. It should be noted that not all CDRs include SDRs.

In a preferred aspect, the variants of the present antibodies and antibody fragments include a combination of CDR and/or SDR substitutions to generate variants having reduced immunogenicity and a binding affinity that is substantially similar to that of the parental antibody or antibody fragment to PCBP-1.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis.

Alternatively, polypeptide fragments comprising only a portion of the primary antibody structure can be produced wherein the fragment substantially retains the immunoreactivity properties of the variant. Such polypeptide fragments include fragments produced by proteolytic cleavage of intact antibodies or fragments produced by inserting stop codons at the desired locations nucleotide sequence using site-directed mutagenesis. Single chain antibodies and fusion proteins which include at least an immunoreactivity fragment of the variant are also included within the scope of the invention.

The antibodies and their variants in accordance with the present invention can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of PCBP-1, including cancer, such as cancer of the breast, ovary, cervix, prostate, colon, stomach, kidney, liver, head, neck, lung, blood, pancreas, skin, testicle, thyroid and brain. The pharmaceutical compositions are preferably administered to a mammal, more preferably a human patient in need of such treatment, in order to treat the disease.

Antibodies and antibody fragments can either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available.

3. Nucleic Acid Molecules and Host Cells

Any of the antibodies or antibody fragments of the present invention can be encoded by nucleic acids. The present invention includes such molecules, fragments of such molecules and such molecules included in vectors and the like. Nucleic acid molecules also include the complement of such nucleic acid molecules. Both DNA and RNA molecules are examples of nucleic acid molecules.

In another aspect, the present invention provides an isolated DNA sequence which encodes the heavy chain of an antibody molecule, wherein said antibody molecule has specificity for PCBP-1 antigens and wherein the variable domain of said heavy chain comprises a CDR having the antigen binding site amino acid sequences CDR1, CDR2, and CDR3 set forth in FIG. 10.

In yet another aspect, the present invention provides an isolated DNA sequence which encodes the light chain of an antibody molecule, wherein said antibody molecule has specificity for PCBP-1 antigens and further wherein the variable domain of said light chain comprises a CDR having the antigen binding site amino acid sequences CDR1, CDR2, and CDR3 set forth in FIG. 11.

In another aspect, the present invention includes and provides a nucleic acid molecule in a host cell. Such nucleic acid molecule can be integrated into the genome of the host cell or can be present on a vector such as a plasmid or viral vector. A nucleic acid molecule may be transiently present in such a host cell. In one aspect, a host cell is selected from the group E. coli; Bacilli, including Bacillus subtilis; enterobacteriacae, including Salmonella, Serratia and Psesudomonas, yeast, including Saccharomyces; Pichia pastoris; Sf9 insect cells; Sp2/0, VERO and HeLa cells, Chinese hamster ovary (CHO) cell lines; W138, BHK, COS-7 and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145 and LNCap cells.

4. Methods of Making PCBP-1 Antibodies or Antibody Fragments

PCBP-1 antibodies or antibody fragments of the present invention can be developed, for example, using the human breast cancer cell line SKBR3 (available from the American Type Culture Collection as ATCC No. HTB30).

The present invention includes processes for producing monoclonal, chimeric, including humanized antibodies using recombinant DNA technology. See, for example, Antibodies, A Laboratory Manual (Harlow & Lane Eds., Cold Spring Harbor Press, 1988).

PCBP-1 antibodies or antibody fragments of the present invention can be produced by any known method including, without limitation, generating murine hybridomas which produce antibodies or antibody fragments specific for PCBP-1. Hybridomas can be formed, for example, by the fusion of a mouse fusion partner cell and spleen cells from mice immunized against PCBP-1. Mice can be immunized with crude or semi-purified preparations containing the antigens of interest. To immunize the mice, a variety of different conventional protocols can be followed. For example, mice can receive primary and boosting immunizations of antigenic preparations.

Cell fusions can be accomplished by any procedures known to those skilled in the field of immunology. Fusion partner cell lines and methods for fusing and selecting hybridomas and screening for antibodies or antibody fragments are known.

Antibodies or antibody fragments of the present invention can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the antibodies and antibody fragments can be produced by culturing hybridoma cells in vitro and isolating the secreted antibody or antibody fragment from the cell culture medium.

PCBP-1 antibodies or antibody fragments of the present invention can also be produced by expressing the appropriate DNA sequence in a host after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of the PCBP-1 antibodies and antibody fragments can be inserted into separate expression vectors, or into the same expression vector.

Suitable hosts include, without limitation, prokaryotic strains such as *E. coli*; Bacilli, including *Bacillus subtilis*; enterobacteriacae, including *Salmonella, Serratia* and *Psuedomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells, can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Isolated or purified DNA sequences can be incorporated into a cloning or expression vector, which can in turn be used to transform a host cell. The transformed host cells can be used in a process for the production of an antibody molecule having specificity for PCBP-1 antigens, including culturing the host cells and isolating the antibody molecules they produce.

5. Diagnostic Methods, Assays, and Kits

In a further aspect, the present invention provides an immunoassay for detecting a PCBP-1 antigen comprising an antibody or antibody fragment of the present invention.

The present invention also provides an immunoassay for detecting a PCBP-1 antigen which binds to a monoclonal antibody having one or more of the heavy chain CDR antigen binding site amino acid sequences set forth in FIG. 10 (SEQ ID NOs: 45-47), and one or more of the light chain CDR antigen binding site amino acid sequences set forth in FIG. 11 (SEQ ID NOs: 48-50).

The present invention also provides an immunoassay for detecting a PCBP-1 antigen which binds to a monoclonal antibody having the one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50), comprising: (a) contacting said sample with an effective binding amount of an antibody specific for a PCBP-1 antigen, comprising the heavy chain CDR antigen binding site sequences CDR1, CDR2, and CDR3, selected from the group consisting of SEQ ID NO: 45, SEQ ID NO: 46, and SEQ ID NO: 47, and the light chain CDR antigen binding site sequences CDR1, CDR2, and CDR3, selected from the group consisting of SEQ ID NO: 48, SEQ ID NO: 49, and SEQ ID NO: 50; and (b) detecting said antigen by detecting the binding of the antibody to the PCBP-1 antigen. The present invention also provides an immunoassay for detecting a PCBP-1 antigen which binds to a monoclonal antibody having the one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50), comprising: (a) contacting said sample with an effective binding amount of an antibody specific for a PCBP-1 antigen, comprising one or more of the heavy chain CDR antigen binding site sequences selected from the group consisting of SEQ ID NO: 45, SEQ ID NO: 46, and SEQ ID NO: 47, and one or more of the light chain CDR antigen binding site sequences selected from the group consisting of SEQ ID NO: 48, SEQ ID NO: 49, and SEQ ID NO: 50; and (b) detecting said antigen by detecting the binding of the antibody to the PCBP-1 antigen. In one aspect of the invention, an immunoassay of the present invention is used to determine an appropriate treatment of a patient in need thereof where said patient has symptoms of a disease characterized by the expression of gene products of Pcbp-1 and its homologues. In vitro analysis can be performed on a tissue specimen obtained from patients in need thereof in order to predict the likelihood of patient survival.

Such immunoassays can be used in any suitable manner, including, without limitation, by comprising: (a) contacting said sample with an effective binding amount of one of the antibodies or antibody fragments of the invention; and (b) detecting said antigen by detecting the binding of the antibody to the PCBP-1 antigen. Immunoassays of the present invention can be used to detect cancer cells expressing a PCBP-1 antigen, particularly cancer, tumor, carcinoma cells or neoplastic disease cells selected from the group consisting of breast, ovarian, cervical, prostate, colon, stomach, kidney, liver, head, neck, lung, blood, pancreatic, skin, testicular, thyroid and brain cancers.

In a further aspect, the present invention provides a kit for the immunohistochemical detection of carcinoma comprising: (a) an antibody or antibody fragment of the present invention; and (b) a secondary antibody conjugated to a detectable label. In a further aspect, a kit of the present invention further comprises an antibody or antibody fragment capable of recognizing the estrogren receptor (ER).

In a further aspect, the present invention provides a kit for making a prognosis regarding the likelihood of survival of a carcinoma patient in need thereof, or for determining appropriate treatment options for a patient in need thereof, comprising: (a) an antibody or antibody fragment of the present invention; and (b) a secondary antibody conjugated to a detectable label. In a further aspect, a kit of the present invention further comprises an antibody or antibody fragment capable of recognizing the estrogen receptor (ER).

In a further aspect, the present invention provides a kit for making a prognosis regarding the status of disease in a breast carcinoma patient in need thereof comprising: (a) an antibody or antibody fragment of the present invention; and (b) a secondary antibody conjugated to a detectable label. In one aspect, the kit may differentiate between ductal and lobular breast carcinoma. In a further aspect, a kit of the present invention further comprises an antibody or antibody fragment capable of recognizing the estrogen receptor (ER).

In a further aspect, the present invention provides a kit for the immunohistochemical detection of carcinoma comprising: (a) a monoclonal antibody having one or more of the heavy chain CDR antigen binding site amino acid sequences set forth in FIG. 10, and one or more of the light chain CDR antigen binding site amino acid sequences set forth in FIG. 11; and (b) a secondary antibody conjugated to a detectable label. In a further aspect, a kit of the present invention further comprises an antibody or antibody fragment capable of recognizing the estrogen receptor (ER).

In one aspect, the immunohistochemical analysis can be performed on a glass slide. In another aspect, the immunohistochemical analysis can be performed on a plastic slide. In another aspect, the immunohistochemical analysis can be performed on a slide made from a material other than glass or plastic.

In a further aspect, the present invention provides for Fluorescence In Situ Hybridization (FISH) of the pcbp-1 gene to determine the copy number of pcbp-1 gene sequences in a normal cells, non-metastatic cancer cells and metastatic cancer cells. In one aspect, increased expression of PCBP-1 protein as determined using the methods of the present invention can be accompanied by duplication/amplification of the pcbp-1 gene. In another aspect, duplication of the pcbp-1 gene may precede the changes of expression of PCBP-1 protein as provided in the present invention. FISH is a method to analyze genes at the chromosome level and is capable of detecting and characterizing genetic changes such as gene/chromosome amplification/duplication, deletion, translocation, rearrangement and other abnormalities associated with genes and/or chromosomes. The term "in situ hybridization" generally refers to hybridization of a nucleic acid probe to a nucleic acid target that is part of a cytological or histological preparation. Typically, FISH methods involve the following steps: (a) fixing the tissue, cells from a culture or other biological material under investigation to a support (e.g., glass slide or wall of a micro titer well), (b) treatment of the tissue or material to increase accessibility of probe DNA to target DNA (e.g., permeabilizing the cell, denaturing the target DNA, and blocking repetitive sequences in the target DNA) (c) contacting the tissue or material containing target DNA with probes to form specific hybridization complexes, (d) post hybridization washes of the complexes to selectively remove probes that are not specifically hybridized to the target, and (e) detection of probes that have formed hybridization complexes with target DNA molecules (e.g., by directly visualizing a fluorescently labeled DNA probe or by using a secondary fluorescent probe). An advantage of FISH is that one can analyze individual cells and visualize the location on chromosomes. FISH can determine both the number of copies of a given DNA probe sequence in a cell as well as identify duplications, translocations and deletions of target DNA sequences. Methods for FISH are known in the art and are described in a number of sources, including: Gall and Pardue, (1981) Methods of Enzymology 21:470-480; Henderson, (1982) International Review of Cytology, 76:1-46; and Angerer, et al., (1985) in Genetic Engineering: Principles and Methods (Setlow and Hollaender, Eds.) vol. 7, pp. 43-65, Plenum Press, New York.

The FISH method is performed on a chromosome spread of a sample. In one aspect, a FISH sample may be a histological preparation obtained from a breast cell or tissue from a sample obtained from a patient. In one aspect, the chromosome spread is obtained from a culture of cells including primary cultures prepared from a sample of a patient or from established cell lines known to one of ordinary skill in the art. A chromosomal spread may be an interphase or metaphase spread or the sample can have cells at a variety of stages of the cell cycle.

Probe size is important because longer probes hybridize less specifically than shorter probes. The overlap defines the resolution of detectable features. For example, if the goal of an experiment is to detect the breakpoint of a translocation, then the overlap of the probes—the degree to which one DNA sequence is contained in the adjacent probes—defines the minimum window in which the breakpoint may be detected.

The mixture of probe sequences determines the type of features the probe can detect. Probes that hybridize along an entire chromosome are used to count the number of a certain chromosome, show translocations, or identify extra-chromosomal fragments of chromatin. This is often called "whole-chromosome painting." If every possible probe is used, every chromosome, (the whole genome) would be marked fluorescently, which would not be particularly useful for determining features of individual sequences. However, a mixture of smaller probes can be created that is specific to a particular region (locus) of DNA; these mixtures are used to detect deletion mutations. When combined with a specific color, a locus-specific probe mixture is used to detect very specific translocations.

A variety of other techniques use mixtures of differently-colored probes. A range of colors in mixtures of fluorescent dyes can be detected, so each human chromosome can be identified by a characteristic color using whole-chromosome probe mixtures and a variety of ratios of colors. Although there are more chromosomes than easily-distinguishable fluorescent dye colors, ratios of probe mixtures can be used to create secondary colors. Similar to comparative genomic hybridization, the probe mixture for the secondary colors is created by mixing the correct ratio of two sets of differently-colored probes for the same chromosome. This technique is sometimes called M-FISH. The same physics that make a variety of colors possible for M-FISH can be used In the opposite situation—where the absence of the secondary color is pathological—is illustrated by an assay used to investigate translocations where only one of the breakpoints is known or constant. Locus-specific probes are made for one side of the breakpoint and the other intact chromosome. In normal cells, the secondary color is observed, but only the primary color is observed when the translocation occurs. This technique is sometimes called "break-apart FISH".

In one aspect of the present invention, bacterial artificial chromosome (BAC) clone number RP11-175A7 (Genbank No. AC016700, 177995 bp, SEQ ID NO: 55) can be used to detect the presence, copy number and chromosomal location of the pcbp-1 gene in a sample using FISH. In one aspect, an increased number of copies can be detected by FISH that correlates with the increased expression of PCBP-1 protein detected using the immunological techniques of the present invention. In another aspect, the changes in copy number or chromosomal location can correspond with the change in cellular location of PCBP-1 protein (e.g., nuclear vs. cytoplasmic). In yet another aspect, an increased copy number of the pcbp-1 gene may be used to identify cells in tissue samples that have an increased likelihood of becoming metastatic.

In a further aspect, DNA probes for FISH analysis of the pcbp-1 gene can be prepared by one of ordinary skill in the art. In one aspect, additional probes may comprise cDNA sequences of the pcbp-1 gene. In another aspect nucleic acid sequences obtainable from the group consisting of UniProt Q15365, Q53SS8, Q14975; OMIM 601209; NCBI Gene 5093; NCBI RefSeq NP_006187; NCBI RefSeq NM_006196, NP_006187; NCBI UniGene 5093; and NCBI Accession AK130439, AAA91317 can be used.

In an aspect of the present invention, FISH probes (e.g., DNA probes containing a detectable label) of the nucleic acid sequences capable of detecting the pcbp-1 gene can be prepared by nick translation. Nick translation is well known to one of ordinary skill in the art. Briefly, nick translation is a tagging technique in molecular biology in which DNA Polymerase I is used to replace some of the nucleotides of a DNA sequence with their labeled analogues, creating a tagged DNA sequence which can be used as a probe in FISH or other hybridization techniques. This process is called nick translation because the DNA to be processed is treated with DNase to produce single-stranded "nicks." This is followed by replacement in nicked sites by DNA polymerase I, which elongates the 3' hydroxyl terminus, removing nucleotides by 5'-3' exonuclease activity, replacing them with dNTPs. To radioactively label a DNA fragment for use as a probe in blotting procedures, one of the incorporated nucleotides provided in the reaction is radiolabeled in the alpha phosphate position. Similarly, a fluorophore can be attached instead for fluorescent labeling, or an antigen for immuno-detection. When DNA polymerase I eventually detaches from the DNA, it leaves another nick in the phosphate backbone. The nick has "translated" some distance depending on the processivity of the polymerase. This nick could be sealed by DNA ligase, or its 3' hydroxyl group could serve as the template for further DNA polymerase I activity. Proprietary enzyme mixes are available commercially to perform all steps in the procedure in a single incubation. Nick translation may cause double-stranded DNA breaks but this does not influence the performance of the labeled probe in in situ hybridization.

In one aspect, the DNA sequence can be tagged directly with a fluorescently labeled nucleotide. In a further aspect, the DNA sequence can be indirectly labeled with a nucleotide incorporating a modified nucleotide. In an aspect, a detectable label can be introduced by polymerization using nucleotides that include at least some modified nucleotides, such as nucleotides modified to include biotin, digoxygenin, fluorescein, or cyanine. In another aspect, the detectable label is introduced by random-priming and polymerization. Other examples include nick translation (Roche Applied Science, Indianapolis Ind.; Invitrogen, Carlsbad Calif.) and chemical labeling (Kreatech ULS, Amsterdam NL). Detectable labeling of nucleic acids is well known in the art and any labeling method appropriate for labeling DNA can be used.

First, a probe is constructed. The probe must be large enough to hybridize specifically with its target but not so large as to impede the hybridization process. The probe is tagged directly with fluorophores, with targets for antibodies or with biotin. Tagging can be done in various ways, such as nick translation, or PCR using tagged nucleotides.

Then, an interphase or metaphase chromosome preparation is produced. The chromosomes are firmly attached to a substrate, usually glass. Repetitive DNA sequences must be blocked by adding short fragments of DNA to the sample. The probe is then applied to the chromosome DNA and incubated for approximately 12 hours while hybridizing. Several wash steps remove all unhybridized or partially-hybridized probes. The results are then visualized and quantified using a microscope that is capable of exciting the dye and recording images.

In an aspect, if the fluorescent signal is weak, amplification of the signal can be used in order to exceed the detection threshold of the microscope. Fluorescent signal strength depends on many factors such as probe labeling efficiency, the type of probe, and the type of dye. Fluorescently-tagged antibodies or streptavidin are bound to the dye molecule. These secondary components are selected so that they have a strong signal. In a further aspect, FISH experiments designed to detect or localize gene expression within cells and tissues can rely on the use of a reporter gene, such as one expressing green fluorescent protein, to provide the fluorescence signal.

In a further aspect, the present invention provides a kit for making a prognosis regarding the likelihood of survival of a carcinoma patient in need thereof comprising: (a) a monoclonal antibody having one or more of the heavy chain CDR antigen binding site amino acid sequences set forth in FIG. 10, and one or more of the light chain CDR antigen binding site amino acid sequences set forth in FIG. 11; and (b) a secondary antibody conjugated to a detectable label. In a further aspect, a kit of the present invention further comprises an antibody or antibody fragment capable of recognizing the estrogen receptor (ER).

In a further aspect, the present invention provides a kit for making a prognosis regarding the status of disease in a breast carcinoma patient comprising: (a) a monoclonal antibody having one or more of the heavy chain CDR antigen binding site amino acid sequences set forth in FIG. 10, and one or more of the light chain CDR antigen binding site amino acid sequences set forth in FIG. 11; and (b) a secondary antibody conjugated to a detectable label.

Kits can include reagents for assaying a sample for a PCBP-1 antigen, where such kits may include: PCBP-1 antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of a PCBP-1 antigen in a sample; and the like. Other examples of kits or kit formats are found in Alper, US Publication No. 2008/0293162, and in the Scoring Guide for the Interpretation of Ventana Pathway HER2—Staining of Breast Carcinomas (Ventana Medical Systems, Inc., Tuscon, Ariz., USA), both of which are herein incorporated by reference in their entireties. In a further aspect, a kit including reagents for assaying a sample for a PCBP-1 antigen may further include an antibody or antibody fragment capable of recognizing the estrogen receptor (ER).

In further aspect, the present invention provides a method for diagnosing cancer in humans comprising: (a) contacting a specimen from a patient suspected of having cancer with an antibody or antibody fragment of the present invention; (b) labeling said specimen; and (c) detecting the presence of the antigen-antibody complex by said label. Such a method of diagnosing cancer can be performed in vivo or in vitro. In one aspect, the cancer can be breast cancer. In another aspect, the breast cancer can be lobular or ductal breast cancer.

In further aspect, the present invention provides a method for making a prognosis of the likelihood of survival of a cancer patient in need thereof, or determining appropriate treatment options for a patient in need thereof, comprising: (a) contacting a specimen from a patient suspected of having a cancer with an antibody or antibody fragment of the present invention; (b) labeling said specimen; and (c) detecting the presence of the antigen-antibody complex by said label. Such a method of diagnosing cancer can be performed in vivo or in vitro. In one aspect, the method further comprises detecting the cellular localization of the antibody-antigen complex. In one aspect, the cancer can be breast cancer. In another aspect, the breast cancer can be lobular or ductal breast cancer. In one aspect, the cellular localization of the antibody-antigen complex is cytoplasmic.

Figure 15:
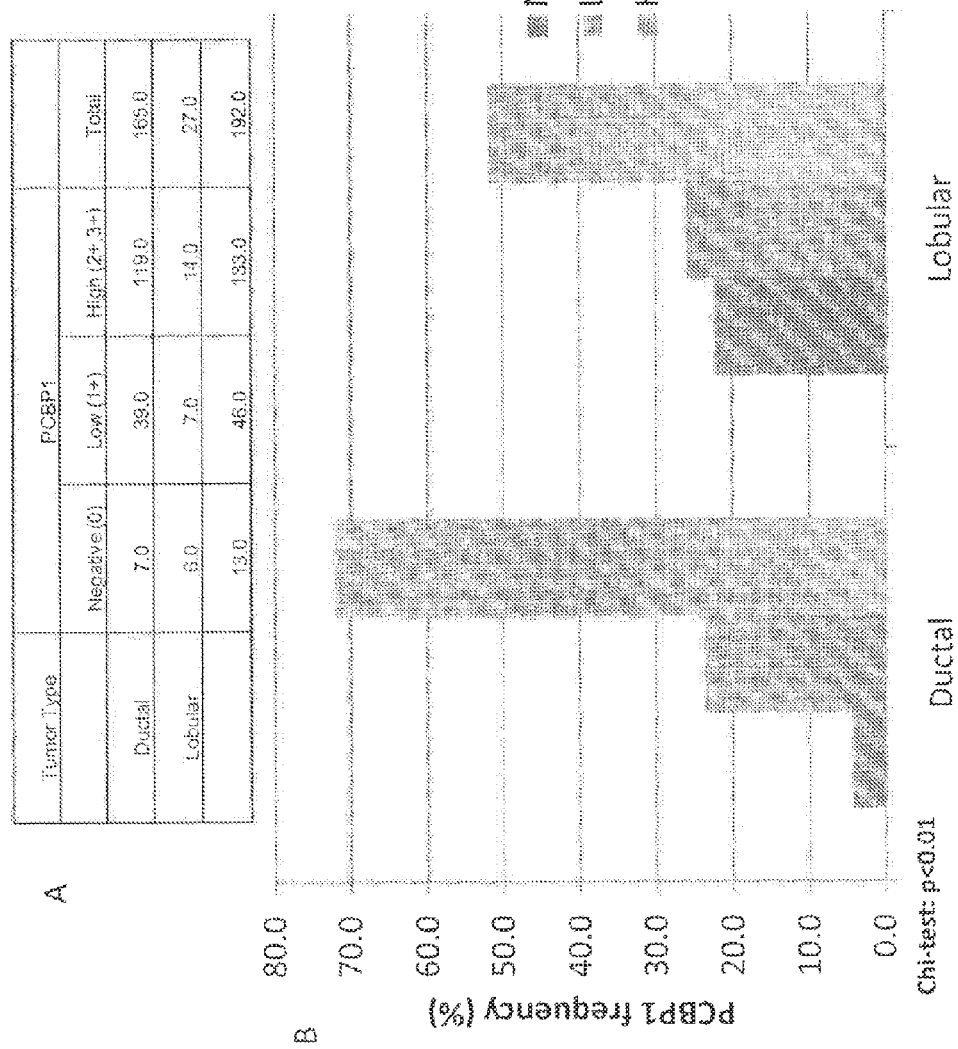
FIG. 15. Chart A of FIG. 15 is the number of ductal and lobular carcinoma samples displaying negative (0), low (1+) and high (2+ or 3+) immunohistochemical staining with Alper PCBP-1 mouse monoclonal antibody. Chart B of FIG. 15 is a graph of the number of ductal and lobular carcinoma samples displaying negative, low and high immunohistochemical staining with Alper PCBP-1 mouse monoclonal antibody. A higher percentage of ductal carcinoma patients expressed high levels of PCBP-1 than in lobular carcinoma patients.

In one aspect, the method further comprises detecting the level of the antigen-antibody complex in the cytoplasm. As shown in FIG. 15, a level of 0 (negative) or 1+ (low) can be indicative of lobular breast cancer, while a level of 2+ or 3+ (high) can be indicative of ductal breast cancer. In one aspect of the present invention, greater than 50%, greater than 60% or greater than 70% of patients having levels of 2+ or 3+ have ductal breast cancer. In another aspect of the present invention, less than 60%, less than 50%, or less than 40% of patients having levels of 2+ or 3+ have lobular breast cancer. In one aspect, diagnosis with lobular breast cancer can indicate a higher likelihood of survival than diagnosis of ductal breast cancer.

In a still further aspect, the present invention provides a method for diagnosing cancer in humans comprising: (a) contacting a specimen from a patient suspected of having a cancer with a monoclonal antibody having one or more of the heavy chain CDR antigen binding site amino acid sequences set forth in FIG. 10, and one or more of the light chain CDR antigen binding site amino acid sequences set forth in FIG. 11; (b) labeling said specimen; and (c) detecting the presence of the antigen-antibody complex by said label. The method of diagnosing cancer can be performed in vivo or in vitro. In one aspect, the cancer can be breast cancer. In another aspect, the breast cancer can be lobular or ductal breast cancer.

In a still further aspect, the present invention provides a method for making a prognosis of the likelihood of survival of a cancer patient in need thereof comprising: (a) contacting a specimen from a patient suspected of having a cancer with a monoclonal antibody having one or more of the heavy chain CDR antigen binding site amino acid sequences set forth in FIG. 10, and one or more of the light chain CDR antigen binding site amino acid sequences set forth in FIG. 11; (b) labeling said specimen; and (c) detecting the presence of the antigen-antibody complex by the label. The method of determining an appropriate treatment of a patient having cancer can be performed in vivo or in vitro. In one aspect, the method further comprises detecting the cellular localization of the antibody-antigen complex. In one aspect, the cellular localization of the antigen-antibody complex is cytoplasmic.

The cancer being diagnosed include those that are selected from the group consisting of solid tumors of the breast, ovary, cervix, prostate, colon, stomach, kidney, liver, head, neck, lung, pancreas, skin, testicle, thyroid and brain. In one aspect, the breast cancer is ductal or lobular breast cancer. In an additional aspect, the present invention provides a method for developing drugs useful in treating, diagnosing, or both treating and diagnosing diseases characterized by the expression of gene products of Pcbp-1 and homologues thereof, including identifying gene products expressed by Pcbp-1 and homologues thereof, and utilizing said gene products as biomarkers in the development and identification of drugs selected from the group consisting of PCBP-1 antibodies and antibody fragments, inhibiting peptides, siRNA, antisense oligonucleotides, vaccines, and chemical compounds, which specifically target said gene products.

In another aspect of the invention, a method is provided for determining appropriate treatment options of a patient in need thereof where the patient has symptoms of a disease characterized by the expression of gene products of Pcbp-1 and homologues thereof comprising a) contacting a tissue specimen of said patient in need thereof; with an antibody capable of preferentially detecting a soluble form of PCBP-1 antigen; b) staining said tissue specimen with a immunohistochemical stain; and c) determining the intensity and/or localization of the staining of said tissue specimen; wherein the intensity and/or localization of said staining correlates with the survival of said patient. For example, high cytoplasmic staining (assigned a value of 2+ or 3+) of PCBP-1 using the antibodies or antibody fragments of the present invention may indicate a low likelihood or patient survival. In another aspect, PCBP-1 staining that is negative or low (0 or 1+) relative to suitable controls may indicate a high likelihood of patient survival. In one aspect of the present invention, the intensity of said staining is measured relative to intensity of staining of suitable controls. In one aspect of the invention, said disease is cancer. In another aspect of the present invention, the cancer is breast cancer. In another aspect, the breast cancer is ductal or lobular breast cancer. In one aspect, high cytoplasmic staining (assigned a value of 2+ or 3+) of PCBP-1 using the antibodies or antibody fragments of the present invention may indicate ductal breast cancer. In another aspect, negative or low cytoplasmic staining (assigned a value of 0 or 1+) of PCBP-1 using the antibodies or antibody fragments of the present invention may indicate lobular breast cancer. As shown in FIG. 15, a level of 0 (negative) or 1+ (low) can be indicative of lobular breast cancer, while a level of 2+ or 3+ (high) can be indicative of ductal breast cancer. In one aspect of the present invention, greater than 50%, greater than 60% or greater than 70% of patients having levels of 2+ or 3+ have ductal breast cancer. In another aspect of the present invention, less than 60%, less than 50%, or less than 40% of patients having levels of 2+ or 3+ have lobular breast cancer. In one aspect, diagnosis with lobular breast cancer can indicate a higher likelihood of survival than diagnosis of ductal breast cancer. In a further aspect of the invention, immunohistochemical staining is any of the known methods in skilled art.

In another aspect of the invention, a method is provided for determining a metastatic status of a breast cell or tissue in a sample comprising contacting the sample from a patient in need thereof with an antibody capable of detecting nuclear and cytoplasmic PCBP-1 and determining the subcellular location of said PCBP-1, where localization of said PCBP-1 in a cell cytoplasm of the sample is indicative of cellular metastasis.

In another aspect of the invention, a method is provided for determining a likelihood of survival for a patient of breast cancer comprising contacting the sample from the patient in need thereof with an antibody capable of detecting nuclear and cytoplasmic PCBP-1; and determining the expression level of PCBP-1, where greater expression of said PCBP-1 in the sample is inversely correlated with overall survival.

In another aspect of the invention, a method is provided for determining likelihood of survival for a patient of breast cancer comprising contacting the sample from the patient in need thereof with an DNA probe capable of detecting pcbp-1; and determining the chromosome localization of pcbp-1, wherein detection of more than two copies of said pcbp-1 in the sample is correlated with overall survival.

In another aspect of the invention, a method is provided for determining likelihood of survival for a patient of breast cancer comprising contacting the sample from the patient in need thereof with an DNA probe capable of detecting pcbp-1; and determining the chromosome localization of pcbp-1, wherein detection of more than two copies of said pcbp-1 in the sample is correlated with overall survival. In an aspect, more than two copies of said pcbp-1, can be three, four, five, six or more copies in a cell. In another aspect, the number of copies can be greater than the two copies found in a normal non-cancerous cell. In an aspect, the number of copies may be any additional copies not found on human chromosome 2.

An antibody or antibody fragment of the present invention can also be used in diagnosis of diseases characterized by the expression of PBCP-1, such as cancer. In another aspect, an antibody or antibody fragment of the present invention can also be used in determining appropriate treatment options of a patient having symptoms of a disease characterized by the expression of PBCP-1, such as cancer. In another aspect of the present invention, the cancer is breast cancer. In another aspect, the breast cancer is ductal or lobular breast cancer.

For example, in vivo diagnosis and imaging of a solid tumor of the breast, ovary, cervix, prostate, colon, stomach, kidney, liver, head, neck, lung, blood, pancreas, skin, testicle, thyroid and brain that expresses PBCP-1 can be performed in accordance with the methods of the invention. An antibody or antibody fragment of the present invention can also be used for diagnosis of diseases characterized by the expression of PBCP-1, for determining appropriate treatment options, or for prognosis regarding the likelihood of survival of a patient in vitro, for example, by using an antibody or antibody fragment to detect the presence of the cancer marker PBCP-1 in a fluid or tissue sample.

Antibodies and antibody fragments can be used in immunoassays to screen body fluids, such as serum, sputum, effusions, urine, cerebrospinal fluid, and the like, for the presence of PCBP-1. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

In one aspect, an antibody or antibody fragment of the present invention can be used to detect an increase in PCBP-1 expression. In another aspect, an antibody or antibody fragment of the present invention can be used to detect a decrease in PCBP-1 expression. In another aspect, an antibody or antibody fragment of the present invention can be used to detect a change in the cellular localization of PCBP-1. A PCBP-1 antibody or antibody fragment, which can include any or all of the antibodies or antibody fragments specific for PCBP-1-related gene products, and/or chimeric, humanized, or other variants thereof, can be used therapeutically, or in developing and performing assays, in vivo or in vitro diagnostic procedures, and imaging. The antibodies can be used alone or in combination with a pharmaceutically-acceptable or diagnostic or prognostic carrier formulation. PCBP-1 antibodies or antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present invention provides therapeutic, diagnostic and prognostic compositions comprising an antibody or antibody fragment of the present invention in combination with a pharmaceutically acceptable excipient, diluent or carrier. The present invention also includes a process for preparation of a therapeutic, diagnostic or prognostic composition comprising admixing an antibody molecule of the present invention together with a pharmaceutically acceptable excipient, diluent or carrier. An antibody molecule can be the sole active ingredient in the therapeutic, diagnostic or prognostic composition, or can be accompanied by other active ingredients including other antibody ingredients, for example anti-T cell, anti-IFNγ or anti-LPS antibodies, or non-antibody ingredients such as xanthines. Compositions can be incorporated into kits for diagnosing or treating diseases or predicting the outcomes of diseases characterized by the expression of PCBP-1, including, without limitation, solid tumors, and particularly solid tumors of the breast, ovary, cervix, prostate, colon, stomach, kidney, liver, head, neck, lung, pancreas, skin, testicle, thyroid and brain. In a particularly preferred aspect, the cancer is breast cancer. In one aspect, the present invention provides therapeutic, diagnostic and prognostic compositions for determining whether a breast cancer is ductal or lobular.

Antibodies or antibody fragments of the present invention are useful for immunoassays which detect or quantitate PCBP-1 or cells bearing PCBP-1 in a sample. Such an immunoassay typically comprises incubating a biological sample in the presence of a detectably labeled antibody of the present invention capable of identifying the tumor antigen, and detecting the labeled antibody which is bound in a sample.

In an aspect of the present invention the level, localization or both of one or more forms of PCBP-1 can determine, confirm or indicate the status of a cell, collection of cells, or sample from a subject. As used herein, "confirm" means that based on the level, localization, or both of one or more forms of PCBP in a cell, collection of cells or sample, subject etc provides a sufficient basis to characterize the status of a cell, collection of cells, sample or subject etc. As used herein, "confirm" means that based on the level, localization or both of one or more forms of PCBP in a cell, collection of cells or sample, subject etc provides in combination with other analysis a basis to characterize the status of a cell, collection of cells, sample or subject etc. As used herein, "indicate" means that based on the level, localization or both of one or more forms of PCBP in a cell, collection of cells or sample, subject etc provides that more likely than not or greater probability of determining the status of a cell, collection of cells, sample or subject etc. is of a particular status. In one aspect, high (2+ or 3+) cytoplasmic staining of breast cancer samples can indicate that a patient has ductal breast cancer, while negative (0) or low (1+) cytoplasmic staining of breast cancer samples can indicate that a patient has lobular breast cancer.

A status of a cell or collection of cells can include any aspect and in one aspect is whether that a cell, collection of cells, sample, etc. are metastatic, non-metastatic tumor cells or normal cells. A status of a subject can include whether the analysis provides information on whether a metastatic cancer or non-metastatic tumor is present in the subject. In one aspect, a status of a subject can include whether a breast cancer is ductal or lobular.

Examples of confirmatory analysis, assays, tests etc. that can be used to confirm or in combination with those disclosed include, without limitation, those set forth in Alper, US Publication No. 2008/0293162, as well as histological examination of samples.

In an aspect of the present invention the level, localization, or both, of one or more forms of PCBP-1 is diagnostic or prognostic of a disease or outcome probability. In one aspect, high cytoplasmic staining (2+ or 3+) of PCBP-1 relative to suitable controls using the antibodies or antibody fragments of the present invention may indicate a low likelihood of patient survival. In another aspect, nuclear PCBP-1 staining that is negative (0) or low (1+) relative to suitable controls using the antibodies or antibody fragments of the present invention may indicate a higher likelihood of patient survival. In another aspect, high cytoplasmic staining (2+ or 3+) of breast cancer samples can indicate that a patient has ductal breast cancer, while negative (0) or low (1+) cytoplasmic staining of breast cancer samples can indicate that a patient has lobular breast cancer. In one aspect, a suitable positive control can be SKBR3 cells or MDA-MB-231 cells, and a suitbale negative control can be healthy bladder cells.

In an aspect of the present invention a reduced level of a soluble form of PCPB-1 in a cell, collection of cells or sample can diagnose, prognose, monitor, determine, confirm or indicate that such derived is from a metastatic tissue. In one aspect, "reduced" can mean reduced relative to a control, with the control being a normal cell of the same type that is non-metastatic. In this aspect, the reduction can be greater than 10, 20, 30, 40, 50, 60, 70, 80, 90, 95, or 99%. In another aspect, the reduction can be two-, four-, ten-, or twenty-fold or more.

In an aspect of the present invention an increased level of a soluble form of PCPB-1 in a cell, collection of cells or sample can diagnose, prognose, monitor, determine, confirm or indicate that such derived is from a metastatic tissue. In one aspect, "increased" can mean increased relative to a control, with the control being a normal cell of the same type that is non-metastatic. In this aspect, the increase can be greater than 10, 20, 30, 40, 50, 60, 70, 80, 90, 95, or 99%. In another aspect, the increase can be two-, four-, ten-, or twenty-fold or more.

In one aspect of the present invention, PCBP-1 expression is measured using immunohistochemistry followed by a quantitative method. In one aspect, a quantitative method can be software such as AQUANALYSIS™ software (HistoRx, Inc., New Haven, Conn., USA). In another aspect, a quantitative method such as AQUANALYSIS™ software can be used in addition to the methods described in Example 13. In one aspect of the present invention, PCBP-1 expression is relative to PCBP-1 expression in normal controls. In another aspect, PCBP-1 expression in cancer cells can be expressed as a percentage of PCBP-1 expression in normal controls. Statistical significance of differences in PCBP-1 expression can be measured using the Student's t-test. In one aspect, t=0.99. In another aspect, t=0.95. In another aspect, t=0.90.

In one aspect of the present invention, "strong expression" of PCBP-1 can be at least a 3-fold, 4-fold, 5-fold or greater increase in PCBP-1 expression as compared to normal tissues. In another aspect, "moderate expression" of PCBP-1 can be at least a 2- to 3-fold increase in PCBP-1 expression as compared to normal tissues. In another aspect, "moderate expression" of PCBP-1 can be between a 2- to 3-fold increase in PCBP-1 expression as compared to normal tissues. In another aspect, "weak expression" of PCBP-1 can be a 1-fold or less increase in PCBP-1 expression as compared to normal tissues. In another aspect, "weak expression" of PCBP-1 can be a decrease in PCBP-1 expression as compared to normal tissues.

Figure 16:
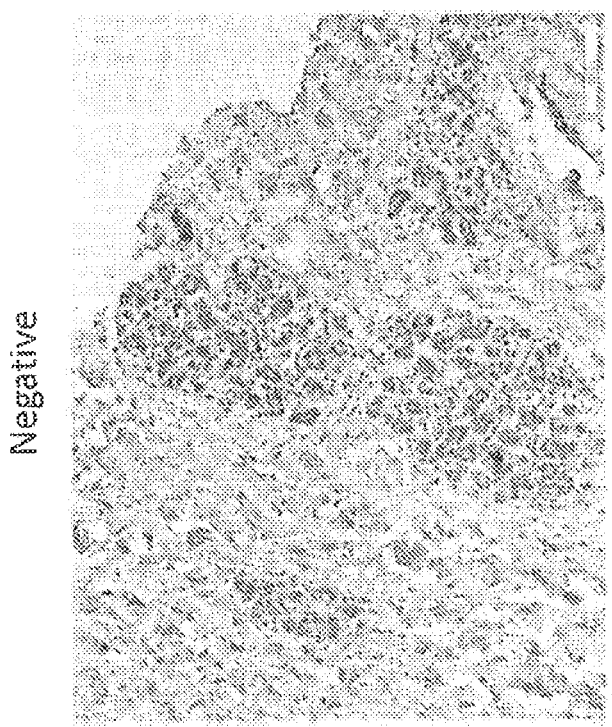
FIG. 16. An example of a bladder tissue sample displaying negative (0) immunohistochemical staining with Alper anti-PCBP-1 mouse monoclonal antibody.
Figure 17A:
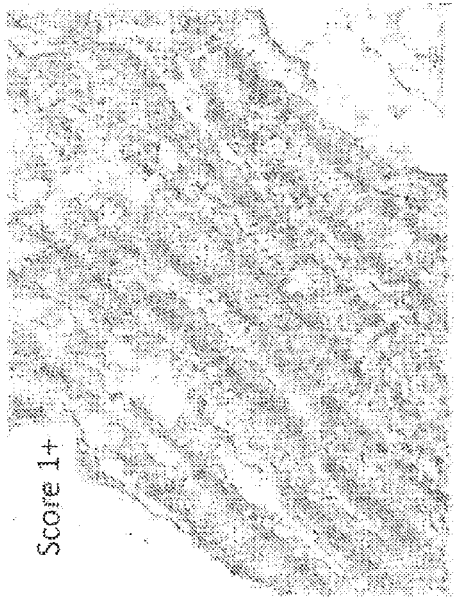
FIGS. 17A, 17B, and 17C.
Figure 17B:
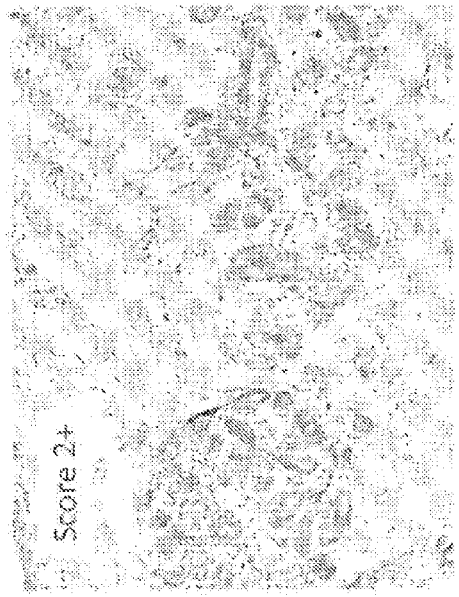
Figure 17C:
Figure 18A:
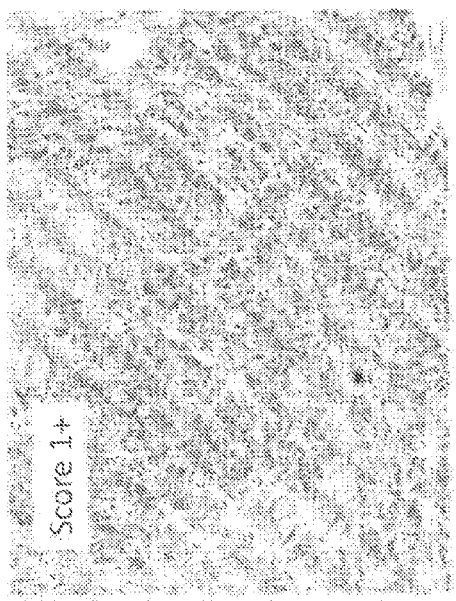
FIGS. 18A, 18B, and 18C.
Figure 18C:
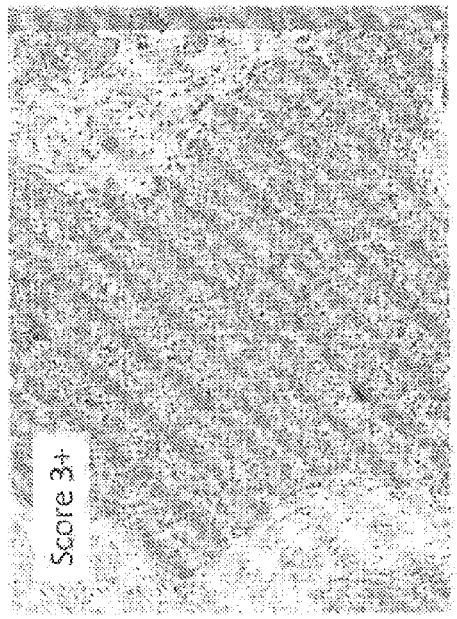
Figure 18B:
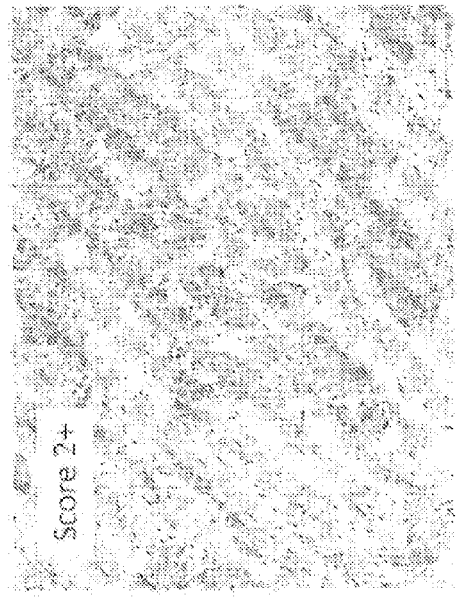

Quantitative or semi-quantitative detection of PCBP-1 may be evaluated within the context of a patient's clinical history and other diagnostic tests evaluated by a qualified pathologist. In one aspect, diagnosing a breast cancer as a carcinoma based on PCBP-1 expression is done based on intensity of staining and percent of stained cells from the total population of well-preserved cells. Suitable positive controls for PCBP-1 staining include SKBR3 and MDA-MB-231 cell lines. Suitable negative controls for PCBP-1 staining include bladder cells. In one aspect, the intensity of cell staining can range from no staining to faint staining to weak staining to intense staining. In another aspect, the percentage of well-preserved, stained cells is 0%, less than 50%, greater than 10%, greater than 30%, greater than 40%, greater than 50%, greater than 60%, greater than 70% or greater than 90%. In an aspect of the present invention, staining is localized to the cytoplasm. In another aspect, nuclear staining may still be present, but this staining is not included in the determination of positivity. In one aspect, tissue specimens can be analyzed for PCBP-1 expression via microscopy at low (10-20×) resolution to locate well-preserved and well-stained areas. Identified well-preserved and well-stained areas can be used to make a determination of the intensity of cytoplasmic staining. The percentage of well-preserved, stained cells can be estimated as 0%, less than 50%, or greater than 10%, greater than 30%, greater than 40%, greater than 50%, greater than 60%, greater than 70% or greater than 90%. In one aspect of the present invention, the cells of a single representative field is used and the area of a single representative field is used to make a determination according the methods of the present invention. In another aspect of the present invention, the number of cells examined can be at least 50, at least 100, at least 200, at least 300, at least 400, and 500 or more. In another aspect, the number of cells used to make a determination according the methods of the present invention are at least 100 cells. In one aspect of the present invention, quantitation of PCBP-1 expression can be determined by assigning a value of 0 to 3+ for cells stained with an antibody of the present invention, preferably Alper PCBP-1 antibody or any antibody having a staining pattern like Alper PCBP-1 antibody. In one aspect, the criteria for quantitation of cell staining are as follows: 0: no staining is observed; 1+: faint, partial cytoplasmic staining is observed; 2+: weak, complete cytoplasmic staining of greater than 50% of the cells in the sample is observed; 3+: intense, complete cytoplasmic staining of greater than 50% of the cells in the sample is observed. Examples of a negative sample and of 1+, 2+ and 3+ staining in ductal and lobular breast cancer cells are shown in FIGS. 16-18.

In one aspect, a score of 2+ includes a sample with a percentage of well-preserved cells in a tissue sample having stained cytoplasm is greater than 50%, while the percentage of well-preserved cells in a tissue sample having non-stained cytoplasm is less than 50%. In another aspect, a score of 2+ or more is associated with ductal breast cancer.

In another aspect, a score of 3+ includes a sample with a percentage of greater than 90% of well-preserved cells in a tissue sample having a stained cytoplasm, while the percentage of well-preserved cells in a tissue sample having non-stained cytoplasm is less than 10%. In another aspect, a score of 3+ is associated with ductal breast cancer. In another aspect, tissue samples assigned a score of 3+ will have a higher number of stained cells, and the cells will be stained at a higher intensity than that seen in a tissue sample assigned a score of 2+.

In another aspect of the present invention, increases in PCBP-1 expression can be expressed as increases in cells or tissues as a whole. In another aspect, increases in PCBP-1 expression can be expressed as increases in the cytoplasm of cells. In another aspect, increases in PCBP-1 expression can be expressed as increases in the nucleus of cells.

In another aspect of the present invention, decreases in PCBP-1 expression can be expressed as decreases in cells or tissues as a whole. In another aspect, decreases in PCBP-1 expression can be expressed as decreases in the cytoplasm of cells. In another aspect, decreases in PCBP-1 depression can be expressed as increases in the nucleus of cells.

In one aspect of the present invention, PCBP-1 expression in colon cancer cells is increased as compared to PCBP-1 expression in normal colon cells. In another aspect, colon cancer cells can exhibit strong cytoplasmic PCBP-1 expression as compared to normal colon cells.

In one aspect of the present invention, PCBP-1 expression in squamous carcinoma cells is increased as compared to PCBP-1 expression in normal skin cells. In another aspect, squamous carcinoma cells can exhibit a greater than 3-fold increase cytoplasmic PCBP-1 expression as compared to normal skin cells.

In another aspect of the present invention, PCBP-1 expression in melanoma cells is increased as compared to PCBP-1 expression in normal skin cells. In another aspect, melanoma cells can exhibit strong cytoplasmic PCBP-1 expression, while normal skin cells can exhibit weak nuclear expression of PCBP-1.

In one aspect of the present invention, PCBP-1 expression in glioblastoma multiforme cells is increased as compared to PCBP-1 expression in normal brain cells. In another aspect, glioblastoma multiforme cells can exhibit moderate cytoplasmic expression of PCBP-1, while neurons and astrocytes do not exhibit any PCBP-1 expression.

In one aspect of the present invention, PCBP-1 expression in astrocytoma cells is increased as compared to PCBP-1 expression in normal brain cells. In another aspect, astrocytoma cells can exhibit moderate cytoplasmic expression of PCBP-1, while neurons and astrocytes do not exhibit any PCBP-1 expression.

In one aspect of the present invention, PCBP-1 expression in ovarian cancer cells is decreased as compared to PCBP-1 expression in normal skin cells. In another aspect, ovarian cancer cells can exhibit little or no nuclear and/or cytoplasmic expression of PCBP-1, while normal ovarian cells can exhibit strong nuclear and cytoplasmic expression of PCBP-1.

In one aspect of the present invention, PCBP-1 expression in endometrial cancer cells is increased as compared to PCBP-1 expression in normal endometrial cells. In another aspect, endometrial cancer cells can exhibit strong nuclear and cytoplasmic PCBP-1 expression, while normal endometrial cells can exhibit little or no cytoplasmic expression of PCBP-1.

In one aspect of the present invention, PCBP-1 expression in sarcoma cells is increased as compared to PCBP-1 expression in normal muscle cells. In another aspect, sarcoma cells can exhibit moderate to high levels of cytoplasmic PCBP-1 expression as compared to normal muscle cells.

In one aspect of the present invention, PCBP-1 expression in bladder cancer cells is increased as compared to PCBP-1 expression in normal bladder cells. In another aspect, bladder cancer cells can exhibit moderate to high levels of cytoplasmic PCBP-1 expression as compared to normal bladder cells.

In one aspect of the present invention, PCBP-1 expression in breast cancer cells can be increased as compared to PCBP-1 expression in normal breast cells. In another aspect, breast cancer cells can exhibit strong cytoplasmic PCBP-1 expression and moderately strong nuclear PCBP-1 expression, while normal breast cells can exhibit weak nuclear PCBP-1 expression. In another aspect, breast cancer cells can exhibit strong cytoplasmic PCBP-1 expression and moderately strong nuclear PCBP-1 expression, while normal breast cells can exhibit strong nuclear PCBP-1 expression.

In one aspect of the present invention, cytoplasmic PCBP-1 expression in ductal carcinoma cells can be higher than cytoplasmic PCBP-1 expression in lobular breast carcinoma cells. In an aspect of the present invention a similar level of a soluble form of PCBP-1 in a cell, collection of cells or sample to a normal control can diagnose, prognose, monitor, determine, confirm or indicate that such cell was derived from a non-metastatic tissue.

In an aspect of the present invention, a lack of localization of a soluble form of PCPB-1 in a cell nucleus can diagnose, prognose, monitor, determine, confirm or indicate that such derived is from a metastatic tissue.

In an aspect of the present invention, localization of a soluble form of PCPB-1 in a cell, collection of cells or sample to a normal control can diagnose, prognose, monitor, determine, confirm or indicate that such derived from a non-metastatic tissue.

In an aspect, a diagnostic or prognostic method or other method of the present invention is indicative of metastatic status, where the level of nuclear PCBP-1 is indicative of the metastatic status of a cell or tissue. In an aspect, a level of nuclear PCBP-1 that is lower than a non-metastatic control tissue or cell is indicative of metastatic ability. In this aspect, an indicative level can be less than 1%, 5%, 10%, 20%, 30%, 40%, 50%, 60%, 70%, 80%, 90%, or 95% of the control, or between less than 1% and less than 20% of the control.

In an aspect, a diagnostic or prognostic method or other method of the present invention is indicative of metastatic status, wherein the level of cytoplasmic PCBP-1 is indicative of the metastatic status of a cell or tissue. In an aspect, a level of cytoplasmic PCBP1 that is higher than a non-metastatic control tissue or cell is indicative of metastatic ability. In this aspect, an indicative level can be greater than 1%, 5%, 10%, 20%, 30%, 40%, 50%, 60%, 70%, 80%, 90%, or 95% of the control, or between greater than 1% and greater than 20% of the control.

In an aspect, a diagnostic or prognostic method or other method of the present invention is indicative of non-metastatic status, wherein the level of nuclear PCBP-1 is indicative of the non-metastatic status of a cell or tissue. In an aspect, a level of nuclear PCBP1 that is similar to a non-metastatic control tissue or cell is indicative of non-metastatic ability. In this aspect, an indicative level can be equal to or within 1%, 5%, or 10% of the control, or equal to or within 1% and greater than 10% of the control. In another aspect, a diagnostic or prognostic method or other method of the present invention is indicative of non-metastatic status, where subcellular localization of PCBP-1 and estrogen receptor (ER), progesterone receptor (PR), or ER and PR is similar. In this aspect, the absence of similar localization can include a lack of ER or PR staining where PCBP-1 staining is present in a ductal breast cancer cell cytoplasm. For example, ER in the nucleus and PCBP-1 in the nucleus is indicative of normal or non-metastatic ductal breast cancer cells.

In an aspect, a diagnostic or prognostic method or other method of the present invention is indicative of non-metastatic status, wherein the level of cytoplasmic PCBP-1 is indicative of the non-metastatic status of a cell or tissue. In an aspect, a level of cytoplasmic PCBP1 that is similar to a non-metastatic control tissue or cell is indicative of non-metastatic ability. In this aspect, an indicative level can be equal to or within 1%, 5%, or 10% of the control, or between 0% and less than 10% of the control.

In another aspect, the present invention includes a method of determining a metastatic status of a breast cell or tissue in a sample comprising contacting the sample from a patient in need thereof with an antibody capable of detecting nuclear and cytoplasmic PCBP-1 and determining the subcellular location of said PCBP-1, where similar subcellular co-localization of PCBP-1 and estrogen receptor (ER), progesterone receptor (PR), or ER and PR, is positively correlated with overall survival, non-metastasis, or overall survival and non-metastasis. In this aspect, the absence of co-localization can include a lack of ER or PR staining where PCBP-1 staining is present in a ductal breast cancer cell cytoplasm.

In another aspect, the present invention includes a method of determining a metastatic status of a breast cell or tissue in a sample comprising contacting the sample from a patient in need thereof with an antibody capable of detecting nuclear and cytoplasmic PCBP-1 and determining the subcellular location pattern of said PCBP-1, where the absence of similar subcellular localization of PCBP-1 and estrogen receptor (ER), progesterone receptor (PR), or ER and PR, is inversely correlated with overall survival. In this aspect, the absence of similar localization pattern can include a lack of ER or PR staining where PCBP-1 staining is present in a ductal breast cancer cell cytoplasm.

In an aspect of the present invention, the cell, collection of cells or sample is a cervical or breast cell collection of cells or sample.

In an aspect of the present invention, the cell, collection of cells or sample is a lobular breast cell collection of cells or sample. In another aspect of the present invention, the cell, collection of cells or sample is a ductal breast cell collection of cells or sample.

Antibodies and antibody fragments of the present invention are also useful for immunopathological analysis, such as the differential diagnosis of tumor type, and the subclassification of the tumor based on its expression of PCBP-1, including, without limitation, assessment of metastatic potential, predicted responses to therapy, and overall prognosis. In one aspect, the immunopathological analysis using the antibodies and antibody fragments of the present invention can indicate whether a breast cancer sample is ductal or lobular breast cancer.

PCBP-1 antibodies and antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles or soluble proteins or glycoproteins. The support can then be washed with suitable buffers followed by treatment with the detectably labeled antibody of the present invention. The solid phase support can then be washed with the buffer a second time to remove unbound antibody. The amount of bound label on said solid support can then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner can be an antibody against the constant or variable region of the antibody of the invention, such as a heterologous anti-mouse immunoglobulin antibody. Alternatively, the binding partner can be a non-antibody protein capable of binding to the antibody of the present invention.

By radioactively labeling the antibodies of the present invention, it is possible to detect PCBP-1 through the use of a radioimmunoassay (RIA). The radioactive isotope can be detected by such means as the use of a gamma counter or a scintillation counter or by autoradiography. Isotopes which are particularly useful for the purpose of the present invention are known in the art.

It is also possible to label the antibodies of the present invention with a fluorescent compound. When the fluorescently labeled antibody is exposed to light of the proper wave length, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards. Alternatively, detection may be accomplished by counting the intensity and number of pixels of a fluorescent image.

In situ detection can be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present invention can utilize any suitable staining procedures known in the art.

Kits according to the present invention can include frozen or lyophilized antibodies to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, cervix, prostate, colon, stomach, kidney, liver, head, neck, lung, blood, pancreas, skin, testicle, thyroid and brain.

The kits including the reagents necessary for immunohistochemical analysis can be provided as follows: a) PCBP-1 antibody or antibody fragment of the present invention, or chimeric or humanized variants thereof; b) blocking reagent (in the form of, for example, goat serum) and secondary antibody (such as, for example, goat anti-mouse antibody); c) detectable marker (such as, for example, immunoperoxidase or alkaline phosphatase); and d) developing reagents. The primary antibody (PCBP-1 antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound a PCBP-1 antibody, which can or cannot be labeled, for example with a protein such as biotin), which is in turn being used to detect a specific target (in the context of the present invention, the target is a PCBP-1 expression product).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of colon, breast, ovarian and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

6. Pharmaceutical Compositions and Methods of Treatment

Another aspect of the invention provides a composition comprising any of these antibodies, optionally in combination with a pharmaceutically acceptable carrier. In another aspect, an antibody of the present invention is optionally in combination with one or more active agents, drugs or hormones.

The present invention also provides a method of treating human or animal subjects suffering from or at risk of a cancer that expresses PBCP-1, such as solid tumors of the breast, ovary, cervix, prostate, colon, stomach, kidney, liver, head, neck, lung, pancreas, skin, testicle, thyroid and brain, the method comprising administering to the subject a therapeutically effective amount of an antibody of the present invention, or a pharmaceutical composition comprising a therapeutically effective amount of an antibody of the present invention.

The term "subject" as used herein refers to any subject in need of treatment.

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

An effective amount for a human subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions can be administered individually to a patient or can be administered in combination with other agents, drugs or hormones. According to some aspects, antibodies can be conjugated with these agents. A summary of the ways in which the antibodies of the present invention can be used therapeutically includes direct cytotoxicity by the antibody, either mediated by complement or by effector cells, or conjugated to anti-tumor drugs, toxins, and radionuclides. Antibodies can also be used for ex vivo removal of tumor cells from the circulation or from bone marrow.

Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include 212Bi, 131I, 186Re, and 90Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it can be necessary to give one or more doses per day. Alternatively, if the antibody molecule has a long half life (e.g. 2 to 15 days) it can only be necessary to give a dosage once per day, per week or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it can take the form of a suspension, solution or emulsion in an oily or aqueous vehicle and it can contain formulatory agents, such as suspending, preservative, stabilizing and/or dispersing agents. Alternatively, the antibody molecule can be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

A pharmaceutical compositions of this invention can be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays can also be used to administer the pharmaceutical compositions of the invention. Therapeutic compositions can be prepared as injectables, either as liquid solutions or suspensions. Solid forms suitable for solution in, or suspension in, liquid vehicles prior to injection can also be prepared.

Direct delivery of the compositions will generally be accomplished by injection, subcutaneously, intraperitoneally, intravenously or intramuscularly, or delivered to the interstitial space of a tissue. Dosage treatment can be a single dose schedule or a multiple dose schedule.

When an antibody or antibody fragment composition is to be administered by a route using the gastrointestinal tract, the composition can to contain additional agents which protect the antibody from degradation but which release the antibody once it has been absorbed from the gastrointestinal tract. Such additional agents are well-known to those skilled in the art.

Antibodies of the present invention can also be administered in methods of conducting gene therapy. In order to achieve this, DNA sequences encoding the heavy and light chains of the antibody molecule under the control of appropriate DNA components are introduced into a patient such that the antibody chains are expressed from the DNA sequences and assembled in situ.

The antibodies and antibody fragments of the present invention may also be used in the treatment of cancer in a patient in need thereof. In one aspect, the cancer is breast, ovary, cervix, prostate, colon, stomach, kidney, liver, head, neck, lung, blood, pancreas, skin, testicle, thyroid or brain cancer. In one aspect, the cancer is breast cancer. In another aspect, the breast cancer is ductal or lobular breast cancer.

In another aspect, the method for the treatment of breast cancer in a patient in need thereof comprises the steps of: (a) diagnosing said patient with breast cancer; (b) determining the level, localization, or both of PCBP-1 in a sample obtained from said patient; (c) determining whether said breast cancer is ductal carcinoma or lobular carcinoma; (d) determining whether said breast cancer is HER2-positive or HER2-negative; (e) determining whether said breast cancer is estrogen receptor-positive or estrogen receptor-negative; (f) determining whether said breast cancer is progesterone receptor-positive or progesterone receptor-negative; and (g) administering one or more chemotherapeutic agents to said patient.

In one aspect, the one or more chemotherapeutic agents are selected from the group consisting of an aromatase inhibitor, a hormone therapy agent, a taxane, an alkylating agent, an anthracycline, an antifolate, a pyrimidine analog, and a monoclonal antibody.

In another aspect, the aromatase inhibitor is selected from the group consisting of exemestane, anastrozole and letrozole. In another aspect, the hormonal therapy is selected from the group consisting of tamoxifen, Fareston™, Arimidex™, Aromasin™, Femara™, Zoladex™, Megace™ and Halotestin™. In another aspect, the taxane is selected from the group consisting of docetaxel and paclitaxel. In another aspect, the alkylating agent is selected from the group consisting of cyclophosaphamide, meclorethamine, uramustine, melphalan, chlorambucil, ifosfamide, carmustine, lomustine, streptozocin, thiotepa and busulfan. In another aspect, the anthracycline is selected from the group consisting of daunorubicin, doxorubicin, epirubicin, idarubicin, valrubicin and mitoxanthrone. In another aspect, the antifolate is selected from the group consisting of methotrexate, trimethoprim, pyrimethane and pemetrexed. In another aspect, the pyrimidine analog is selected from the group consisting of 5-fluorouracil, floxuridine, cytosine arabinoside, and gemcitabine. In another aspect, the monoclonal antibody is selected from the group consisting of herceptin, Alper PCBP-1 antibody and Alper HER2 antibody.

7. PCBP-1 Expression Products as Drug Development Targets

In addition, the present invention relates to the discovery that Pcbp-1 and homologues thereof can cause the expression of PCBP-1 antigens by cells in patients suffering from various diseases, such as cancers, and more specifically solid tumors of the breast, ovary, cervix, prostate, colon, stomach, kidney, liver, head, neck, lung, pancreas, skin, testicle, thyroid and brain. This expression of PCBP-1 antigens presents a drug development target, and accordingly the present invention also relates to the use of such PCBP-1 antigens as biomarkers that can be targeted not only by the PCBP-1 antibodies or antibody fragments of the present invention, but also by various other molecules, such as siRNA, antisense oligonucleotides, vaccines, and chemical compounds.

Methods for developing drugs useful in treating and/or diagnosing diseases characterized by the expression of gene products of Pcbp-1 and homologues thereof can include the steps of identifying the gene products expressed by Pcbp-1 and homologues thereof in a subject having a disease, and utilizing those gene products as to development and identify drugs that specifically target the gene products.

Once candidate drugs have been developed based on the PCBP-1 antigens, the PCBP-1 antigens and PCBP-1 antibodies and antibody fragments of the present invention can be used to aid in screening the various drug candidates, in order to identify those drug candidates that exhibit a desired level of specificity for diseased cells presenting PCBP-1 expression products.

The following examples are non-limiting illustrative examples.

Example 1

Before tumor resection, 10 ml samples of blood are collected from ovarian or breast cancer patients into EDTA-containing tubes and placed on ice immediately. Within two hours of collection, blood samples are centrifuged at 1000×g for 20 minutes. The buffy coat and red blood cell layers are removed and the plasma is stored as 250-500 µl aliquots at −70° C. until analysis. Patients with stage II, III, and IV ovarian or breast cancers are selected for this study. Controls are obtained from healthy, cancer-free women who donated blood to the Brigham and Women's Hospital Blood Bank. Blood from breast cancer patients is collected in sodium citrate tubes (Becton-Dickinson) and processed according to the manufacturer's instructions. Plasma samples are aliquotted and stored at −80° C. until analyzed.

Plasma samples isolated from 20 patients with stage II-IV ovarian cancer are obtained from Brigham and Women's Hospital. Plasma samples (C: control breast blood sample, NM: non-metastatic breast blood sample, M: metastatic breast blood sample) obtained from control and patient groups are diluted with PBS at a ratio of 1:100. An increase in soluble plasma filamin-A levels have been reported to be associated with cancer. Plasma filamin-A levels are measured with an enzyme-linked immunosorbent enzyme assay. The ELISA plates (Nalge NUNC™ International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, A-FLNA is added in dilution buffer (45 µg/ml) (PBS buffer, 1% BSA, 0.01% Tween-20 ™). The wells are washed with PBS/0.03% Tween-20™ and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB™ substrate solution (Pierce, Rockford, Ill.) is added. Color reaction is stopped by the addition of 100 µl/well 1N H2SO4 and the analysis is performed with an ELISA Reader. The figures represent optical density (OD) values of plasma readings for filamin-A levels. P-values are derived using the Mann Whitney Test and show a significant difference among control, non-metastatic and metastatic groups (p<0.001). P values are determined by comparison with controls by ANOVA. Data are representative of four independent experiments performed in triplicate. All analyses are performed under blinded conditions. See FIG. 1.

Figure 2A:
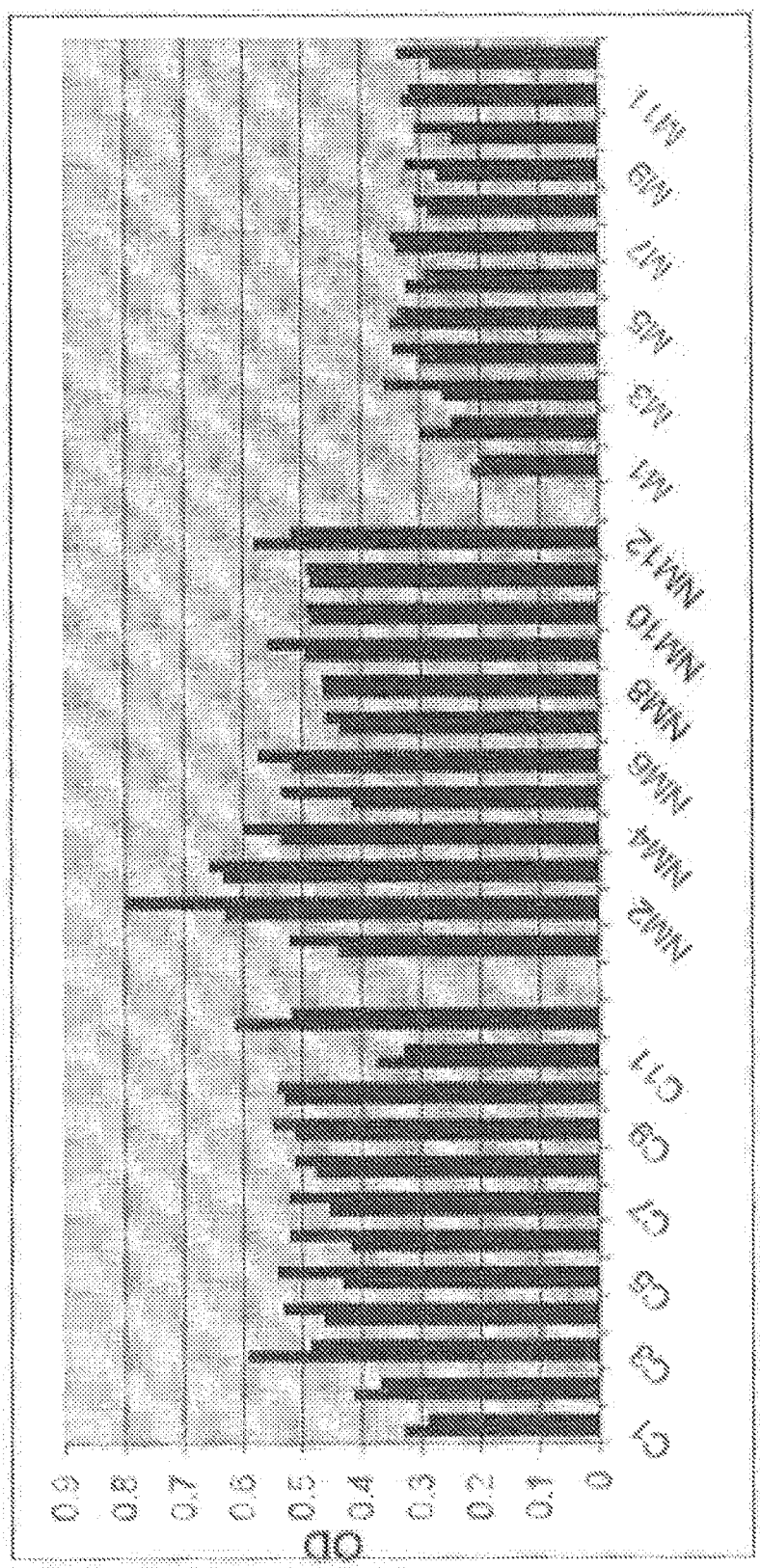
FIGS. 2A and 2B. Plasma samples from breast cancer patients are subjected to ELISA analysis using an anti-PCBP-1 monoclonal antibody. The figures represent optical density (OD) values of plasma readings for PCBP-1 levels. P-values are derived using the Mann Whitney Test. Control and metastatic group showed a significant difference ($p<0.001$). Control and non-metastatic groups did not show a significant difference. There is a significant difference between non-metastatic and metastatic groups ($p<0.001$). P values are determined by comparison with controls by ANOVA. Data are representative of four independent experiments performed in triplicate.
Figure 2B:
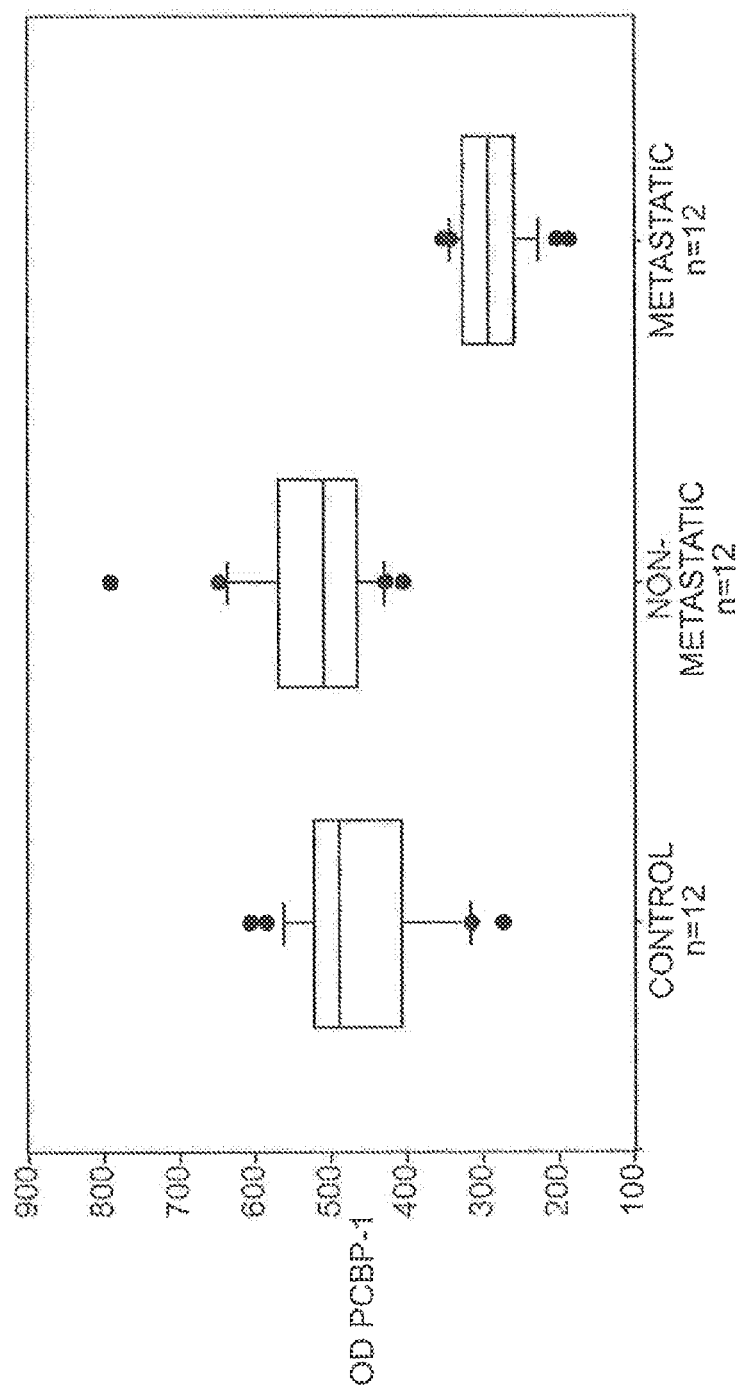

Plasma samples from breast cancer patients are subjected to ELISA analysis using the anti-PCBP-1 monoclonal antibody. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 μl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, anti-PCBP-1 is added in dilution buffer (45 μg/ml) (PBS buffer, 1% BSA, 0.01% Tween-20™). The wells are washed with PBS/0.03% Tween-20 and incubated at room temperature for one hour with 100 μl/well secondary antibody (HRP-Donkey anti-mouse IgG, Jackson ImmunoResearch, West Grove, Pa.) diluted 1:3000. After washing the wells, 100 μl Immunopure TMB™ substrate solution (Pierce, Rockford, Ill.) is added. Color reaction is stopped by the addition of 100 μl/well 1N H2SO4 and the analysis is performed with an ELISA Reader. The figures represent optical density (OD) values of plasma readings for PCBP-1 levels. P-values are derived using the Mann Whitney Test. Control and metastatic group showed a significant difference (p<0.001). Control and non-metastatic groups did not show a significant difference. There is a significant difference between non-metastatic and metastatic groups (p<0.001). P values are determined by comparison with controls by ANOVA. Data are representative of four independent experiments performed in triplicate. All analyses are performed under blinded conditions. See FIGS. 2A and 2B.

Example 2

Cellular Localization of PCBP-1 in Human Breast Cancer Cells

Human normal mammary epithelial cells (HMECs), SKBR3 cells (human non-metastatic breast cancer cells) and MDA-MB-231 cells (human metastatic breast cancer cells) are seeded and grown on glass slides. The cells are fixed with formalin (10% with 0.1% Triton™-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm of HMECs. SKBR3 cells exhibit cytoplasmic and nuclear staining. MDA-MB-231 cells exhibit cytoplasmic staining. See FIG. 3.

Example 3

Cellular Localization of PCBP-1 in Human Cervical Cells

Cervical cells obtained from pap smears of healthy and cervical cancer patients are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm and nucleus of normal cervical cells. Cervical cancer cells (CIN III) display cytoplasmic staining only. See FIG. 4.

Example 4

Approximately 2 μg of a purified 7SK mAb is suspended in PBS, and is applied under reducing (boiled 3 minutes in sample buffer with beta-mercaptoethanol and 10% SDS) and non-reducing (not boiled, and without beta-mercaptoethanol) conditions to 6 and 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the right. The 6% Tris-glycine gel shows the IgG1 antibody (7SK) at ~150 kDa under non-reduced conditions. The 8% Tris-glycine gel shows the heavy chain of the IgG1 antibody (7SK) at ~50 kDa. See FIG. 5.

Example 5

Figure 6:
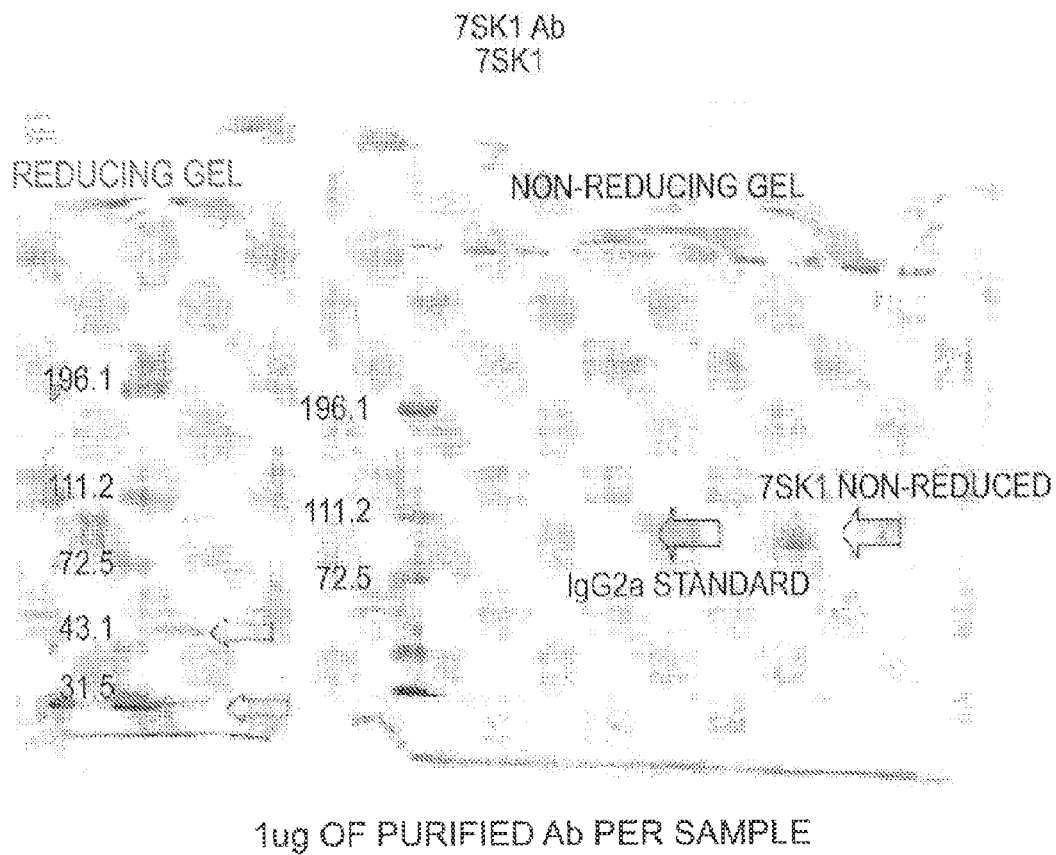
FIG. 6. Approximately 1 µg of purified Alper PCBP-1 mouse mAb (identified as 7SK) is suspended in PBS, and is applied under reducing (boiled 3 minutes in sample buffer with beta-mercaptoethanol and 10% SDS) and non-reducing (not boiled, and without beta-mercaptoethanol) conditions to 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the left. Under denatured conditions, the heavy chain of Alper PCBP-1 mouse IgG1 Ab (7SK) is detected at ~50 kDa and light chain of Alper PCBP-1 mouse IgG1 (7SK) is detected at ~25 kDa. In a non-reducing gel, intact Alper PCBP-1 mouse IgG1 (7SK) is detected at 150 kDa.

Approximately 1 μg of a purified 7SK mAb is suspended in PBS, and is applied under reducing (boiled 3 minutes in sample buffer with beta-mercaptoethanol and 10% SDS) and non-reducing (not boiled, and without beta-mercaptoethanol) conditions to 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the left. Under denatured conditions, the heavy chain of IgG1 Ab (7SK) is detected at ~50 kDa and light chain of IgG1 (7SK) is detected at ~25 kDa. In a non-reducing gel, intact IgG1 (7SK) is detected at 150 kDa. See FIG. 6.

Example 6

Figures 7A, 7B:
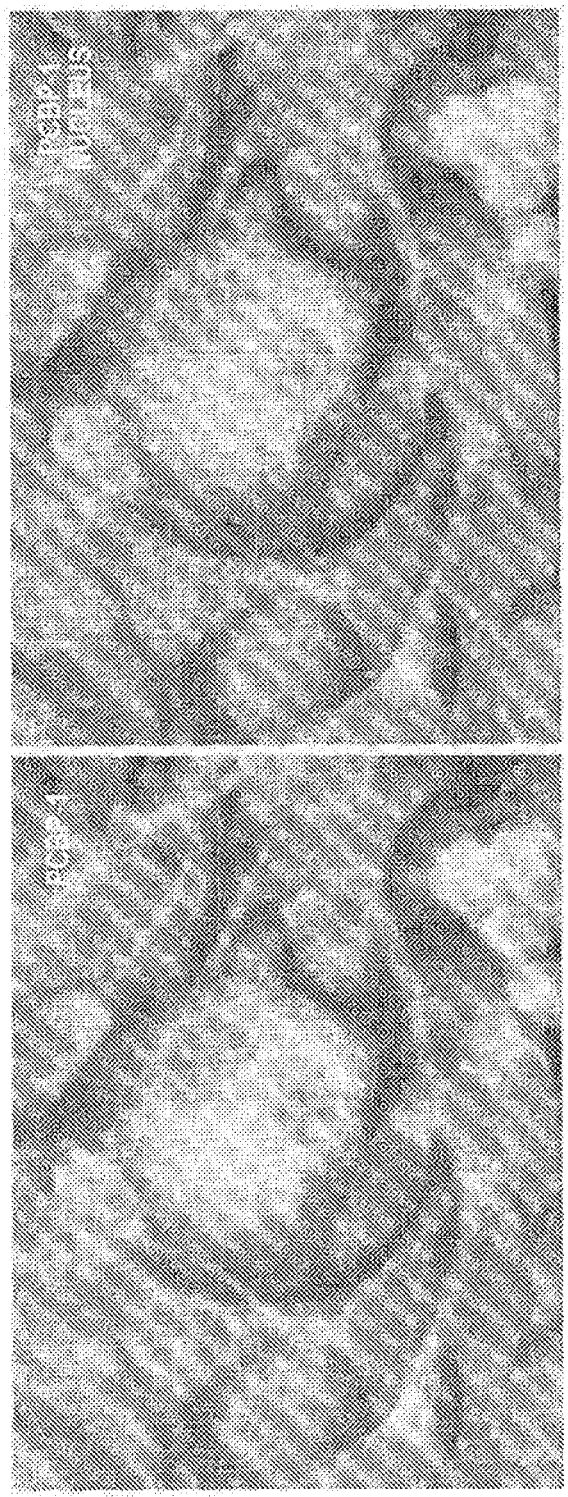
FIGS. 7A and 7B. SKBR3 cells are fixed with 10% gluteraldehyde, permeabilized with 0.1% Triton-X100. PCBP-1 expression is then visualized with the Alper PCBP-1 mouse mAb (7SK) and secondary FITC-labeled anti-mouse antibodies (Jackson ImmunoResearch, West Grove, Pa.). Nuclei are visualized by DAPI staining (Molecular Probes, Eugene, Oreg.). The images are analyzed using an Olympus microscope equipped with 63× objective lens.

SKBR3 cells are fixed with 10% gluteraldehyde, permeabilized with 0.1% Triton-X100. PCBP-1 expression is then visualized with the 7SK mAb and secondary FITC-labeled anti-mouse antibodies (Jackson ImmunoResearch, West Grove, Pa.). Nuclei are visualized by DAPI staining (Molecular Probes, Eugene, Oreg.). The images are analyzed using a Olympus microscope equipped with 63× objective lens. See FIG. 7.

Example 7

Spot 1 is digested with trypsin and analyzed by MALDI-MS. The major protein identified is poly(rC)-binding protein 1, SwissProt Q15365. Also present, probably as contaminants, are albumin (fragment) and hemoglobin alpha and beta.

Example 8

Figure 8A:
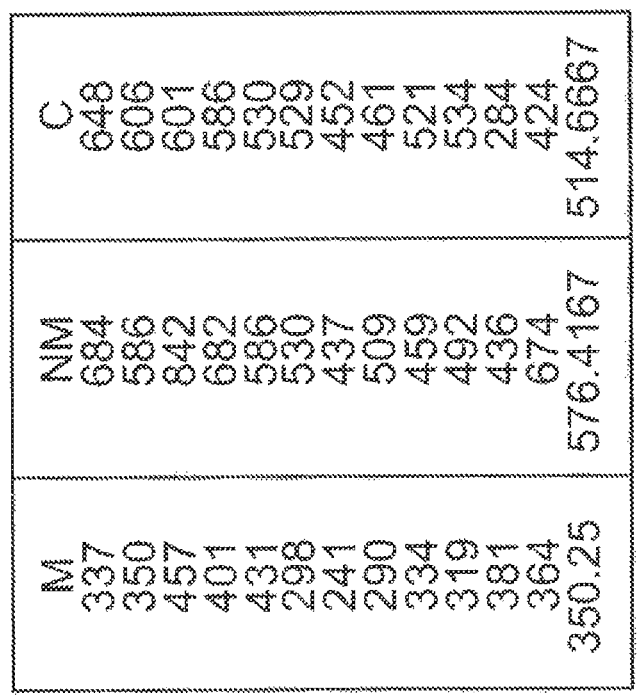
FIGS. 8A, 8B, and 8C. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, 7SK (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N H2SO4 and the analysis is performed with an ELISA Reader.
Figure 8B:
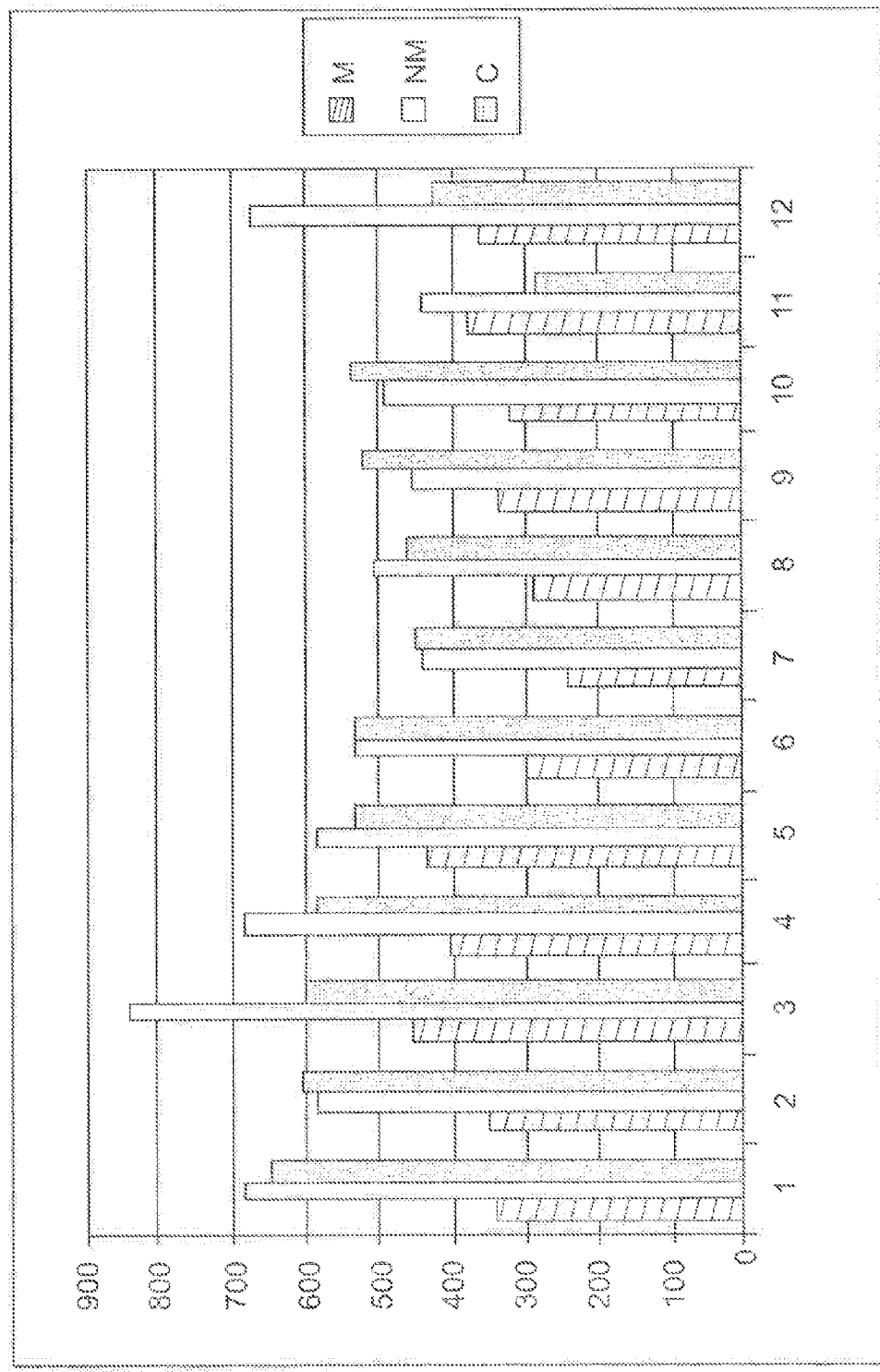
Figure 8C:
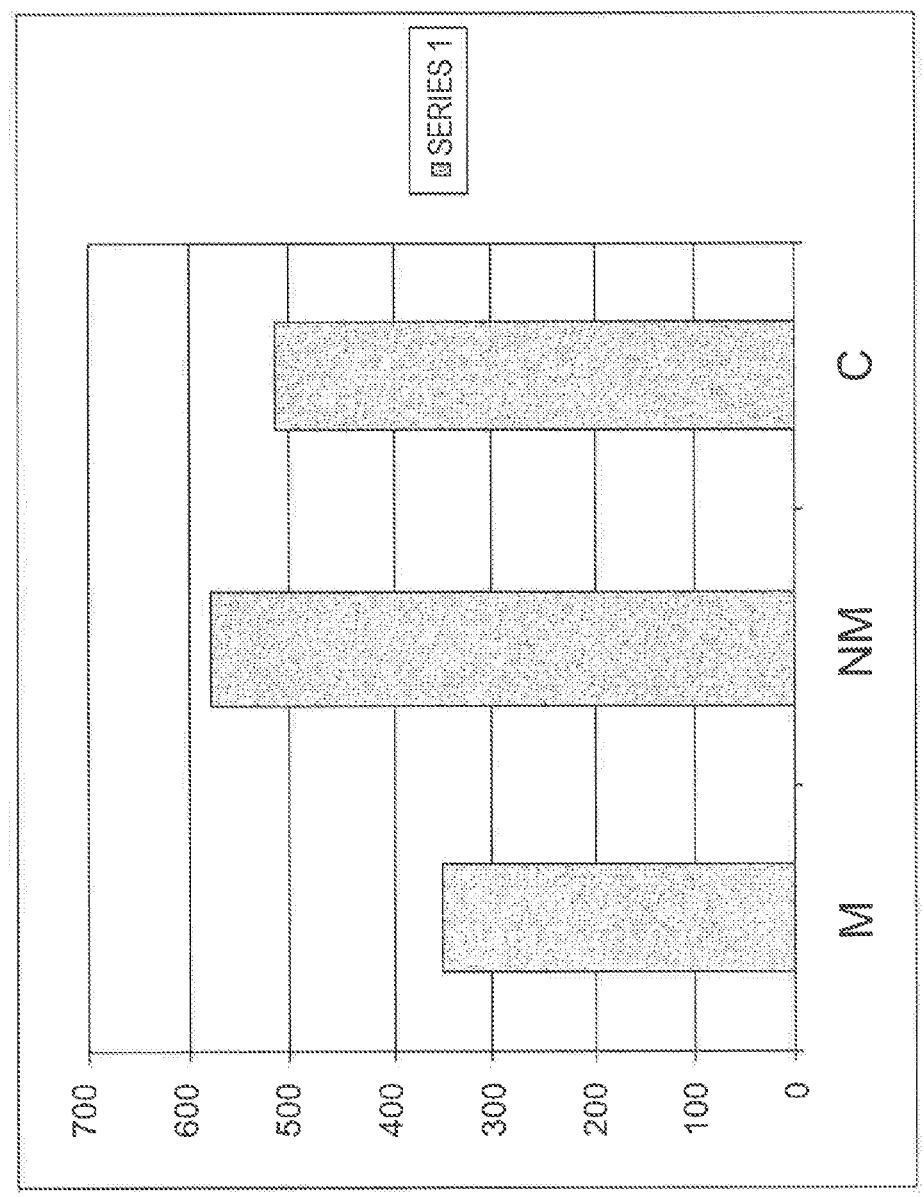

Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 μl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, 7SK (clone name: Alper-pCBP-1) is added in dilution buffer (45 μg/ml) (PBS buffer, 1% BSA, 0.01% Tween-20). The wells are washed with PBS/0.03% Tween-20 and incubated at room temperature for one hour with 100 μl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N H2SO4 and the analysis is performed with an ELISA Reader. The figures represent optical density (OD) values of plasma readings for PCBP-1 levels. See FIG. 8.

Example 9

Figure 9B:
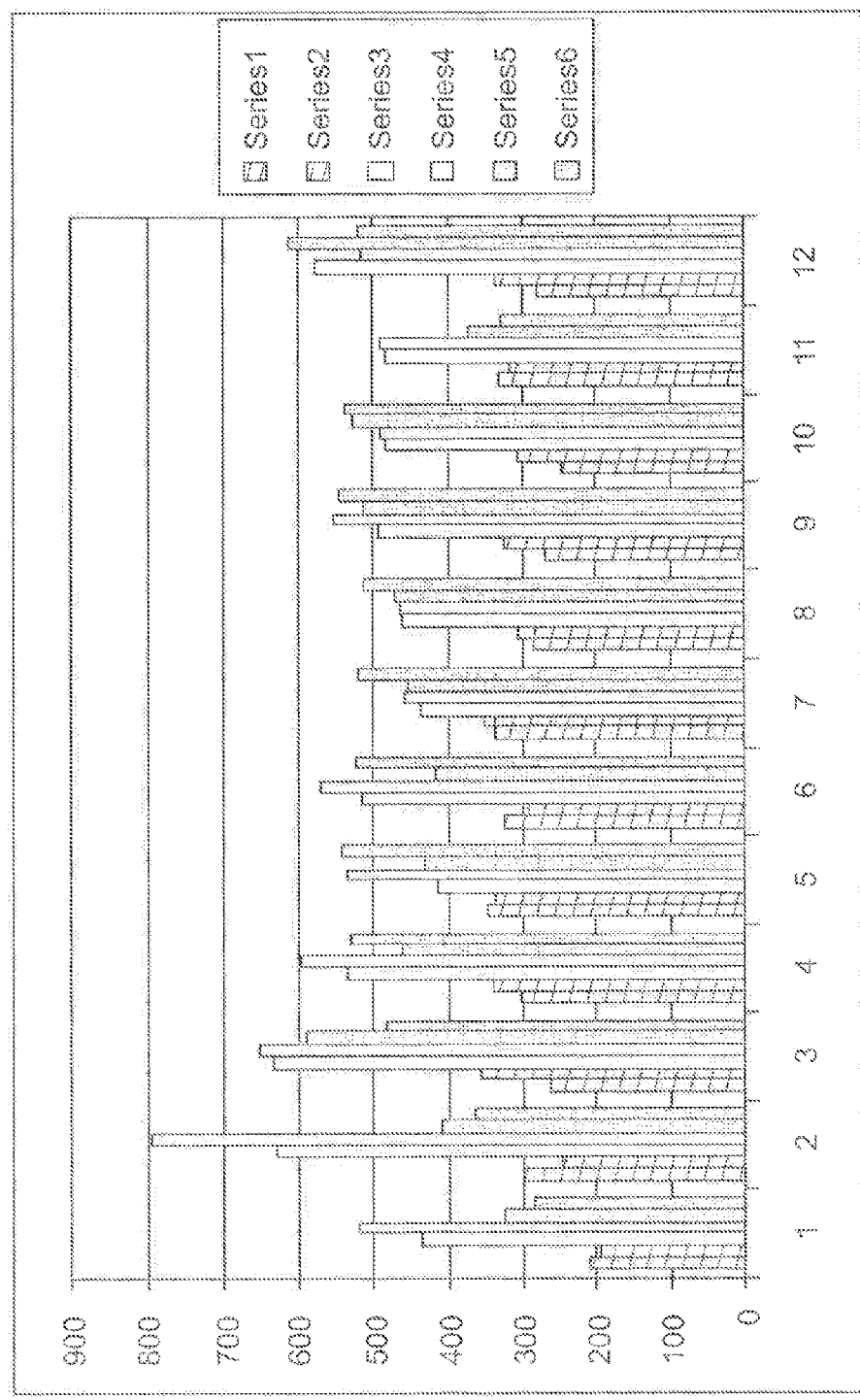
Figure 9C:
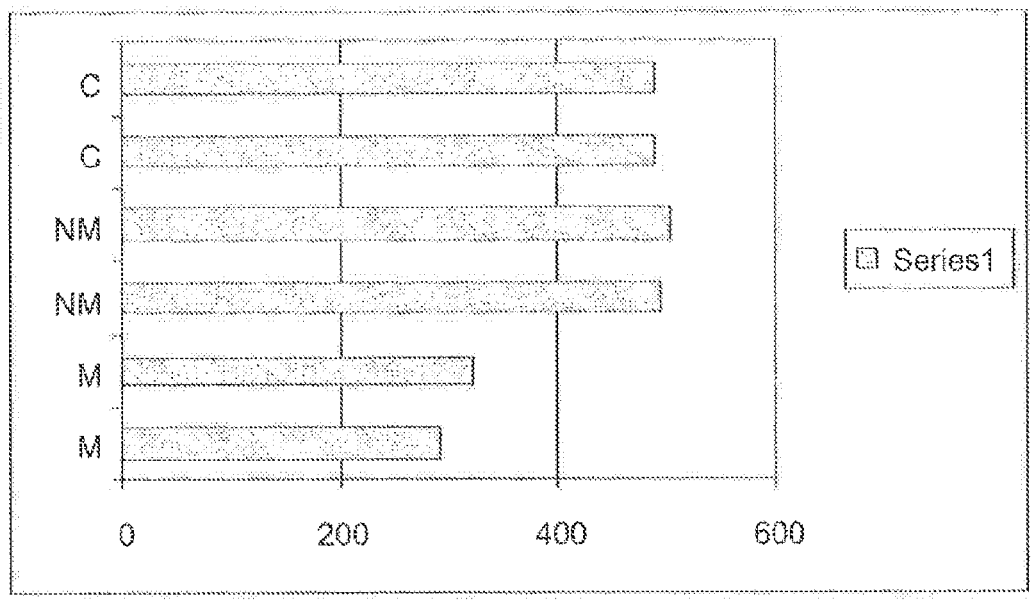
Figure 9D:
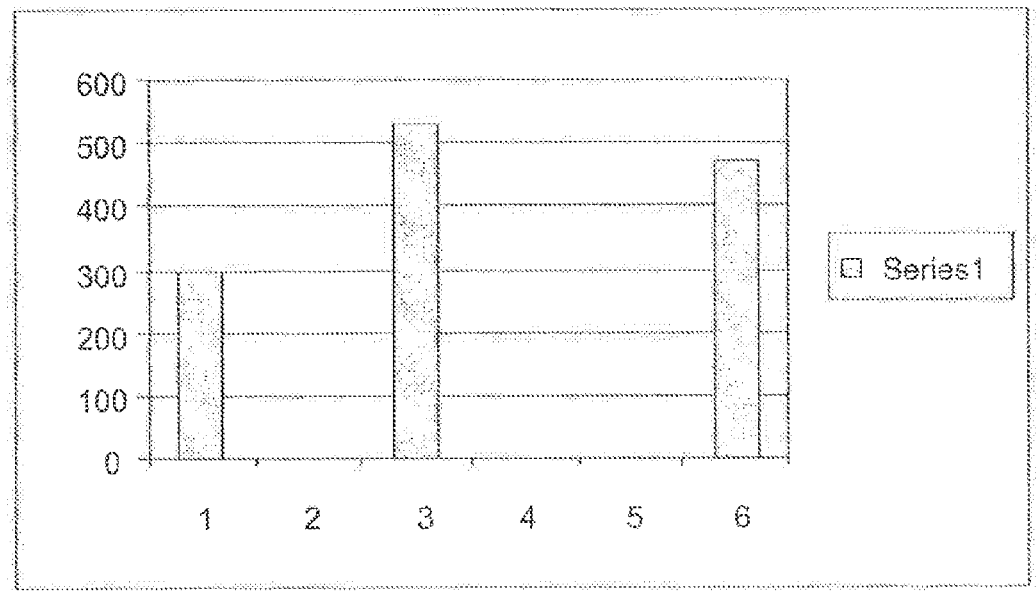

Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The plasma samples are analyzed in a blinded fashion. The wells are washed with PBS and incubated at room temperature for one hour with blocking buffer (5% BSA in PBS). After washing with PBS, the primary antibody, 7SK MoAb (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N H2SO4 and the analysis is performed with an ELISA Reader. Optical density is represented by OD and shows PCBP-1 levels in plasma. Series 1-2 represent controls, series 3-4 represent nonmetastatic and series 5-6 represent metastatic plasma samples. 1: metastatic, 2: non-metastatic, 3: control plasma samples. See FIG. 9.

Example 10

FWRs and CDRs of the heavy chain of the PCBP-1 mAb 7SK, in which the polypeptide sequence provided in the top line corresponds to the sequence of the PCBP-1 mAb. Amino acid residues are numbered using the convention of Kabat et al. The bold residues set forth in underlined text indicate the specificity determining residues (SDRs). See FIG. 10.

Example 11

FWRs and CDRs of the light chain of the PCBP-1 mAb 7SK, in which the polypeptide sequence provided in the top line corresponds to the sequence of the PCBP-1 mAb. Amino acid residues are numbered using the convention of Kabat et al. The bold residues set forth in underlined text indicate the specificity determining residues (SDRs). See FIG. 11.

Example 12

Cell lysates from SKBR3 cells are run on a 2D polyacrylamide gel and proteins are transferred to a nitrocellulose membrane. Membranes are probed with PCBP-1 mAb. Spot 1, corresponding to PCBP-1, is cut out of a corresponding Coomassie-Blue stained 2D gel and subjected to tryptic digest. Tryptic peptides are analyzed by MALDI-TOF to determine the sequences of the digested peptides. All peptides obtained from the digest have sequences that correspond to the sequence of PCBP-1. See FIG. 12.

Example 13

Tissue arrays containing tissue samples of various normal and human cancer tissues are subjected to immunohistochemistry using Alper PCBP-1 mouse monoclonal antibody (7SK). Slides of the 117-2 multi-tissue array, the YTMAF96 array and the YTMAF179-3 are depaaafinized and rehydrated with distilled water. Heat-induced epitope retrieval is performed at 95-101° C. in citrate buffer at pH 6.0 for 20 minutes, then the slides are allowed to cool to room temperature and are rinsed with Tris buffer. A peroxidase block is applied to the slides for 5 minutes, and the slides are again rinsed with Tris buffer. BACKGROUND SNIPER™ (Biocare Medical Products, Concord, Calif.) is applied to the slides for 5 minutes, and the slides are rinsed with Tris buffer. A 1:50 dilution of Alper PBCP-1 mouse monoclonal antibody is then applied to the array slides for 30 minutes at room temperature, followed by a Tris buffer rinse. MACH 3™ Probe (Biocare Medical Products, Concord, Calif., USA) is applied to the slides for 15 minutes, the slides are rinsed with Tris buffer, and MACH 3™ Polymer (Biocare Medical Products, Concord, Calif., USA) is then added to the slides for 15 minutes. After a rinse with Tris buffer, diaminobenzenetetrahydrochloride is applied to the slides for 5 minutes. The slides are then contacted with hematoxylin counterstain. Tissue arrays are analyzed via microscopy for staining intensity. Results are summarized in FIG. 13. Intensity of PCBP-1 staining is increased in colon cancer, melanoma, squamous carcinoma, glioblastoma, endometrial cancer, sarcoma and bladder cancers as compared to normal controls, while PCBP-1 intensity is decreased in ovarian cancer as compared to normal controls.

Normal breast epithelial cells showed a 1- to 3-fold increase in nuclear staining intensity while breast cancer cells showed 3-fold cytoplasmic and sometimes 2- to 3-fold nuclear staining intensity for PCBP-1. Breast cancer cells showing increased cytoplasmic staining intensity for PCBP-1 are correlated with lower likelihood of patient survival than breast cells with normal nuclear staining. Globular breast carcinoma cells show a lower PCBP-1 cytoplasmic staining intensity as compared to ductal breast carcinoma cells.

Colon cancer tissue epithelial cells showed a 3-fold increase in cytoplasmic PCBP-1 staining intensity compared to normal colon tissue epithelial cells. A 3-fold increase in cytoplasmic staining intensity was observed in both melanoma and squamous carcinoma cells, while normal skin cells showed weak nuclear staining for PCBP-1. A 2-fold increase in cytoplasmic staining was observed in Glioblastoma multiforme and astrocytomas, while no staining was observed in normal brain neurons and astrocytes. Sarcomas and bladder cancer cells showed 2- to 3-fold increases in cytoplasmic staining compared to normal muscle and normal bladder cells. While normal endometrial cells showed negative or weak cytoplasmic staining for PCBP-1, endometrial cancer cells showed a 3-fold increase in nuclear and cytoplasmic staining for PCBP-1. Normal ovarian epithelial cells showed a 3-fold increase in cytoplasmic and nuclear staining for PCBP-1 as compared to ovarian cancer cells.

Example 14

The soluble, native form of PCBP-1 is purified from SKBR3 human breast cancer cell conditioned media. An affinity approach is taken, in which Alper PCBP-1 mouse monoclonal antibody is cross-linked to sepharose (i.e. CNBr-activated sepharose or similar kit available from GE Healthcare Bio-Sciences Corp., Piscataway, N.J., USA, or from Pierce Chemical Co., Rockford, Ill., USA) to purify the native PCBP-1 antigen. Conditioned media is generated and affinity purification of PCBP-1 is performed.

The purified PCBP-1 is characterized with respect to size (SDS-PAGE), purity (SDS-PAGE, SEC-HPLC, Western blot), and aggregation (Western blot). The stability of the purified PCBP-1 preparation is monitored over time by SDS-PAGE and SEC-HPLC. The purification can be scaled up using non-affinity techniques which can include, but are not limited to, ion exchange chromatography, filtration, aqueous phase partitioning and/or counter-current chromatography.

Example 15

Purified PCBP-1 is injected to six-week-old Balb/c mice and six-lb. NZW rabbits via iv, ip, or intramuscular routes using Kohler and Milstein's original injection and monoclonal antibody production conventional technique over a period of 3-5 months (Kohler et al., Nature 256(5517): 495-497, 1975). During the injections, at certain time intervals several test bleedings are performed to test immunologic response as well as antibody production in mice and rabbits. Production of monoclonal and polyclonal antibodies is tested using ELISA, western blot and immunofluorescence staining techniques.

Example 16

The YTMA 49-10 array, a node-positive and node-negative invasive breast carcinoma tissue microarray containing 700 samples, is subjected to immunohistochemistry using Alper PCBP-1 mouse monoclonal antibody (7SK). Slides of the YTMA 49-10 multi-tissue array are deparrafinized by immersing twice in xylene and incubating for 15 minutes. Slides are then immersed in a 1:1 solution of xylene:ethanol for 5 minutes. Slides are then immersed in 100% ethanol for 5 minutes, followed by immersion in 95%, 75% and 50% ethanol for 3 minutes each. Slides are rinsed with reagent-quality water for 5 minutes and are rehydrated by immersing in distilled water until ready to perform antigen retrieval. Heat-induced epitope retrieval is performed at 95-100° C. in citrate retrieval buffer at pH 6.0 for 40 minutes, then the slides are allowed to cool to room temperature and are rinsed with Tris buffer (Tris buffered saline with Tween 20, pH 7.6). A peroxidase block (3% hydrogen peroxide) is applied to the slides for 5 minutes, and the slides are again rinsed with Tris buffer. BACKGROUND SNIPER™ (Biocare Medical Products, Concord, Calif.; Catalog No. BS966 G) blocking reagent is applied to the slides for 5 minutes, and the slides are rinsed with Tris buffer. A 1:50 dilution of Alper PBCP-1 mouse monoclonal antibody is then applied to the array slides for one hour at room temperature, followed by three washes with Tris buffer. MACH 3™ Probe (Biocare Medical Products, Concord, Calif., USA; Catalog No. M3M530) is applied to the slides for 15 minutes, the slides are rinsed three times with Tris buffer, and MACH 3™ Polymer (Biocare Medical Products, Concord, Calif., USA; Catalog No. M3M530) is then added to the slides for 15 minutes. After three rinses with Tris buffer, diaminobenzenetetrahydrochloride (DAB) is applied to the slides and slides are incubated until desired stain intensity develops. The slides are then contacted with hematoxylin counterstain if desired.

Figure 14B:
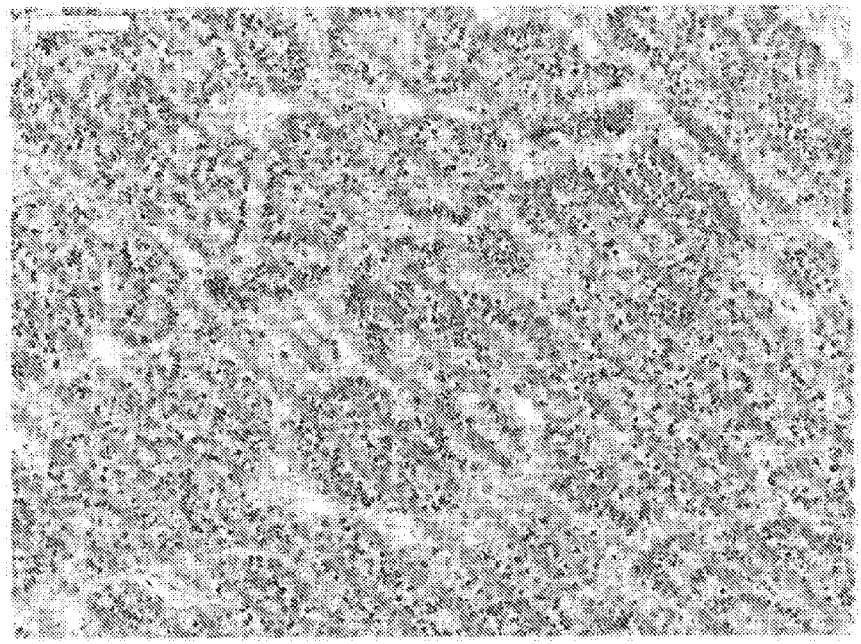
FIGS. 14A and 14B Immunohistochemical staining of samples from lobular and ductal carcinoma patients. The YTMA 49-10 node-positive/node-negative invasive breast carcinoma tissue micro array (obtained from Yale Cancer Center Department of Pathology Tissue Microarray Facility) is stained with Alper PCBP-1 mouse monoclonal antibody. Samples are then labeled with a FITC-labeled secondary goat-anti-mouse antibody and subjected to laser confocal microscopy. Samples are assigned a value (0, 1+, 2+ or 3+) based on amount of staining with Alper PCBP-1 mouse monoclonal antibody. High (2+ or 3+) indirect immunofluorescent staining is observed in about 50% of patients with lobular carcinoma. High indirect immunofluorescent staining is observed in about 70% of patients with ductal carcinoma.
Figure 14A:

Slides are then fixed by immersing in 70% ethanol, 80% ethanol, 95% ethanol and 100% ethanol for two minutes each, followed by immersion in xylene twice for two minutes. Tissue arrays are analyzed via microscopy at low (10-20×) resolution to locate well-preserved and well-stained areas. Identified well-preserved and well-stained areas are used to make a determination of the intensity of PCBP-1 expression. Percentage of stained cells is estimated as 0%, less than 50%, or greater than 50% of the total number of well-preserved cells. Stained cells are then assayed for staining intensity, which can range from negative to faint to weak to intense. Results are summarized in FIGS. 14 and 15. Examples of negative and 1+, 2+ and 3+ staining in ductal and lobular breast cancer cells are shown in FIGS. 16-18.

Example 17

A. Labeling of RP11-175A7 BAC Clone

DNA of *Homo sapiens* BAC clone RP11-175A7 (SEQ ID NO: 51; Genbank Accession No. AC016700.8) is fluorescently labeled with by nick translation using standard protocols. DNA from BAC clone RP11-175A7 is prepared by standard methods. A nick translation reaction is prepared including BAC DNA (8 µl), dNTPs (5 µl), 10× Nick translation buffer (5 µl), 10× beta-mercaptoethanol, Orange-dUTP (1 µl), DNA polymerase (2 µl), DNAse (3 µl of 1:1000 dilution), nuclease free H2O (21 µl) and incubated at 15° C. for 90 minutes. The reaction is stopped with 1 µl of 0.5 M EDTA. The reaction is ethanol precipitated by the addition of 10 µl of salmon sperm DNA, 40 µl Cot-1 DNA, 10 µl of 3 M NaOAc, pH 5.2 and 200 µl of 100% EtOH followed by incubation at −80° C. for 30 minutes. The precipitated Orange-dUTP labeled DNA is collected by centrifugation at 14,000 rpm for 15 minutes. The pellet is dried and resuspended in 32 µl of nuclease free water, 8 µl 20×SSC and 40 µl 20% dextran sulfate in formamide to prepare 80 µl of hybridization mix.

B. Hybridization

Figure 19A:
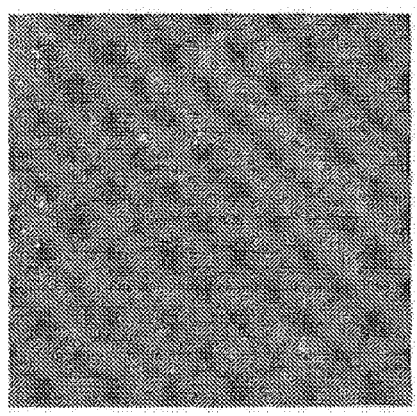
FIGS. 19A, 19B, 19C.
Figure 19C:
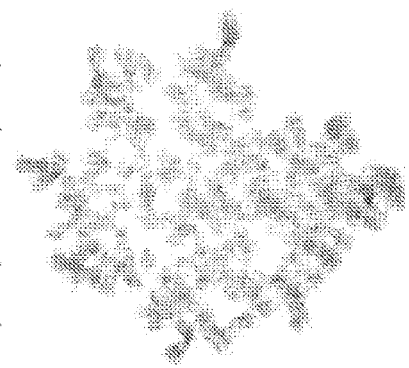
Figure 19B:
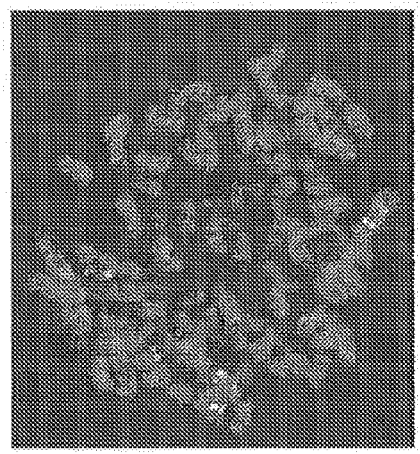

Slides of chromosomal DNA in metaphase of breast cancer cell lines SK-BR 3, MDA-MB-231 and C2T2 are prepared and pretreated to denature the chromosomal DNA and block non-specific hybridization to repetitive DNA. The hybridization probe prepared in step A above is briefly denatured by boiling followed by quick chilling and applied to the chromosome slide preparations and incubated for approximately 12 hours to allow hybridization. Hybridized slides are washed according to standard methods to remove unhybridized and partially hybridized probes. The results are visualized and quantified by fluorescent microscopy. Images of chromosome spreads of individual cells for each of the three lines are recorded and presented in FIG. 19.

Example 18

The staining protocol listed above in Example 16 is used on approximately 300 untreated breast tissue samples from healthy subjects, nonmetastatic ductal cancer patients and metastatic ductal cancer patients. Stained tissue samples are included on the 'Breast normal adjacent tissue and cancer tissue array' (Biomax #BRN801a). The BRN801a array has tissue samples with both normal and breast carcinoma pathology diagnoses. The array includes 70 cases of adjacent normal breast tissue, plus 10 tissue sections of malignant invasive ductal breast carcinoma tissue obtained from different samples. The staining protocol listed above in Example 16 is also used on the 'Breast invasive ductal carcinoma and matched metastatic carcinoma tissue microarray' (Biomax BR10010). The BR10010 array contains tissue sections from 50 samples of breast carcinoma (46 invasive ductal carcinoma, 1 micropapillary carcinoma, 2 invasive lobular carcinoma, 1 neuroendocrine carcinoma), and 50 matched metastacised breast carcinomas obtained from a lymph node. The staining protocol is also used on the 'Breast Tumor Tissue Array' (Biochain Institute, Inc; Z7020009). The Z7020009 array has duplicate tissue samples obtained by surgical resection from six pathological tissue types including normal breast tissue, hyperplasia breast tissue, fibroadenoma breast tissue, invasive ductal carcinoma, invasive lobular carcinoma and Paget's disease.

Results show that PCBP-1 is localized and expressed in high amounts in the nucleus in healthy breast tissue epithelial cells. As a cell undergoes transformation, PCBP-1 expression becomes more cytoplasmic with some nuclear expression as well, and overall increased expression than in the healthy cells. As the ductal carcinoma cells become metastatic, PCBP-1 expression is entirely in the cytoplasm of the cells with no staining in the nucleus. Of 100 cases of metastatic ductal breast cancers, no nuclear expression of PCBP-1 is observed.

Example 19

Figure 20:
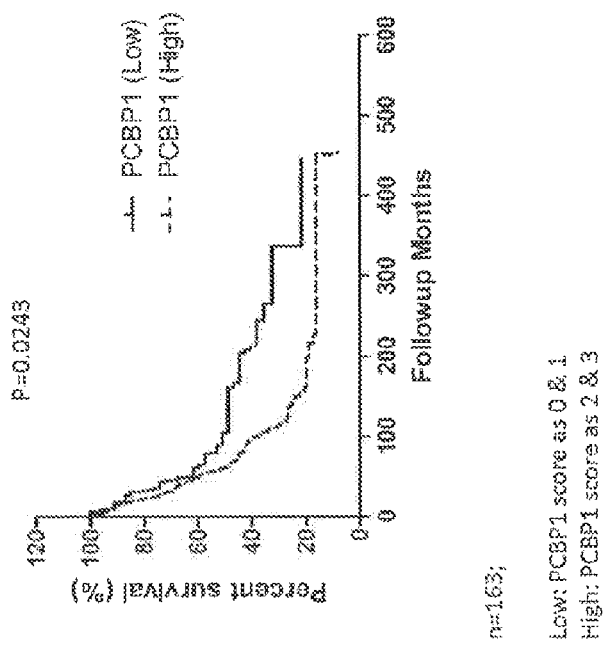
FIG. 20. Higher PCBP-1 expression levels correlate with a decrease in overall survival of ductal breast cancer patients.

The staining protocol listed above in Example 16 is used with the Alper PCBP-1 mouse monoclonal antibody (7SK) and the Yale Breast Cancer Cohort YTMA 49_9 array. The Yale Cancer Center/Pathology Tissue Microarray Facility collects and provides pathological analysis on tissue samples and arrays the samples on a slide. The Facility provides a map of the arrayed samples so researchers can correlate results to cancer pathology, including determination of ductal cancer. These samples are analyzed blindly for PCBP-1 staining. Results show that higher levels of PCBP-1 expression (PCBP-1 score of +2 or +3) are correlated with a decrease in a ductal breast cancer patient's overall prognosis or survival relative to ductal breast cancer patients with a lower level of PCBP-1 expression (PCBP-1 score of 0 or +1). See FIG. 20. This correlation is statistically significant with a p-value of 0.0243. PCBP-1 scores are determined in a blind analysis, where a score of 0 or +1 is a low level of PCBP-1 staining. The difference between 0/+1 and +2/+3 in ductal cancer samples is particularly apparent in the higher amount of cytoplasmic staining of arrayed tissue samples scored +2 or +3.

General guidelines are as follows, and samples can be scored by standard pathology guidelines.

Score 0=No staining is observed in invasive tumor cells

Score 1+=Weak, nuclear staining is observed in any proportion of invasive tumor cells, or weak, cytoplasmic staining is observed in less than 30% of cells Score 2+=Weak cytoplasmic is observed in 50% or more cells or strong cytoplasmic staining of more than 30% is observed in invasive tumor cells Score 3+=Strong cytoplasmic staining is observed that is in more than 50% of tumor cells Example 20

Figure 21:
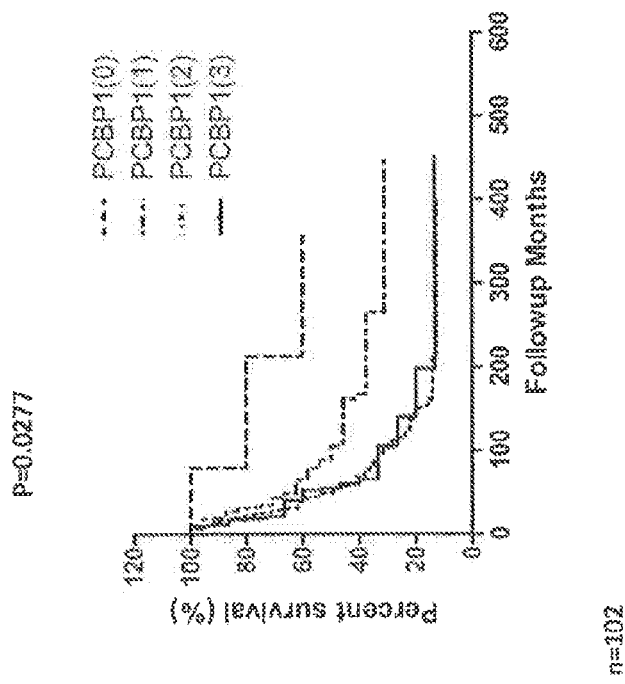
FIG. 21. Higher PCBP-1 expression levels from patients with more than three positive lymph nodes correlate with a decrease in overall survival of those ductal breast cancer patients.

The protocol listed above in Example 16 is used with the Alper PCBP-1 mouse monoclonal antibody (7SK) and the Yale Breast Cancer Cohort YTMA 49_9 array. Mapping of patient pathology, including lymph node status, is provided by the Yale Facility. Results show that higher levels of PCBP-1 expression are correlated with a decrease in the overall prognosis of a ductal breast cancer patient with three or more positive lymph nodes. See FIG. 21. This correlation is statistically significant with a p-value of 0.0277. PCBP-1 scores are determined in a blind anaysis, where a score of 0 or +1 is a low level of PCBP-1 staining. The difference between 0/+1 and +2/+3 was particularly apparent in the higher amount of cytoplasmic staining of arrayed tissue samples scored +2 or +3.

Example 21

Figures 22A, 22B, 22C, 22D:
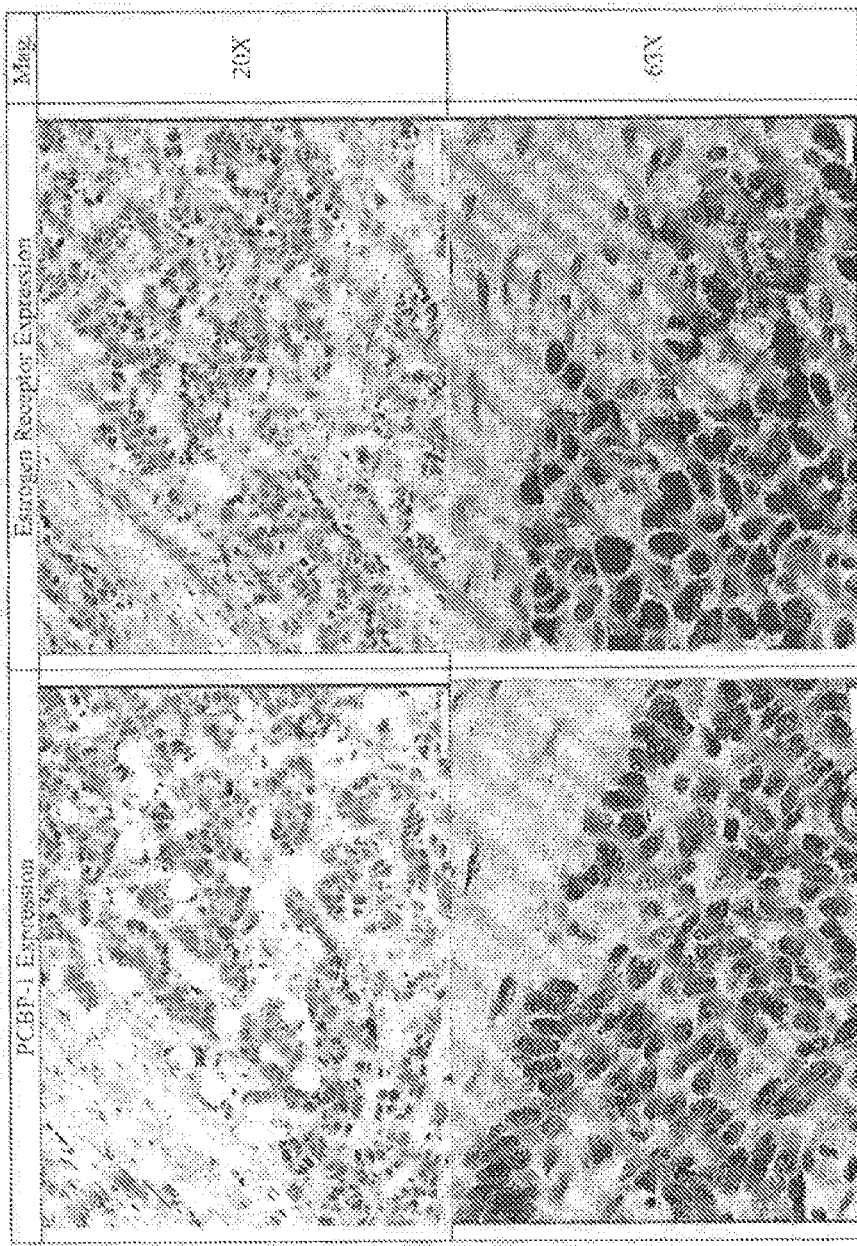
FIGS. 22A, 22B, 22C, and 22D.

The protocol listed above in Example 16 is used with the Alper PCBP-1 mouse monoclonal antibody (7SK) and a array of normal breast tissues and untreated non-metastatic breast cancer tissues from the Cytology Services of Maryland. Detection of the estrogen receptor (ER) and progesterone receptor (PR) subcellular localization for these arrays is provided by Cytology Services of Maryland using commercial antibodies. Results show a strong positive correlation between ER (nuclear) positivity with PCBP-1 (nuclear) positivity in untreated non-metastatic breast cancer patients and controls, the correlation is >75% of staining in the nucleus for ER and PCBP-1. See FIG. 22. There is also a strong positive correlation in expression and staining intensity between high levels of PR staining (2+/3+) and high levels of PCBP-1 staining (2+/3+) with 81% of staining in the nucleus for PR and PCBP-1 (39/41).

What is claimed is:

1. A prognostic method for determining the severity of disease in a patient diagnosed with or suspected of having breast cancer comprising:
   a) obtaining a cell or tissue sample from a human subject diagnosed with or suspected of having breast cancer;
   b) contacting the sample with an antibody that binds a PCBP-1 antigen, wherein the antibody comprises a heavy chain variable domain comprising three complementarity determining regions (CDRs) comprising the amino acid sequences of SEQ ID NO: 45, SEQ ID NO: 46, and SEQ ID NO: 47, and a light chain variable domain comprising three CDRs comprising the amino acid sequences of SEQ ID NO: 48, SEQ ID NO: 49, and SEQ ID NO: 50;
   c) detecting the antibody;
   d) scoring the detection pathologically, wherein a pathology score of 0 indicates no staining in the cell, a score of 1+ indicates weak nuclear staining in any number of cells, or cytoplasmic staining in less than 30% of cells; a score of 2+ indicates weak cytoplasmic staining in 50% or more cells or strong cytoplasmic staining in more than 30% of cells; and a score of 3+ indicates strong cytoplasmic staining in more than 50% of cells; and
   e) providing a prognosis to the patient, wherein the pathology score correlates with the severity of disease, wherein a score of 0 or 1+ indicates a higher likelihood of patient survival and a score of 2+ or 3+ indicates a lower likelihood of patient survival.

2. The method of claim 1, wherein the antibody is detectably labeled.

3. The method of claim 1, wherein the antibody is detected with a labeled secondary antibody.

4. The method of claim 2, wherein the label is fluorescent.

5. The method of claim 1, wherein the cancerous breast cell or tissue is ductal.

\* \* \* \* \*

SEQUENCE LISTING

<160> NUMBER OF SEQ ID NOS: 52

<210> SEQ ID NO 1
<211> LENGTH: 8
<212> TYPE: PRT
<213> ORGANISM: Homo sapiens

<400> SEQUENCE: 1

Ile Arg Glu Glu Ser Gly Ala Arg
1               5

<210> SEQ ID NO 2
<211> LENGTH: 11
<212> TYPE: PRT
<213> ORGANISM: Homo sapiens

<400> SEQUENCE: 2

Ile Asn Ile Ser Glu Gly Asn Cys Pro Glu Arg
1               5                  10

<210> SEQ ID NO 3
<211> LENGTH: 13
<212> TYPE: PRT
<213> ORGANISM: Homo sapiens

<400> SEQUENCE: 3

Ile Ile Thr Leu Thr Gly Pro Thr Asn Ala Ile Phe Lys
1               5                  10

<210> SEQ ID NO 4
<211> LENGTH: 31
<212> TYPE: PRT
<213> ORGANISM: Homo sapiens

<400> SEQUENCE: 4

Ala Phe Ala Met Ile Ile Asp Lys Leu Glu Asp Ile Asn Ser Ser
1               5                  10                  15

Met Thr Asn Ser Thr Ala Ala Ser Arg Pro Pro Val Thr Leu Arg
            20                  25                  30

<210> SEQ ID NO 5
<211> LENGTH: 14
<212> TYPE: PRT
<213> ORGANISM: Homo sapiens

<400> SEQUENCE: 5

Leu Val Val Pro Ala Thr Gln Cys Gly Ser Leu Ile Gly Lys
1               5                  10

<210> SEQ ID NO 6
<211> LENGTH: 20
<212> TYPE: PRT
<213> ORGANISM: Homo sapiens

<400> SEQUENCE: 6

Glu Ser Thr Gly Ala Gln Val Gln Val Ala Gly Asp Met Leu Pro Asn
1               5                  10                  15

Ser Thr Glu Arg
            20

<210> SEQ ID NO 7
<211> LENGTH: 16
<212> TYPE: PRT
<213> ORGANISM: Homo sapiens

<400> SEQUENCE: 7

Ala Ile Thr Ile Ala Gly Val Pro Gln Ser Val Thr Glu Cys Val Lys
1               5                  10                  15

<210> SEQ ID NO 8
<211> LENGTH: 17
<212> TYPE: PRT
<213> ORGANISM: Homo sapiens

<400> SEQUENCE: 8

Gln Ile Cys Leu Val Met Leu Glu Thr Leu Ser Gln Ser Pro Gln Gly
1               5                  10                  15

Arg

<210> SEQ ID NO 9
<211> LENGTH: 23
<212> TYPE: PRT
<213> ORGANISM: Homo sapiens

<400> SEQUENCE: 9

Val Met Thr Ile Pro Tyr Gln Pro Met Pro Ala Ser Ser Pro Val Ile
1               5                   10                  15

Cys Ala Gly Gly Gln Asp Arg
            20

<210> SEQ ID NO 10
<211> LENGTH: 25
<212> TYPE: PRT
<213> ORGANISM: Homo sapiens

<400> SEQUENCE: 10

Gln Gln Ser His Phe Ala Met Met His Gly Gly Thr Gly Phe Ala Gly
1               5                   10                  15

Ile Asp Ser Ser Ser Pro Glu Val Lys
            20                  25

<210> SEQ ID NO 11
<211> LENGTH: 29
<212> TYPE: PRT
<213> ORGANISM: Homo sapiens

<400> SEQUENCE: 11

Gly Tyr Trp Ala Ser Leu Asp Ala Ser Thr Gln Thr Thr His Glu Leu
1               5                   10                  15

Thr Ile Pro Asn Asn Leu Ile Gly Cys Ile Ile Gly Arg
            20                  25

<210> SEQ ID NO 12
<211> LENGTH: 11
<212> TYPE: PRT
<213> ORGANISM: Homo sapiens

<400> SEQUENCE: 12

Ile Ala Asn Pro Val Glu Gly Ser Ser Gly Arg
1               5                   10

<210> SEQ ID NO 13
<211> LENGTH: 21
<212> TYPE: PRT
<213> ORGANISM: Homo sapiens

<400> SEQUENCE: 13

Gln Val Thr Ile Thr Gly Ser Ala Ala Ser Ile Ser Leu Ala Gln Tyr
1               5                   10                  15

Leu Ile Asn Ala Arg
            20

<210> SEQ ID NO 14
<211> LENGTH: 10
<212> TYPE: PRT
<213> ORGANISM: Homo sapiens

<400> SEQUENCE: 14

Leu Ser Ser Glu Lys Gly Met Gly Cys Ser
1               5                   10

-continued

```
<210> SEQ ID NO 15
<211> LENGTH: 345
<212> TYPE: DNA
<213> ORGANISM: Mus sp.
<220> FEATURE:
<221> NAME/KEY: CDS
<222> LOCATION: (1)..(345)

<400> SEQUENCE: 15 gtg cag ctg gag gag tct gga cct gag ctg gtg aag cct ggg gcc tca      48
Val Gln Leu Glu Glu Ser Gly Pro Glu Leu Val Lys Pro Gly Ala Ser
 1               5                  10                  15 gtg aag att tcc tgc aaa gtt tct ggc tac gca ttc agt agg tct tgg      96
Val Lys Ile Ser Cys Lys Val Ser Gly Tyr Ala Phe Ser Arg Ser Trp
             20                  25                  30 atg aac tgg gtg aag cag agg cct gga cag ggt ctt gag tgg att gga    144
Met Asn Trp Val Lys Gln Arg Pro Gly Gln Gly Leu Glu Trp Ile Gly
         35                  40                  45 cgg atc tat cct gga gat gga gat act aac tac aat ggg aag ttc aag    192
Arg Ile Tyr Pro Gly Asp Gly Asp Thr Asn Tyr Asn Gly Lys Phe Lys
     50                  55                  60 ggc aag gcc aca ctg act gca gac aaa tcc tcc agt aca gcc tac atg    240
Gly Lys Ala Thr Leu Thr Ala Asp Lys Ser Ser Ser Thr Ala Tyr Met
 65                  70                  75                  80 cag ctc agc agc ctg acc tct gtg gac tct gcg gtc tat ttc tgt gca    288
Gln Leu Ser Ser Leu Thr Ser Val Asp Ser Ala Val Tyr Phe Cys Ala
                 85                  90                  95 aga tcg gaa cta tgg tca aaa atg ttt gct tac tgg ggc caa ggg acc    336
Arg Ser Glu Leu Trp Ser Lys Met Phe Ala Tyr Trp Gly Gln Gly Thr
            100                 105                 110 acg gtc aca                                                         345
Thr Val Thr
        115

<210> SEQ ID NO 16
<211> LENGTH: 115
<212> TYPE: PRT
<213> ORGANISM: Mus sp.

<400> SEQUENCE: 16

Val Gln Leu Glu Glu Ser Gly Pro Glu Leu Val Lys Pro Gly Ala Ser
 1               5                  10                  15

Val Lys Ile Ser Cys Lys Val Ser Gly Tyr Ala Phe Ser Arg Ser Trp
             20                  25                  30

Met Asn Trp Val Lys Gln Arg Pro Gly Gln Gly Leu Glu Trp Ile Gly
         35                  40                  45

Arg Ile Tyr Pro Gly Asp Gly Asp Thr Asn Tyr Asn Gly Lys Phe Lys
     50                  55                  60

Gly Lys Ala Thr Leu Thr Ala Asp Lys Ser Ser Ser Thr Ala Tyr Met
 65                  70                  75                  80

Gln Leu Ser Ser Leu Thr Ser Val Asp Ser Ala Val Tyr Phe Cys Ala
                 85                  90                  95

Arg Ser Glu Leu Trp Ser Lys Met Phe Ala Tyr Trp Gly Gln Gly Thr
            100                 105                 110

Thr Val Thr
        115

<210> SEQ ID NO 17
<211> LENGTH: 294
<212> TYPE: DNA
<213> ORGANISM: Mus sp.
```

```
<220> FEATURE:
<221> NAME/KEY: CDS
<222> LOCATION: (1)..(294)

<400> SEQUENCE: 17 cag gtc cag ctg cag cag tct gga cct gag ctg gtg aag cct ggg gcc      48
Gln Val Gln Leu Gln Gln Ser Gly Pro Glu Leu Val Lys Pro Gly Ala
1               5                   10                  15 tca gtg aag att tcc tgc aaa gct tct ggc tac gca ttc agt agc tct      96
Ser Val Lys Ile Ser Cys Lys Ala Ser Gly Tyr Ala Phe Ser Ser Ser
            20                  25                  30 tgg atg aac tgg gtg aag cag agg cct gga cag ggt ctt gag tgg att     144
Trp Met Asn Trp Val Lys Gln Arg Pro Gly Gln Gly Leu Glu Trp Ile
        35                  40                  45 gga cgg att tat cct gga gat gga gat act aac tac aat ggg aag ttc     192
Gly Arg Ile Tyr Pro Gly Asp Gly Asp Thr Asn Tyr Asn Gly Lys Phe
    50                  55                  60 aag ggc aag gcc aca ctg act gca gac aaa tcc tcc agc aca gcc tac     240
Lys Gly Lys Ala Thr Leu Thr Ala Asp Lys Ser Ser Ser Thr Ala Tyr
65                  70                  75                  80 atg cag ctc agc agc ctg acc tct gtg gac tct gcg gtc tat ttc tgt     288
Met Gln Leu Ser Ser Leu Thr Ser Val Asp Ser Ala Val Tyr Phe Cys
                85                  90                  95 gca aga                                                             294
Ala Arg

<210> SEQ ID NO 18
<211> LENGTH: 98
<212> TYPE: PRT
<213> ORGANISM: Mus sp.

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg

<210> SEQ ID NO 19
<211> LENGTH: 291
<212> TYPE: DNA
<213> ORGANISM: Mus sp.

<400> SEQUENCE: 19
gttcagctgc agcagtctgg acctgagctg gtgaagcctg ggcctcagt gaagatttcc     60 tgcaaggctt ctggctacgc attcagtagc tcctggatga actgggtgaa gcagaggcct    120
ggaaagggtc ttgagtggat tggacggatt tatcctggag atggagatac taactacaat    180
gggaagttca aggcaaggc cacactgact gcagacaaat cctccagcac agcctacatg     240
caactcagca gcctgacatc tgaggactct gcggtctact tctgtgcaag a            291
```

<210> SEQ ID NO 20
<211> LENGTH: 291
<212> TYPE: DNA
<213> ORGANISM: Mus sp.

<400> SEQUENCE: 20

```
gttcagctgc agcagtctgg acctgagctg gtgaagcctg gggcctcagt gaagatttcc      60
tgcaaggctt ctggctacgc attcagtagc tcctggatga actgggtgaa gcagaggcct     120
ggaaagggtc ttgagtggat tggacggatt tatcctggag atggagatac taactacaat     180
gggaagttca aggcaaggc cacactgact gcagacaaat cctccagcac agcctacatg     240
caactcagca gcctgacatc tgaggactct gcggtctact tctgtgcaag a              291
```

<210> SEQ ID NO 21
<211> LENGTH: 33
<212> TYPE: DNA
<213> ORGANISM: Mus sp.

<400> SEQUENCE: 21

```
gtttgcttac tggggccaag ggactctggt cac                                    33
```

<210> SEQ ID NO 22
<211> LENGTH: 33
<212> TYPE: DNA
<213> ORGANISM: Mus sp.

<400> SEQUENCE: 22

```
tttgactact ggggccaagg caccactctc aca                                    33
```

<210> SEQ ID NO 23
<211> LENGTH: 291
<212> TYPE: DNA
<213> ORGANISM: Mus sp.

<400> SEQUENCE: 23

```
gttcagctgc agcagtctgg ggctgagctg gtgaagcctg gggcctcagt gaagatttcc      60
tgcaaagctt ctggctacgc attcagtagc tactggatga actgggtgaa gcagaggcct     120
ggaaagggtc ttgagtggat tggacagatt tatcctggag atggtgatac taactacaac     180
ggaaagttca aggcaaggc cacactgact gcagacaaat cctccagcac agcctacatg     240
cagctcagca gcctgacctc tgaggactct gcggtctatt tctgtgcaag a              291
```

<210> SEQ ID NO 24
<211> LENGTH: 291
<212> TYPE: DNA
<213> ORGANISM: Mus sp.

<400> SEQUENCE: 24

```
gtccagctgc agcagtctgg acctgagctg gtgaagcctg gggcttcagt gaggatatcc      60
tgcaaggctt ctggctacac cttcacaagc tactatatac actgggtgaa gcagaggcct     120
ggacagggac ttgagtggat tggatggatt tatcctggaa atgttaatac taagtacaat     180
gagaagttca aggcaaggc cacactgact gcagacaaat cctccagcac agcctacatg     240
cagctcagca gcctgacctc tgaggactct gcggtctatt tctgtgcaag a              291
```

<210> SEQ ID NO 25
<211> LENGTH: 290
<212> TYPE: DNA
<213> ORGANISM: Mus sp.

<400> SEQUENCE: 25
gtccagctgc agcagtctgg acctgagctg gtgaagcctg ggcttcagt gaagatgtcc    60 tgcaaggctt ctggctacac cttcacaagc tactatatac actgggtgaa gcagaggcct   120
ggacagggac ttgagtggat tggatggatt tatcctggag atggtagtac taagtacaat   180
gagaagttca aggcaagac cacactgact gcagacaaat cctccagcac agcctacatg   240
ttgctcagca gcctgacctc tgaggactct gcgatctatt tctgtgcaag              290

<210> SEQ ID NO 26
<211> LENGTH: 288
<212> TYPE: DNA
<213> ORGANISM: Mus sp.

<400> SEQUENCE: 26
cagctgcagc agtctggacc tgagctggtg aagcctgggg cttcagtgaa gatatcctgc    60
aaggcttctg gctacacctt cactgactac tatataaact gggtgaagca gaggcctgga   120
cagggacttg agtggattgg atggatttat cctggaagcg gtaatactaa gtacaatgag   180
aagttcaagg gcaaggccac attgactgta gacacatcct ccagcacagc ctacatgcag   240
ctcagcagcc tgacctctga ggactctgcg gtctatttct gtgcaaga                288

<210> SEQ ID NO 27
<211> LENGTH: 291
<212> TYPE: DNA
<213> ORGANISM: Mus sp.

<400> SEQUENCE: 27
gttcagctgc agcagtctgg acctgagctg gtgaagcctg ggcttagt gaagatatcc    60 tgcaaggctt ctggttacac cttcacaagc tacgatataa actgggtgaa gcagaggcct   120
ggacagggac ttgagtggat tggatggatt tatcctggag atggtagtac taagtacaat   180
gagaaattca agggcaaggc cacactgact gcagacaaat cctccagcac agcctacatg   240
cagctcagca gcctgacttc tgagaactct gcagtctatt tctgtgcaag a             291

<210> SEQ ID NO 28
<211> LENGTH: 291
<212> TYPE: DNA
<213> ORGANISM: Mus sp.

<400> SEQUENCE: 28
gtccagctgc agcagtctgg acctgagctg gtgaaacctg ggcttcagt gcggatatcc    60 tgcaaggctt ttgggtacac cttcacaagc tactatatac actgggtgaa gcagaggcct   120
ggacagggac ttgagtggat tggatggatt tatcctggaa atgttaatac taagtacaat   180
gagaagttca agggcaaggc cacactgact gcagacaaat cctccagcac agcctacatg   240
cagctcagca gcctgacctc tgaggactct gcggtctatt tctgtgcaag a             291

<210> SEQ ID NO 29
<211> LENGTH: 246
<212> TYPE: DNA
<213> ORGANISM: Mus sp.

<400> SEQUENCE: 29
tcagtgaaga tttcctgcaa agcttctggc tacgcattca gtagctactg gatgaactgg    60
gtgaagcaga ggcctggaaa gggtcttgag tggattggac agatttatcc tggagatggt   120

```
gatactaact acaacggaaa gttcaagggc aaggccacac tgactgcaga caaatcctcc      180
agcacagcct acatgcagct cagcagcctg acctctgagg actctgcggt ctatttctgt      240
gcaaga                                                                  246
```

```
<210> SEQ ID NO 30
<211> LENGTH: 325
<212> TYPE: DNA
<213> ORGANISM: Mus sp.
<220> FEATURE:
<221> NAME/KEY: CDS
<222> LOCATION: (3)..(320)

<400> SEQUENCE: 30
```

```
tt ctg atg acc cag tct cct gct tcc tta gct gta tct ctg ggg cag        47
   Leu Met Thr Gln Ser Pro Ala Ser Leu Ala Val Ser Leu Gly Gln
   1               5                   10                  15 agg gcc acc atc tca tac agg gcc agc aaa agt gtc agt aca tct ggc        95
Arg Ala Thr Ile Ser Tyr Arg Ala Ser Lys Ser Val Ser Thr Ser Gly
                20                  25                  30 tat agt tat atg cac tgg aac caa cag aaa cca gga cag cca ccc aga       143
Tyr Ser Tyr Met His Trp Asn Gln Gln Lys Pro Gly Gln Pro Pro Arg
            35                  40                  45 ctc ctc atc tat ctt gta tcc aac cta gaa tct ggg gtc cct gcc agg       191
Leu Leu Ile Tyr Leu Val Ser Asn Leu Glu Ser Gly Val Pro Ala Arg
        50                  55                  60 ttc agt ggc agt ggg tct ggg aca gac ttc acc ctc aac atc cat cct       239
Phe Ser Gly Ser Gly Ser Gly Thr Asp Phe Thr Leu Asn Ile His Pro
65                  70                  75                  80 gtg gag gag gag gat gct gca acc tat tac tgt cag cac att agg gag       287
Val Glu Glu Glu Asp Ala Ala Thr Tyr Tyr Cys Gln His Ile Arg Glu
                85                  90                  95 ctt aca cgt tcg gag ggg gga cca agc tgg aaa taaaa                     325
Leu Thr Arg Ser Glu Gly Gly Pro Ser Trp Lys
                100                 105
```

```
<210> SEQ ID NO 31
<211> LENGTH: 106
<212> TYPE: PRT
<213> ORGANISM: Mus sp.

<400> SEQUENCE: 31
```

Leu Met Thr Gln Ser Pro Ala Ser Leu Ala Val Ser Leu Gly Gln Arg
1               5                   10                  15

Ala Thr Ile Ser Tyr Arg Ala Ser Lys Ser Val Ser Thr Ser Gly Tyr
            20                  25                  30

Ser Tyr Met His Trp Asn Gln Gln Lys Pro Gly Gln Pro Pro Arg Leu
        35                  40                  45

Leu Ile Tyr Leu Val Ser Asn Leu Glu Ser Gly Val Pro Ala Arg Phe
    50                  55                  60

Ser Gly Ser Gly Ser Gly Thr Asp Phe Thr Leu Asn Ile His Pro Val
65                  70                  75                  80

Glu Glu Glu Asp Ala Ala Thr Tyr Tyr Cys Gln His Ile Arg Glu Leu
                85                  90                  95

Thr Arg Ser Glu Gly Gly Pro Ser Trp Lys
                100                 105

```
<210> SEQ ID NO 32
<211> LENGTH: 294
<212> TYPE: DNA
<213> ORGANISM: Mus sp.
```

<220> FEATURE:
<221> NAME/KEY: CDS
<222> LOCATION: (1)..(294)

<400> SEQUENCE: 32

```
gac att gtg ctg aca cag tct cct gct tcc tta gct gta tct ctg ggg      48
Asp Ile Val Leu Thr Gln Ser Pro Ala Ser Leu Ala Val Ser Leu Gly
1               5                   10                  15 cag agg gcc acc atc tca tgc agg gcc agc aaa agt gtc agt aca tct      96
Gln Arg Ala Thr Ile Ser Cys Arg Ala Ser Lys Ser Val Ser Thr Ser
            20                  25                  30 ggc tat agt tat atg cac tgg tac caa cag aaa cca gga cag cca ccc     144
Gly Tyr Ser Tyr Met His Trp Tyr Gln Gln Lys Pro Gly Gln Pro Pro
        35                  40                  45 aaa ctc ctc atc tat ctt gca tcc aac cta gaa tct ggg gtc cct gcc     192
Lys Leu Leu Ile Tyr Leu Ala Ser Asn Leu Glu Ser Gly Val Pro Ala
    50                  55                  60 agg ttc agt ggc agt ggg tct ggg aca gac ttc acc ctc aac atc cat     240
Arg Phe Ser Gly Ser Gly Ser Gly Thr Asp Phe Thr Leu Asn Ile His
65                  70                  75                  80 cct gtg gag gag gag gat gct gca acc tat tac tgt cag cac agt agg     288
Pro Val Glu Glu Glu Asp Ala Ala Thr Tyr Tyr Cys Gln His Ser Arg
                85                  90                  95 gag ctt                                                              294
Glu Leu
```

<210> SEQ ID NO 33
<211> LENGTH: 98
<212> TYPE: PRT
<213> ORGANISM: Mus sp.

<400> SEQUENCE: 33

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu
```

<210> SEQ ID NO 34
<211> LENGTH: 290
<212> TYPE: DNA
<213> ORGANISM: Mus sp.

<400> SEQUENCE: 34

```
ttgtgctaac acagtctcct gcttccttag ctgtatctct ggggcagagg gccaccatct      60
catgcagggc cagccaaagt gtcagtacat ctagctatag ttatatgcac tggtaccaac     120
agaaaccagg acagccaccc aaactcctca tcaagtatgc atccaaccta gaatctgggg     180
tccctgccag gttcagtggc agtgggtctg gacagactt caccctcaac atccatcctg     240
tggaggagga ggatactgca acatattact gtcagcacag ttgggagatt                290
```

<210> SEQ ID NO 35
<211> LENGTH: 287
<212> TYPE: DNA
<213> ORGANISM: Mus sp.

<400> SEQUENCE: 35

```
ttgtgctgac ccaatctcca gcttctttgg ctgtgtctct agggcagagg gccaccatct      60
cctgcaaggc cagccaaagt gttgattatg atggtgatag ttatatgaac tggtaccaac     120
agaaaccagg acagccaccc aaactcctca tctatgctgc atccaatcta gaatctggga     180
tcccagccag gtttagtggc agtgggtctg ggacagactt caccctcaac atccatcctg     240
tggaggagga ggatgctgca acctattact gtcagcaaag taatgag                   287
```

<210> SEQ ID NO 36
<211> LENGTH: 36
<212> TYPE: DNA
<213> ORGANISM: Mus sp.

<400> SEQUENCE: 36

```
tacacgttcg gaggggggac caagctggaa ataaaa                                36
```

<210> SEQ ID NO 37
<211> LENGTH: 33
<212> TYPE: DNA
<213> ORGANISM: Mus sp.

<400> SEQUENCE: 37

```
acgttcggtg gaggcaccaa gctggaaatc aaa                                   33
```

<210> SEQ ID NO 38
<211> LENGTH: 287
<212> TYPE: DNA
<213> ORGANISM: Mus sp.

<400> SEQUENCE: 38

```
ttgtgctgac ccaatctcca gcttctttgg ctgtgtctct agggcagagg gccaccatat      60
cctgcagagc cagtgaaagt gttgatagtt atggcaatag ttttatgcac tggtaccagc     120
agaaaccagg acagccaccc aaactcctca tctatcttgc atccaaccta gaatctgggg     180
tccctgccag gttcagtggc agtgggtcta ggacagactt caccctcacc attgatcctg     240
tggaggctga tgatgctgca acctattact gtcagcaaaa taatgag                   287
```

<210> SEQ ID NO 39
<211> LENGTH: 287
<212> TYPE: DNA
<213> ORGANISM: Mus sp.

<400> SEQUENCE: 39

```
ttgtgctgac ccaggcccct ccttccttgg atgtttctca agggtagagg gccaccatct      60
cctgcaggac cagcaaaagt gtcagaacat ctagctatag ttatatgcac tggtaccaac     120
agaaaccagg tcagccgccc aaactcctca atctatgtgc atccaaccaa gtatctaggg     180
tcccagccag gttcagtggc agtggatctg ggacagactt caccctcaaa atccatcctg     240
tggaggagga ggatgctgca acctatttct gtcagcaaag taatgag                   287
```

<210> SEQ ID NO 40
<211> LENGTH: 287
<212> TYPE: DNA
<213> ORGANISM: Mus sp.

<400> SEQUENCE: 40

```
ttgtgctgac ccaatctcca gcttctttgg ctgtgtctct aggacagaga gccactatct    60
tctgcagagc cagccagagt gtcgattata atggaattag ttatatgcac tggttccaac   120
agaaaccagg acagccaccc aaactcctca tctatgctgc atccaaccta gaatctggga   180
tccctgccag gttcagtggc agtgggtctg ggacagactt caccctcaac atccatcctg   240
tggaggagga agatgctgca acctattact gtcagcaaag tattgag                287
```

<210> SEQ ID NO 41
<211> LENGTH: 287
<212> TYPE: DNA
<213> ORGANISM: Mus sp.

<400> SEQUENCE: 41

```
ttgtgctgac ccaatctcca gcttctttgg ctgtgtctct agggcagagg gccaccatat    60
cctgcagagc cagtgaaagt gttgatagtt atggcaatag ttttatgcac tggtaccagc   120
agaaaccagg acagccaccc aaactcctca tctatcgtgc atccaaccta gaatctggga   180
tccctgccag gttcagtggc agtgggtcta ggacagactt caccctcacc attaatcctg   240
tggaggctga tgatgttgca acctattact gtcagcaaag taatgag                287
```

<210> SEQ ID NO 42
<211> LENGTH: 290
<212> TYPE: DNA
<213> ORGANISM: Mus sp.

<400> SEQUENCE: 42

```
ttgtgctgac ccaatctcca gcttctttgg ctgtgtctct agggcagagg gccaccatct    60
cctgcagagc cagcgaaagt gttgataatt atggcattag ttttatgaac tggttccaac   120
agaaaccagg acagccaccc aaactcctca tctatgctgc atccaaccaa ggatccgggg   180
tccctgccag gtttagtggc agtgggtctg ggacagactt cagcctcaac atccatccta   240
tggaggagga tgatactgca atgtatttct gtcagcaaag taaggaggtt               290
```

<210> SEQ ID NO 43
<211> LENGTH: 286
<212> TYPE: DNA
<213> ORGANISM: Mus sp.

<400> SEQUENCE: 43

```
ttgtgctgac ccaatctcca gcttctttgg ctgtgtctct aggacagagg gccaccatat    60
cctgccaagc cagcgaaagt gtcagttttg ctggtacaag tttaatgcac tggtaccaac   120
agaaaccagg acagccaccc aaactcctca tctatcgtgc atccaaccta gaatctggag   180
tccctgccag gttcagtggc agtgggtctg agtcagactt cactctcacc atcgatcctg   240
tggaggaaga tgatgctgca atgtattact gtatgcaaag tatgga                 286
```

<210> SEQ ID NO 44
<211> LENGTH: 290
<212> TYPE: DNA
<213> ORGANISM: Mus sp.

<400> SEQUENCE: 44

```
ttgtgctcac ccaatctcca gcttctttgg ctgtgtctct agggcagaga gccaccatct    60
cctgcagagc cagtgaaagt gttgaatatt atggcacaag tttaatgcag tggtaccaac   120
```

```
agaaaccagg acagccaccc aaactcctca tctatgctgc atccaacgta gaatctgggg    180
tccctgccag gtttagtggc agtgggtctg ggacagactt cagcctcaac atccatcctg    240
tggaggagga tgatattgca atgtatttct gtcagcaaag taggaaggtt               290
```

<210> SEQ ID NO 45
<211> LENGTH: 5
<212> TYPE: PRT
<213> ORGANISM: Mus sp.

<400> SEQUENCE: 45

Arg Ser Trp Met Asn
1               5

<210> SEQ ID NO 46
<211> LENGTH: 17
<212> TYPE: PRT
<213> ORGANISM: Mus sp.

<400> SEQUENCE: 46

Arg Ile Tyr Pro Gly Asp Gly Asp Thr Asn Tyr Asn Gly Lys Phe Lys
1               5                   10                  15

Gly

<210> SEQ ID NO 47
<211> LENGTH: 14
<212> TYPE: PRT
<213> ORGANISM: Mus sp.

<400> SEQUENCE: 47

Ser Glu Leu Trp Ser Lys Met Phe Ala Tyr Trp Gly Gln Gly
1               5                   10

<210> SEQ ID NO 48
<211> LENGTH: 15
<212> TYPE: PRT
<213> ORGANISM: Mus sp.

<400> SEQUENCE: 48

Arg Ala Ser Lys Ser Val Ser Thr Ser Gly Tyr Ser Tyr Met His
1               5                   10                  15

<210> SEQ ID NO 49
<211> LENGTH: 7
<212> TYPE: PRT
<213> ORGANISM: Mus sp.

<400> SEQUENCE: 49

Leu Val Ser Asn Leu Glu Ser
1               5

<210> SEQ ID NO 50
<211> LENGTH: 8
<212> TYPE: PRT
<213> ORGANISM: Mus sp.

<400> SEQUENCE: 50

Ile Arg Glu Leu Thr Arg Ser Glu
1               5

<210> SEQ ID NO 51
<211> LENGTH: 177995
<212> TYPE: DNA
<213> ORGANISM: Homo sapiens

<400> SEQUENCE: 51

```
gaattcactc aggtatccac aagataatgc aggtctgagg aagggagtgg agattttacc    60
aaaagtgcag aaaacattta cataaacctc ccaccccgcc aaagaaaaat aaccaaagtc   120
atcaaatatc atcagtccct ggacataagt agaaggaccc ttagagatca tttaatctct   180
tgctttataa aagggagaac tgaaaccctg acagatgagt tgtagaagtc tcagagctag   240
acaggggcag agctaggact agggcccaga gcctcagatt ccaaggtcca atgacctctt   300
tgccagacca cagcatcacc caaggtgtct gtatgacatg ttaccaaccc aagacacat    360
tacaatttaa ccaacgtcca aacgtgggct accgaaggga gaaactgtta agactctcgg   420
ggaaggaggg aggctaagag ctggggaagc tgggaaaggg aaggcttcac tgaggaggtg   480
cactaagtcc caggagtaca taacaggaaa ttatggaaat atttcagtag gtagtcttgg   540
aaagaaagac ctgacagata aaattttctc tagagaaaag aaataagtta gatttaaaag   600
accagaagaa ggctttgttt gaacattcct tgattatatg caatttagtc cttttgttgt   660
cacctgagtt tctaacactt ggtaatattt ttaattccct catctattct gtctccctat   720
gagacaggac tctctgcaga gaccacatcc agtttagtgg ttaagaatgg agtctctgga   780
ctcagattgc ctaaattcaa atccttgctt taccacttaa tagctgtgtg accttggata   840
aattccttca ctaatctgta cctctgtaaa actgacctaa tatcaccacc catttcagga   900
ggttttgtga ggattaaatg tgtataagcg gtcacaactt attaatgggt ttttaatcac   960
tttataatgt gtcctttta tatataaaga atagaaatta cccaagtaca tatactgcat   1020
gtagtaacaa atattgtttt gcaaaaattt tgttacatat gtgtgcataa atgtcttaaa   1080
tcataatgta aaatttgttt cttagtggtt tttttaaaaa tgtgagacac tgaatacata   1140
aaataaggct tagaacaatg cccagcacac agtaagcacc tagtgctgta actgtcatcg   1200
ttgctgttat gtacctatta aatgttcgta gagttatata aactaacatg aaaccacttt   1260
ggaaaatata tctgatagta acataagtta aaggcaaaaa gcccttctct ttgtctctca   1320
tatccacaca caatcagagc cctgctcagg caccagtttg ttgcttggcc cactagctac   1380
gtgttgcatt gaactgaaga gtccacagac tgacctaaca ctctgtcatg ctctgtcaat   1440
ctctgcagag aaatggaggc ttggtgccag agcgaattta ttttttacctg gttggggtgc   1500
tggggtgggg gaggcaagag tcaagcccat ggggagctga cggaagcaag tcagtcatac   1560
aaaaaaccat ttgctccccc agaggcaggt aggctcaaat gtgccacaga cagggccaga   1620
ccgacagaca cctgagcctc tgggcaggct gaatcacttc cccctcccta tcctcaccag   1680
acactgcata agacagcatt tcagcccgcc cgcccgttac aggtgtagct cttatcagga   1740
aaagctggga gctgcctgat acaaaaaggg gctgactgca caacaaaaga ttacctgaag   1800
ggctcattta aatgacaagc tcacctaaac gttttaaata gtatttaaat tccaaaaccc   1860
tgatttacag aaaaacctgg aaaatgtgct caccagtaag gaaatctgga ggtccatccc   1920
cgacattgtg tgaccttgaa ttaagcactt catctttatg tttgtcttcc tctgtttaaa   1980
agagagagag agagagagag ataagaacac ctacctcaga ggaccatggt aaaaattaaa   2040
gatagaatac ggtgaactgc cttgcatcgg atgtgctggc actggccaat gcacaataaa   2100
cgcctgtccc ttctagacta aaaatgaaca cttaattgtg gtaaactatt aataagattc   2160
accggccaac tgtcctatga aaagtcaga ggcactgtag tctcttcgta gctctcgttc   2220
tctccagcac aacagcccat gctaggaagt ctagaaaagc agtaacttat ctcattcctt   2280
```

```
aaattaaaca gaggtttcta aatgctttgg tactgtgggg acccaaatta tcccttgata    2340 ctgccccct  attatccact attaagcttt aaaaaggcga gagattaaat attgtgccca    2400
cattttacag tcattcgcgt tcccgtttca aattaaaggg aggaaaacgc gttaaaatta    2460
ggcctccgac cttcagacca gcctgtgggc ttttttaagt cataaaactc gcggaggtgg    2520
aaggccccgg ggaggaagag gggtgcattc tagagctttc gggccgaccc caatttctcg    2580
ttggcgacga atgctaacca cgtgtcgcca ttttgtgttc aggaaacatg gcggccgccc    2640
caagggtaag aacagggga  ggcggagtag cgccacgtta gccgctttcc ctgagagatt    2700
gtgaagcacg ttgcgcacgg ggccctttct ggtctggctt agcccaagga ggaaggggaa    2760
aaggcagaaa tcacaactca taggccagcg tcttgagcga cacttcctca gcgggaagaa    2820
ccggcaaaaa aggccttcca agatggcggg ccctgacggg gccgccccc  ttgagcctgg    2880 cgcagtggct gcgcccatgg gcccgaaaag cagccgcggg agcccaggcc gcgcgcgggaa   2940 agccgcagaa acgtcctgaa gccctggccg gcagcccctg aacaaacgag gcctccacag    3000
gcgtacacta ttgtttctaa tgtcggaaaa gggtgccgcg gtggaaacga cacaagggca    3060
ggaggtgggg tttctgtggc tttaaccgaa agaaacttgc gaaacgcaaa caaagcatta    3120
tgtaaatgga cgccattctt tttaggacca cgtttctagc acgccccaca aacagcagag    3180
ccgcgattcg gcaggcggcc gtgagtgggt ttcggtcttt ctgcccaccg gccgccgccg    3240
gggagcagga gctggggtgg gggatccatg cagggcgccc ggacgccggg gacgaaaggg    3300
ccccacgtgc ccgcccgcgc gcacccgctc cgcaggcctc gcctcgccgc ccctcccccc    3360
cggaagaggg ctgctgcccc tcccatcccc ccacaccctc gcgcacgcgc tctggtcacc    3420
tcacgcgcat gttttaaacc cgcggcgtcc cggcttgtgc ctgcagtttc gccggggct    3480 gcccatgtcg ttccgcgcac gagccctca  tgtagggcag gaaaataatg tctatcccgc    3540
atacacagca ctagtatttt cagtcacccg ccagtgccgt tagagttaat aaaatacgtc    3600
atcattttaa aactttgccg gactcacagc ttccgcccat cgtgcgcttc attttcacta    3660
ctgcagtgtc agaaggtttt ttttttaagg accatgtaag ggttggcgca atcttgtgac    3720
ctaaaaaaga cgggtcctca ttttttttca aggggtcctg cgcagcaagc acttccgggg    3780
tcagagggta cgcggggttg aaagcgggct tcccgccccg cccagaccgc cgaggctgcc    3840
gccggagtcg ccaccgccgc gcctcgcccc accgcccgc  ccgccgctcc cggcccgct    3900 cgcccctcc  gccgccgccg cccgcccctg cgactacgct gcggcctccc gcccgctccc    3960
gctcgctccc gcgccctcg ctcgcctcgc gccggcagtt ttgggcctac acctcccctc    4020 ccccgccag  ccgccaaaga cttgaccacg taacgagccc aactcccccg aacgccgccc    4080
gccgctcgcc atggatgccg gtgtgactga agtggactaa atgtgactc tcaccattcg    4140 gcttcttatg cacggaaagg aagtaggaag catcattggg aagaaagggg agtcggttaa    4200
gaggatccgc gaggagagtg gcgcgcggat caacatctcg gaggggaatt gtccggagag    4260
aatcatcact ctgaccggcc ccaccaatgc catctttaag gctttcgcta tgatcatcga    4320
caagctggag gaagatatca acagctccat gaccaacagt accgcggcca gcaggccccc    4380
ggtcaccctg aggctggtgg tgccggccac ccagtgcggc tccctgattg ggaaaggcgg    4440
gtgtaagatc aaagagatcc gcgagagtac gggggcgcag gtccaggtgg cggggggatat  4500 gctgcccaac tccaccgagc gggccatcac catcgctggc gtgccgcagt ctgtcaccga    4560
gtgtgtcaag cagatttgcc tggtcatgct ggagacgctc tcccagtctc gcaaggggag    4620
agtcatgacc attccgtacc agcccatgcc ggccagctcc ccagtcatct gcgcgggcgg    4680
```

```
ccaagatcgg tgcagcgacg ctgcgggcta cccccatgcc acccatgacc tggagggacc    4740
acctctagat gcctactcga ttcaaggaca acacaccatt tctccgctcg atctggccaa    4800
gctgaaccag gtggcaagac aacagtctca ctttgccatg atgcacggcg ggaccggatt    4860
cgccggaatt gactccagct ctccagaggt gaaaggctat tgggcaagtt tggatgcatc    4920
tactcaaacc acccatgaac tcaccattcc aaataactta attggctgca taatcgggcg    4980
ccaaggcgcc aacattaatg agatccgcca gatgtccggg gcccagatca aaattgccaa    5040
cccagtggaa ggctcctctg gtaggcaggt tactatcact ggctctgctg ccagtattag    5100
tctggcccag tatctaatca atgccaggct ttcctctgag aagggcatgg ggtgcagcta    5160
gaacagtgta ggttccctca ataacccctt tctgctgttc tcccatgatc caactgtgta    5220
atttctggtc agtgattcca ggttttaaat aatttgtaag tgttcagttt ctacacaact    5280
ttatcatccg ctaagaattt aaaaatcaca ttctctgttc agctgttaat gctgggatcc    5340
atatttagtt ttataagctt ttccctgttt ttagttttgt tttgggtttt ttggctcatg    5400
aattttattt ctgtttgtcg ataagaaatg taagagtgga atgttaataa atttcagttt    5460
agttctgtaa tgtcaagaat ttaagaatta aaaaacggat tggttaaaaa atgcttcata    5520
tttgaaaaag ctgggaattg ctgtcttaaa ctctttgttg gtgccttttt tttccctccc    5580
cttttagcct gaggtgtttg gagggaggag ggagaagggt gggcccgtcc ttggtattct    5640
ctcaagctct tctcaccttaa tcggtaagat tccattccct ctgtgcccca acaaaggaac    5700
atggcaggct gggcctgctt tgggatgttt ccagggacag agaggttcaa gttccagaga    5760
gaggcctctg cccatttctc tggtagaaac aaggttttct cgagggggaaa aggtgtgccc    5820 actcagtagg acctctaaat ggcagagcgt cctctccatc taaccagttc ccccaccccc    5880
acctcacagg ataaacttag gaacaaaaaa atattctggg gtgggaggag cctggggaag    5940
gggtgtgggg gcagggaaag gaaaggaagg gagggcagtg ggccggggag gattgggggc    6000
ttggaggagg gcaacagctg ccgggtggtg gtgggactag aggggtcttg gttgggcagc    6060
aggggtggga agggggggagg ggacggtacc aacgagacgc acgtgtcaag catgcacctg    6120
tggcaagcag cctgtcagag gatgttatta cacctgccaa gtggtgtatc cagaaacaaa    6180
agaggcccag tttccaattc ttcagctgtg tgcaatgttt agagaatccc tataccagga    6240
aataatcctg cctaaatggg tcagtcttca caaggcggga atgtagactg atgcactgac    6300
tataacctaa gaatgatctg agtgttaaag atgcagattc ctctgtccca ccccaaaact    6360
aatcagctgt attttttaaca aacaccccaa aggagtctta gatttgaatg ccactgattg    6420
tcttcagtgg aggaggaaga tcccgctgtg aaggccgtag caccctcacg cccacgtcag    6480
ccaataggac tatccctgac ctgatgagag aaggaaaact gctaggcaaa gcaacatta    6540 gaaacaatag tatgagaaaa tagagcctga gatgagggaa agaagaaaca atagtatcag    6600
acaatagacc agtaggtgcc aaagtgggta gttcaaaccc caggcactat gggagatcac    6660
tcatggcaaa gagaagttcc tgtgggaggg gagtattatc cacagtaaat attcgttgag    6720
gcttattatg tggtcacgca gggttaggca agcagtcact gaaaggagcc caaattctgg    6780
agttagactt gcttttcaaat ttgagttctg cctcctattc atggctttgg acaaattaat    6840
ctctataaat gaagatgtta aaattaacac cttctgggct tgtgaaaata aaatgaaagc    6900
atgtatataa aacagaacag tgcttagaac acagtaaatt tcagtgtact cgattataaa    6960
aagccaaaag gcccatttct gggggctgag ggttggccac aaaatctggg cagagaagac    7020
```

```
agatgattaa aaggtaggaa acaaagcaat gtgtattaaa tgagttggac tgagaggcca    7080
agacaggtgg ggagggaggg ggacctagtg aagacccaga agtgggtacc atgccttctg    7140
ggaacaataa gcacaaatcc aaatcaaggc aagagggat ataagcttga accctcaaac     7200
accaagccaa atagtctttg aagaatccct gaaatgctgg gtgaagcagt ttgaatgccc    7260
tatgaaaagc aggtcttaat accaaaaatt aggccaggtg cagtggctca tgcctgtaat    7320
accaacactg ggaggccgag gtgggcagat cacttgagct caggagtttg agaccaacct    7380
gggcaacatg gtgaaacctc gtctctacaa aaaaaaaaa aaagaaaaa aaaattagac      7440
aagtgtggtg gtgtgcacct gtagttccag ctacttggga ggctaaagtg ggaggattgc    7500
cctgcacctg ggaggtcgag gctgcagtgg cctgtgatca taccaatgca ctcagcctga    7560
gcgacagagc aagaccctgt ctcaaaaaag aaaaagaaa gaaaagtagg cctcagactt     7620
tcctgaacct cctccccact gcatcttata ctgggcaaag ctggcaataa tttgtaaaat    7680
aatgatttag gcagcaaggc ataggacgaa ttgctacttg aaagatgaa aagcaagaat     7740
agcagttggc aaactacctc aaggaagaag caggttctaa tataggctgg caagtggtat    7800
caataggaat gcaaggaaag gaactaggca atggcagaga tattgaaact gggtgtggag    7860
gccagaggaa gatgtaaaaa gggggagcaa tgaattcagg cacggtgata gaagtatatg    7920
cagacagaaa tagtcaacaa gtagctagaa ataagactga ggtgaagtca aagctgcata    7980
ggaacagagg taaatgaggg aagggacta gagatggagt tttggggtat ttcgttgggt     8040
tgaaggacct agttttctta ttcactgggt accctagtac ctgtcaccat acctgacaca    8100
tagcagggac tcagtaaata tttgtaaagt gtatatggaa gaggcagcca gtgaggacag    8160
aaggaatagt tgaagcagca ggagagaaat caggagagtg cccttgagag aagtcaagga    8220
ggaacagtcc agggctgacg gagtgacaat aatgctgtaa ggaggttatt taacagattt    8280
gattgagcag ctactgtggg caaagtactc tgaactacat cgtgctgttg tggtgcgctt    8340
ggaagatgtc tagtagctga ttatagttaa gagtatgatc tgtggtaaag ggaggaagag    8400
gaggtgaagg aagccgtaaa attacttaag gctaaattat caccagcatt gaatgccgta    8460
acaaaggctt tgagcgtcat actgaaaatc ggtggtctcc aaacatttc ttaaagtata     8520
ggccttccat agcaagtctt tagcatatgt ctttataact tgtttattta taaattatat    8580
atgtatgcta atccttatgc ttgtttataa gctatatata agcagaatcc taaatattat    8640
atacattata aacacaaaag ttaaatatta ccagtttaaa aacaaatgaa atctgaatca    8700
aagcaatttt ttttaattga aatctaaact atttatttac ttatttattt ttgagacaaa    8760
gtctctattg cccagactgg agtgcaatgg catagtcttg gctcactgca acctctgcct    8820
cctggcttcg aacaattctc ctgcctcagc ctcccaagta gctgagatta caggtgccca    8880
ccattacacc cagctaattt ttgtattttt agtagagaca cggtttcacc atgttggcca    8940
ggctggtctt gaactcccaa cctcaggtga tcaacccacc ttggcctccc aaagtgctgg    9000
gattagaggt gtgagccacc acacccggcc taaattattt aatttatttt gagacaaggt    9060
ctaactctgt catccatgtt ggagtgcagt ggcacagtca cggctcactg caacctcaac    9120
ctccccgact cagctgatcc tcccacctca gcctcctggg tagctgggac tacaggcatg    9180
tgccaacacg cccggctaat ttttgtattt ttttgtagaa acagggcctc actatttgcc    9240
caggctggtc tcaaactcct gggctcaagc aatccgccct tcttagcctc ccaaagtgct    9300
ggaattacac atgtgagcca ccgccccgg ccaaaatcta atcttaata gttttttgttg     9360
ttgttgttgt tgttgttgtt gttgttgttg ttgttgttgt tgagactgag tctcgctctg    9420
```

```
tctcccagcc tgtagtgcag tggcatgata gctcactgca acctctgcct cctgggttca    9480
agcgattctc ctgcctcagc ctcttgagta gctgtgatta caggtgcgca ccaccacgcc    9540
tggctaattt tttgtatttt tagtagagat ggggtttcac cacgttggcc aggctggtct    9600
caaacttctg acctcaggtg atccacctgt ctcggcctcc caaagtgctg ggattacaga    9660
cgtgaaccac cacgcccagc caatcttaat agtttttta tcctttctcc ccagtccttt     9720
cagacaccaa aggaattctg ggaagacaa tttcactgga atgagtatgt ttggggagca     9780
gaatttcaga agagtgatgc ggggaaacca gtttgcagga ggagaggagg gcatagtggg   9840
tgaggaaatg gaggcaaggg tgtccactgc tcaaatactt gatggtgcaa aggaggaaaa   9900
gaaataagtc aaaaagttgg ccgggcgctg tggctcacgc ctgtaatccc agcactttgg   9960
aaggcggagg caggcggatc atgaggtcag gagatcgtag accatcctgg ctaacacggt   10020 gagacccgt ctctactaaa aatacaaaaa attagctggg cgctgtggcg ggcccctgta    10080
gtcccagcta cttgggaggc tgaggcagga agggcgtg aacccgggag gcggagcttg     10140
cagtgagccg agatagcgcc actgcagtcc ggcctgggca aaagagcgag actccgtctc   10200
aaaaaaaaaa aaaaaaatt aagtcaaaaa gttgagcagt tgagcgggaa aatattgttt    10260
tgttttattg tttttgaaag gaacctcact aacaggagat aataaggaac caatagtaag   10320
ctgaacgtta aagatacagg taagagaaga ctatggctct agccatagtc tgttggactg   10380
ctggaattta actctgtccc ctcttccata gggacttgca tctcagaatt cctctccttt   10440
gtcctttctc tttggggcag cttgagcatg tcctgtcctc ttctggatgg aggactggaa   10500
attgatgagg cccctatgca gttgctgatt cttgtcactg ccctgttcct gcctccagct   10560
gttaggccat agccactgcc atagttggga agagctggaa caggttgaca aacacctgtt    10620
gtgtcatagc catagtattt gtatcatgtg tttagaaggc tggtctcccc cggtcccaa    10680 tcccctccct tgccccactc aaatatagac acacacacat gcacacacgt acatgaccac   10740
cacgagctct cctccagcca gtagtttgga cagtgaatca ccactcttgg gttcaccct    10800 agagcagcta cttactccct gtgacctgaa aagtaagcag tatttaccaa gagcttcagg   10860
tttgtgagtt gaacccacct caccccttgc tactcttggc taccccaagt ggtgaaccac   10920
atactgtcca gcatccctgg gcctgccacc tcctgccagt gagacagcgc ccagtcagac   10980
atacaaatag gcagtcacag caagagaagc cttccactac caagtcctct gctcacctca   11040
cctagcctgg ccacctgagg ggccttccta aaattcagat ctaaacacat gtgtcccccg   11100
atcaaaggcc ttcaagtccc acctcacccc catggtctat gaaagaaaac ccaaactgtt    11160
cagcacagtt ttccaggccc ttgaacatct gttccccacc agcctcacca gtgcaaggcc   11220
taacaagtct cctgccacta ccttcagcct tccatacaaa ataactggca gtcccccaa    11280 agtcattctg tgtgggcatc cttgcctgtg ggacatcatt gtttcttcac tcttctgatc   11340
ctggctgtgc tcttcttcct tacctccctg gggttctggg gttcctgttc tttgagcatc   11400
aacattctgc aaggaaaatc acactgtgct gagaattggg agacctgagt tctagtcctg   11460
gctctggcat cagctcactg ggagagcttg acaaattcc tccctctttc tgggtcttag    11520
tcctccatct gagaagacgg gataagttca gacccatgat tctctggctg ccttggaaaa   11580
taaggcttcc tttgtgggca cccatcccag cttctgcctc ctgccacagg gctgacttct   11640
gacacacagg cctttctgtaa atactctaac agagaaaagc ggaagttgac aaaaaactgg  11700
cagcaacaag ccccagcttg gcattttggg taactattca taggcacttg attgaggagg   11760
```

```
aagtagaaag gaagaactgc agtgagattt gctcggaaca tccctgatct attattgtgc  11820
ctgtcgcttt agactttttc ttacttattt attttattta tttatttta agacggggtc   11880
attcactctg tggcctgggc tggaggacaa tggtatgatc acagcccact gcagcctcaa  11940
actcctgggc tcaaccaatc ctcctgcttc agcctcccaa gtagctggga ttataggcta  12000
tcactttaga ctttgagggg aagatgtaag gacagtagag gggaagaaga cagacactcc  12060
agagaaggtt acacacgagg agaagttaat ccctaaaagc aggcccaagc cctgccccct  12120
cctttcccct gccctcctgc cctcaaagca agggctttgg gagagggctt ggctgccctg  12180
attttcccct ataccttgtg tccactgaag tagggagata gtaactgtgc tgccctcctt  12240
ctcctcccag gggtggattg tgcctccaaa catctgccac tgggctgagt gagccttggt  12300
agggagctga gaccaccgtc cttcagcgtc agcaaactca tatcatgtca gctagccact  12360
cgaatggtgc aagatgccaa actggttatt ccctgagcag ttcagtcaca gtaaggtgac  12420
tctaaatgga cggtctgcac attttttcatc ttgtctgtaa tgactttat tgctcaattg   12480
ttcttttta ttttttatt tttatttta ttttattatt tatttattta aattttatt     12540
tatttattta tttatttga ggcagggtgt caccgtatcg cccaggctgg agtgcagtgg   12600
tgtgatctag gctcactgta acctccgcct cctaggttta agcaatcctc ccacctcagc   12660
ctcccaagta gttgggacta cagtcataag gcaccacact ggctatttt ttgtatttt    12720
agtagagaca gggtttacc gtgttgccca gggtggtctc gaactcctcc aagcgatcca    12780
cctgcctcag cctcccaaag tgctaggatt acaggtgtaa gccggcgtgc ccagcctgcc   12840
caattttca gtcaagaaaa catacatgaa gcctggcacg gtggctcaca cctatactcc    12900
caacactttg gaaggccaag gcaggaggat cagttgaggc caggagttcg agaccagtct   12960
gggcaacata gtgaaacctt gtctctatta tgtttaaaaa aataaaaat gtaaaggcca    13020
ggaacggtgg tttatgcctg taatcccagc actttgggag gccaaggcga gatgatcagt   13080
tgaggccacg agttcgagac cagtctgggc aacatagtga gacctcatct ctattatatt   13140
aaaaaaaata gggaccaggc atggtggctc atgcctgtaa tctcagcact ttgggaggcc   13200
gaggctggcg gatcacgtgg tcaggaaatc aagaccatcc tggctaatac ggtgaaaccc   13260
tgtctctact aaaaatacaa aaattagcc gggcgtggtg gctggtgcct gtagtcccag    13320
ctactcggga ggctgaggca ggagaatggc gtgaacccgt gaggcggagc ttgcagtgag   13380
ccaagattgc ggcactgcac tccagcctgg gctacagagc gagactccgt ctcaaaaaaa   13440
aaaaaaaaaa agtacaaaaa attagccggg ggtggggacg ggcgcctgta gtcccagcta   13500
ctccggaggc tgaggcagga gaatggcctg aacccgggag gcggagcttg catcgcgcca   13560
cggcactcca gcctgggcga tgaagcgaga ctccgcctca ataaataaat aaataaataa   13620
atacataaat aaataaataa ataaataaaa atttaaaggc cagaaatggt ggttcatgcc   13680
tgtaattcca gcactttggg aagccaaggc tcgggaagat tgcttgagcc catgagtttg   13740
agactagcct gggcaacatg gcaaaacgct gtctctacaa aaatacaaa aaaaaaaaa    13800
aaaaaatagc tggtcttggt agtgcacacc tatggtccca gctacttgga aggctgaggt   13860
gggaggatca cctgagtccc ggaggtccag gctgtagtga tccgtgacca tgtcactgca   13920
ctccagcctg ggtgacagag accctgtctc aaaaaaaaaa aaaaaaaaaa gaaagcaata   13980
tatgtctta tagagcatac atgaaatatct aacacatata aaatcctta ttgctattaa    14040
catcctctat tctttgttgt atgcatatat aaatataata cttttcaata tatagagatg   14100
cagtatatat atatatatat atgcgcatat atgtatagag agagagagaa agtgtgtgtg   14160
```

```
tgtgtatata aatatccccc ttttttttta agacagagtc tcgctccatc acccaggctg  14220
gagtgtagtg gtgccatctc ggctcactcc aatctccatc tcctgggttc aggtgattct  14280
cctgcctcag cctcctgagt agctgggatt acaggtgccc accacaccgc ctggctaatt  14340
tttgtatttt tagaagagat agggtttcac catgttggtc aggctggtct caaactcctg  14400
acctcaagtg atctgcccac ctcgacctcc caaagtgctg ggttacagg cgtgagccac  14460 tgcgcccagc caaattcacc atttaaagt gtacaattta atggttttta gtatattcac  14520
aagattgtgt aatcatcatc actctctcat gccagtcatt ttcatcaccc caaaaagtaa  14580
cctttgcacc tattaccagt catttccatc ctccctcacc tccagtcccc accccccgagt  14640 ccctggcaag cactaatcta ctttctggct ctatggattt gtttattctg cacatttcat  14700
ataaatagaa ttatataata tgtggccttt tgcatctgac tgctttcatt taatataagt  14760
tttcaaggtt tgtccatgtt gtagcatgta tcagtaccta ttttcttctt tttttttttt  14820
gagacggagt ctcgctctgt caccaaggct ggagtgcagt ggcacgatct cagctcactg  14880
caacctctgc ctcccaggtt cacaccattc tcctgcctca gcctcctgag tagctgggac  14940
tacaggtgcc agccaccatg gctggcctaa tgttttgtat ttatttattt ttttagtaga  15000
gatggggttt caccgtgtta accaggatcg tctcgatctc ctgacctcgt gatccgcccg  15060
cctcggcctc ccaaagtgct gggattacag gcgtgagcca ccgcacccag ccttcttttc  15120
ttttaatggt tgaatatatt catattcaag tgtgatatgg tcatacaata tatggtatca  15180
catgaccata tgcattttta tttagccatt cattagttgc tggacatttg tattgtttcc  15240
acttcctgac tattatgaat aatgctatgg tgaacattga acatttgtgt acaagttttg  15300
tatggacata tgttttcatt tctttggagt atatacctat cagtggaatt actgggttat  15360
gtggtaactc tatgtttaac ttttgagga ctgccaaatt ttttcacag tggctctatc  15420 attttacatt cccaccagca gtatatgagg gttctaatat ttctacattc ttgccaacac  15480
ttttttttct ttttttggga tagggtctca ctcctgttgc tcaggctgga gtgcagtggt  15540
gcgacctctg ctcactgcag cctcaacttc ccgagctcag gtgatcctcc cacctcagcc  15600
tcccaagtag ctgagactac aggcacgcgg caccacacct ggctaatttt ttgtatttt  15660 agtaaagata aggttttgcc acattgccca ggctggtctc aaactatctg cctgcctgcc  15720
ttagtctccc aaagtgctgg gattacaagc ttgagccact gcacctggcc acttttttt  15780 ttttcttttt tttactgtag ccatcctagt gggtgtaaag tgacacctca ttgtggtttt  15840
gacctgcatt tccctaattg agtatctttc catttgctta ttggctgttt atatatcttc  15900
tttggagaaa catttattaa aatcctcccc aacctgggca acatagtgaa aacccatctc  15960
tattaaaaat taaaaaatta aaattaaaa aaatttagcc aggtgccatg gtgtgcgcct  16020
gtggtcccag ctactcggga ggctgaggca ggagaattgc ttgaacccgg gaagtggagg  16080
tttcagtgag ccgagatcac gctatcacaa ttccagcctg ggtgacagag cgagaatcca  16140
tctcaaaaca acaaaataaa ataaaatcct ttgcccattt aaaaaattaa gttgtctttt  16200
tattattgcg ttgtaagagt tctatatata ttctatatac tagaacctta ttagatatat  16260
aatttgtaaa tattttctcc cgttctgtga gttgtcataa ctttcttaat aatgtccttt  16320
gaagcacaaa agttttaat tttgatgaag accaattttt tctttctgtt ttttggttg  16380 tggttgcttg tgcttttatt gtcatatgta agaaaccatt ccctaatcta aggtcacgaa  16440
gatttatact catgttttct tctatgagtt ttatagtgta agaactagaa ctataaaaat  16500
```

```
cttagaagaa acaaaaata taaatcttca tgacctcgga tttaggtctt tgactcattt   16560
tatgttaatt tttgtatatg gtgtaagatt ccagatttgt tctgttgcat atggatatcc   16620
agttgttcca acattgtttg ttgaaaagac tattctttca ttattttata ttttttttcct  16680 atttttttacc ttaataaatt gtgaacattt tcactacaat aaatactaca attttgtgcg   16740
tttttttttt agccatatgt tattttttta acctctctcc tatttaatgc atatttgttt   16800
gtacattttg ctgtctttct ttcttttttct tttctttttt ttttttttttg agacagagtt   16860 tcgctctgtc gcccaggctg gagtgcagtg gcacgatatc agctcagttc aagtgattct   16920
tatgcctcag cctctccggt agctgggggct acaggcaccc gccacagcgc tcaggtaatt   16980 tttgtattttt taggagaaat gaggtttctt catgttggcc aggctggtct ggaactccag   17040
aacagacaac ggaggccggg cgcggtggct cacgcctgta agtaatccca gcattttggg   17100
aggccgagac gggcggatca cttgaggtca gaagttccag accagcctgg ccaacatggt   17160 gaaacccgt ctctcctaaa aatacagaag agtagctggg cgcggtggcg ggtgcctgta    17220
gtcccagcta tcggggaggc tgaggtggga gaatcgcttg aacccggaag gcagaggttg   17280
cagtgagccg agatcgcacc attgcacatc agcctggggg acagagcgag actccatctc   17340
aaaaacaaaa gaacaaaatc aaattattca aaagaggaaa gccttgattt aagggcagct   17400
ccatttccaa ggcttttcat gcacattatc actttgctat agaacagcag ttctcaaact   17460
ttttgatctt atccctttac actcttaaaa attactcagt ttggccgatg tggtggctca   17520
cgcctataat cccagcactt gggaggtca tggaggaagg atcacttgag cccggaagct   17580
catagacaat cctggcctgg gcaacatggc aaagcctctt ctctacaaaa aatacgaaag   17640
ttagccaggt atagtgccta gtgcctgtgg tcacagccac tcgggaggct gaggtgggag   17700
gataacttga gccatgagg ccgcagtgag ccatgatcgc accactgcac tccagcctgg   17760
gcaacagagt gagaccctgt tgcaaaaaaa aaaaattgag attcctaaaa agcatttttg   17820
ttatgtggtt aaccatctca caaaataaag catataaaca ttttaaatgt ttacatatta   17880 attatttac aaataactat aataaaccca ttaaatgcta acataagttg atattttta    17940 ttaaaaataa ctattttcca gccgggcgcg gtggctcacg cctgtaatcc cagcactttg   18000
ggcggccgag gcaggcggat cacctgaggt cgggagttca agaccagcct gaccaacatg   18060
gagaaacctc gtctctacta aaattacaaa attagacggg cgtggtgacg catgcctgta   18120
atcccagctg ctcgggaggc tgaggcagga gaattgcttg aactcggtag gcggaggttg   18180
cagtgagccg agatggcgcc attgcactcc aaccagggca acgagagtaa actccatcta   18240
aaaacaaaaa caaacaaaaa aatttccaaa gcaaaaaaaa cttagtgtga gaaactattt   18300
tgcacactaa gatttacatt tttgaaaatc tccttaatgt ctgacaatag aatacactgt   18360
ctcctgtttg tttctgcctt aatcacgtga tatcacaatc atctaacctc tggaaaatta   18420
cattctgtgc cagtgagcaa acgagagtga aaaaggcaaa caaattttgt tttgttttgt   18480 tttttgaga tggagtcttg ctctgcctcc taggctggag tgctgtggcg cgatctcggc   18540
tcactgcaac ctctgcctcc taggttcaag cgattctacc tcagcctcct gaatagctgg   18600
gactacaggc gcgcaccacc gcacccagtt aattttttttt ttttttttt tttttttttg   18660 gtattttttag taaagacagg gtttcaccag gttggccagg ctggtctcaa actcctgacc   18720
tcaggtgatc cacccacctc aacctcccaa agtgctagga ttacaggcgt gagccaccac   18780
acccagccac atcttagtat tattataaaa atagttccgc cgccatcttt cttcctggca   18840
ggggccgacg cagggaccgg cgcggggtg agagcgcgcg gccggattca ccacaacatg   18900
```

```
gcaactctttt ttataaggaa aatggtgaac cctatgctat atctcagtcg tcacacagtg    18960
aagcctcgag ccctctccac atttctattt ggatcccttc gaggtgcagc ccccgtggct    19020
gtggaacccg gggcagaagt gcgctcactt ctctcacccg gcctcctgcc ccacctgctg    19080
cccgcgctgg ggttcaaaaa caagactgtc cttaagaagc gctgcaagga ctgttacctg    19140
gtgaagaggc ggggtcagtg gtacgtctac tgtaaaaccc atccgaggca caagcagaga    19200
cagatgtaga ccctttccct ccagagtcac gcacatactc gtcatcgcgt ctcttgggag    19260
aatggttgta tcttatggaa ggaattatca catcaaggag tcaggggaaa gtgactggaa    19320
gcaaacgccc taaaagttac ccatcacgtt tcagtgtaaa tgagtaacta tagaagacat    19380
tgcattatct tatttccaaa atgttccaat taaaaaacat tttcctatta aaaaaagaa    19440 aatagttttg acctctcaga cccctgaaag gatctgaggg cgccctaggg ccccccacca    19500
ctctttgaga aatgctactc tacagaaaga ttttaccaaa gtgtactgtc atcactgtgc    19560 cccttttttct gtaccttcac caacattggg catcatcttg cttttttttt tagcctttgc    19620
tgatttgtta aacaaaaagc aggatctctt cgtgatttta atttgcattc tgaaaggttc    19680 atgattttttg aatttatatt ttttctttta taaaccacct ctttatatcc tttgcatgtt    19740
ttctttctgg gatgggcatt ttgtcttatt tattataaga gcactgttgt tgttttttttt    19800 tctggctcta tcccaggctg gagtgcagtg gcgcgatctt ggctcacttc aacctccgcc    19860
tcccaggttc aaacgattct cctgcgtcag cctccccagt agctgggaca ggcgccggcc    19920
accacgtccg gctaattttt gtagctcacc actgagaaca aggtgacaaa catggagttt    19980
attgtacctg tgtcagatca ggattagaag actggagacc tgtgagtccc ctgttcctca    20040
caggggagga agtggcccat ctgggtgggc ttcttggcct caagccaatg ctgtgatccc    20100 cagtagggg ctgtctcact gtaccctaag gtggggccag tttataccca aaattttaac    20160
aagggatttg ggtatccaag atgttaaagc tttgttaggg gaaaataggc taagccctca    20220
tgacccattt cttcagaaaa gatgttttag aataagaaaa ggaaactaga atttaacagt    20280
ctgacaggat attcttgcta accacaaatt tacagaatta tagtttagcc atagaggtct    20340 tctccttttct caacttttgc agatctctcc agtaaatgcc tctactgctt gactgctttc    20400
tgaaatagga aaccattata aagtagaatt tgtgtccaaa gtgactaggc ccagttagct    20460 gggatttttct ccatttcagt gttgtttccc ccatccttaa gcacactgga gattttttctc    20520 tgccagtttg gcaggtgaaa aaatggtat agcattgttt taattttcat tcttggatt    20580 actggtgagt aaaaagaaat gttatgtatc tctcagctgt ttgcatttct cctttagtga    20640
attgcctatt cgtatctttt tcaccttttt ctattggagt gttcgtattt ttcttaatga    20700
ttgaggatct cgttatacag taaaatatta acgcttcgac atataatgca tttttttaat    20760
gtgtcagttt tcttttaact tctgctctgc agaagtgtct aatgattaag tagctaaatc    20820
tatcaatctt taactttatg gtttctgtct ttaaagtcag gtttggaaag tccttcccta    20880
acttcaataa ttgttttttca aaatttcctc ttttttcctc ctagtatttt atatttccat    20940
tttgttatac tatttaaatc taaaccatct gacatttact tgggtatata ttatatatga    21000
tgggaagagc tagtaatttt tttttcccccaa attgcaggct cgttgtccaa tgatatttat    21060
tgaataatcc aagaagggaa aatatgtggt ccgagtgaat ctgtctcccc ttcccgggcc    21120
cccggaagac atttctaatc aaatgcagaa ctcctggcta aactcagact aggcctcaca    21180
gcccgattag aactgcaagc agctacctcc aacctacgag atttgtcatc aagatgaaac    21240
```

```
attttgtcat tccctaagta atctatcctt tttcctattg atgtgttact gacatacctg    21300
tcttttcttt ctgtgttact gacatacctg tcttttcttt ctgtgttact gacatacctg    21360
tcttttcttt ctgtgttact gacatacctg tcttttcctg tgccagctcc acactgtttg    21420
gttatcactt ccaagtacta aatggtaatg actggtagca ccagtcttat accatttttc    21480
aacattttaa aattatttcc tcaaacaaaa gtcagactca gaatatgtca gaaaatattt    21540
aaaaataaaa aataaaatta ttttttctga tttaaacttt tgattttat tacatcaaag     21600
tatttccaaa ataaattaaa atttaaaatt catattagat tttccaatct aggtatacat    21660
agtgtttctt tccatttttta aagattccct ttatttctct gaatgttttt ttttcataat   21720
gtctttcaca ttactggtcg actttattcc tgcatatttc atatttgtgg ttgctatcag    21780
aagtggaagt tttggcaggg cgcagtgact cacgcctgta atcccagcac tttgggaggc    21840
cgaggtgggg ggatcactta aggtcaggag ttcgagacta gcctggccaa catggtgaaa    21900
ccctgtctct actaaaaata caaaattag cctggcttgg agctgggcat ctctaatccc     21960
agctgctagg aaagctgagg taggagaacc tcttaaaccc aggaggggga ggttgcagtg    22020
agccaagatc acaccactcc actccatcct gggtgacgga gtgagactgt ctgaaaacaa    22080
taaataaata aattttaaaa aataaaagag taaaagaagt ggaagttttt taaatataac    22140
atctcatttc tcactctgtc acccaggctg gagtgcagtg gcatgatctc agctcactgc    22200
aacctctgcc tccaggttc aaacgattct cctgcctcag cctcccgagt agctgggatt     22260
acagggcgt gccaccatgc caggctaatt tttgttgttg tttttgtttt ggttttttga     22320
gatggagttt cgctcttgtt gcccaggctg gagtgcagtg gcgcgatctc agctcactgc    22380
aacctctgcc tccaggttc aagcaattct cctgcctcag cctcgcgagt agctgggatt     22440
ataggcatgc actaccacgc ccttctaatt ttgtatttt agtagagacg gggtttctcc     22500
atgttggtca ggctggtctc gaacttccaa cctcaggtga tccgcccacc tcagcctccc    22560
atagtgctgg gattacaggc gtaagccacc atgcctggcc ttaatttttg tattttagt    22620
agaggtgggg tttaccatg ttggccagac tgatcttgaa ctcctgacct caagtgatcc     22680
tcccaccttg gcctcccaaa gtgttgggat tacaggcggg agccactgtg cctggctttg   22740
tttcttatta ctagaatgta agcttcatga gagcagagtc cacatatctt tgttcataa     22800
cagccataga gctggccggg catggaggct cacacctgta atcccagcac tttgaaaggc    22860
caaggtgggc ggatcacgag gtcaggagat cgagaccatc ctggccaaca tggtgaaact   22920
ccatctctac taaaaataca aaaattagac aggtgtggca gcacatgcct gtaatcccag    22980
ttacttggga ggctgaggca ggagaatcac ttgaacccag gaggcagagg ttgcagtgag    23040
ttgagatcga gccactgtac tccagcctgg agacagacct agactccgtc tcagaaaaaa    23100
aaaaaaaaaa tagccataga gcttaagaaa cagtgcctcc acattgtagt ttctcaataa    23160
aagtttttaa atgaatgaag gaataatggc acaaagcaat gctattattt tagtgttatt    23220
aatttgtaac aggcgccggg cgcagggggct cactcatgcc tgtaatccca gcatttgggg  23280
aggccaaggt gggtggatca cctgcactca ggagtttgag accagcctgg ccaacatggt    23340
gaaacctcgt ctctactaaa aatacaaaaa ttagccaggc gtggtggcgt gtgcctgtaa    23400
tcccagctac tcgggagact gaggcaggag aattgcttga acccaggagg tggaggttgc    23460
agtgagccga gattgcatca ttgtactcca gcgtgggcga cagagcaaga ctctgtcccc    23520
ctcaaaagaa aaaagaaag agagagagag aagaaagaaa gaaagagag agaaagaagg      23580
agagaaagaa ggagagagaa ggaaagaaag aaagaaagaa ggaaagaaaa gaaagaaaga    23640
```

```
aagaaagaaa aagaaaatga gcaaaggaag gatttggtgg caaggaggtc attggtgatc    23700
ttagtgagtg tggggagtat ctttgttggg ctggggcgaa agccgcctgt gatggttgag    23760
gagaggtgac aatatgcaga ctgcctctgg gctactcctt caagaagctt agcagggcca    23820
ggcggtggtt cacacccaca atcccggcac tctgggaagc caaggcatga ggatcactgg    23880
agcccaggag ttcaagacca gtgtaggcaa catgctgaaa tcctgtctct tacaaaaaat    23940
acaaaaatta gctgagtgag gctggtgcg gtggctcatg cctgtaatct cagcattttg     24000
ggaggccgag acaggcggat cacttgaggt caagagttca aaaccagcct gaccaacaca    24060
gtaaaaatcc atctctacta aaatacaaaa atacaaaaa ttattgcacc actgcactcc     24120
atcctgggtg aaagagtgag actccatctc aaaaaaaaaa aagaaaaga aagaaaaga     24180 aatgaaatta gctcagtgtg gtggctggcg cctgtagtcc cagctactcc aggggctgag    24240
gtggaaggat tgctttagcc tgggagttcg aggctgcagt gaaccgtgat tgcgccactg    24300
ccctccagcc tgggcgacag agcgagacct tgtctcaaaa aaaaaaaaa agaagaagaa    24360 gaagccacta agctaagagg taggtactaa gttgaagggg agacagaatg gagataagga    24420
tttgggtttt ttaggtggta gtgacacaag gatgttcata agctgaagaa gaaaagacca    24480
acaaacagac taaacatttg agaatgagac agaggaaaaa gcatacggag caaagcacag    24540
aggtcacagg gtgtgtggcc agcagtggtg gggacgctgc tagctttctc tgaagtggga    24600 gaaaggagt gttcctttcc ctgcactttc tcaaccacac tgactgagga aggacagagg     24660
gggcccagag agcagtgggg gtgtccaatc actgttcttg ggcctggaaa ctgttggggc    24720
tgtggacccc agagtactga aggactgctg gacggagcgt atggctccat ctgagcctgt    24780
aaatcataaa tctacctggt caaagagtaa aggcctcaaa ggttctgagt taattggtct    24840 ggttttttgac ctgagcatca gaaatttttt aagctccctg agtgagtcta acatgcagcc    24900
atggttgaga accactgggg ttaagaagtg aattgagacg tatggagact taaatctcca    24960
accctgggtg ggaggacaag gagaggctct gccgccctgg ctggaatagt ggggccctgt    25020
ttgggttgtg gacgtccctt cagtcacagg aggatgaatt cctgccttgt tcctttggtc    25080
ggatctgaat tcttccccaa cctcccgccc taactgatag catacagggc ttcccagaca    25140
gagaccatca gcccctaggg tggcagagaa aggccaggtt caggaatgtg acattaatta    25200
tgacaaacaa tatgttctcc cacttaagaa ctaagcctgg ttggctgcgc atgtgcgcgc    25260
gcgtgcttgt gtgtgggtgt gtggtggggt atgtgtgtgt ccggggctgc cgattcaact    25320 gaaaacaaa agcggctctg agtctgaagc taaggtttaa caagtgacca agatgactca     25380
tgctgcttgg ctgcaaaggc cacagggctg ccaccccag cggggcgggg cctgggtggg     25440
aagagtcaca ggtacagagg ctcctgtgac attcacactc tgcccctgca tcggctgcct    25500
ttggggccaa atacttttgt gaaaattaag acagaaggcc gggtgcggtg gttcacgcgt    25560
gtaatcccag cacttttgga ggccgaggca ggcggatcac gaggtcaaga gatggagacc    25620
atcctggccc acatggtgaa accctgtttc tactaaaaat acaaaaatag gcagggcgtg    25680
gtggctcacg cttgtaatcc cagcactttg gaggctgag gcgggcagat cacgagctca     25740
ggagatcgaa atcatcctgg ctaatacggt gaaaccccgt ctctactaaa aatacaaaaa    25800
attagccggg tgtggtggca cgtgcctgta gtctcagcta ctcaggaggc tgaggcagga    25860
gaattgcttg aacccaggag gtggaggttg cagtgagcca agactgcgcc acctcactcc    25920
agcctggcaa cagagtgaga ctccatctca aaaaaaaaac aaaacaaaa acaaaaagta    25980
```

| | | | | |
|---|---|---|---|---|
| actgggtgtg | gtggcccgca | cctatagtcc | cagctactcg | ggaggctgag gcaggagaat 26040 |
| cacttgaacc | caggaggcgg | aggttgcagt | gagccgagat | cgtgccactg tactccagac 26100 |
| tggcgacaga | gccagactcc | ctctcaaaaa | aacaaaaaa | caaaaagaa ccagaaaatg 26160 |
| taactttctt | cctatggtca | taaatctggt | gtaagcaggc | aagtcaaagc gatgttgaag 26220 |
| ccaatggatc | ttgcaaaggc | atggcaatgt | tgcacaagg | atgggatata gtaagttaaa 26280 |
| atacattggc | tttttccaaa | cgggctcaaa | ctggaagaga | aggtctaagc agagcatgtg 26340 |
| ctgctgtcag | gagggttcct | cagcaggaga | cagggcaccc | caggggtgca tatttaataa 26400 |
| aaacttacaa | tatgcaggtt | tgggacatg | aaggaaacat | ttaacctgtc ctgtccaaca 26460 |
| cggcagccac | ttgtcacatg | cggcagttga | atacttggaa | tatggctagt ctgaataaag 26520 |
| atgtaaaaca | tacgccggat | tttagactta | gtacaggggt | gggaaagagt ttaaaatagc 26580 |
| tcagtatagg | ccgggcacag | tggttcacac | ctgtaatccc | agcactttgg gaggccaagg 26640 |
| tgggcagatc | acctgcagtc | aggagtttga | ccagcctg | gccaacatgg caaaaccctg 26700 |
| tctctaataa | aattacaaaa | attagctggg | aatggttgcg | gcgcctgta cttccagaca 26760 |
| ctcgggaggc | tgaggcagga | gaattgcttg | aacctgggag | gaagaggttg cagtgagctg 26820 |
| agatcacacc | actgcactcc | agcctgggag | acatagagac | tccgtctcaa aaaaaaaaa 26880 |
| aaacctctct | ctccatgtat | atatctgtgt | gtgtgtgtgt | gtgtgtgtgt gtgtgtattt 26940 |
| tttgtttgtt | ttgttttcac | ggctcactgc | agcctcaaac | ctctgggctc aagtgttcct 27000 |
| cctgcctcag | cctcctgagc | agctgggact | acaggcgctc | accaccatgc caagctaacc 27060 |
| ttttactttt | ttgtagagat | aggttcttgc | tattatgtcc | aggctggtct cgagctcctg 27120 |
| ggctaaggtg | atcctcctgc | cttggcctcc | caaagtgctg | ggattaataa accaccatac 27180 |
| ctggccaaac | tcaataattt | attaatactt | taaaaatact | gactacgagc tgggcacagt 27240 |
| ggctcatgcc | tgtaatccca | gcacactttg | agaggctgag | gaaggcagat cacttgaggt 27300 |
| caggagttca | agaccagcct | ggacaacatg | gcaaaacccc | gtctctacta aaaatacaaa 27360 |
| aattagctgg | gcatagtggc | acacaccttt | aatcccagct | actcgggagg ctgaggcagg 27420 |
| agaatcactt | gaacctggga | ggcaatggtt | gcagtgagcc | aagatcccgc cactgcactc 27480 |
| cagcctgggc | aacagagcga | gactatttct | caaacaaaac | aaacaactct tatcacccag 27540 |
| gctggaatgc | attgacagaa | tcctagctca | ctgcagcctc | taattcctgg gcccaagtga 27600 |
| tcctcccgct | ttagcctcct | gtgtagccac | cccaccagcc | ttaaatgttt tttcaacctg 27660 |
| atagaaagat | atagcaatct | gtctgctctc | tttcctagtc | ttccttttt ttttgtttt 27720 |
| tttttacaaa | gattgctaaa | catttatgac | atgctggtag | agtaagagat acaggaaatg 27780 |
| ggcggggcgc | ggtggcttac | gcctgtaatc | ccagcacttt | gggaggccaa ggcgggcgga 27840 |
| tcacctgaga | ttgggagttc | gagaccagcc | tgaccaacat | ggaaaaaccc tgtctctact 27900 |
| aaaaatacaa | aattagccag | gcatggtggc | acatgccagt | aatcccagct actcgggagg 27960 |
| ctgaggcagg | agaattgctt | gaaccgtgga | ggcagaggtt | gccaagatca tgccattgca 28020 |
| ctccagtctg | ggcaacaaga | gcaaaactcc | atcccaaaaa | agaataata ataattcttt 28080 |
| ctaaagaagg | ggtctcgcta | tgttgctcag | gctgaggcgc | agtgactgtt cacagatgtg 28140 |
| atcataacac | actacaacct | caaactcctg | gcctcaaggg | attctctcgg ctcagcctcc 28200 |
| ggagtagcag | ggaccacagg | catgcgccac | ggcacccagt | gtggcacatt ttaaaaaatg 28260 |
| cagccactta | agggcacttt | ctgttgtttt | atttatcttt | caagttttac ttatttataa 28320 |
| atctatgcac | acatacacat | gtactattgg | atgagagcag | caggaggctg tggaaaggat 28380 |

```
acttggcata aagccaagag cacttgtctc caggtctgat ctcccacttc ctggggctca    28440
atttccccat tcataaaatg ggtgggttgg cctagatagg cctaaggact cttccagctt    28500
agatattgca ggattctaga ttgaagtcaa actgttcctt agattttgtg tctgatccca    28560
cagccagaga gcagggctgg tttccttgtt aatgcgatcc agtgctgtca gccatgagag    28620
acttcacctt tggaacagaa atttccatct gcatcctctc tgcagatcat gcctatccct    28680
cctccccact gacacccccc ctcatgtaaa tcagcctggg gaatcagatc ttggagaaac    28740
ttcgatctct ttatctggaa ggcacaaaga tagcattgca aagcctgctg ctggtgtgga    28800
ggtggtgttc aggaatgctt cacatttttc tagcaagttt cattcctagt agtataatct    28860
tgaggagagg cctttcccca gggaggcttt ggggaaacta gcaatggaat gagggaaaga    28920
acatggactg ggtgggagag agccttcttt agaaggaaat actggcaaaa tccgtattg    28980 caaagttttg aaaaaatcca tcctgccggg cacggtggct cacgcctgta atcccagcac    29040
tttgggaggc cgaggcgggc ggatcacaag gtcaggagat cgagaccatc ctggctaacc    29100
tggtgaaacc ccgtctctac taaaaataca aaaaaatta gccgggcgtc gtggtgggcg    29160
cctatagtcc cagctactcg ggaggctgag gcaggagaat ggcgtgaacc cgggaggtgg    29220
agcttgcagt gagccgagat caagccactg cactccagcc tgggtgacag agtgagactc    29280
cgtctcaaaa aaaaaaaaaa aaaaaagaa aaatccatc ctattgcatt tgcttagaaa    29340
gaacctgggg ctgggcagtc ggcctggctc tgtcactgtg tgattttaaa agacatttaa    29400
tgtttccaag ctactgagtg caacaggttt ctcactgagc ttgattttgc accctccag    29460 cccaccctct atctacaatg ctgccagcac tgactctaaa atgcacatga ctccacctcc    29520
actcccaccc cactgactcc attacctgta gcaaaaaata aagaaaatc taaactcttc    29580 tctatgacat ttgaagcctt taaaatctgg tcccaggcta catttttaat ctcatctcat    29640
actctccagc tcactgagcc ccttttcccta ttgtcctgag tccgtatctg cctctggaca    29700
gccatgagct ccactgggaa ggacagtggc ttggccaccc cagctgtgtt cttcccccag    29760 tacccttttcc agttcctggc acagaggctc agtaaaggtt tgatgcctga ataaccaact    29820
aaatgggcaa tcatgtaaat caaggaaggc ccatggactg gacaactcct aaattccctt    29880
ccagcactaa cttctgagta atgttcccca gggcagagct caaaactgct taggacttga    29940
cctagttcat actgttactg cagtttgaaa aacagagaca ggtggtctga caaagggttt    30000
aaaagttttt tattcatatg acaattttgc atacagcaga aaaattaaaa tacaatgcaa    30060
tttaaatatt taaaattgct ttaaaacaag atcatcctat ggttacacaa caatgtgaat    30120
gtgcttaatg ccatgtacac ttagatggct gagatggtaa actttatgtt atgtgtattt    30180
cactacaatt gaaaaaaaac aagactgcca ggcacgatgt ctcacgccta taatcccagc    30240
attttgggaa gccaagacag gaagatcact tgaggccaag aattcaagac cagcctgggc    30300
aacaacagca aaaaatctt acaattagtt agccatggtg gtgcatgcct gtggtcccag    30360
ctactcggga ggctgaggca ggaagatcgc ttgaacccag gaggttgagg ctgcagtgag    30420
tagcgttcgt gccactgcac cccagccagg gcgacagagt gagaccctgt ctcaaaaaaa    30480
caaacaaaaa actcaagact ttcctggatg tgtagttgct accaccatgc ccctggccct    30540
tctgtagagg gggcttttaa agagataaaa caaacaaaaa tctcaagtag gagaagtatt    30600
gaaacctttg attcctagag aagatggaga aagaaaggat tcctggttta acaaaatgtt    30660
aaatgtagtg aaatttaaag taccctaata tcaccaatgc ccagaagcct cagccatctg    30720
```

```
tcacactgag ggctaggaaa tgagcaaaaa tgcctctgtg ggaccacaag aaatatcatt   30780
agactaatca agaaccaat tttatgaagt agatgatccc aattttaaa actgtaaaga     30840 aagcatttac gttttgttt ttgttttata aagacagggt ctcgctgggt gcagtggctc    30900
actcctgtaa tcccagcact tgggaggcc aaggtgggtg aaccacaagc tcaggaggtc    30960
gagaccatct tgtccaacat ggtgaaaccc cgtctctact aaaaatacaa aaattagttg   31020
ggtgtgatag cacgtgcctg taatcccagc cactcgggag gctgaggctg agaatcgct    31080 tgaacccggg aggcggagat tgcagtgagc cgagattgcg ccactgcact ccagcctggg   31140
tgacagagtg agactccatc tcaaaaaaaa aaaagaaaa gaaagacag ggtagacctc     31200 tgttgcccag gctggacgga gcgtagtggc gcaattatag ctcaccatag cctcaacctt   31260
ctggcatcaa gcaatccttc cacttcagcc tcccaagtag ctaggaccct aggtgtgtac   31320
caccatgccc agctaatttt tttggcgggg gtgtggggga gggttcacac tatgttgcct   31380
aggctgatgt cgaattcctg gctgcaagca atcctcctgc cttagcctcc caagggctg    31440 ggattacaag agtgagccac tgcacccagt ggttaccatt ttatagtcaa ggaaattaaa   31500
gcttagaaaa agtaacttgt ggctgggtgc cgtggctcac gcctgtaatc ccagcattct   31560
gggaggccaa aggggtgga tcacctgagg taaggagttc aagaccagcc tgaccaacat     31620
ggagaaaccc tgtctctact aaaaatacaa aattagccag atgtggtggt gcatgcctgt   31680
aatcccagat actcggaaag ctgaggcagg agaatcactt gaacctggga ggcggaggtt   31740
gcagtgagcc aagatcgcac cattgcactc cagcctgggc aacaagagca atctccatc    31800 tcaaaaaaaa aaaaaaaga aagaaagaaa gaaaggtaa cttgtgtaaa tttatatata    31860
cagctggcca gttgaaaact aagattcaaa actaccttgg gtgtgggaag agtttaaaaa   31920
aaaatcaacc aagtccatgc tgtttccagt gccccattcc ttataatggc tttcttgtta   31980
ggcttggttt tgctttgagt cctcccaaag caactctgac tacctaatca aaacaggaca   32040
ttattagaag gagcctaggg tggctccggg gactaaagga agtgctaaca aacagcccta   32100
gacaggcagg gaccgcggca gctgagggac cttcattcta aaacacgagc attcatgtga   32160
cactgctcca agcttgccag gctcagagat tctgttcagg tttcaaattc ctaggagaga   32220
gaatctggtt tgcctgcctg tgttaggtgc ccacagccct atcagtcagc tctgcccagg   32280
gagacagagt cctgaaccct agacatggcc actgggtgc atcctaggtg ttggctcttc    32340
ccagaggagg gaaatccctg tgagtcaggc agtcccctca ggtaagtccc cagcagaaaa   32400
ttttctgtgg ggaggaaaaa gggaacagaa gtagcctgtc acccgagaag cctccatggc   32460
aacatttgga gctatcaatt cagcctcagc ctcacagttt gctcccttca aggtttcacc   32520
attatcaggg gctgcaaacc tgggcagcat atctgcaatt ctggcctcgc tttatccttc   32580
agtgttaaaa ctcatcttaa ctacaccaag gttgctggag cttgtcttcc aaagtcaccc    32640
ttgggggctt agtgggtgca agggccgctc agggcaaatg aaaatgaaag gcacacaacc    32700
aagaaagctc agaggtgcct ggaaggcagg ctgtgctcac tctccagaaa ccctgaagg    32760 ctctttcgga agaaagaaaa gaaaaatgtg tgccatgcat ttgactcggt ttagctgtgc   32820 tttgggctc atgacatgga aacctgccca tgcacagtca gccctaacaa gcaataacca    32880
gaggtgtctg gcctaaactc taaaatgctc ttaaggatat tagaaccatt aactctaact   32940
ggagttaatc tataggcaca aatcactcgc caaattaact ggccagtggt ttaacagcct   33000
ttcaaactca ggaaggcctg tatataaatc gacagcagca actaccactg cttagcacct   33060
accttactgc tatttcaatt gcatttctct acaatcctga gaaagctgct attattataa   33120
```

```
ccatttatgg atgagaaaga tgaggcacag agttttgacg tgacccagaa cacacaatgt   33180
tgggaaattc cagacagaat ggggacttga atttaggtct tctgatccca aatcctagac   33240
gggtgtttct tatgaggact ttctcatgga ttcatcactt ctttattcac tttatgtcat   33300
cagttctttt ttcagagtaa gttacctaat gattctccac ccttgcacag tggggctggc   33360
ttctccatgc cagtgtaaat gtacgtacaa agaatgcatc agattagttt ctatgcccaa   33420
gaaagtaatg tcacccttgt cttgggctct aattgcaaga acagctgagc tggagcagat   33480
cctggtgacc atttgttgcc aagtccagga ttacacagtg gacaagagga gttttctagg   33540
actacactaa aatgagtata gttagggtga ggatttcagg accatggaac tagaaggaac   33600
tttattctaa acctcaggct tgaaattcaa aaccagagtt tttactcttg cctgttagat   33660
gtcaatcaga gcttagttca gcctgagtgc tcctgcacaa gtcttcagtg ttcctctatg   33720
gatttatgat tgtctggcct ctccatcacc cctctggagt gggaaataag tgaaagtggc   33780
atggaaggag gtatgatttg ggcagagaga aaaatcagcc tcttcacggt cctgacctgt   33840
ttttcaaacc ctgagtcaag aatccactga tgggtttgtt aaagcaattt actaggtaaa   33900
gaccaacact taaaaaataa gataaaatta gtcaagcggg aaatatcaga ctatatcaca   33960
tgtagttatg gtacataatg tttcataaaa cgttttaaaa taattttcaa aaataaatat   34020
atttatgtat aatggtatgt aaaaatgtat cttttaccac aagtcttagt ttaaaaaaaa   34080
aaagtttgaa aggcactggc taagtggatt gagaactgga atgtctgaga tttataaccc   34140
tctccactta atatgggatc tcagatgtca ggaatatta tgaggcctat ttaaaacttg    34200
ccacccagaa acataaaacc aaaaccaaaa gctgcaagga aaagattttt gaaactagat   34260
tttgtaaaat atttctaaat tgtctatatt aaaacataca acagaattga aaggtgtaaa   34320
actgaaaaaa catctgcatc cacatgtcaa agtgtcaaat tcttactatt aaaataatga   34380
ttataaatca agaagtgaaa aagtctgata ttccaacaga agaaaaggga cggaggcaaa   34440
tcatgagaaa aagggaaata gataaaaaga tgttcgccgg gtgcagtggc tcaagcctgt   34500
aatcccagac tttgggaggc tgaggtgggt agatcacgtg aggtcaggag ttctagacca   34560
gcctggccaa catgtgaaac cccgtctcta ctaaaaatac aaaaattagc tgagcatggt   34620
ggcgcatgcc tgtaggctca gctacttggg aggcggaggc acaagaatca cttgaaccca   34680
ggaggcagag gttgcagtga gccaagaatg cccactgcac tctagcttgt gcaacagaga   34740
ctcagtctca aaataaaata aataaataaa aataaaaaga tgttcaactt caccaataac   34800
gtcaattaag acaggatcta attttttttc aactcccaat gttttttaaa tacccagttt   34860
tgtcaaggat gtaacactat aaaaggcgcc acatattgct agtgggagta taattagata   34920
aactgggaga aaaattggca atacacacca gaagccttga aaattgtacc ctttgtctta   34980
ataatccctc ttcaaataat ttatctcaag gaaacaatca tgggtgtgtt caaggttgtt   35040
aacaatagta aaaaacttga ggaaaaaaaa acaaaccctg gctgtccaac aataggaatg   35100
ttatgatctt gtttacaaaa tataattaat taattaataa gttaactagc aaagccccaa   35160
catggggctt gagtttgggc cattctgggg gctgaaagcc tgaccactcc tataggagtt   35220 catttteccg agctgactga tgaaggcaga aggagggagg agtttagaga acacaggctt   35280
gggggaggtg cgatgcagac aatgggactg ttgaacctca gcagagacgg tttgagatgg   35340
aagctgagga gctattttca agagatactt tgcaagactc taagtctgag gcctgggatt   35400
aacaaaaaag acatcatagg tgtgttggta aaaagtgccc tggagaagag tacagcagac   35460
```

```
aagagggtct agggactgtg agggactttg caggtttatt tagggtaggc agggaaggcc    35520
cctctgatga gttgagattt accagagacc tgaagaaatg gtgagaacta ccaagggagg    35580
ctaggcagag ggaacagcca gtgcaaaggc cttgaggcag cacatgcttg ctgtgtttta    35640
agaacagcaa ggaggccagt gtggctggag tatggtgagc acaggtgtca ctggcaggag    35700
acaagggcag caaagcagcc caggttgggt catgtaggac cctgtgggca ttctaaggat    35760
ttgtcattta ctctgagtga gatggggagc cgtggggagg attttgagta gggaagggac    35820
atgtcctgac ttaggttctt attttttattt atttatttat ttttgagatg gagtcttgct    35880
ttgtcgccga ggctggagtg cagtggcaca atctcggctt gctgaaacct cccactcccg    35940
agcacaagcg attttcctgc ctcagcctcc ctagtagctg ggattacatg ggtgtgccac    36000
catgcccagc taattttttat atttttagta gagacaggga ttcaccatgt tggccaggct    36060
gatcttgaac tcctgacctc aagtgatcca tctgccttgg cctcccaaag tgctagggtt    36120
acaggcataa gccactgagc ccggccctga cttaggtttt taaaggatca ctctagagag    36180
tgcaatgtgg aagacaggct tagggacagg tatgggggc tgaagacaga agttggacaa     36240
cacttaggag gttactgcaa taatccaggt aggaggtggt gacttggacc aggatgatgg    36300
cagaggaaac agtgacatgt gttcagatct tggatctatt ttgaaggtag actgatagaa    36360
tttgctaatg gatggggtga gattttgtgt gtgtgtgtgt gtgtgtgtgt gtgtgtgtgt    36420
gtgtgtgtgt atgagcaaga gaacaggcca ggcatggtgg ctcacgcttg taatcccagc    36480
actttgggag gccaaggtgg gtggatcaac tggggtcagg agtttgacat ggtgaaaccc    36540
catctctact aaaaatacaa aaattagcgg ggtgtggtgg tgcacatctg taatcccagc    36600
tactcgggag actgaggcag gagaatcact tgaacctgtg aggcagaggt tgcagcgagc    36660
caagattgca ccattgcact ccagcctggt caacagagca agactccgtc tcaaaaaaaa    36720 aaaaaaaga gagagagaga gaacatgggg cccacctcgc cccacgtgaa ccagattctc    36780
tgcagatggt tcatggtatt tcttttcttt ttttcccttt caagttattg gtggagaaag    36840
ttcatggtat ttcctaaaca ctccccagga gacactaatg tgcagccagg gttaagaacc    36900
actgctctag atggtgaggt tataggaaac ttttattcct ttttttttgtt tgaggcagag    36960 tctcgctctg tcgcccaggc tagagtacaa tggcgcaatc tcagctcacc gcaacctctg    37020
cctcccaggt tcaagcaatt ctcctgcctc agcctcccaa gtagctggga ttacaggcgt    37080
gagccaccac atctggctaa ttttgtattt ttagtagaga cagggtttct ccattttggt    37140
caggctggtc tcgaactccc gacctcaggt gatccgcccg ccttggcctc ccaaagtgct    37200
aggattaaag gcgtaagcca ctgcacctgg cctggaaact tttattctta tctttattta    37260
tttatgtttt aatattctta tctttatttt ccacattttc tacaataaaa gttttaataa    37320
gaggagaaag ggggccgggt gcagtggctc atgcctgtaa tcccagcagt ttgggaggcc    37380
gaggtgggtg gatcacgagg tcaggagatg gaaaccatcc tggctaacat ggtgaaaccc    37440
cgtctctact aaaaatacaa aaaaattag ccaggcgtgg tggcgggcac ctgtagtccc    37500
agctacttgc gagactgagg caggagaatg gtgtgaaccc gggaggcaga gcttgcagtg    37560
agccgagatc gggccactgc actccagcct gggtgacagt gcaagactcc atctcaaaaa    37620 aaaaaaaga ggagaaaggg tattttaaac aaaacatctc ccctccccca tcctgaacta    37680
tgaaatgtaa gataataaca atacaacttt cttttaatga tcatatctcc acttgccaaa    37740
taccatccca tgaccagcat aaatgtcacc ttctctctgg agcccttgc acttcccaa     37800 ccaccagtga cagctcattt ttgtcctctc ctgtggccca catggcccct cttttggaa    37860
```

```
cttagttctc tcttttcttt ttctttctt tttttttttt ttgaggcggt gtctcgctct   37920
gttgccttgc ctgggctgga gtgtagtggt gtgatctcag ctcactacaa cctctgcctc   37980
ctgggttcaa gcaattctca tgcctcagcc tcccaagtag ctgggattac aggcacacac   38040
cagcacgctc ggctaatttt tgtattttta aagtagaga cagggatttg ccatgttggc    38100
caggctgctc ttgaattcct gacctcaagt gatctgcccc cctcggcctc ccaaagtgct   38160
gggattaggc gtgagccact gcacctggct agagcttagt tctctagtgt tggtagttgg   38220
agcctgcttt tttggaggag gtctttccta taaacccact ctggaaacag tgtcaaagca   38280
ggaagtgaga ggtatgtttt gaggtccaca gtccggctgg aagaagtggt agacagagga   38340
ccttagattg tcaggccatt gggccacaga atcagggcct ggatctggga cagtccttgg   38400
tctcccctga ggctctaggc tcctggttca cctgttctga atccctgtct cttgggaggc   38460
agggagtgag ctatttgtgt aagactaagg ccttagaata tgtcccacgt tctctggcat   38520
cagacacccc actcaggggc caaacagaaa gctgtgaagg gtggtgagaa aagtctcttc   38580
ttacacctcc tctccaccac tatttagtac cttgcttttt tagctttcat gttatattat   38640
gactggtttc ccatgtcatt aaatattctt cagaaattta actttgatga taacatatta   38700
ttcccattac ccataacttc atcatcctcc aactgttcaa aagttagatt atttctagct   38760
tttactatta cagtatattt aacatcacct ggtaattgat ctaaaaggaa taattaggaa   38820
tcagtcccca aatttggaga tggcaaccaa gaagtctttt tcattttcca cagttttccc   38880
acattttgt tttttttttc aagagatgct ctgcaactca ggctgcagtg cagtgggatg   38940
atcataattc actgtaacct caaattcctg ggctcaggct cccaaatagc taggattaat   39000
ggcgcatgcc accatgccag gctaatttta ttttgtaga cggggagtc ttgctatgtt    39060
gcccaggctg gttttgaact cctgggctca agtgatcctc tcgcctcgac ctccctaagt   39120
gctaagtgtt gggtttatag agatgagcca ccatgccttc tttctttttt tttttttaat   39180
tctgttttgc aaagaatatc cctcttgcca gcatctgaat aatatctatc tttactatta   39240
tttatgtgtg taaatagctt tacagttcac aaagcatttt cttatataat gtctcatcta   39300
atcaacacag caacactatg aaataagtta ctatttccat tttacatttg gggaaattaa   39360
gctcagaaag gccatgtgac atgttcaaga taacacattt agtgtcagag ctggacgtg    39420
gacccgggtc ttgggactcc cgaaaccata tcctttaccg tgggcaaagt gctatgctga   39480
ggtcttacca cacacataga tggcactgga agaagggcaa gtatggaaca gcaccccagg   39540
cagagtgggc gatgccactg gtaagataca gagaaagtac tacacacagt ggcgttgcaa   39600
ggacagagca gttcctccca caagggcat gcagtaggct ttgggaagaa acgtggccaa    39660
gtcgggtctt caaaggtgaa taggatctag atattcagaa taagagggct ttccacaggc   39720
tcagtgaatg ggaaaggaaa gtgtggctga ttggggaaag cgctagcaca gggagcaaga   39780
gatggggcgt ggctggggag gaatggaatt gtaattctag cctcacaaag gctagagcca   39840
gcagggcctt gggatcatgt ggggaggaaa ccagagatgt gtggaacaat ttgctgaagg   39900
cagaaccagg cagggaaagg gcagggtcag gttcgtaccc ttgcctctgg ccaccagggc   39960
caatgctcct tccctgcagt aaacccgatt aatctcctca aactcaggtg ccatttcctt   40020
ggaatagtat ttaccgcggg gcgcggtggc tcacgcctgt aatctcacgc tttgggaggc   40080
tgaggtgaga ggatccccttg agcctagggg ttcgagacca gcctgggcaa catagcgaga   40140
ccctgtggtt aaaaaaaaat taaaattagc caatagtggt ggcacgcgcc tgtagtacca   40200
```

```
gcttcttggg aagctgaggc aggaggatca cctgtgccca gagagggcga ggctgcagtg    40260
agccatcatc gtgccactgt actccagcct gggcgacagt tcgagacctt ttctcaaaaa    40320
aagaaaaaaa aaagttgttc aagttgtgta gtgcacggga ggaaagaagt atgacaataa    40380
cataggacag cagccggctc tttttttcat caggatgtgg agagtgggcg ccttgggaag    40440
acgaaattga gtatgtgcgg gggaggggtc atatgaaaca aggtcgggaa ggggcgggg    40500 agagctgggg ctctggagga gcttgggct cgcgctgcgg gggaggaagc gccttccgcg    40560
gtcgctgggg ggaagtggtt aggaggaagc acgggcagtg gagggactg ctggagggtc    40620 ccatctggga aagcaggcac ggatgcgggg acatttccgc ccgtcaccct ggcaaagcgc    40680
tcgcagggct ggagggacag agttctcaga tccaagtaga gaaaaccggg aacggttccg    40740
gctctgggga ctgacattca tcgcggcagt ttctggtggc aaaacagagg aaacaaagga    40800
atgatgaaat gaactgagct gccttcatgc cccggatgaa tgttcagcca ttagaaaaga    40860
gtgaatccca gctgggattt ggggttccac ggtgtactag aaaagcaaaa caaagagaag    40920
cgcctactag atgccatctt ggaaaacaaa agcaaacgtg tgtgtgtgtg tgtgtgtgtg    40980
tgtgtgtgat gttacatggg catggggaaa ttacggaagt aaatactaat gcttgtggcc    41040
gggcgcgtgg ctgacgcctg taatcccagc actttgggag gccgaggcgg acggatcacg    41100
aggtcaggag atcgagacca cggtgaaacc ccgtctctac taaaaataca aaagttagc    41160 cgggcgtagt gacgggcgcc tgtagtccca gctacacggg aggctaaggc aggagaatgg    41220
cgtgaacccg ggaggcggag cttgcagtga gccgagatcg cgccactgca ctccagcctg    41280
ggtgacagag cgagacgccg tctcaaaaaa aaaaaaaaaa atactaatgc ttgtgtaaat    41340
tgggatggtg gaaatgagg aagagggcgg caggggaatc cttagtactt acagagaaaa    41400
cggagcaagt gtacaagcac gccaacccc ccggtgccca agctcggcgc tcacgcggct    41460
aggatgacgc ccgtgggacg ccccagggc cctgctcgca gccactctgc tcagggtcat    41520
ttatagtctc tccgttcttt gttaaataaa gacggtgaga cacggacggg ctggagccgg    41580
caggggtagt ggagggcaga ggggacgggt cggggcgccc ctcgctcctg ccacgctgcc    41640
gccgccccag acaaagacag ctgcgtacgc cgggagcgca ggggcgcctg cgcgcagggc    41700
ctaaatcgcc tgtcccgtct cccctgacg cccacacacc caagcggcag cccactcccc    41760
ttctaccccg cagccatttg cttcccaccc cttgattttc ttttttcttt tcccctcccc    41820
tcagcatccc cccaacctcc tctgatacac tttggctaat tgtctaatga atttacctat    41880
tctaggtatt tcgtataagt ggaatcatat aatattcgtc cttctgtgtc ggcttatttt    41940
gcttagtaca aggtttttta tttttatttt tttttctttt gagacacggt ctcgttctgt    42000
cgcccaggct ggggcacagt ggcgctcagc tcactgcaac ctccacctcc gggtttcaag    42060
tgatcctccc acctcagcct cccaaatagc tgggactaca ggtgcgctgc caccactgcc    42120
tagctaattt ttgtattttt ggtagagacc aggtttcgcc atgttgccca cgctggtctc    42180
cagctcctta gctcaaacga tcctcctgcc acagcctccc aaagtgctgt aattacaggc    42240
gtgtgagcca ccatgcccgg ccacttagca taatcttttc aaggttcatc cctgctgcag    42300
cacgtatgag aacttcattt cttttattgt atttgtggta atatgtacac aacataaagc    42360
ttattttaat caattttaa gtgtacagtt tagtggcact aaatagtcac gtggttgtgc    42420
actcaccacc atcatccatc tctagaactc ttccatcatc ctaaactgaa actctgtacc    42480
cgtgaaacaa ctccctcatt cccctctacc cagctcctgg caaccaccat tctactttct    42540
gtccctgtgc acttgggagc atcacctttc tgggacatct gcaacggttc tctggaggat    42600
```

```
tgtctccct  tttttaaaaa  tttatttct  tttctttctt  tctttttttt  ttttggtaga   42660 gaagggttt  cacttcattg  cccaggctgg  tgtccaactt  ctgggctcaa  ggaatctgcc   42720
tgccttggct  tcccaaagtg  ttgggattac  aagcatgagc  cactgtgccc  cgcctgtggt   42780
ctcattttgg  agggcaagag  ggatagagat  agccataacc  tggagaatat  tgagatgtgg   42840
acaacaagga  tgacaaaatt  tggtcctatg  agaaatcatc  tgtgaggaag  agtggagaga   42900
actgagcttg  ttcaagacag  tgaggtcctg  ggatgatctc  aattcatgta  agaaaaccag   42960
gaagcaagga  ggtttcagtt  tatcaacaga  tttaaaaggc  gcaagccttt  tgatataact   43020
agagaagaga  agactcaggt  gatcacacag  actgtcttca  cccaagtgaa  ggatgattat   43080
gtaggaaagt  ggatagaaga  tgctgtcaac  agaaatgtaa  acagaatcat  gttaacaatt   43140
tttcagtagg  cacttttttt  ttttttttg  agatggagtc  ttgctctgtt  gcccaggctg   43200
gtgtgcagtg  gtgcgatctt  ggctcactgc  agcctcctgg  gttcaagcga  ttctcctgcc   43260
tcagccttcc  gggtggctgg  gattacaggc  atgccatcat  gcccggctaa  ttttttgtatt  43320 tttagtagag  acagagtttc  accttgttgg  tcaggatggt  ctcaaaactc  ttgacctcag   43380
gtgatctgcc  tgcctcagcc  tcccaaagtg  ctgagattac  aggcgtaagc  catcacacct   43440 ggccaattt  taaattaata  atgagaggct  gggcatggtg  gcacacacct  gtgattccag   43500
ctactcagaa  ggctgaggtg  ggaggatcgt  ttgagcccag  gaagttgagg  ctgcagtgag   43560
ctgtgttcac  actagtgcac  tccagcctgg  gtgacaaagc  aagaccctgt  tgaaaaaaaa   43620
attttttaat  aatgagatat  ctgacattct  ttttttaca  cttggtctct  gaaatcaggc   43680
tggctacatg  tgaagtgctc  tatagctacc  tgcggtcact  gtattggaca  gtgcagggtt   43740
ggaaactgga  cttaggagtc  agggctgggt  tcaagcccca  cattccatcc  cttactaggc   43800
tgggtaacta  ggcacattac  ttagcctctc  ctatttctgt  ttcttcatct  acaaaatgaa   43860
actaaaaata  gtacctactt  tatagggtaa  ttttgtggat  taatggcaca  tgaagcatat   43920
ggtgcatgtt  cagtaaatgt  tggcgattat  tagcagtaaa  tttggtggtt  attgaattag   43980
tgacattgca  gtatcactgt  tagggtgacc  tccattccca  tcagatgatg  tggcttgaag   44040
ctattccaaa  cgggcaaggt  taaaaaacaa  taggcaaact  gggaaaacct  atttgcaaca   44100
cacatgaaaa  caaatgttg  ttattcttgc  tatgtaggaa  gtgcttgcaa  ataaataaga   44160
aaatgaatac  caatggaaaa  ttcaaaagaa  acaaacatct  gaagtgattt  ttttttaaga   44220
cccactttaa  ataagttcaa  ctctccttgg  aatcagacat  aaaaataaac  aaaagacatt   44280
ttttgttgtt  gttgagtaac  agatcaacag  ccagaatttg  gtggcaccta  atattgaaga   44340
aggtgtgggg  agataccttc  tcttttaaa  taaagatttc  ctgaagtttc  cattgttata   44400
tctgaccaca  gactatccag  agaaacaagc  tgagttcttg  cttcaaggag  gaactagcca   44460
gagagccttt  tctacccact  ttttcccttg  tccagataaa  gctaaacagc  caacaaaccc   44520
ctcctagcaa  gttgactttt  ttcttgtcat  gtgtgcagac  tctgcacatt  agctttgcta   44580
atagtccttt  accacaggtg  ttgacatttc  acgtggcttg  aaatagcccc  cagcattgtt   44640
ctacatttgg  acagggctga  catacttaag  ccacaatacc  cccagaatat  tattaggctt   44700
ctggctacct  ccttcaggaa  tgttttatct  gccagcagga  ttggctacat  aattttggg    44760 gcccagggga  aaatgaaaat  atgggcccct  ttctcataaa  aggatgaaaa  agccctttc    44820 attttttcta  cagtctctct  ctcaacctgt  catgatgttt  ttatttacta  tttattgttg   44880
tactcccttg  gacatggaga  tacttcagag  gtcagtgcag  gccctcacag  atgcccagga   44940
```

```
ccatgccgca agacagcatg catttkccag tttgggaaag cttttttttt ttttgacacg   45000
gagtctcaca ctgtcaccca ggctagagtg cagtggtgcg atctccgctc actgcaagct   45060
ccacctcccg ggttcacacc attctcctgc ctcggcctcc cgagtagctg ggactacagg   45120
tgcccgccac catgcctggc taattttttg tattttagt agacgggg tttcaccatg    45180
ttagccagga tggtctcgat ctcctgacct cgtgatccac ccgcctcggc ctcccaaatt   45240
gttgagatta caggcgtgag ccatggcgcc cggcccagtc tgggaaaact tgatggggag   45300
tggggtgaag agactaatgc tttttttttt tattcaagat ggagttttca ctcttgttgc   45360
ccagtgcaat ggcgcaatct cggctcactg caacctccgc ctcccaggtt aaagtgatta   45420
tcctgcctca gcctcccatg tagctgggat tacagctgcc caccaccatg cccagataat   45480
tttgtatttt tttttagta gagacggggg ttcaccatgt tggccaggct ggtctcgaac   45540
tcctgacctt aggtgatcca cccacctcgg cctcccaaag tgctgggatt acaggcttga   45600
gccaccacac ccaccctatt taaccaatt tttttttttt tttttttttt tgagacggag   45660
tctcgctgtg tggcccaggc tggagtgcag tggcacaatc tcgtctcact gcaagctcca   45720
cctcccgggt tcacgccatt ctcctgcctc tgcctcccaa gtagctggga ctacaggcgc   45780
ccgccaccat acccagctaa tttttttgt attttagta gagacatggt ttcaccgtgt    45840
tagccaagat ggtctcgatc tcctgacctc atgatccgcc cgcctcggcc tcccaaagtg   45900
ctgggattac aggcgtgagc caccgcgccc ggccccattt taaccaattt tttaagtgta   45960
gtttagtggc actaaatata gtcacgtggt tgtgcactca ccaccatcat ccatctctag   46020
aactcttcca tcatcctaaa ctgaaactct gtacccatga acaactcct ccctcattcc    46080
cctctaccca gctcctggca accaccattc tactttctgt ccctgtgcac ttgggagcat   46140
caccttctg ggacatctgc aacggttctc tggaggattc tgtctcccct tttttaaaaa    46200
tttattttgt tttcttct ttctttttt tttgatagag aaggggtctc acttcattgc      46260
ccaggctggt gtccaacttc tgggctcaag cagtctgcct gccttggctt cccaaagtgt   46320
tgggattaca agcgtgtggt ctcatttkgg agggcaggag ggatagagat agccataacc   46380
tggagaatat tgagatgtgg acaacaagga tgacaaaatt tggttctatg agaaatgatc   46440
tgtaaggaag agtggaggga actgagcatg ttcaagacag tgaggtctcg ggatgatctc   46500
agttcaggag gtttcagtat atcaacagat ttgaaaggag caagcaggct gggcgtggtg   46560
gctcacgcct gtaatcccag cactttggga ggccgaggcg gcggatcac aaggtcaaga    46620
gattgagacc atcctggcta acatggtgaa accccgtctc tactaaaaat acaaaaatca   46680
gctgggcata gtggtgcgtg cctgtagtac cagctactcg ggagactgag gcagaagaat   46740
tgcttgaacc tgggaggcgg aggttgcagt gagccgagac tgcgccactg cactccagcc   46800
tggcaacaga gcgagactcc gtctgaaaaa aaataaaaaa taaaaggcgc aagcagtgtg   46860
atataactgg agaagagaag actcaggcaa tcacacggac tgtcttcacc caagcgaagg   46920
atgattatgt aggaaagtgc atagaagatg ctgtcaatag caatataaag tgaatcatgt   46980
taacaatttt tcagtggcca cattttttt ttttttttga aaggagtct tgctctgttg     47040
cccaggctgg agtgcagtgg cgtgatctcg gctcactgca acctccaact cctgcaaaa    47100
ccctgtctct actaaaaata caaaaattag ccagtcgtgg tgttgcacac ttgtaatccc   47160
agctactcgg gaggctgagg caggagaatc acttgaacct ggaggcgga ggttgcagag    47220
agccgagatt gcatcactgc actccagcct gggtgacaga gcaagactgt ctcaaaaaat   47280
aatcaaacac atttttttt tagagtcagg gtcttgctct ttcacccagg ctggagtgca    47340
```

```
gtagtgggct caagagatcc tcctgcttca gcctcccaag tagctgggat tataggcatg    47400
tgccaccatg tctggctaat tttttattt ttacttttga agaggtaggg tcttgttctg    47460
ttgctcagtc tggtcttgaa ttcctggtct caagcagtcc ttcttgagac cttggcctcc    47520
caaagcgtgg ggattacagg catgagccag gggtcctgat cagtattctt tttttcaaga    47580
ataaatttga atatgcttca ttgcaaggta tattgtttcc actgagcacc taggatttct    47640
caagttcttt gtatattata tgagtctttc acagcaatgt taaggacag gtgaaataaa    47700 cataaaataa ttcctggccg ggtgcagtgg ctcatgcctg taatcccaac actttgggag    47760
gccgaggcgg gtggatcatc tgaggtcagc agttcgagac cagcctgacc aacatggcga    47820
aaccccgtct ctagtaaaaa tacaaaatta gccgggcatg gtggcacatg cctgtaatcc    47880
cagccacttg ggagactgag gctggagaat tgcttgaacc caggaggcgg gggttgcagt    47940
gagctgagat cgcgccactg aactccatcc tgggcaacaa gagcaaaact ctgtctcaaa    48000
caaacaaaca aacaaaaaat tcctctttac agaggaggca attaagaccc attgtcaatc    48060
acctagtagg catcgggact gggggtttgaa agcacatgtc tctaaagtcc atgcttttat    48120
ttgtaatgcc aaaagactgg aaacaatcta aacaccccctt gatgggaacc agttaaatta    48180
tagtagtcca tacaatgtaa tactctacag ccgcaaagat agataaaaat gaggatactc    48240
tcatataccg ataaggaaat gtcaccaaga tagggtgtta agcgggggga aaaacccaac    48300
aaacgtgtag aacgtgtaca gactggcact aaatatgtta aaatggagta aggaagggta    48360
tagatttgtt ttagcttgta tgtgtagaaa aacaacgtta gaaggataaa caaaaaccctt    48420 ataacagggt tatctattta gggtgggga aagtgggcat ttgggggaca gggacagaag    48480
agatgtacat ctttttcattt tttttagttt taaacatata aataaattat ctgttcaaaa    48540
aagcaaatgc atataaacat ttttttaagc aacatgaaat taaacaaaac tgctgtccct    48600
tccttccact gtaccatgtg ccttagacat cttttggaggg cagtctgtcc tcttttccag    48660
tgagttgcac agggcagcag gcctcaggac accctggcag ctctaaggat ggcttcagca    48720
cagcctgggg aaggaagccc tgccagcagg cagcgccagg ccaagtgtac cctctttcct    48780
tatccctgac ttagaaaaac aaaaccgata ggcaaatcca ctcatcggca tttctgaatc    48840
cagttgttaa ccaatcctct tcctgccctt tactctcctt ttcttccttt ttccagaaaa    48900
tcctggaaag ctctgcagct actttgcaaa gtgcttact agctctggct gccttgttgt    48960
tttccttttc tcatttggcc tgtgtcatcc tctcaggcaa gtactgcagt cagacttcct    49020
gccagcttgc ctgctgggtt catctgtctt taaaacacaa aacaaaacaa acaaaaaagc    49080
ctgtattttc atagaaccta caaacctcaa attcgaagtt attttgtcca actctccacc    49140
cagagcagaa gatcctagtt gtaaaattta gcagagtaaa tccacttggt tttaaagccc    49200
aattctgtgg tttcactttg cccatccaat caactcggag taacagctct cataaaatat    49260
ttgctcttgt gaagaatccc acggggcagg tctatttgtg tgtggagtct agtggtgcag    49320
tcagcaccag taaatttcca ttcagtaatt cagtgactgt taatcgacac ctaatatgta    49380
tccatcactg tctgaggccc tgtgctaggg acagaaacaa acaccgagac tcagcccctg    49440
ccctcaaatc tctaacagcc atgttaggat accttcaggt catcaagcca ggtcattagt    49500
gcctggccta atttgttttg tttttaaaaa gccatttgca aggtatcagt tatatcactg    49560
tgttgtggac atttctcatgg tgagctatgt gtcggaaata tgatttatgg gaatggcttt    49620
cttttctctc tttttttaagg ttttgggggaa atagcttta tactgcaaag ataatggcca    49680
```

```
aagctcaaac tctaggtaat gtaatccata taagattaat tagcctttca gggtgttaat    49740
tttgtcataa cagtgtcata gctttcagct ttcattagct agaattcctt ggctaatgtg    49800
caggaaattt gagatgtctg ccaggtgtgt tcggtgaaag attttacaaa atcaaatgtg    49860
agtctaaaag caagtcattt tgagagacac tgagcttggc agagattcag gtgtctagaa    49920
ccataccata tactccccag agaatgctgg gccagaacat gtcttccctt gagcgttgtt    49980
caattcactg ggcacacgga gcagaggact ccgtggaggc agcatgctca ctccccatta    50040
cacacgcaca gcatcaccag gaaccatacc tcgacattca ttctttgctg gcttattctc    50100
aaaggaaaac cccaaccaga agataatgaa caccacagac tgttggaagc agcaagaagc    50160
taccacacat ttgtggctcc cacacatcca cccaaaacac accagcagga agaaagagca    50220
atatattact caggtttcct gtcaggacat cctggcttga aacacaggtc tgtcacttaa    50280
aaatattaag ataacccgca gatgggaaac tgcttcatta tgtccttggg aatctcagaa    50340
aactgtcagc ttatgaaata gagctcaaaa gcaagtagaa aatcaccat tcccattgat    50400
gacgggtagt ttttcttcca ggcaaagagg atcacaggaa catgggggca tgaaatgact    50460
gaaggaatct gggctgggga aggccccatg cagtttctgg gcagactggg tcttgtctca    50520
gaccaacaac cttggtccaa atttgtcata aggacatgac aaactcagta tacaagcatt    50580
accgcgtaag tagtaggccc tattttgttg gtgactgaag attgcctttg aattccccag    50640
tgcccatagg ccctgcacgc ctcaccatct gccattgaac agtgtaaggt gtaagcagat    50700
cagctcagca gaacagtata aggctacact ttgaacagta gctgtctcct tgggggaacc    50760
ctacaatgaa ggggaatcca ttaaaaggag gtataggct agatgtctgt tctccaggct    50820
tgtcatggca agctcaggat cagagagacc acccatccat tcatcaatgc attcattcac    50880
tcattcaata gacatctata gagcactttt ttttttttaga cggagtctct cggttgccca    50940
ggctggaatg cagtagtgcg atctaggctc actgcaactt ccgcctcctg ggttcaagca    51000
attcatctgc ctcagcctcc tgagcagctg ggactacagg cattagccac cacgcctggc    51060
taatttttaa aatatttta gtagacatgg ggttttacca tgttggtcag cctcgtctcg    51120
aactcctaac ctcaaatgat ctgcctgcct cgcctcccaa agtgctggga ttacagaaat    51180
gagccaccac atccggattt tttttttttt tttttttttt ttgagacagg gtcttgctct    51240
gtcactcagg ctggagtgca gtggtgcaat cacggctcac tgcagtctca acctcctggg    51300
ctcaagcaat cctccctcct cagcctccca agtaactggt actactggcg tgtgccacca    51360
tgcccagtta ttttgtat gttttgtaca gacagggtct tatgttactc aggctagtct    51420
tgaactccta ggctcaacca atcctccagc tttggccttc caaagtgttg gaataacagg    51480
tactgttatt ccgagtaact ggtactactg gcgtgcgcca ccatgcccag ctaatttttg    51540
tattttttgt agagacaagg tcttactatg ttacccaggc tattctcgaa ctcctaggct    51600
caaccaatcc tccagctttg gccttccaaa gtgctggaat aacaggtgtg gccactgtg    51660
cctggccact gcaaattctt gggagcctgc tgtctctctt agccaggtta caatggatac    51720
tatctgttaa cactagtatt cctactatcc catattcaat ctttactcct caatcacaaa    51780
ctttttttt ttttttttt gagacagagt ctcatgctgt cccccaggct ggagagcagt    51840
ggcgcagtct cggctcactg caagctccgc ctgccaggtt cacaccatcc tcctgcctca    51900
gcctcccgag cagctgggac tatagttgcc cgccaccaca cccggctaat ttttttgtat    51960
ttttagtaga gatggggttt caccacgtta gccaggatgg tctcagtctc ctgacctcgt    52020
gatccaccca cctcggcctc ccaaagtgct gggattacag gcgtgagcca ccgcatcctg    52080
```

```
ccctcaacca caaacttttta tttccttctg ctattctatc ccatgattct cataaaccat    52140
caaaatgtct tcagaatgcc aattttttgt gtgttccgat ttcatctctg gcatgataaa    52200
ctttatagct ctgaaactct tggttcaaaa aatagtgccg tggagagcta ggtggtcacc    52260
ctgagaccac aacttgcagt ccctccaggc tcatgcctgt atctgtgaac agggaatctc    52320
ctgaggaaat acacgtggtc tccacagatt ccacagccac acccatctca tgacctggat    52380
tcctcccctc cccctgccc agcctccacc ccctgggcag gaaaggagc cgagaaagtg    52440 agtcttcagc tccttcctct tctgcactta gatctatcac atctcaccac atcaacactg    52500
ttattttctt agaactatat agtgtttata tttggggtct agggtaaaat tccattttca    52560
tctatcattg caactggctt ttctggcttt ctcttttgga gatcttggct tattttttccc    52620 cagggagtga gtcatattca caaacacgcc ttatctcctg ggacacaacc tggtcagtta    52680
gctaccccaa ctcacagaaa atgatcacaa agattttgtg tccctttttac ttttttttttt    52740 tttttttttt tgagatggag tttcgctctt gttgcccagg ctggagtgca atggcatgat    52800
ctcggctcac cgcaacctcc gcctcccggg ttcaaacgat tcgcctgcct cagcctactg    52860
aggagctggg attacaggca cccgccatca cgcctggcta agttttgtat ttttagtaga    52920
gacggggttt caccatgttg gccagactgg tctctaactc ctgacctaag gtgatccacc    52980
cgcctcagcc tcccaaagtg ctggaattac aggcgcgagc catcgcgtct ggccccttt    53040 tacctttata tcactcactt ccacaaaatt tatttaaaat ttagaggaaa acctctgtac    53100
ttcctcctgc ctcccacccc ttgttttttt tattaattt ttttttgag acagactctt    53160 gctctgtcac caggctggag tgcggtggca caatatcaat tcactacaac ctccgccacc    53220
cgggttcaag caattcccct gcctcagcct cccaagtcgc tgggattaca ggcacccatc    53280 actaccccg gctaatttt tgtattttag tagagacggg gtttcaccat gttggcaaag    53340
atggtcttga tctcctgacc tcgtgatctg ccagcctcag cctcccaaag tgctgggatt    53400
acaggcgtga gccaccgtgc ctggccccct tgttttaatt ttctccgtag cacttgtcac    53460
tatcgacata ctagatagct tattcatttg ttcatcattc attcattgtt tgtctctctc    53520
tctttcctca ctggaatgta aacttttggc cagacatggt ggctcacacc tgtaatccca    53580
gcacttttgg aggccgaggc tggcagatca cttaaggtca ggagttcaag aacagcctct    53640
ggccaacatg gtgaaacccc atctctacta aaaatacaaa aaaaattagc caggcatggt    53700
ggtgcatgcc tgtaggctgc agtgagccga gattgcgcca ctgcactcca gcctgggtga    53760
cagaaccaga ctccatctca aaaaaaaaaa aaaaaaaaaa aagaatgtaa acttttgag    53820 ggcagggctt ttgtttgttt tgtatattgc tgtattccca ggcccagctc agtgcctggc    53880
acataaaaaa tactcaataa aggttgaaca aataaattgg tgaataaata gttgattttt    53940
ccttccttgt ctgaggccta ccacttccct ctcctgccac aatgtctttc cattggctca    54000
gtccctaaga gatcagatga ctgtatgttc tgtgtaagct gtggaggcga accaccaaaa    54060
cagtgggtag ttcctctcca tctcctgcat ctccatctac tgatagcaca aacatttgc    54120 aagtcctact cacctcctct gtggcaccat cccttaacct cccacagtga tctcaccttc    54180
ttctgaactc acagcatcca gtgcatgtat cattcatcta caatttagca ctttctgcct    54240
tgtgtggata atataattct cctgaatgtg agcaaagctg gcttcctgca ccaacccctt    54300
cccctctttc cagcagctcc tcacttctta cctcgcggaa tttaaacaag gacccagatg    54360
tgggacttac actttcaggc tggcccagta cgagggact catctctcaa acacctagag    54420
```

```
agttcacata atgttgaggg acatataaat caaatgccaa tttactcaca ctgaggaatg   54480
acagatattc aaaatggact gcaacgcttg aactggcctg actggccgat gtccccatgg   54540
gctaaggatt gcttagtaaa atgcagactt agaacaaaag taaccaacct aaagtcaggt   54600 ctcactttt aaggcagaag atcctctttc ctgcaacagg agcagcagcc tgaccaagga    54660
actcacggag cttacctggt ctcccactag ccttgggtcc tgccagggct gtacttggaa   54720
gcacaggtac tttcaaggat ggccaaaccc ctcctgttaa gtttgccaaa ctggtttata   54780
acccaattga ttaaacttca cctaaattac aaccactttc cagcccctct cctattagac   54840
tataagctcc cgagggccca tgccttgcag gtttcttttt tcttttttt ttttgagatg    54900 gagtttcgct cttgttgccc aggctggagt gcaatggcac aatctcggct caccgcaacc   54960
tctgcctccc aggttcaagc aattctcctg cctcagcctc ccgagtagct gggattacag   55020
gcatgcacca ccatgcccag ctaattttgt ttttttgttt ttttgagacg gagtcttgcc   55080
ctgtcgccca ggctgtagtg cagtggcgca gtctcggctc actgcaacct ccgcctccca   55140
ggttcaagtg attctcctgc cccagcctcc cgagtagctg ggattacagc cgtgtgcctc   55200
catgcccagc tcatttttgc attttttagta gagacggggt ttcaccatgt cggtcaggct   55260
ggtctagaac tcctgacctc atgatctgcc cgcctcggcc tcccaaagtg ctgggattac   55320
aggcgtgagc caccgcgccc agccttaatt ttgtattttt agtagagatg gggtttctcc   55380
atgttgaggc tggtctcgta ctcctgacct caggtggtcc acccgcctcg gcccccaaa    55440 gtgctgggat tacaggcgtg agccaccccg cccggccagc aggtttcaat aagtatgttg   55500
tgacagaaag ggccgctttg tcagcaaaga aagaaataga aaaactcact ccgcccacag   55560
ttttttttaa gagacagggt ctctctccga cgcccaggct ggagtgtgat cacagctcac   55620
tgcagcctta atctccaggg ctcaagcttt cgtcctaccc tcagcctccc agatagctag   55680
gactacaagc gtgcatcaca acgctgacta gtggtttttt ttttttctt tttttaatag    55740 agatggggtt tcaccatgtt gcccaggctg gtctggaact cctgggttca agggatcctc   55800
ccacctcagc ctcccaaatt gctgggatta caggcatgag ccacctcccc tggcctcact   55860
ccctgtttaa agtgtccctg gccaggtgc tgtggctcat gcctgtaatc ctagtgctttt   55920 gggaggctga ggcgagagga tcactcaagg ccaagaattc cagaccaggc tgggtagcgt   55980
atcgagaccc catctctaca gaaaatttta aaaattagcc gggcgccgtg gcatgtgctt   56040
gttgtggtcc tagctactca ggacgctgag gtgggatggt ggcttgaccc caggagtttg   56100
aggttaactg agctataatt gtgcgactgc acttagcctg gcaacagag agggtccttg    56160 atctaaaaca aaacaaaaca aaacaaaaaa caaacaaaca aacaaaacgt gtccctgggt   56220
caatcaggct caaccactcg ttttttgtttt ttttttctg agatggagtc ctgctctgtt    56280
gctcaggctg gagtgcagtg gtgcgatctt ggctcactgc aaccccgcc ttccggttcg     56340 agcaatcctc catcctccca cctcagcctc cggagtagtt gggattacaa gtgtgtgcca   56400
ccacacccag ctaatgtttt tattcttagt aaagacaggg tttcaccatg ttggccacgc   56460
tggtctcaaa cttctgacct caagtgattt gcccacttca acctacatcc actccttgat   56520
ctgaaacact gaagctacct gccttgttca agccaaaaa gcgtctacct acaaagccct    56580
ggggattttt tgtttgtttt atttgagacg gagtctcact cgcccaagat ggagggcaat   56640
ggcgtggtct tggctcctga ccttgtgatc tgcccgcctg ttttgaagga caaatgcctg   56700
cacccttatt tgtttgcttt ctcctgggaa tttctctatc caatcctgca ggcaagttgt   56760
tttttttttt ttggagacag agtctcgctc tgttgccagg ctgcagtgca gtggcgcaat   56820
```

```
ctcggctcac tgtaatctcc gcctccctgg ttcaagcgat tctcctgcct cagcctcctg   56880
aatagctggg actacaggca cgcgccacca cgtccagctg attttttgtat tttcagtaga   56940
gacggggttt cattatgttt gccaggatgg tctcgatctt gacctcgtga tccgtctgcc   57000
tcggcctccc aaagtgctgg gattacaggc atgagacacc gtgcccagcg acaagataat   57060
tttaaaagga gagggaacgt ctgcttttgt tgcctttctc gtcttttgtg gttccacata   57120
caacacagca gtgtctatgg gctgtcaatc gcaacataat gcaaacaaca caattgtctc   57180
tggggtccac tgaatccaaa tcacacacgc accacacttc tgccttttgc actgctgact   57240
gccaagtgaa caatgttttg tagaagcagc aagtgtgagg agaggtgact tctgccagat   57300
ggtgctaaaa aagacccaag tctgatacac aggagtcctt ccattaaccc atccatgacc   57360
aaagcaaagt gtgtgtgggg tgaggggtag aaggaattgc cctgtctttg ccctctgggg   57420
cttcttctgc ctcgaacact atccatctgc cacctaacct ggttttgcct tgatataaat   57480
ggtagcggtg gccaagagaa tggggtgaca gaggggggga aacccacggt gttacatgct   57540
ttcacccata ccctccagga tggccctgag cgtctcacac cctagggggcc tgaccaggta   57600
ctgacacttt cttgccaaag ccctacaacc atcacctccc tactgtgaaa tgtgaggtaa   57660
gttgcttaaa ccggcggaac cagtttcctc aactacatag agggatgatg attcccccta   57720
gctcacagga ccgctgtggg aatcaaatga gatcactcat gtgaaaagcc tagcacaacc   57780
cctgacacat gacacaagca cttcaggaca tattcatgtt cctccttcca ggacagggcc   57840
ttacactgtc tactctggta aaccagcctc atataagctc ctggaggctg gcgtgtcccc   57900
aggggtcagg ccatcccaga aacgatgact tgaccatagt cacgtcatga ggtgagagat   57960
tccgggaagg ggcagcaaga ggagaaagaa gcgaagggcg ccccaaggta atgtgtgccc   58020
tacacagggc tcctagccat aagcacttat gcaagtgcgg ggcacagaga aaattctggt   58080
aacactcctc ccctcaattc tgatcaggtc ccaggctcaa ctaatcagtt cagggatggg   58140
cccctttgcca cctttttcct aaccaaagcc actctcaagg ggaaacttct attaacggcc   58200
agtaagcaag acacacaacg ctttttgttt gaaggactac ccaggcgtta gtgcccttcc   58260
agaccggctc tagtgactgg cggggaagaa ggggaaaaag aattagtgta tctggacaca   58320
acacccagca tgtgctaggc agaaactaag tgtgcgaagc ggatcccgat gtacaaaggg   58380
gaaaacagcg gctgggaaag cctgagccac gggctccagg cggccagtcg cggtcctccc   58440
ggcgcgtgcc ctcctcctcc ccgacctggc cggagctgac cggggcgggt gtaggcccgg   58500
gggcgggagg gctactggat cccaggtggg gcgggtgtag gcccggggac gggagggcga   58560
cgggatccca ggtagggcgg ggcctggctc cgggcgcgac ggctctttgc tcgcagcgcc   58620
gcgccgtctc gaggtcgggg tgcggcccga ccccacgtgc cccaaatccc cccgctgcc   58680
ctgtaaaacc tgcgggcccc ggtccaggcg tggtcccgct cgcacgaggg agcggtcgcc   58740
cagggtgccg ggaagtcggg gaccggccag ccgccgaccg gccgcacccc tccccgccga   58800
gctcgcgcgc ccgcctcgtc agcacctttc ccgcagcgca gccccacagt ggtcacgagg   58860
cgggcgcggc ccggtcagcc ctggctagac taggcatcgg caccacccac ctcgcccctc   58920
cccgtcccgc tggtttcccc tcccctcct tccctcccc ctctctgttc tccttcccct   58980
cccgatcccc gggcgggccg cagcgcgcca cgtacctggc cccgcccctg cgagccacgc   59040
agggaacccc ggtgacgtca ccaccctccg gcgctctcat tccgcgctc tccagaaaag   59100
acgcgaaggt ggtgacgtgt cccgtgcgcc agggcggctg cgcaggaggc attggcaact   59160
```

```
gagcgtcctg cggcgccgcc tggtggaagc aaagcagccg agccccccgg aagcggcggc   59220
gcgggcgagt ggagaacgtg acttacgtca tctggcggag gcgtggggc ggctgccgcg    59280 tgaccagccc cagccaggcg cggtcggcgc gtttctcttt ctcttctcct actctcagcg   59340
gagcgggtgg aagcttgatt tcatgccgtt tattttactt tgactgtttt caaacctatc   59400
aagttaatat tgttaattat agaaaacgtg gggggaaaag ggaaaagata ggtagaaaat   59460
gattcttagc atccccaagc atctttaacc tttcattatg tttacttcca gccttttca    59520 tgaaacaaaa ttgtggtctg actgtataca gtggtattaa ctacaaagat tcctaagaag   59580
ggacaaaaag caccttttag cttcaaggct aatttagagg aacaggtaga agaggaaaag   59640
ttcaaacaat ggacaaaatg agtgattcgt ccacggtatc taatcactgt tcacatcatc   59700
cggaggaaac gggctcagag tcatgcccaa ggccgcgcat aaaagagtgg cagactgggg   59760
tttcaaaccc aggctctaaa ctgtgaacct gcaagatggt gggagtgggg aagacagtga   59820
aaagttgtgc agggaattca cagaactaca gaacccactt tgtacttctg gaactgctga   59880
gtggggaact agttctaagg aacaaggtta gtgcccagc agttggagca gtttggtgag    59940
agagtggcac aaagctgaca ctggtacatg gccctggcca ctagttgtta agttccaccc   60000
atctccagca ctgccctccc catgagtgac agtgaaaggt gggagggacg ttacaggact   60060
gtatcaggca ttagacctgc tactccaagt gcagtctggt gcagtctgca ggccagcagc   60120
ctccctgctg tccagcactt tccgcatcac ttggaagctt gatggaaatg cagaatcttg   60180
gaccacactt taaagcttct gaatcgggcg gcatgcgatg cctcatgctt gtaatcccag   60240
cactttggga ggccaaggtg ggtggatcac ctgaggtcag gagttttgag accaccctgg   60300
ccaacatgtt ggcccgtct ctactaaacc ccatctctac taaaagtaca aaaattagcc    60360
gggcatggtg gcgggcgcct gtaatcccag ctacttggga ggctgagaca ggaggatcgc   60420
ttgaacccgg gaggcagagg ttgcattgag ccaaaactgt tccgttgcac tccagcctgg   60480
gcaaccaaga tgtcccttct taggaacctt tgtagttaat accactgtat acagtcagac   60540
cacaattttg tttcatgaaa aaggctggaa gtaaacataa tgaaaggtta agatgcttg    60600 ggggtgctaa gaatcatttt ctacctatct tttccctttt cccccacgt ttttgaaact    60660 ctgtctcaaa aaatttaaaa aataaagctt ctacatcaaa atacgcattt taactaggtc   60720
cctgggtgat tcctgtgcac attgaagttt gagaagtgct gttgtaaata agtaagtcg    60780 tcctgctcgc ttggtacagc aggtgggatg gtagatgcga agggcgcttg cagaactgga   60840
tgatgggaag acaggcaggc agggagcaag gtcggtaagg aggattaaaa aaaaatcaag   60900
gctgggcgcg gtggcttacg cctgcaatcg ctgcgctttg ggaggccaaa gcaggcggat   60960
cacctgaggt cgggacttcg agaccaggct gaccaacagg gagaaacccc gtctctacta   61020
aaaatacaca attagccggg catgggtggc gcatgcctgt aatcccagct actggtgagg   61080
ccgaggcagg agaactgctt gaacccggca ggtggaggtt atggtgagcc gagatcatgc   61140
cattgcactc cagtctgggc aacaagagcg aaactgcgtc tcaaaaaaa aaaaaaattc    61200 ctacgagtgt cagaaaatat gatctgccac aaaggaaaac caggaaatca gaatctggga   61260
gctaaaggaa gaagaaatag gtgaagcagg taagcagatc tcttgagaaa attcactaat   61320
agacaaaggg ctgccccct gtgggtgatt tttttgtgtt gtctgtgact tacagggtct    61380
agttattata attcacagag cttagggaga gcagccctg cccatcccct ccagcagggt    61440
atagtgagat ttctctgggt tcttctagct gagggcatat tctgggcgtt tttggacagg   61500
ggagaaccag ggataggagg agctggctga ggttctgaca gaacagtgtc tgttggatga   61560
```

```
gggctggagt atgtatggtg tgcgcttgtg tatgcacatg tgggctggag ggaagggcag    61620
ggcattggca ccaacccagg acagcagtca ctgaaagatg gggtgaattt aggtgattgg    61680
gaattagtgg gcccacaaag ccacagggct gatgacatct ggtaccttga aagtcaggtg    61740
gcaggcctac agatctcttg ggtggatagt tcttggagtt agagtttgga ggtccccaag    61800
tagcttctaa atattagcaa tctggctggg cgccgtgact cacgcctgta atcccagcac    61860
actttgggag gtcgaggcag gtggatcacc tgaggtcagg agttcaagac cagcctggcc    61920
aacacggtga aaccccatct ctactaaaaa tacaaaaatt agctgggtgt ggtggcgcat    61980
gcctgtaatc ccaactactc gggaggctgg ggcagaagaa ttgcttgaat ccggaggcg    62040 gaggttgtag tgagccgaga ttgcgccact gcactccagc ctaggtgaca gagcgggact    62100
ccatctcaaa aaagaaaaaa atttgtatat atatatgcaa tctgtttat atatatatat     62160 aagcaatctg ttgagacaac agtagtactg gtagaggcag ggccatagta gattagaacc    62220
agagtgttct gagtggagga gtagcaagtt gttgttctca tgaggatgtc aggggcccca    62280
gccatgttgc ctggaggagg aagagttaag aaggcatccc tctcagacct attgatacac    62340
ttagtctgag aatgatcagt ctgtgcggta gacaggaggc cgtgtgggta tggagggttt    62400
taagctgttc tctccagaat acaaatggtg gcttagcttg gagaggcagc acctgggcag    62460
tccttagaga tcccattgac tgatggagga ggggtgcaat ggacagtaca cgtgggaatg    62520
tgtatgggtg gggaggtagg tggatgcggg gtttgaggag tgctgctgtg ggagtatcta    62580
ggacgactct gggagagagt ggggcaggcc cgaaatgaga tcaacactga tgttgtccca    62640
gaggtgtctg gaggctggga gtgggtgcag cagttctgct ggtcctccta ggcccgtgct    62700
tgacttggta gaggggtgt caagttagaa aaaagggt gactctgaac tccattccag       62760
attgtgatgg gctgtgatag tgtcctggag tggtgctggg gggaagatct gactgcttga    62820
gcagagtcct ctttgggtgg atgatttgct ccacccgtgt gttttgtggc ccctgtggtt    62880
cttctgagtc attcaggtat tactagagca ggcatctgcc tgtcacccac aggtgtgttt    62940
tgtgaaaaag ctgtgactga tgtcctccaa gttttcaggt tgaaggattt ctcaggatgg    63000
ccaaccacgg tctttccttg ggtgttcctg ctcttcaggc aagcctctgc cttatctagt    63060
ttttgtttgt ttgttttttt ttttttttga gatgagtctc gcctctatgg ccagggtgga    63120
gtgcagtggt gcgatcttgg ctcactgcaa cctctgcctc ccaggttcaa gcgattctcc    63180
tgcctcagcc tcccgagtag ctgggactac aggcacgcgc caacacgcct ggctaatttt    63240
tgtattttta gtagagacgg ggtttcacca tgttggccag gatggtctca atctcttgat    63300
cttgtgatct gcccacctca gcctcccaaa gtgctgggat tacaggcatg agccactgtg    63360
ccgggcatgc ctcatctagt tttatcttct ccacctatcc aaacccttcc tctccttga    63420 agcccaattc aagttctagg tctctgtgca cctccctgga ttctcaacaa ttttccctat    63480
tgtctgacgc acttaggagc tgacacaaac cagcccctca atcccagagg gtagacaaca    63540
caatgtggtt attccttctc ttttagaggc atagtacctc tcttaccaaa aatgtctccc    63600
cctctgttag gccaatcagt gccttttgg gggctgggag gggttctgcc ttttggatca    63660
gagagtggag cagtgagtcc tgctccagtg aggaagccat acattcaggc acttcaggag    63720
ccagaattcc tactagggga gctgctctgt gctgagatca aatgaagccc cagagagagg    63780
cagaaatggg tcagatggac cctagctcca caggtcccga ggcccagcca catcagctcc    63840
agcccagtgt ggttgtctag ctctgccttta gtgtccacaa gccagtcatt catacctatt    63900
```

```
ttgcccaagc tggttaactg gctttctgtc actcgcaatt caaagtacct ggtatggccg   63960
agcgtggtgg ctcacgcctg taatcccagc actttgggag gtcgaggagg gcagatcacg   64020
aggtcaggag ttcaagacca gcctggccaa catagtgaaa ccccgtctct actaaaaata   64080
caaaaaaaaa ataaaaaaaa ttagctggga atagtggcgg gtgcctgtag tctcagctac   64140
ttgggaggct gaggcaggag aatcgcttga acccaggagg cggaggttgc agtgagccga   64200
gatcacgcca ctacactcca gcctggcgac acagtgagac tccatctcaa aaaacaaaca   64260
aaaacaaaga aagtacctgg cacatagtag gcatgcaaga aatgttcatt cccttctttc   64320
ctccttaaag ataggcttat acttctgggt ctttcagtat ctctattctg tgatcattca   64380
atcagaaaca gcaattgaat tttactaact gagaatatat agagatacaa gtatgaagtg   64440
aacaagctat tacaggcatt agttttaaac agcaatattc ccttgatacc tgtgagaggt   64500
gacagcgtgc tggcagtcct cagagccctc gcttgctctc ggcacctccc ctgcctgggc   64560
tcccactttg gtggcatttg aggagcccctt cagcccccca ctgcactgtg ggagcccctt   64620
tctgggctgg ccaaggctgg gaggtgtgga gggagaggca cgagcgggaa cctgggctgt   64680
gtgcggcgct tgcgggccag ctggagttcc cggtgggcgg ggacttggtg ggccccgcac   64740
tcggagcagc cagccagccc tgctggcccc gggcaatggg gcacttagca cctgggtcag   64800
tggctgcgga gggtgtactg ggtccccag cagtgctggc ccaccagcgc tgcgctcgat   64860
ttttcgccgg gccttagctg ccttcctgcg gggcagggct taggacctgc ggcccgccat   64920
gcctgagcct tccacccact ccatgggctc ctgtgcggcc cgagcctccc tgacgagcac   64980 cacccctgc tccacagtgc ccagtcccat cgaccaccca agggctgagg aatgtgagcg   65040
catggcgcag gactggcagg cagctccacc tgcagcccca gtgtgggatc cactgggtga   65100
agccagctgg gctcctgagt ctgggggga atgtggagtc tttatatcta gctcagggat   65160
tgtaaataca ccaatcagca ccctgtgttt agctcaaggt ttgtgagtgc accagtcgac   65220
actctgtatc tagctgctct ggtggggacg tggagagtct ttatatctag ctcagggatt   65280
gtaactacac caatcagcac cctgtgttta gctcaaggtt tgtgagtgca ccaatcaaca   65340
ctccgtatct agctgctctg gtgaggatgt ggagaacctt tatgtctagc tcaaggattg   65400
taaatacacc agtcggcact ctgtatctag ctcaaggttt gtaaacacac caatcagcac   65460
cctgtgttta gctcaaggtt tgtgagtgca ccaatcgaca ctctgtatct agctgctatg   65520
gtggggcctt ggagaacctg tgtgtggaaa ctctgtatct aactaatctg atggggacgt   65580 ggagaaccttt tgtatctagc tcaaggattg taaacgcacc aatcagcacc ctgacaaaac   65640
aggccactcg gctctaccaa tcagcaggat gtgggtgggg ccagataaga gcataaaagc   65700
aggctgccag agccagcatt gacaacccgc tcgggtcccc ttccacactg tggaagcttt   65760
gttctttcgc tctttgcaat aaatcttgct actgctctca ctctttgggt ccatgctgct   65820
tttatgagct gtaacactca ccgcgaagat ctgcagcttc actccttagc ccagcgagac   65880
cacgagccca ccgggaggaa tgaacaactc cagacgcgct gccttaagag ctgtaacact   65940
caccgcgaag gtctgcagct tcactcctga gccagcaaga ccacgaaccc accagaagga   66000
agaaactccg aacgcatctg aacatcagaa ggggcagaca ccagacgcgc caccttaaca   66060
gctgtaacac tcaccgcgag ggtccgcggc ttcattcttg aagtcagtga gaccaagaac   66120
ccaccaattc cggacacacc tggatctctt tttccagtat cactatcagt taaatcccgc   66180
ctcccccccc cgaaatttat aatttttataa acaggcaacc atgagatata attaggaaaa   66240
actagtgaca ctgcttttatt tgagaacaga ataaagagcg tggctggaac tctgccaaga   66300
```

```
tggtctttaa cattctgccc taaccagggt gttaactttc caacactgtt ggtgtatggc    66360
tgagtgctgc agatttctca gagaattagc aaaaggttga aataaacgct aaagatgagt    66420
ccgtaagaag gaaaataagc tggttttctt tctgttcctt ttaaaactct agccagaaat    66480
actgcccaat gcataatgaa gactgtacac agcagcatca aaaaggctat ttacaagaga    66540
ttttcttcaa cagaatccac ttgaaagcac tgagaatttg catcttagct aagagcagtt    66600
taccaaggaa cagggccatc taagtgccta actagcattt aaagttgtca aggggtgggg    66660
atgtgcaaat taagcagcaa aagattatta tcttgttttg ctttaaggga aagtaatagt    66720
ggtcagaggg gccagttcca agggctggtc caagggggc cgctggtctt ggtactccgc      66780
cacatgccca ttccggtggt ggccatactc aaacttgatc cgcagctcgc caatcttaga    66840
ttggggaagg atatctggga tccactcgat gatgaaaggt gttggctcct tttgatctgg    66900
ggaagtgttg cctaaagaga agaaaggagt attagtacaa ttccacctaa ctctaatggg    66960
tgttcctaat tgcaaaaaaa gtgtccggaa ttggagcagc tgttcagct ttgataatca     67020 gaaggccgaa tgaggtttat aaattcagtg gtgattggga tatcagattt attgatcatc    67080
atgaagtttt tgggttattt tgttttttt gagacggagt ctcgctttgg cacccaggct     67140
ggagtgcagt ggcgcaatct cagttcactg caacctttgc ctcccgggtt caagcgattc    67200
tccttcctca gcctcctgag tagctgggat tacaggcacg tgccaccaca cctggctaat    67260
tttttgtatt tttagtagag atggggtttc atcgtgttag ccaggatggc tcaatctctt    67320
gaccttgtga tccgcccacc tcagactccc aagtgctggg attacaggcg tgagccacca    67380
cgcccagcca tcatgaagtt aaaacatata tatttaggcc aggcatggta gttcatgcct    67440
gtaatcccaa cagtgttggt gggcaaggcg agaggatagc ttgaggccag gagtttaaga    67500
ccagcctatg caacaaagtg agaccctgtc tctacaaaaa attaaattag ccaggtgtgg    67560
tgaaatgtgc ccatagtccc aactacttgg gagactgagg tgggaggact gcttgaaccc    67620
agtagttcaa tgccagcctg gcaatacag tgagactttg tctcaaaaaa acaaagtaat     67680
acaagaaaac aagaaggata ggccaggac agtggcttac acctgtaatt ccagcactgt      67740
gggaggctga ggtgggcgga tcacttgagg tcaggagttt gagaccagcc tgaccaacac    67800
ggcaaaaccg tctctactaa aaatacaaag attatccagg tgtggtagca tgctcctgta    67860
atcccagtta ctcgggaggc taaggcagaa gaatcgcctg aacccaggag gtggaggctt    67920
cagtgagcca agatcgcacc acttcactcc accctgggca acagagtgag actccgcctc    67980 aaaaacacc cccaaaaaat aaaaaaacaa gaaggatgga ttaattaatg tatatacatt      68040
tttatattat aaaaattaac aatgtatata cattttctc tcagcactac taaatctttg     68100
acttcataag ctaatatttt actttttgt ttgtttgttt gttttttgag atggagtatt     68160
gctctgttgc ccaggctgga gtgcagtgtt gcaatctcgg ttcactgcaa cctccacctc    68220
ctgggttcag gtgattctcc agccttccaa gtagctggga ctacaggcac gcaccaccat    68280
gtccagctaa ttttttgtatt tttagtagag acagggtttc agcaggttgg ccaggctggt   68340
ctcgaactcc tgacctctga tgatcctccc acctcagcct cccagagtgt ggggattaca    68400
ggcgtgagcc actgcgcctg gcttatattt tacttttaac ttcactatgt tactctccct    68460
ccactttagc ctaaatagtc accccttta aattccttcc ctctacttct tttggtcctt     68520
tctcacaaag actaagacat cactgatatg atgagaaaca aagcatccat ccacccaccc    68580
cagactaaca acttcattgg cagggtattt tggtctgtttt ggtttctttt agtcatagaa   68640
```

```
tataaatgtt aggtattatc tagttcatgt ttgtcacaga cattctagct tccatttcaa   68700
atgatatctg gagctgctgc caacttttca cttaaatatc aatgaagaca tagaaaaaga   68760
taaaaactta caactgatga acactaagac tactggcagc ttctgggagg aaatataaaa   68820
caggtggaga tggatggaaa gaaacctacc cagactttgg ccatagcata tcccatcttt   68880
ccttcataaa gggaggctac atggaaaaag gcaggaaaat actttgtctc tctcactgtt   68940
tgtgccctgg ctagtacttg tacagagcag caaatgagca gcgccacttc gtttccttta   69000
gaacatctca cacacacccc tccccactca tgtacctgaa ttcttgatga ctgcaaaggg   69060
gacttggagg agagtaggtg catttaaggt gaatagcagg gccaggtgca gtcgctcacg   69120
tctgtaaacc cagcactttg ggaggccaag ccgggcagat catgaggtca ggagttcgag   69180
accagcctga tcaagatggt gaaactccgt ctctactaaa aatacaaaaa ttagccaggc   69240
gtggtggcac gcccctgtaa tcccagctac tcagaaggct gagataaaag aattgcttga   69300
acctgggagg caggggttgc agtgagccaa gatcgcacca ctgcactcca gcctaggcaa   69360
cagagcaaga ctccatctca aaaaaaaaa aaagtgaat agcagtggca gagtgtgttc   69420
tggaaggtac agtctgcact agtaaagcaa tttgggtgtg agaaggagga gaaacccttg   69480
aaaactatat atgcgggaa tcttagtttt gtgtgttttt ttcctatatt ccattattag   69540
caatgaagga ggcagagatg gtcaggagat gccactgtgg taggaaagag aaacattaga   69600
tctgagaact ctgcatcagc gctccacata cagatctgag agggagccag ccatcatgca   69660
ggagtggtcc caagcaacct gcctgttacc agaatttgag tctggacaga tctttttttt   69720 ttttttttg agacagagtt ttgctctgtc gccaggctgt agtggtgcga tctcggctca   69780
ctgcaagctc tgcctcccag gttcatgcca ttctcctgcc tcagcctcct gagtagctgg   69840
gactacaggc gcccgccacc acgcccagct aattttttg tatttttagt agagatgggg   69900
tttcaccatg ttagccagga tggtctcgat ctcctgacct cgtgatccac ccgccttggc   69960
ctcccaaagt ctgacagat cttaatctgt tcagtaataa gtaaagaaaa gaacaggaaa   70020
ttaaaaaaaa aaaaaactac ataaggaaaa gggagtaaac agctagaaga atcaaaggaa   70080
gggaaagcaa tgactgatat atctatccaa aagaaaattt aaacggccgg gcgcggtggc   70140
tcatgcctgt aatcccagca ttttgggagg ccgaggcggg tggatcacga ggtcaggagt   70200
tcgagaccag cctggccaat gtggtgaaac cccgtcttta ctaaaaatac aaaaattagc   70260
tgggcgtggt ggcgggctaa tcccagctac tcgggaggct gaggcaggag aatcgcttga   70320
acccgggagg tggaggttgc agtgagccga gatcgcgcca ctgcactcca gcctgggtga   70380
cagagcaaga ctctgtctca aaaaacaaa caacaaaca aaaaaaaaa cacagaaatt   70440 tcagggaact gtttagcatc cacaaaagaa aaaaataag atccagcctt tatgaaagta   70500
aggccagaat cattaaggag agctcagact gggaggaaaa ggcagctgga tgagagtaaa   70560
aggaagacga acaagaaaag gccaaatttc aagaatcaca aagaatagaa ttaaaatcta   70620
catggtcagc tgggcacagt ggctcatgcc tgtaatccca gcactttgag aggatcaggg   70680
tggaggatca cttgaggtca ggagttcaag accagcctgg gcaacatagt aagaccccca   70740
tctctgtaag aaattttac taaaaaaaaa aaaaaaaaa aaaaaaaaa aatctgacat   70800 ggttctaaaa tatattataa acccgtaata acccaaagag tgtggtacta gcatgcatct   70860
agacagatta aaggaagaaa acagaaagat tagaaataga cacaaataca acaggaattt   70920
agcctaagat aaagatggca tttgtaacta ctaaagaag aacaaataag tgtttcttct   70980
aataaatggt ttgtatcaac cagatatcca tctggaagaa aataaaaggt ggtagaatct   71040
```

```
tacctataac ttacctaact tacatcatga taaattccag agaatcaaag ttttttgttt     71100
tgttttgttt tgttttgttt tgttttgttt gagacaaggt cttgctctgt cacctaggct ggagcgtagt     71160
gacacaatca tggctcactg cagcctcgac ctccagggcc caagcgatcc tcccacctca     71220
gcctccaaag tagctgggac cacaggcatg taccaccatt cctggctaat ttttttttt     71280 ttgaaagtaa gtttattaag aaagtaaagg aggccgggca tggtggctca cgcctgtaat     71340
ccagcacttt ggaggccaa ggcgggcaga tcacaaggtc aagagatcaa gaccatcctg     71400
gccaacatgg tgaaaccccg tctctactaa aaatacaaaa attagctggg catgatggca     71460
caggcctgta gtcccagcta ctaaggaggc tgaggcagaa gaattgcttg aacctgggag     71520
gtggaggttg cagtgagcaa gatcgcacca ctgcactcca gcctggtgtc agagcaagac     71580
tccatctaaa aaaataaaaa ataaaaagaa ggtaaaaaga aggtaaagga ataagaatg     71640 gctacttcat aggcagagga gcccctggct aattttaaaa attcttttat agagatgggg     71700
tctccttgtg ttgctcaggc tggtctcaaa ctcctgggct caagctatcc tccaacccca     71760
gcctcccaaa gtgctgggat tataggtgtg agctgctgtg ctctgtcaga tcaaagattt     71820
aaacatagaa ggttaaagaa tacttttgaa aaatacaaaa ttaggccggg tgtggtggct     71880
catgcctgta atcccagcac tttgggaggc caaagcgggt ggatcacctg aggtcaggag     71940
ttcgagacca gcctgaccaa tatggtgaaa ccccatctct actaaaaata caaaaaatta     72000
gccaggcgtg gtggcgggtg cctgtagtcc cagctactcg ggaggctgag gcaggagaat     72060
ggcgtgaacc tggaggcgg aggttgcagt gagccgagat tgcgccactg cactccagcc     72120
tgggtgacag agtgagactc catctcaaaa aaaagaaaa aaaaaagaa aatacaaaa     72180 ttaaacacta gcagaactaa actaagaata tggtatcact ggccgagtgc agtggctcat     72240
gcctataatc ccagcacttt gggaggctga ggcgggcaga tcacctgagg ttgggaattc     72300
aagaccagtc tgaccaatgt ggagaaaccc catctctact aaaaatacaa aattagctgg     72360
gcatggtggc acatgcctgt aatcccagct gtttgggagg ctgaggcaga acaatctctt     72420
gaacccggga ggcggaggtt gcggtgagcc gagattgccc cattgcactc cagcctaggc     72480
aataagagtg aaactccgtc tcaaaaaaaa aagaatatgg tatcaccttc aaaaactatg     72540
aagacaagac agagaacgta gtccatttag caaaaaataa gacaaagac caactatata     72600 aattataata aatataaaga ggatagacca ttaaaattag aaaaactcaa aaccaagtat     72660
ataatgttga taagagattc atctaagttg ggcctggtgg tgtgtgcctg tagtcccacc     72720
tccttgggag gcagagtgga aggatcactt gaacccagga gttcaaggct gtagtgcact     72780
atgatcacac ctggaaatag ccattgcact ccagcctgag caacatggca agaccctgtc     72840
tctgaaaaaa gattccatta aaacagtgtc acaaaaaagt taaaactaaa tggatggcga     72900
acatattaaa aaaaataaaa aacaggccag gcatggtggc ttatgcctgt aatctcagca     72960
ctttgggagg ctgaggcacg aggactgctt gaacccagga gttcaagacc agcgtgggca     73020
acagagtaag acctcgtccc tactaaaaat aaaagaaat tagctgggaa tggtggcaca     73080
tgcctgtagt cccagctact caggaggctg aggtgggagg atcgcttgag cccaggagtt     73140
tgaggctgca gtgagccgtg attgtgccac tgcactccag cttgggtaac agggcaagac     73200
cctatctcaa aaaaaaaaa agagtaaaat ttaaaaaatt aaagaataa aaacaaaag     73260 aaagctggtg tcactgttgt aatactggac aaagaattta gggcaaagtt atttttacat     73320
tgataacata caatttacgt taacaacatc tggcaataac tctgatgtac caacaacact     73380
```

```
gcatttaaaa taattaaagg cttttagaaa tataagaagt cattcaggga aacataattt   73440
tagaagcaaa tggtaaaatg actcttctag tctttggcag gtcaaagaga taacaaagag   73500
gacttaaaca ccaaaataag gccgggtgcg gtggctcacg cctgtaatcc cagcactttg   73560
ggcggccgag gtggatggat cacgaggtca ggagatcgag accatcctgg ctaacatggt   73620 gaaacccgt  ctctactaaa aatacaaaaa attagccggg cgaggtggcg ggcctctgta   73680
gtcccagcta ctcaggaggc tgaggcaaga gaatggcgtg aacccaggg  ggcggagcct   73740 gcagtgagcc gagatcgcac cactgcactc cagcctgggc gacagcgaga ctcccgtctc   73800
aaaacaaaca aacaaacaaa caaacaaaaa accaccaaaa taaaatgaaa aagctatata   73860
tagctgggcg cggtggctca cgcctgtaat cccagaactt tgggaggcca aggtgggcgg   73920
atcatctgag gttagaaatt cgagaccagc ctggccaaca tggcgaaacc ccatatctac   73980
taaaaataca aaaattagca gggtgtggtg gcatacgcct gtaatctgag ctactcagga   74040
ggctgaggca ggagaatcac ttgaacccgg gaggcggagg ttgcagtgag ccgagatcgt   74100
gccactgcac tcccgcctgg gtgacagagc aagactgtat ctgaaaaaca aacaaaaact   74160
atatacgagt ttatattgga taaataacat ctatgctagc acaaattcat atcatatatt   74220
gttagtgaaa aaacatttta aaattcctaa aagaaagaa  attaaggccg ggcttggtgg   74280
ctcacgtcta aatcccagc  actttgggag gccgaggtgg gcggatcacc agacgtccag   74340
agttcgacat cagcctggtt aacatggtaa accctgtctc actaaatata caaaattag   74400 ctgggcatgc tggcatgcgc ctgtaatccc agctactcag gaggctgagg caggagaatt   74460
gcttaaacct gggagatgga gggtgtagtg agccaggatc gcactgctgc actccagcct   74520
gagcgacaga gtgagactcg gtctcaaaaa aaaaaaaaa  gaaagaaatt aaagatacat   74580
cttctgacct caaaataata aaactagaaa ttggaaacta agaatatgaa gattaaaagc   74640
ctcaactaat ttgaaatttt aaatacaagg tactgaggac agggagaaac taaattataa   74700
ttatagatga ttcagataat aactttaaat gttatcaaac attaatttaa aaaattgcat   74760 attccttta  ttatttattt atttatttat ttatttgttt gtttgtttgt ttttgagaca   74820
gagtctggcc ctctcgccca ggctgaagtg caatggcacg atctcggctc actgcaacct   74880
ccacctcctg ggttcaagca attcccctac ctcagcctcc cgagtagctg tgactacagg   74940
cacacaccac cacacccagc taatgttttg catttttagta gagatggggt ttcaccatgt   75000
tggccaggat ggccttgatc tcctgacctc gtgatctgcc cgcctcagcc tcccaaagtg   75060
ctggaattat aggcatgagt caccacgccc ggccacgcct ggctaatttt tgtattttta   75120
gtagagatgg ggtttcacca tgttggccag gctggttgga actcctggcc tcaagtaatc   75180
cacttgccta ggcctcccaa agtgctggga ttacaggcat gagccaccgc gctcggccga   75240
gtattccttt ttttttttt  ttttttgag  acggagtctt gctctgttgc ccaggctgga   75300
gtgcatggag tgcagtggcg cgatctcggc tcactgcaag ctctgcatcc tgggttcaca   75360
ccattctcct gcctcagcct cccgccaccg cgcccagcta atttttttgta ttttagtaga   75420 gatggggttt caccatgtta gccaggatgg tctcgatctc ctgaccttgt gatccgcctg   75480
tctcagcctc ccaaagtgct gggattacag gcgtgagcca ccgtgcccgg ccctcggcgg   75540
agtattcctt ttaaaagcta caaaaataaa acagttccaa gaaaatatta ggaaaatttt   75600
aaaagagaaa ttattgtaga caaagaagg  aaataaattta aagcaaattt agggcccggc   75660
ctggtggctc acacctgtag tcctagcact ttgggggggcc gaggtgggca gattgcctga   75720
gctcaggagt tcgagaccag cctgggcaac atggtgaaac cccgtctcta ctaaaataca   75780
```

```
aaaaattagc tgggtgtgac ggtgggcgcc tgtaatccca gctactcggg aggctgaggc   75840
aggggaatcg cttgaatccg ggaggcagag gttgtggtga gccaagatca tgccactgca   75900
ctctatccag cctggtgaca gagcgagact ccctctccaa aaaaaaaaaa aaaatttaga   75960
actgaaaaaa gccagttacc tgatttggaa aacaccataa agcagatgaa attcaagtac   76020
agtctaaaac agacttagaa gagattttaa ttttttcttct tttagtaaag tgggggtctt   76080
gctatattgc ccaggctggt cttgaattca tggcctgaag cgatcctgct gcctcagccc   76140
ccaaagctct gggattacag gcataagcca ctgtgcccag ctttcattta ctattatcac   76200
tactgggact tcatcaaggg taccaattta atattaagta tattaaaact aagagatttc   76260
cataactgga aataacaagt tagaatcagg atagatattt cattcacaag agcagcaaaa   76320
aaataatatt cacaagaatt tgacagaata attataaatt ctaaatttct tctggaagaa   76380
taaatacaaa actgaagaaa caagggagg ccaccagata gatcacaaag ctaaattagt   76440
taaaactatg gctggcatgc atttattcat tcagcaagtc ttttttttttt tttttctttt   76500 ttttgaggct gagtctcact ctgccgccca ggctggagtg cagtggtgag atctcggctc   76560
actgtaacct ctgcctcctg ggttcaagcg attcttgtgc ctcagcctct cgagtagctg   76620
ggactacagg catgcgccac tatgcctggc taagttttgt attttttatag tagagactgg   76680 gtttcaccat gttggccagg ctggtctcaa aactcctaac gtcaagcaat ccacctgtct   76740
tggcctccca aagtgctggg attataggtg tgagccacag cacctggcct gtaatttttat   76800 ttttgaaaac actggttcaa ttgaaacaaa ataccttatc ccacgattgc ctttacaagg   76860
tgaatgaatg tgtcttcttt gtttaaggtc aagatccaaa gctttggaca gtgtactgta   76920
ctgttcacca gctgacactc aaaggaagat gcagttttga agttcactta ccaactttga   76980 gaaaagttttt tagttccaag ggtcgcagca ctggttgttt ttctatacga ccgtaggttt   77040
ctgctatgct ttctacttcc actttagggc atttaaatag ctcataagtc ccatctcggt   77100
tctggataaa gctacgggtg atttccaagg gcatctggac accaagacaa taccaaaaaa   77160
aggtgagaga gaaaactttc aaaacagacc aatacctgga tgacgacaaa tcttttatta   77220
ttccttcttt cttgttaagt atattcaaat gaattacaac ttccctgttt ttcaagaaaa   77280
tcctgtcaac aaatctgcct tttctcccctt acatcattca tggctttcct ttttttctcta   77340 aaatcttaaa tttccacccc agccaaacta tataccaatt gagcctctaa catcttcatg   77400
ggtacatgac tgctgctggc acagacctgc tctaaaatca gtttcattcc ttcccctact   77460
gctctgctag cagcattctt ctcttaaatt cctttgttca tagcacctgc agctcacctc   77520
acatcctgta tgcttcatac tgtccttggg actgagccaa gcagaactgg aactggatgc   77580
tgtggtgacc cagagcaaat tacaaacttc tcagagcctg ttttctcacg ggcaaaatgc   77640
agttaatgcc agggcatggc tgggaggtca aatgaggtga cggaggtaag taatgcctga   77700
cagtgagaag ctccatgatg gttagctcta ttctcccaca tgcctgcacc ctgagttgct   77760
tcagtgtctc cctaaatgtc atccattcca ggctaaaaac tgcctctgtg ccatgtgcat   77820
ttaaaggagt tcctcaagtg ttttttaatgc caacacagcc ctttctagg gttcacatgt   77880 atttactttt tttaagaggc aaggtcgcta ggagtggtgg ctcacgcctg taatcccaga   77940
actttgggag gctgaggtag gcggatcacc tgaggtcggg agtttgagac cagcctgacc   78000
aacatggaga aacctcatct ctactaaaaa tacaaaatta gccaggcgtg gtggcagacg   78060
cctgtaatcc cagctactca gaaggctgag gcaggagaat cgcttgaacc tgggaggtgg   78120
```

```
aggttgaggt gagccaagat cacatgattg cactccagac tgggccacaa gagtgaaagt    78180
ccgtgtcaaa aaaaaaaaaa aaaaagagt caaggtctca cttggttgcc cctgctggag    78240
tacagtggca caatcatggc tcactgtagc ctccaactcc caggctcaag tgatcctctt    78300
gcttcagctt tcttagtggt tgggactata ggcacacacc accaggcctc acttttttt    78360 ttttttttt tttttggaga tggagtctag ctctgtcacc caggctagaa tgcagtggca    78420
cgatctcagt tcactgcaac ctccgcctcc caggttcaag tgattctcct gcctcagcct    78480
cccgagtagc tgggattaca ggagcaagcc accacgcccg gctaatttttt gtattctagt    78540 agagacgggg tttcaccatg ttggcgaagc tggtctcaaa cccctgacct caggtgatct    78600
gcccaccttg gcctcccaaa gtgctgggat tacaggcatg agccacctcg ccagcctctt    78660
ttgctttctt tctttctttc tttttatttt tttaagagta ggggcctttg ctggcctggc    78720
gcactggctc acgcctgtaa tcccagcact ttgggaagcc aaggagggtg gatcacctga    78780
ggtcaggagc ttgggaccag cctggtcaac atggtgaaag cctgtctcta ctaaaaatac    78840
aaattagctg ggcaggatgg tgcgcttgta atcccagcta ctcgggaggc tgaggtggga    78900
gaattgcttg aacctgggag gcagaggctg cagtgagcca agattgtgcc ctgcattcca    78960
gcctagacaa cagagtgaga ctctgtctca aacaaaaaaa aaatagtagg ggcctcgctg    79020
tgttgcctag gctggtcttg aactcctggc ctcaagcaat ccttcatctc agcctcctaa    79080
atcgctggta ttatagccac catgcctggc tcacatgtaa attctgtagc tatcaaacaa    79140 cttattttt tttcctgaac agaagaatgc cttgcaatta agctactctt aatgtatcaa    79200
atcacattat gctgaattt ctactttttt ggagacgaag tctcgatctt gtcccccagg    79260
ctggagtgca atggcgcaac ctcagctcac tgcaacctcc gcctcccggg ttcaagcgat    79320
tctcctgcct cagcctccca gtagctggga ttacaggtg cctgccacca tgcctggata    79380 attttgtat tttagttgt gacggggtt caccatgttg gccaggctgg tctcaaactc    79440
ctgacctcag gtgatccacc tgccttagcc tcccaaagtg ctgagattac aggtgtgagc    79500
caccgtgcgc ggcctgaatt ttctacataa ttctattact gtaggaaaaa aaactccatc    79560
tcagattttc aggatctact tgaaaaacat acatacatat atatttttg agacagcgtc    79620 ttgctctgtc gcccaggctg gagtgcagtg gtgcgatctc ggctcactgc aagctccgcc    79680
tcccgggttc acaccattct cctgactcag cctcccgagt agctgggact acaggagcct    79740
gccaccatgc ccggctaatt ttttgtatt tttagtagag acggggtttc actgtgttag    79800
ccaggatggt ctcgatctcc tgacctcgtg atccacccgc ctcggcctcc caaagtgctg    79860
tgattacagg cgtgagccac cgcacccagc ccgaaaaaca ttttaaaatg tgtaagacag    79920 gcacagggge tcacgcctgt aatccatgca ctttgggaag ccaaggtggg cggatcactt    79980
gagatcagga gcttgagacc agcctggcca acatggcaaa accctgtctc tactaaaaat    80040
acaaaaatta gccaggcatg atggtgcgtg cctatagtcc cagctactca ggaggttgag    80100
gcatgagaac tgcttgaacc tgggaggtgg aggttacagt gagccgagat cgtgccactg    80160
cactgcagcc tgggcaacag agcaagagac tctgtctcca aaaataaaa ataaaaacat    80220 aaaatgtcta gtgtggctgg aagaggcaga ttacacctgt aatcacagta ctttgggagg    80280
ccaagatggg aggactgctt gaacccagga atttgagacc agcctgggca acatagcaag    80340
accctatctt aaattttttt tttttttaa ttaatagggt gggcctggtg gctcatgcct    80400
gtaatcccag cactttggga gactgcggca gacagattgc tcgagtccag gaatttgaga    80460
ccagcctggg caacatgggg aaaccccatc tctacaaaaa ttagctgggc atggtggcat    80520
```

```
atgcctgtag tccaagctac tcaggaggct gaggtgggag gatcacttga tcccaagagg   80580
tggaggtaga gtgagccgtg actgcaccac tgtactccag actaggcaac agagtaagac   80640
tctgtcccaa aaaaaccaaa attcaaaaaa aaaagaccaa aaaaaaattt tttttaaagg   80700
gtcatttctc gggcaggcac agtggctcat gccttgtaat cccagcagtt tgggaggatc   80760
atgaggtcag gaatttgaga ctagcctggc ctacatggtc aaaccctgtc tctactaaaa   80820
atacaaaaat tagccgggta tggtggcacg tgcctgtaat cccagctagc cggggggctg   80880
aggcaaggga attgcttgaa cccgggaggc agaggttgca gtgagccaag attgcgccac   80940
tgcactccag cctgggtgac agagcaagac tccatcccaa aaataaaata aaataaaata   81000
aaaagggtca tttctctaat gagaacaaag ctgtagtttg gggaggaggg tttaactgtg   81060
ctggtgccac tgacttcaca aatattatat catctcaaat tatttatata ctttctagct   81120
gcctgccagt caaatctagg actcatcata agtattaggg gatcattatt taatttataa   81180
gaaaaattat gttttttttaa tcccaaaggc aaggaaaag tatattccaa tttaagatac   81240 tttttttcaag ccatagggaa cacacattaa aattggagtc agaactataa agccagggat   81300
atttctgaat atctcttagc atgaaaaaaa gaaactctgg tgtctgtaac tcaaggaacc   81360
agtgcaaata tagtccctgt acttgcctcc ctctcttccc ttcacaaccc tcccactgtt   81420
atagaaataa actctcacct ctggggtatc taagatttgt ttaacttgca ggatattagt   81480
gatatgccaa gtatacttgg aaaaggttcc cagtggcaag gcatctttcc gaacaaaagc   81540
ttcaacgtga aaaaggaca aaattagatt accaaaaaat aacatttttct tttgttgtat   81600 ttgttaccta gtttctaata cagtactatt atttccttat agattctcag cacttttaaa   81660
aagaaattct agaggcaaat atataaaagg ttttggtgac aaatcagttg atgtagataa   81720
ttgatatgct gatcattgaa ggctttgtgc tccagacatg tgagtagaag tcctaactct   81780
gaatactcac ggtgaatatt ccacacagat tttttccaaa cataattctc tatgttcgag   81840
acatccatca ctataccaaa gggaaatcct gtacctgtgg tggagttggg gagccgtttt   81900
tttgcacttc ctatagatat tctttgttgc agggcatcaa aaaatgactg aggaatgtgg   81960
aacaccaatg gttctggttt gcctatggga aacaagaaga aacaactcat ttaaagaaac   82020
tcagtggact ttctgatgta cagggagagg tgaaagaaaa ggaatcaagg gacggtaata   82080
actaaaaata ccactgagat ttcttttatac agagcaaaa agaaggcttt gattgacctt   82140
tctgggccaa gaactgtcac tagtcctact gttgatccct tgcaaacata aaaaacacag   82200
tgtagcctgg gcaacaaaga aagacccagt gtctataaaa aaaaattttt tttttgagat   82260
ggagtctcac tctgttgccc aggctggagt gcaatggcat gatctcggct cactgcaacc   82320
tctgcctccc gggttcaagc aatcctcctg cctcagcctc ctgagtagct gtgactacag   82380
gcgtgcacca ccacgcctgg ctaattttg tattttttagt agagatgggg tttcaccatg   82440
ttggccaggc tggtctcaaa ctcctgacct cgtgatccac ccacctcggc cacccaaagt   82500
gctgggatta caggcgtgag ccaccgtgcc tggccaaaat tttttttaa attagccagg   82560 cgtggtggta tgcacctgct gtcccagcta cttgggaggc tgaggtggga ggatcaactg   82620
agtcgaggag gttgaggctg cagtaagcca tgatcacgcc actgcactcc agcctgggca   82680
acagagtgag accctccctc aaaaaggaaa aaaaagaaa agaaaagaga ggccaggcgt   82740
ggtgactcac acctgtaatc ccagcacttt gggaggccga ggtgggtgga ttacctgagg   82800
tcaggagttc gagaccagct tggccaacat ggtgaaaacc catctctact aaaaaaaaaa   82860
```

```
aaaaaaaaaa aaattagctg gcatggtgg tgtgtgcctg taattccagc tactcaggaa    82920
gctgaggcag gagaatcgct tgaacccagg aggcagagt tgcagtgagc cgagatcatg    82980
ccactgcact ctagcttggg caacaggtg agactccact gaaaaaaaag aaaaaagaca    83040
atgaaaaaac aaaccaacac agtagaccct tgtcatccac caagtataac atttcaaatc    83100
cgcaaatttt aaaagacca acacagcaca gactttcccc cttaaagggt atgcgaagta    83160
agatgggatg agaacaatga ggccgagtg gctgcctcca cttgattccc ttttgctcgc    83220
tatccccagg ttcttgctat ttgcattcat gtctaagcaa actaatgaca tgctctctca    83280
cccgatggtc agcaccatga atgctgaggg actacaagtt aggacactgc ttacccagca    83340
agcatctgtc tttctctctg aatatgacct caaggcaggt aaaatacttg aaagtactta    83400
accaacctct taaagaacct tgcggccagg cacagtggct cacacctgta atcccagccc    83460
tttgggagga tgaggcaggt ggatcaccag gtcaggaaat tgagaccatc ctggctaaca    83520
tggtgaaact ccatctctac taaaaataca aaaattagc cgggcatggt ggcatgcgcc    83580
tgtagtccca gctacttggg aggctgaggc aggagaatcg cctgaacctg ggaggcggag    83640
gttgcagtga gccaagatca cgccactgca ctccagcctg ggcgacagag tgagactctg    83700
tctcaaaaaa aaaaaagaa aagaaacttg tcagacatta ggtcaacaaa aagagttaag    83760 gggaggggt caagtgagtt cagtcttcct taaaattct gtccagacca ggtgtggtgg    83820
ctcacacctg taattccaac actttgggag gccaggcag gcggatcact tgaggtcaga    83880
agttcgagac cagcctggcc aacatggtga accctgtct ctattaaaa tacaaaaatt    83940 agccaggagt ggtgacacat gcctataatc ccagctactc aggaggctga acacgagaa    84000 tttcttgagc ctgggaggtg gaggttgcag tgaactgaga ttgtaccact gcactccagc    84060
ctgtgtgaca gagcaagact gtctcaaaaa ataaaaaaga attaacttca aaaggtaaa    84120 acacacacac tcatagtcaa ggagcgagct gatggaaacc tggacaaagg tggtagtaat    84180
ggagatggta agatggaata gagggtggta caggaatggg atggaagagg gaataggatg    84240
ggatggaaga ggactacaag tgtttagctt atagtattat caatattctg ttttctgggc    84300
tgggcacggt ggttcacgcc tgtaatccca gcactttggg aggccgaggt aggtggatca    84360
cctgaggtca ggagttcaag accagcctgg ttaacatggt gaaaccccat ctctactaaa    84420
aatacaaaaa attggccagg catggtggtg cgtgcctgta atcccagcta cttgggaggc    84480
tgaggcagga gaattgcttg aacctgggag gtggagatta cagtgagcca agatcacgcc    84540
actgcactcc agcctgggcg acaagtgatt cacctacctc agcctcctga gtagttggga    84600
ctacaggcct ctgccaccat gcccagctat aggatccttt tttttttttt ttgagatgga    84660
gtctcactta gtcacccagg ctggagtgca gtggtgcaat ctcagatcac tgtaagctcc    84720
acctcctggg ttcacgccat tctcctgcct cagcctcccg agtagctggg actacaggca    84780
cccgccacca cacctggcta attttttgt attttagta gagatgggt ttcactgtgt    84840 tagccaggat ggtctcaatc ttctgacctc gtgatccgcc cgcctcagcc tcccaaagtg    84900
ctgggattac aggcatgagc caccgcaccc ggctgctaat aggatacttt taaggcaaca    84960
agcagagact ggctagatct gaaactggtg acgttccatg agactataac aaataacacc    85020
caaatccagc ctgtgttctc caatcttcct cagcatgttt atgtcccttt tttttttttt    85080
agatggagtc tcactgttgc ccaggctgga gtgcaatggt gcgatcttgg ctcactgcaa    85140
cctccgcctc ccgggttcaa gcaattctcc cacctcagcc tcccaggtat ttgggactac    85200
aggcacccac tataatgcct ggctaattgt tttgtatttt tagtagagat agggtttcgc    85260
```

```
catgttggcc aggcttgtct tgaactcctg acctcaagtg atccgcccac ctcggcctcc    85320
caaagtgtcg gattacaggt gagagtcacc atgcccggcc agtatgttta gtaattctat    85380
ataactatct tagtctcatg tgtttagatt ttcaattttt cttttttcca tacagggtct    85440
cgcttcgttt cccaggctgg agtgcaatgg cactattttt tgtagagatg gggttcacta    85500
tgttgtgcag gcttagattt tctctaatct ttttccctt tgctttaagt ttgagagtta     85560
gaatagtctc ataaagcttc agtatctccc tcaccacaca cacacacaca cacacacaca    85620
cacacacacg tgcacacgaa cttatgcaag caataagact acctgccttt acttattatt    85680
tgctatgttt tttctcttct gtctctaaat tataataatt ttgctgcgcc tgaattttaa    85740
ctatgtgatt gttttttttct ttcaattaga tttctacttt cttgtggccc agtgctctct   85800
ggactgaagt ccaattactt ttcctatcag aggagaatta cagcacaatt acctaatttt    85860
ctcctacttt cagcaagagc ccagttagat gaacaatact taccatcaaa ctgatagtgc    85920
atggtttgat ggatgcgttc tgtgacactg gccagccagt cttggaagga taaagtcact    85980
tgtgcctcat ctaacagctg accacaggct agggaaaaaa aaaccacaca tacacacttc    86040
tttagtaact tttcttacaa aataaacagc taattgaagt ttgaaaaagt taacaagttt    86100
ttttatttt attttatttt tttgagacag aggttcgccc ttgttgccca ggctggagtg    86160
cagtgcacaa tctcagctca ctgcaatctc tgcctcctgc gttcaagcga ttctcctgcc    86220
tcagcctcct gagtagctgg gattacaggc accgccacc acacccggct aattgttgta     86280
tttttagtag agatggggtt tcatcatgtt ggccaggctg gtctccaact cctgacctca    86340
ggtgatccac ctgcctcggc ctcccaaagt gtagggatta caggcgtgag ccaccgcgcc    86400
cggcctgttt tttatttatt gacaaggctt tgtcatgttg cccagctggc ttcgaactcc    86460
taggctcaag caatccacct gcctcagcct tctgaagtcc tgggagaagt gttaataagt    86520
ttgtccagaa aaaaaaaaa aaaacttgaa gctgaacttc aaagaaagca aataaactaa    86580
gtgaaataag atattctggg attttttttt ttttcttcag tctcactctg tcgccctggt    86640
tggggtgaag tggcatgatc tcagctcact gcaacctcca cctcccaggt ttaagcgatt    86700
ctcatgcctc agcctcctga gtagctggga ctacaggtgc gtcaccatgc ccagccaatt    86760
ttgttttctt tttaatagag acagggtttt tgccgtgttt cccaggctgg tctcaaactc    86820
ctggcctcaa atgatctgca cgccttggcc tcccaaagtg ctggattaca ggcgtgagcc    86880
acctgaggtc aggaattcaa gaccaggctg gccaacatgg tgaaacccc gtctctacta    86940
aaaatacaaa aattagctgg gcgtggtggc atgcacctta atcacagcta ctctggaggc    87000
tgaggtggga gaattgcttg aacccgggag gcggaggttg cagtgaactg agatcgtgcc    87060
acagcactcc agcctgggca agagtgagac tctaaaaaaa aaaaagaaa aagaaaatac    87120
gaaatgagaa gcaacactaa actgcatata aaagaatggt cctatataat gactgtttta    87180
ggctgggctt ggtggctcac gcctgtaatc ccagcacttt gggaggccga ggcgggtgga    87240
tcatgaggtc aggagatcga gaccatcctg gctaatacag tgaaacccg tctctactaa     87300
aaatacaaaa aattagccag gcgaggtggc aggcacctgt agtcccagct actcgggagg    87360
ctgaggcagg agaatggcat gaacccggga ggcggagctt gcagtgagcc gagattgtgc    87420
cactgcactc cagcctgggt gacagagcga gactccatct caaaaaaaaa aaattaacct    87480
ggcatggtgg tgcgtgactg tggtcccaac tactcaggag gctgaggtga gaggattgtt    87540
tgagcccagg aggcagaggc tgcagtgagc cgagatcatg cctctgcact ccaggctggg    87600
```

```
tgtagagtga gaccccatct caagtaaaaa taaataagta aataaataaa aataatggct   87660
gttttagagg tttataaatt agttttattc ctgatgaaca tgtatccata tgccccagac   87720
cctctcaata atgaacatat tctttcatgc caaggttgac cacaaataga tgactgagtg   87780
atgcacgcac tgtgggttgc aatgataata ccttttagact taaaacctaa aaccttgtat   87840
tcagaaatgt aaaatgaatg aattcacttt tttttgagac cgagtcttgc tctgttgccc   87900
aggctagagt gcagtggcat gatctcagct cactgcaacc cctgcctccc gggttcaggc   87960
gattctcctg cttcagcctc ctgagtagct gggatttaca ggcacctgct accgtgcctg   88020
gctaattttt gtattttag tacagatggg gttttgacat cttggtcagg ctggtcttga   88080
actcctcacc tcgtgatcca accacctcgg cctcccaaag tgctggcatt acaggcatga   88140
gccactgcac ccagccaaat tcactcttaa atataagtga aagagtgaaa tcttgcagcc   88200
ctggagtaaa taactggaaa aaacagtaac gagtgatgga atttaatgga gccagagttt   88260
agaggtcgga gtcaaaaggc tatgggaagc tgggtgcagt ggctcacgcc tgtaatccca   88320
gcactttggg aggccaaggc gggtggatca cctgaggtca ggaattcgag accagcctgg   88380
ccaacatggt gaaaccctgt ctctactaaa aatacaaaaa attagccagg cgtagtggtg   88440
tgcgcctgta atctcagcta ctcgggaggc tgaggcagga gaatcgcttg agcccaggag   88500
gcggaggttg cagtgagctg agattgtgcc actgtactcc agcctaggcg acagagtgag   88560
actctgtctc aaaaaaaaaa aaaaaaaaa ggctatggga cctaggatcc ccacccactg   88620
agtgacgagg gtccatatct caagttcctc tcttctaaga tgaagatatg catctggata   88680
tctccaaatt caagagcctt ccacagatct atcattctat ttcttttctt aaaatatctt   88740
tattccgggc acgtggctc atgcctgtaa tcctagcact tgggaggcc gaggcgggtg   88800
gatctcttga gcccaggagt ttgagaccag attgggcaac atgacgaaac tccgtctcta   88860
ctaaaaatac aaataaataa tcaagtgtgg tggcatgtgc ctgtagtccc agctacttgg   88920
gaggctaagt tgggaggata atttgagccc agaaggctgc agcgagctgt atccccgcca   88980
ctgcgctcca gcctgagtga cagagcaaga cctgtgtcaa agaaaaacac aacaaaaaaa   89040
taccgccaac aacaaaatat cttcacgtgt ctgaagtaca gtatcacctt ttgtagagat   89100
aatgcctcaa tgactattca tttaaaacta agattatcag aggtaaaggc atacagtgac   89160
aatttagatt gaagctacct tcctttttct ttgcaccaaa ggaagtgaca aaaaattatt   89220
aaaaatcagc caagcacagt ggctaattgc tataatccca gcactttggg aggccaaggc   89280
aggcggatca cttaaggcca ggagttcgag agcagcctgg ccaacatagc aaaaccccat   89340
ctctaccaaa aatacaaaaa ttagaagggt atagtggcaa atgcttgtga tcccagctac   89400
ttgggaggct gaggcacgag atgaacctgg gaggcgaagg ttgcagtgag ctgagatcac   89460
gccattgcac tccagcctgg gtgacaaagc aagactctgt cttgaaaaaa tatatgtata   89520
taaataataa aaaaacctat ttgatgctgt tgatctgctt actttgtgac tttccttaaa   89580
cacttatgcc tagaatgcct aagtgcgtaa gttctttttt tttttttttt tttttttga   89640
gacggagtct cactctgttg cccaggctgg agtctagtag catgatcttg gctcactgca   89700
accttcacct tccaggttta agcgattctc ctgcctcagc ctcccaagta gctgggatta   89760
caggcacatg ccaccatact tggctacatt tttatactt tttagtagag acagggtttt   89820
accatgttgg ccaggctggt ctcaaactcc tgacctcaag tgatccatcc gcctgcctca   89880
gcttcccaga gtgctgggat cacaggcgtg agccaccgtg cttggtcata agttcttaat   89940
gaattactta attagtattg ttttatatta ttcttttttt tctttatttt agacaagatt   90000
```

-continued

```
tcatcctgtt acccgtgcag tggtgcaatc atgactcact gcagcctcga catcccaggg   90060
tcaagcaatc ttctcacctc agcctcctaa gtagctgagt ttacaggcat gtgacacaac   90120
acccagctaa ttttttttg ttttttgtgt ttttttggt agagatggag tctcactact    90180
cctacctcgg cctcccaaag tgctgggatt ataggcgtga gccaccacac ccagtcacat   90240
aaaacgcctt tttccttcaa ctttgaatct ctataccaat tgcacatgag taataagcaa   90300
taagatgaac acatcctgca agacacctgc tgctaaacat gtcagaattt ttttgtttaa   90360
agacataatt taggccagtc gtggtggctc acacctgtaa tctcagtact ttgtgaggct   90420
gaggtgagca gatcacttgg ggtcaggagt ttgagaccag cctggacaac atggtgaaac   90480
cccatctcta ctaaaaatac aaaaattagc cgggcatggt ggcgtgcacc tgtaattcca   90540
gctacttggg aggctaaaac aggagaatcg cttgaaccca gaggcggagg ttgcagtgac   90600
caagatcatg tcattgtact ccagcctggg caacagagtg agactccatc tccaataaat   90660
aaataaataa ataaaaataa atacaataaa ttactttta aggtaattgt acattcacac   90720
gcagttgtaa gaaatataag gcttctatac ccttcatccg gattcaccca agagtaacat   90780
tttgtaaaac tatagtacat cacagtcagg aaaatgacat ggttacaatc tagtgacctt   90840
attcacatct caccagcttt atgtacttgt gtgtggtatg catgcatata gttccatgca   90900
attttagggc atgtgtagac ttgtgtgacc aacaccacag tcaagacata aaacagtcca   90960
tcacaaagac tccctgtgct actcttttat tgctgctgtt acaaccctcc caaccccctc   91020
tttcttttt ttttgagact aagtcttgct cttattgccc aggatggagg aaaatggtgc    91080
gatcttggct cactgcaacc tctgcctccc gggttcaagt gattctcctg cctcagcctc   91140
ttgagtagct gggattacag acgtctgcca ccacatctgg ctaatttttt ctatttttag   91200
tagagacagg gtttcaccat gttggccaga ctggtctcaa actcctgacc tcaggtgatc   91260
tgcctgcctc agtctcccaa agtgctggga ttacaggcgt gagcaccgtg ctcagcccca   91320
acccctctt taaatcctgg caactactaa tctgttctct atctttatgg ttttagacat    91380
aatttagttt ttttttaaaaa ttattttttt aaattaaaaa agattattc atcacccagg    91440
tatttttaaa atttaattac acatatgttt tgtttgtttg tttgtttagg tagagacagg   91500
gttttgccac gttggccagg ctggcctcga actgctggcc tcaagtaatc cacctggctt   91560
ggcctcccaa agtgctggga ttacaggcat gtgccatcac acccagcctc atcacccagg   91620
ttattaagcc tagtatccat tagttatttt tcctgatcct ctcacccct tccacctttc     91680
ctccctcctc ccacgtttca ccctccaata agcccagtg tgtgttgctc ccctctatgt    91740
gtccatgtgt tctcatcatt tagctcccac ttataagtaa gaacatactg tatttggttt   91800
tctgttcctg cattagtttg ctaaggataa tggcctccag cataatttag ctttgagcat   91860
gatttgaaac tggtgggaca ggagggacct cagcctcagt gcttctgtta gtatttatgc   91920
tgggactctt tgggtgacaa tgtgcatgat tatactgctt ctggcttctt taggatgact   91980
ttccaccact gtagcctatt ctagggaagg gaaacttacc ctgccttttt aacgaggaag   92040
caaccacagg cttttcagg ccactttcc ttagattact gctcactgca tcttgaggca     92100
gtagtgaact gttcatctgt gcacctaaac cacaaatcat tacaggttta acaatgtatc   92160
tgctaaatat aaattgattt gatgttaatt tttagagtct aaaacatata aacagtcttt   92220
gctaatttct aggttagctt cacagttct aggagttagc attagtcttt acacataaaa    92280
ttttagcttt cttatgctct ttataggaaa ttgggtgaat aaacagaaat gaaggaaga   92340
```

```
aaaaaattca cttattgctc ccacctgtca gacaattacg atgacttttc tagtgaactg    92400
tcttccgttt tcttctctgt gaatatgtta ttggttttgt gattttttaag tagttgtgat    92460 tttaccagag ttgccaaatt tagcaaaaag aaaatgttct tttaaatttc agataaacaa    92520
caaataatgt cttagtatca aagtatgtca caaatattgc atggaaatac ttatactaaa    92580
aattattcgt tctgtaatcc cagcactttg ggaggcccag gtgggctgat catgaagtca    92640
ggagcttgag accatcctgg ctaacatggt gaaaccccaa ctccactaaa aatataaaaa    92700
attagccggg cgcggtggca ggtgcctgta gtcccagcta ctcaggaggc tgaggcagga    92760
gaatcgcctg aacccaggag gcggagcttg cagtgagccg agactgcgcc actgcactcc    92820
agcctgggcg acagagcgag actgtctcaa aaaaaaaaa aaattatttg ttaactgaaa    92880
ttcaagttta actgagtatt ctatacttta tctggctacc caagtgatct gagcattttc    92940
ccaaattctt tattatcact tgtttttaat ttttatttt tagagatgag gtcttgctat    93000
attgcccagg ctggaatgca gtggctattc acaggtccaa tcacagtgtg ctagagcctt    93060
gagctcccgg gctcaaggga ccctcctgcc tcagcttcct gagtagctgg gactacaggc    93120
atgcaccact gcacccagac tataatcatt tttatgcctg cctgatattc tatggtaaag    93180
tggctttacc atggttcatt taactatccc cagtggttaa cccttagttg tttctaattt    93240
tttaattttc taaataatca taaaatcaac atctccagac aaaatgtttt tcctatacca    93300
ataattattt ccttagaaaa gattattcag aagtggggcc gggcatggtg gctcacacct    93360
gtaatcccac cactttggga ggccgagacg ggtggatcac ctgaagtcag gagtttgaga    93420
ccagtctggc caacatggtg aaacctcatc tctactaaaa atacaaaaat tagctgggtg    93480
tggtggcgag cacctgtaat cacagctact taggagaccg aggcaggaga atcacttgaa    93540
cccgagagat ggaggctgca gtgagctgag atcgcgccat cacactgcag cctgggaaac    93600
aagagccgaa ctccacctca aaaagaaaa aaaaaaata gccaagcgtg gtggcaggag    93660
cctgtaatcc cagctactcg ggaggctaag gcagcagaat tgcttgaacc caggaggtgg    93720
aggttgcagt gagccaagat cacgccactg cacaatccag agcaagactc catttccaaa    93780
aaaaggggaa agactaataa gtaaacattt aacaacaatt tctgctctat attcctgcca    93840
gaattgcctc tctaaaatac acaaatgacc atgtcacttt gtttctccat cttttcttcaa    93900 cttcccagca ccaaaactct tgtgcatgac cacctgatcc atccctagca atatttccta    93960
taggtaggac catttttaagg atcttaacag atactacaag ctatatacca atgattatag    94020
caatgtatac tacactagcc atgccagaga gcctggattt tacctttgcc tgtggtctca    94080
tcattttaaa aaactttgcc agctgggcat ggtggcttac acctgtaatt ccaacaattt    94140
gggaggctga gacaggagga tcacttgagg tcaggagttt gagaccagcc tggtcaacac    94200
agtgaaaccc tgtctctaca aaaacaaac caaaaatta gccaggcatg gtggcttgtg    94260
cctgtagtcc cagctacttg ggaggctgag gcaggaggat ctcttgagcc taggaggtcc    94320
aggctgcagt gagccatgat tgtgcccctg cactccagct gggcaacag agtgagaact    94380 catctcttaa aaaacaaaca aacaaacaaa caaaaaaaca cacaaacttt gctaatttgg    94440
tagcaaaagg tatcctgttt taattttgca tttctaaaat gtttgcattt ctctgtctac    94500
tagtaagttt ggagtttggt ccatgggtgt ggaccaagta atattttcat tttgtttaga    94560
ctctaggtct cttgatgctt acctactagg atacttcacc attttcatat tgatttatca    94620
gagtccttaa ctgacactag tattaagcat ttgaatttaa aaatgtggcc tggccaggca    94680
tagtggctca cacctgtaat cccagcactt tgggaggcca aggcgggtgg atcacctgag    94740
```

```
gtcaggagtt caagaccagc ctggccaaca tggcgaaacc ccgtctctac taaaaataca   94800
aaaattaggc aggcatggtg gtgggtgcct gtaatcccag ctactcaaga ggctgaggca   94860
gaagaattgc ttgaacctgg gcagtggagg ttgcagtgag ccgaagatcg catcagtgta   94920
ctccagcctg ggcaacagag cgagactcca tctctaaata aataaataaa taaataaggc   94980
tgggtgcagc ggctcacgcc ttacttatta caggctcagg cctgtaatcc cagcactatg   95040
ggaagccaaa gcgggtggat cacctgaggt caggagttca agaccagtct gaccaatatg   95100
gtgaaacccc atctctacta aaaatataaa aattaactgg gcgtgcaccc ttagtcccag   95160
ctactcagga ggctgatatg agaattgctt gaacccggga ggcagaggtt gcagtgagct   95220
gagatcgcac cactgcactc cagcctgggc acagagcaa gactccatct caaaaaaaaa    95280
aaaaagaaaa aaatgtgtgt gtgggtgtgt gtatgtgtgt gtttctccat atactgaaaa   95340
tgaagacaat aacctatatt tctaaattag tgtggggaat ataaccattg tcacaaaatt   95400
tttttaaaca ctctatggat gaaaacttca taatactatc ctaaggcaga ttaaggtata   95460
aaattaatct gtttaaggga tgtacaaaca tatacagtaa aagtagaatt tggttggatc   95520
ttatttttgg ctaagggatc aaacttttag cttaacttga aaaagaatca tcaatggaga   95580
gtaaaacttt tctcaggaaa aaaacccata agaacaaaaa cataatattt cttggccagg   95640
tgtgatagct cacacctata attccagcac tctgggaggc caagatggga gaatcactta   95700
aggcctggag ttcgaggcca gcctgggcaa gatggtaaga cccctgtctc tttattttaa   95760
taaaaataaa ataaaatata gtattttctt ataattgctg aggttcagtc aaagacataa   95820
aacgcagtaa aacaatctct aaagacaata ccaccaaacc aaccaaccag actcttacca   95880
gatacttcat cctttctcct cttctttgac ttagaggcag tagactcaca agcagatact   95940
gttgattctg aatggcaacc taactggggt acaataatct ctttaagacc taaaaaaaag   96000
aagatttctg aattattaat cctatccaag ggtaagtata agtataggcc tctatgtagc   96060
gaaaagttaa tttctttta aaaatccccc aaacgaatta tcccaggctg gcaacatag    96120
gcagaccccca actctacaaa aaataaaaaa ttaccacgcc tgtgttccca gctactcgag   96180
aggctgaagt gggaggatca ctttagccca ggagggtcaa ggctgtaatg agccgtgatt   96240
atgtcactgc atgccagcct gggcgacaga ggcagacgct gtctcaaaaa acaaaccaaa   96300
aacaaaaaca aaaaaaaaat tatggagtga ttgcttgttt taaaataagt tccttgggcc   96360
gggtgcggtg gctcacgtct gtaatcccag cactctggga ggccgaggcg ggtggatcac   96420
ctgaggtcag gagtttgaga ccagcctggc caacatggtg aaacctcatc tctactaaaa   96480
atacagaaat tagccaggca tggtggcaca tgcctgtagt cccagctact caggaggctg   96540
aggcaggaga agcgcttgaa cccaggaggt ggagattgca gtgagctgag attgcgccat   96600
tgcattccag cctgggtgac agagtgagac tccatctcaa taaatatata aataaataaa   96660
taagttcctt tagactgggt gcagtggctc atgcctgtaa tcccagtact ttgggaggct   96720
gaggcaggca gatcacctga ggccaggagt ttgagaccag cctggccaac atggagaaac   96780
cctgtctcta ctaaaaatac aaaaattggt caggcatggt ggcaggcgcc tgtaatcccg   96840
gctacttggg agactgaggc atgaggattc cttgaaccca ggaggcaggg gttgcggtga   96900
gccaaggttg tgctactgca ctccagcgtt tgtgatggag caagattctg tctcaaaaaa   96960
aaaaaaaaa aaaaaaatc aagagattct gtctcttgat cattaatttc aaccaaccaa   97020
ccaaccttta tgcaagtgtg ctgactgaga ctgaaagaag gaatgcaacc aggtgtggcg   97080
```

```
gctcacacct gtgatctcag cactttggga ggttgaggca ggaggactgc ttcagcccag    97140
gagttcaaga ccagcctcgg caacaaagta agacccctat ctgcaaaaaa ttaaaaaaat    97200
tagccaggca tggtggcacg tgcctgtggt cctagctatc tgcggggact gaggtggtag    97260
gatctcgagc ctgggaggtc aaggctgctg tgagctgtga tcaggccact gcactctagc    97320
ctgggcaaca aagtgagacc ttgtctcaaa aaaaaaaaaa aaaaaaaaa aaaagaagga    97380 acacttttca tttgaattat ctagcaactg tttctgaagg ttgctaagac aatctccaaa    97440
tgcatcagtg gaactctttt cattgcagtt ttagaaaaac gtaataacca catcaaccat    97500
accacctacc gctggaatca aaatttagga agtctgagaa ttcctgagcc agtgtctcat    97560
cactggcaaa ggcacagatg caagcaaaga aatgaatgca tctctgggct gtctcatcct    97620
tggaggcatt tgacttgtgc gatttcgag tctgacagga gcagaagaag cggcgctcag    97680
gcaagctttt gccactgact ttctgcacaa aagatgtatg caaataccc aaactgtgct    97740 tctggcttgc cttgcatttc accaccaaga tgtttttagt aattctctgc accagaggac    97800
ctgtgggttc cgtggccaac tgccagatgg tctgtttggt ttccggggag gcctgcattg    97860
cattcaggac cgagctcttc agggtcagag gggtggcctc tgcctggcag ttcaccgcca    97920
gcttgatgtg ctggcactgg ttttccacaa cgccttgagt ggcagctttc aggcatgagg    97980
ggacataaca ccgtccagag ctcagctgag tgatgatcgt cccatccact gtctggattg    98040
ttgtctctga aaccccgagc tccacaaagc atcggtaatc agggcccgg tctctttgcc    98100 gcactgagta gacctgaaga tcagagcctg taatgatttt gacagcttca acactaggct    98160
gcttgcgtgc accgtagcgg aatatggttc cacatgtctt gttcttacag ctcagtcccc    98220
gggttccatt gtatgtgcca catcgggac actttctgat tcccctcaat gtggccttcc    98280
ccaaatcaga taagaaagct gggactttag tcctcagaga atttggttcc attttttcaga    98340 ggccctacaa aagacaatac atccaacagt atgagtatac cttcacacac aaaaagttaa    98400
aatcacttat gatatttagt acagaaggca aaatataaaa aagctatcta ctattttttt    98460
tttttagacg gagtctcgct ctgtcgccca ggctggagtg cagcggcgcg atctcggctc    98520
actgcaacct ccgcctcctg ggttcaagtg attctcctgc ctcagcctcc cgaatagctg    98580
ggactatagg caccccgccac cacgcccagc taattttgt atttttagta gagatggggt    98640
ttgaccatgt tggccaggct ggcctcgaac tcctgacctt gtgatccgcc tgcctcagct    98700
tcccaaagtg ctgggattac aggtgtgagc cacggcgcct ggctgctatc cactattttt    98760
aaactgtacc acaaaacaac ataaatttaa acctacaaac aaaatgaaag tggaaactgc    98820 cttctcatacc tatttttta aatcctaata atcaaagcat ttctccagat ttaactctgt    98880
tctatataac aacggaagtt agttaaccta atctttacat gcccagatgt ctaacttcag    98940
caagaattag agaacatgaa agatgagttt ttttcccttc catcattccc cacaaaacct    99000
agcccaatcc tacctgtacc agctgccaag gcatctggaa aacagtgtaa cctgaattca    99060
taagacttaa aaggtgtttc attagtttct aatgatcagg tgaaaacacg atcatttgca    99120
gactaatgat aactgcttaa cccaaaatct tctgaagttt gagctgtatg gtgtaacaat    99180
gcagacattc tgcctcctcc ttctccacca gccaatggca aagcttctgc ccaatgttcc    99240
gcaaataaga ttcccacttc cctaagtgga gatcttgata gtctgcgagt aaaacaagaa    99300
aaaatattaa agttatacaa agacaggatg attcttcgt tagaaatcaa acagaatagg    99360
aatcaaagtc tttcacaatt acttgagaaa tatttgacag aaatgattat ggaaatgggt    99420
taagtgtttt gtacttccaa ctgtaaggaa ggtaaaaagg tgctaatgtc attacaaagg    99480
```

```
gggttgtcaa gaacacttta gaggtctggc atggtggctc actcctgtaa tcccagagat   99540
ttaggaagct gaggtggagg atcacttgag cccaggagtt caagaccagc ctggacaaca   99600
tagtgagacc tcatttctat aaaaaaattt aaaaattagc tgggcatggt ggtgtgcacc   99660
tgtagtccca gctacgttgg aggcagaggt gggaggatca cctgagtcca ggagagcaag   99720
gctgcaaatt gtgccattat accccagcct tggcgacaga gcaggacccc atctcttttt   99780 tttttcttc tttgagatgg agtctcactc tgctcaccca ggctgagtg cagtggcgca     99840 atctcggctc actgcaacct ccacttccca gattcaagcg attctcctgc ctcagcctcc   99900
ttagtagctg ggactacggg cacatgccac catgcccggc taatttttg tatttttagt    99960 agagacgggg tttcactgtg tttcgatctc ctgacctcgt gatctgccca cctcagactc  100020
ccaaagtgct gggattacag gcgtgagcca atgcgcccgg ccgacccat ctctttaaaa   100080 aaaaaaaaaa agaacacacc tagagctatg ttatataatt ggtcaataac tcatccttcc  100140
taatagtaat acatcacatt ttgagtgctt tatgcatttt tctgctctct tacccaggct  100200
ggagtgcagt ggtgtgatca cagcttactg cagactcaac ctcctgggct caagtgatct  100260
tcctgcctca gcctcccaag tagctgaaac tataggtaca tgctgccatg cctggctaat  100320
ttttaaaaaa ttttttggta gagacagggg tctcactttg ttgctcaggc tggtctcgaa  100380
ctcctggcct caagcgctcc tcctgccttg tcctcttaaa gtgctgggat tataagtgtg  100440
agccacacag cttcatttac tcagtaaaaa ttacagtcgg ggactagttc atagcaccaa  100500
tgaaaaggtg gacattttaa aactattctt atttgtactt tccaatttgt taatcagtgg  100560
atagaagatg tagagagaaa aaaaaattgt tttgagacag tcttgctctg tcacccagga  100620
tggagtgcag tgacgtgatc tcgattcact gcaacctccg cctcccgggc tcaagcaatt  100680
ctctggctaa ttttttgtatt tttagtagag atgtggtttc accatgttgg ccaggctggt  100740
tttgaactcc tgacctccag tgatctgccc gccttggcct cccaaagtgc tgggattaca  100800
gacatgaacc actgtgcctg gccctatttt tttttttttt tttttttttt ttgagacaga  100860
gtctcactct gttgtcaaag atggagtgca gatcatggct cactgcagcc ttgacctccc  100920
aaggtcaagc aatcctcctg cctcagactc tcaaatagct gagaccacag gtacgtgcca  100980
ctacactcag ctaattataa attttttata gagatggggg tctcactatg ttgcccaggc  101040
tggctttgaa ctcctgggct caagcaatcc tcctgcctcg gcctcccaaa gttctgggat  101100
tacaggtgtg agccaccatg cccagtggtc tctattcttc ttaaaaaatg ttttaggccg  101160
ggcgcagtgg ctcatgcctg taatcccagc actttgggag gccgaggtgg gtggatcaca  101220
aggtcaggag atcaagacca tcctggctaa cacagtgaaa ccctgtctct actaaaaata  101280
caaaaaatta gccgggcgtg gtggcgggca cctgtagtcc cagctacttg ggaggctgag  101340
gcaggagaat ggcgtgaacc cgggagacag agcttgcagt gaaccgagat catgccactg  101400
cactccagcc tgggcgacag agtgagactc catctcaaaa aaaataaaaa taaaaaaatg  101460
ttttaggctg ggcgcagtgg ctcgtgcctg taatcccacc actttgggag gccgaggcgg  101520
gtggaacacc tgagggcagg agttcaagac tagcctggcc aacatggtaa aaccctgtct  101580
ctactaataa tacaaacaaa aaaaattatc tgggcgtggt ggtgcacgtc tgtaatccca  101640
gctactccgg aggctgaggc agggaatca cttgaacctg ggaggcagag gttgcagtga  101700
gctgagatca cgccattgca ctccagcatg ggtgacaaga gtgaaattcc gtgtcaaaaa  101760
aaaagtttta aaaagactag gcacagtggc tcacacctgt aattgccagc actttgggag  101820
```

```
gctgaggtgg gagggtcact tgaggccagg agttcgagac cagcctagcc aacatgatga 101880
aaacctgtgt ctactaaaaa tacaaaaatt aggcaggcat gatggcacat gtctataacc 101940
ccagctactc aggaggctga ggcatgagaa ttgcttgaac acaggaggca gagaggttgc 102000
agtgagccaa gatcgcacca ctgcacttca gcctgggaaa cagagtgaga ctttgtcaca 102060
aaaaaaaata tatatatata cacacacaca caaacacaca cacacataca tatatacaca 102120
catatatata tatacacaca cacatatata tatatatttt aaggaaaaca agtgctttgt 102180
gaaataagat gcatagcagg gtttctccac cttggcactg ctgacattta ggactggata 102240
attctttgtt gtgggggcta tcctatgcat tgcagaatgt ttaacagtat ccctggtttc 102300
tacccactag atcccggtag caggccccat ccctaattgt aaaaaaaaaa aaaaaaaaaa 102360
agtctccaga taatgccaaa tgtcctctgg aggcaaaact gccccagtta aaagccactg 102420
atgtagagtc attagcctgt tcacacagca ttccttccta gctcaatgaa cttctttagt 102480
aggtattctc attcagtccc acatggattc ttagaatatt gttccaaagt caaacatga 102540 aggatcagtt tgcttttac catgaacgat ctctgtgacc aagtccttta acttctgagc 102600
ttcaggattt tttcatctgc aaagctacga tacgacatat atacgtat atgtatatat 102660 acacacacac acacacatat atacaatttg tatatgaa agagcttaga aaaattaat 102720 ttaaaaatta tgttgctaat gatgatttaa catatcaaag tggaaaaaa cctttctgtc 102780 atatcattaa aaagtcagga aacaacatgt gctggagagg atgtggagaa ataggaagac 102840
ttttacactg ttggtgggac tataaactag ttcaaccatt gtggaagtca gtgtggcgat 102900
tcctcaggga tctagaacta gaaataccat ttgaccatcc cattactggg tatatacca 102960 aaggactata aatcatgcta ctataaagac acatgcacac gtatgtttat tgcggcacta 103020
ttcacaatag caaagacttg gaaccaaccc aaatatccaa caatgataga ctggattaag 103080
aaaatgtggc acatatacac catggaatac tatgcagcca taaaaatga tgagttcatg 103140 tcctttgtag ggacatggat gaaactgaa atcatcattc tcagtaaact atcgcaagga 103200
caaaaaacca aacaccgcat gttctcactc atagatggga attgaacaat gagaacacat 103260
ggacacagga aggggaacat cacactctgg ggacagttgt ggggtggggg gaggagggag 103320
ggatagcatt aggagatata cctaaggcta gatgacgagt tagtgggtgc agcacaccag 103380
catggcacat gtatacatat gtaactaacc tgcacattgt gcacatgtac cctaaaactt 103440
aaagtataat aataattaaa aaacaaaaca aaacaaaaaa aaaaccttc tgtcattaag 103500 ggaggaggtg gtttgccagc tgttggtgct gtagctttag cataggaata gctgtagcat 103560
caacaatgga gttccactct tttatctttt cttttacttt tgttgttgtt gttgacaacg 103620
gagtttcgct cttgttgccc aggctggagt gcaatgacgc aatctcagct cactgcaacc 103680
tccgcctccc gggttcaagt gattctcctg cctcagcctc ctgagtagcg gggattacag 103740
gtacctgcta ccacgcccag ctaacttttt tgtatttta gtagagacag ggtttcacca 103800
tgttggccag gctggtctca aattcccgac ctcaagtgat ctgcctgcct cggcctctca 103860
agtgctggga ttacaggcat gagccactgt gcccagtctt ttctttttact ttttgattat 103920 gccctccagc aggcgatttg tgagtatctt taacattata aatccatatt tctttattaa 103980
aaatgctttc aattttgcaa taattttaga aaattattt caacacattt attacatttt 104040 agttttttt aaattgagac ggagtctcac tttgtcaccc aggctggagt gcagtggcgt 104100
gatctcacct cactgcaacc tccgcctccc gggttcaagc aattctcctg cctcagcctc 104160
ccgattaact gagactacag gcacatgcca ccacgcccag ctaatttttg tattttagt 104220
```

```
agagacgggg tttcaccatg ttggccaggc tggtctcgaa ctcctgacct cagatgatcc 104280
acccacctcg gcctcccaaa gctctgggat tacaggcata agccaccata cccgactgca 104340
ttttggcttt tataggaaag ctaaagacag tacagagact tcctacctac ctttcacaca 104400
gactccccaa atgttaacat ctcacataac tatgggcat ttgtcaaaaa taaggtctta 104460
acattggtac aacactatta actctactac aggctttatt cagattttac cagttgtcca 104520
ctaatgcccc ttttattt atttatttt ttgagacgga gtcttgctct gtcacccagg 104580
ctggagtgca gtggcgtgat cttggctcac tgcaacctct gcctcccggg ttcaagcaat 104640
tctcctgcct cagcctcctg agtagctggg attacaggcg tccaccacca gcccggcta 104700 attttctgt atttttagtt gagacggggt ttctccatgt tggccaggct ggtctcgaac 104760
tcctgacctc aagtgatctg cctgtctcgg cctcccaaag tactgggatt acaggcgtga 104820
gccgctatgc ctggcctcaa tctccctttt aaaaagaat aaatctttta gactaatttt 104880
agattttcag aaaagtggca gatagaacac agttcccaaa caccactcac ccagtttccc 104940
aatgttaaca tcatatataa acatgggaca tttgtcaaaa ccaagggacc aacattgcca 105000
cattattatt aactgaactc tagactttgc ccctttttc tgtttctgga tcaaatccaa 105060
gataccacat tgcattgagt catcacgtct ccttagtccc ctcaagtccg tgagtttgtc 105120 tttcttttc ctaatcttga cagttttgaa gagtcgaata ttttacaaaa tgtccctcaa 105180
tttgagcttg tttgatatct tccttgcata tttggaatca gtatattttg atttgatatt 105240
ctgacccagc aattcacta ctaagaattt atttacaga ctgactccca catgtgtgaa 105300
atgagggaaa ttataaggca actcaatgaa gaatatttgt agcagcaaaa tataagaaac 105360
aacctgatgt ccctcaagaa gatactggtg taattaatta tggtatgcct acaaaatgga 105420
atacttccca gaaaataaaa tattttaca gctgtttaaa aaaaaatggc atggccgggc 105480
acggtggctc acacctgtaa tcccagcact ttgggaggcg aggcaggcgg atcacctgag 105540
gtcgggagtt cctgaccagc ctgaacaaca tggagaaacc ctatctctac taaaaataca 105600
aaattagccg ggcgtggtga cgtatgcctg taatcccagc tactccggag gctgaggcag 105660
gaggatcgct tgaacccggg agccagaggt tgcggtgagc caagatcgtg ccattgcact 105720
ccagcctggg gaacaagaga gaaactccat ctcaaaaaaa aaaaaaaaaa aaaaaaaaa 105780 tgggccgggc gcggtggctc acgcctgtaa tcccagcact ttgggaggcc gaggcgggca 105840
gatcacaagg tcaggagatc gagaccatcc tggctaacac agtgaaaccc tgtctctact 105900
aaaaatacaa aaaattagct gggcgaggtg gcgggcgcct gtagtcccag ctactaggga 105960
ggctgaggca ggagaatggc gtgaaccctg ggggtggag cctgcagtga gccgagatcg 106020
tgccactgca ctccagcctg gcgacagcg agactccgtc tcaaaaaaaa aaaaaaaaa 106080 atggcctgag tagctggacg tggtggctca cgcctgtaat cccagcactt tgggaggctg 106140
aggcgggagg atcactgagc tcaggagttc aagaccagcc tgggcaacat agtgagaccc 106200
tgtctcttaa aaaaaaaaa agatacactg tggagtgaaa aaagtgcagc actttgtaat 106260
atgctattct tggttttact cttttaaaag aaaaaaaaa agacgagaga tacacatatg 106320
tatctatcta gacacacaca catacaatgt ctattgcatc agaagaaacg acatgggatt 106380
tgggaaacag aagttaggag ggagacttac atctcactgt ttggcagtat ttgaatttta 106440
aaacatgtac tagtattact tcctagagac tctatatcga aagcatatac aaacaattaa 106500
cacaacttgt aaagaacgtg gatttgaaac ctgaaagatc tgctgggtat tctcttctca 106560
```

```
gcaagtttac aaatcagcct cctcggcggg agagtgtcaa gggactggtg ttggaagcgt   106620
taacccgcga tgggtttcca tccaaccact acccagacct aaatgtttgg tggattctgt   106680
ttcatgcttg tgaggcacag ttaggggaaa agaacaaatg atcattacgg ataaataata   106740
aaactagctg agtacactgc gtgttaaatc ctttctatgc atgtactgcc cacacgatcc   106800
tgtgaggtag atactatgtt acccatctta gagatgagga aactgttact cagatttgac   106860
ggaagcgtca cagccagcag gtaactcaca aacgtgggtt tgtagtcggc tggatggctt   106920
gccaaaccac aagtgggagg atggagcaca tcagccctca acggcctcgg aacagcggag   106980
gaagaccgcc ggggccctgc agtcaacgga gcggccgccc gactccggga cgctcacctc   107040
ccggccggct tccgggatgg gtctgcagcg acacacacat atcccctggg acctgcttcc   107100
cggcatcctc cccgcgcgag cgctcacttc cggtcccaag taggcccagg cagaagcatc   107160
acctcgccgg cagccgctcc ttggacatgc tttccgctgg gaacccgagc tctacacccc   107220
tgccccaccg ccgccccggt ccttgctcag cactaccccc ttacctgccc tgcgcacccc   107280
ccgcgagccc cggggccctt agctgacgac cgccctcacc tcttctctct tcgcctgccg   107340 cggccttta caaacggggc caaactgttc gctgtaacga caatcgttat tggtcagagc   107400
cgcccacgcg cggcaagtgg ccgcccacct gagctcgcgt tgtcttatgg gagttttagt   107460
tctctccttc agagaccgct gagacactgg gggaatgcgg tggtagaaca tacgccgacc   107520
tagcggctgt aaagctcagg ctctgccttg gagttggagt gcttctggcc tatcttactg   107580
ggcgctcacc tccaaggctc gtcttgactc ccttctggcc tgagagagtc ctatttctga   107640
atagactttt gctggtaatt gatgcaaaaa tgacttgagt tgctggacgt ggtggctcac   107700
gcttgtaatc ccagcacttt gggaggctga ggcggaggat ctcttgaggc taggagttcg   107760
agaccagcct gagcgacata gcgagaccct gtccttacaa aaaatgaaaa ttaaaaaaaa   107820
aatcgcccga gattttctac attattagca gatgtcagct gcgaatttgg agtttgtttg   107880
gaggttcttg cccacctgag tattcacctc tatcacatgt atgtttatga caagttaact   107940
ttttctccct taagtacact ttgaactaca cttgaacgtt ttctcttaaa atgagataaa   108000
aaagagcttc ctgtatatct tagttctggt ccttggaatc acggaataaa tctaaatgct   108060
catcgttcat gattgaagat agctcccgag tgcaatgtgt tcatggtgag gccactgtgt   108120
tggaaacccc tggaatgagg ttttctgctc tcctgaccct agtctggcta cttactagtg   108180
gtagcaggtt aatttactat tgggaaacct tagtcaacta tttataagag aagtggaacg   108240
ttccggccgg gcgtcgtggc tcacggctgt aatcccagca cttgggaggg ccgaggcggg   108300
cggatcacaa ggtcaagaga tcgagaccat cctggccaac atggtgaaac cctgtctctc   108360
tactaataca aaaaaaaaaa gttagctggg cgtggtagcg cgtgcgggta gtcccagcta   108420
ctcggggcac taaggcagga gaatcgcttg aacctgggag gctgaggttg cagtgagctg   108480
agatcgcgcc actgcactcc agcctgggcga cagagcgact ccgtctaaaa aataaataaa   108540
taaaataaaa aaagagaaat ggaacattcc aggactaatg tttgtagtat tagttcttaa   108600
actggaaaga gagggagagg gacacaattt ttccagaaga ctttttagtt ttctttccat   108660
ttattatgta aactaaaaat aaaatcccat gccccacagc caactgaatg aaccctcacc   108720
ccttggccaa ggggatgtta aactgaattc tgaattctcc tgggtggaaa gggaggtcgg   108780
acatgcctcc ttatactccc tcttttggag tttaggcaca actgaccacc attaatgtta   108840
aaagagaaat tataagaatg gcagaacaga ctctctgtag caatagaata ccaaataata   108900
aacaagacca aaggccatgc aaggcaagaa ttaagccaca ccctacaaac cataacatct   108960
```

```
ttttaaatga gttttttaaat taaccctgta tcgtgtggct tactttccag cctgaatcag 109020
gtatagcacc acatgataaa aagcagatgc cccaccctta taatgtaagc attcctttgt 109080
actgacttcg agtccttaga caaagcttaa ctctatttttt tttttttttt ttttttttttt 109140
gagaaggagt ctccctctgt tgcccaagct ggagtgcagt ggcatgatct cagctcacta 109200
caacctccgc ctctgggatt caagtgattc tcccacctga gcctcccgcg tagctgagat 109260
tacaggtgca tgccaccaca cccggctaat ttttgtatgt ttcagagaga tggggtttca 109320
ccatttggt caggctggtc tcgaactcct gacctgaaat gatccacctg cctgggcctc 109380
ccaaagtgct gggattacgg cagtgagcca tggcgctcta ccaaagctga actccttcaa 109440
ccaattgcca actaaagaat ccctaggcgg gacacgatgg ctcaccgcat ctggcctttt 109500
tccttttttcc tttttttttt tttgagacag agtctcgctc tgttgcccag gctggagtgc 109560
agtggcgcaa tctcggctca ctgcaagctc cacctcccgg gttcacacca ttctcctgcc 109620
tcagcctccc cagtagctgg gattacaggc acccgccacc gcacccggct aattttttgta 109680
tttttagtag agacagggtt tcaccatttt ggccaggctg gtcttgagct cctgacctca 109740
tgatccaccc accctggcct cccaaagtgc tggcattaca ggtgtgagcc actgcacccg 109800
gctccgcccc ccccttttt tttttttttt ttaatttttg agacagggtc ttactctgct 109860
gcccaggctg gagtgcagtg gcgtgatctg cagtctcaat ttctcaagct caattgatcc 109920
tccctcctaa gcctcctggg tagctgagac tacaggagct cgccaccatg cccagctaat 109980
ttttgtatttt tttgtagaga ttgggggtgg tggtgggtct ctctgtgttg ctcaggcagt 110040
ggtcttgaac tggccccagg caatcctccc acctcagcct cccaaagttg ctgggattac 110100
aggcatgaga caccatgctc ggctaaagcc attttcaatg aaaagaattt ggccagatat 110160
acagtggctc acacctgtaa tcccagcact ttgggaggcc gaggtgggcg gatcacctag 110220
gtcaggagtt tgagaccagc ctggtcaacg tggcaaaact ccctctctac taaaaatca 110280
aaaattagtg gggtgtggtg gtgggcgcct gtgatcccag ctacctggga agctgaggca 110340
ggaggatcgc ttgaacctgg gaggcagagg ttgcagtgag ctgagatggc accactgcac 110400
tcctgcctgg acaacagagt aagactccat ctcaaaaaaa aaaaaaaaa aaaaaagggc 110460
gggcacggtg gctcacgcct gtaatcccag cacttttgga ggccgaggcg ggtggatcat 110520
gaggtcagga gatcgagacc atcctggcta acacggtgaa accccgtctc tactaaaaat 110580
acaaaaaaat tagccagtcg tggtggcggg cgcctgtagt cccagctatt ggggaggctg 110640
aggcagaaga atcgcctgaa cccgggaggc agaggttgca gtgagccaag atcgcaccac 110700
tgcactccag cctgggtgac agagtgagac ttcgtctcaa aaaaaaaaa aagaaaaaaa 110760
aagaatttat atgctatttg cacattagag cagatattca tagttctttg attttttgcca 110820
actgacaata attatttttt aacttctctc atccttctag cccctgttat catttctttt 110880
tcttttttctt tttcttttttt tttttttgaga cggagtttcg ctcattgttg cccaggctgg 110940
agtgcaatgg cgcgatctca gctcacctta aactctgcct cccaggttca gcgattctc 111000
ctacctcagc ctcccgaata gctgggatta caggcatgcg ccaccacgcc cggctaattt 111060
tgtatttta gtagagatgg ggtttctcca tgttggtcag gctgtcctca aactcctgac 111120
ctctgggatt cacccgaatc aacctcccaa agagctggga ttacaggtgt gagacaccgc 111180
tcctggtgcc ctgttgtcat tttaatccaa tatttttttc tttttaaaaaa tttttttggag 111240
tattggtaca tgcctgtaat ctcaattatt tgggaagctg atgcaggagt attgcttgag 111300
```

```
ctcagaagtt taagagtttg aggccagcct gggcaacata gcaagacccc ttctcttaaa   111360
aataaagtat tgatacataa tagatgtaca tattttgggg gtacatgtaa taatttaata   111420
aattcatata atctgtaaag atcaaatcag tgtaactggg atatccatca ccctaaatat   111480
ttgtctttat gttagaaaca ttgaattatt ctcttctatt ttgaaatgta caacagatta   111540
ttattgtaag ctatagtcac cctatgatct atcaaacatg atgtcttatt tcttctacta   111600
aactgtatac ttgtactcat taatcaacct ttcttcatcc cttcctgacc cccttaaatc   111660 actattttt tttttttaga tggagtttcg ctcttttgcc caggctggag tgaagtggtg   111720
caatctcggc tcactgcaac ctccgccccc caggttcaag cggttctcct gcctcagcct   111780
cccaagtagc agggattata ggcacccaca accacacctg gctaattttt ttttttttt   111840 tttttttttt ttgagaggga gtcttgctct gtcacccagg ctggagtgca gtggtgcgat   111900
cttggctcac tacaacctcc gcctcccggg ttcaactgat tttcctgtct cagactcccg   111960
agtagctggg actctagttg cctgccacca cgcccggcca atttttgtat ttttagtaga   112020
gacaggtttc accatattgg ccaggctggt ctcgaactcc tgaccttgtg atcctcccac   112080
cttggcctcc caaagtgctg ggattacagg cgtgagccac tgtgtctggc tgtacccttc   112140
atattttgta ccctcttctt gtactgttcc gaattacaga ttctcttctt cagctgtatc   112200
taatttgttt agtcagccta ttgaattttt aatttaagct attgtatttt taatttctag   112260
aggttctatt agttttcaa aaatctgcct aatcatttga cagtcatttc ttccttgttc   112320
atatttgtat tacatctttt attttaaag acatgaaatg tagttattac aaattcaata   112380
tgtgattttc taaagttctt gtaggtccag ttctgctgtt ctttgtttct gttggatctc   112440
ttgtagagtc ttgttttcctc atgtgtttca taggttttt gtttgtttgt tttttgagac   112500
ggagttttac tctcacccag gctggagtgc agtggtgcaa tctcgtctca ctgcaaccgc   112560
tgcctcctag gttcaagtga ttctcctgcc tcagcctccc gagtagctgg gattacaggc   112620
atgcaccact acatctggct aattttgta tttttagtag atggagtt tcaccatgtt   112680 ggccaggctg gtctcgatct cctgacctca agtgacctgc ccactctca gagtgctggg   112740 attactggcg tgagccaccg cgcttggccg tgtttgatag ttttttattg tgaactcaca   112800
cctgattatt ttgttttatt ttattattat tttttgaga cagagtcttg ctctgtcacc   112860
aggctggagt gcagtggtgc gatctcggct cactgcaacc tccgcctcct gggttcaagt   112920
gattctcctg cctcagcctc ccaagtagct gggactacag gcatgtacca ccacacacag   112980 ctaattttg tattttagt agagacaggg tttcaccatg ttggccagat gatcttgatc   113040
tcttgacctt gtgattcacc caccgcagcc tcccaacgtg ctgggattac aggtgtgagc   113100
caccacacct ggcttcaaat gattatttta atctgaggta atcctgagtg acctcggtgg   113160
aggacacatt ttttcagaga ggattttgc atatcaaact atataaggga ttcttactaa   113220
ttgataaaaa aaaacagtga aacaatctaa tgaagaaata dacaaaggat atgaacagat   113280
atctcacaga aataaataca aatggccaat tatcatgaaa aatgactaac tttacttgta   113340
atcagggaaa tacagctaaa gagattattt tacattcatt ggattggcaa aagataaaag   113400
cttgataaca accagcattg gtgaaggaat gtaaggaaa taagagcttt ctgacataaa   113460
tggttggagc gtaaaacggt atatgacctt ttttttctg agatgaagtc tcgctctgtc   113520
agccaggctg gagtgcaatg acctaatctt gcctcactac aacctccacc tcccaggttc   113580
aagcaattct cctgactcag cctccccagt agttgggact acaggtgtgc gccaccacgc   113640
ctggctgatt tttgtatttt tagtagagac agggtttcac catgttgacc aaccaccatg   113700
```

```
ttggtctcga actcctgacc tcggggaat  ccacctgcct tggcctccca aagtgctggg  113760
attatagatg tgagccaccg ctcccagctg gtatacagcc tttttttttt tttttttttt  113820
tttgatatac agcattttaa gagggtaatt tggcactata caatacaatt tttacaattc  113880
acatttcctt aacccattca atttctaagt atcctagaaa aacagtatag acatgcacaa  113940
aaacacatga attctctttt ttttttttct tgagacaggg tcttgttttg ttgcccaggc  114000
tgcagtgcag aggcatgatc acagctcact gcagtctcaa cctcctggac gcaaatgatc  114060
ctcctacatc agcctcctga gcaggtggaa ccacaggcac atgccaccat gcctggctat  114120
ttttttttaa ttttttgtag agatgaggtc ttgctatgtt gcccaggctg gtcttgaact  114180
cctgggctca agtgatctgc ccacctcagc cttccaaatt gctgggatta caggcatgag  114240
ccaccgcacc cggcctgcct ctgcctcctt gaacactaat gatcctgagt tttatccaca  114300
gtcctcatct cacttggtga tctctactcc aagggttgaa ctaacacgta aacacagacg  114360
attcccattt ctatatccag cccagatcac cctccgaaat tccatgtcat tacctactgg  114420
atatttctac ctgtgtcacc cacgtccaat ctcacatatc gaaagataag gccaggcgag  114480
gtggctcacg cttgtaatcc cagcactttg ggaggccaag gcaggcggat cacctgaggt  114540
caggagttca agactagcct agccaacatg gcgaaacccc gtctctaccc aaaatacaaa  114600
aattaactgg gtgtggtggc acatacctgt aatcccagcc acttgggagg ctgaggcacg  114660
agaattgctt gaacccagga ggcggacgga ggctgcagtg agccgagatc acacactgca  114720
ctccagcctg gcaacagag  tgagactctg tctgaaaaaa aaaaaggtaa gactaatttg  114780
ctctcatctc ctgctctctc accatgatag ctcctgtcct tactcactct cacaaacatg  114840
cttctctgcc ttctcacatc ccagtaacta aggatccacc atgcatctaa ctgctcatca  114900
agtctgcaac ctggaacacg tcttgactaa atacaaattg gatcagtggc tccctggggt  114960
cttcaggata aaaaaagttt aaatgacatc acatggctta aagaacttgg ccctgatttg  115020
gtccttcaat gccagctttt tattaactta ctcccagtac tccagctggt agtactgtcc  115080
acacgaggtg gaaagccatt tggtcaaaac tagattgttt gaaataacaa tttaattaac  115140
tcattcatta atcaattaat tcaacattta ttaagcttta ttatttacca tgtactggat  115200
attatggcat tgaagaaata gtcaccaggc caggagcagt ggctcatgcc tgtaatccca  115260
gcactttggg aggctgaggc tggcagatca cttgagggca ggagttcgag accagcgtgg  115320
ccaacatggt gaaaccccgt ttctactaaa aatacaaaaa ttagctaggc gtggtggcat  115380
gcacctgtaa tccctgctac ttgggaggct gaggcagaag aatcacttga accctggagg  115440
tagaggtttc agtgagccga gattgtgcca ctgcactcca gcctgggaga cagagcaaga  115500
ctctgtctca agaaaaaaa  aaaaaaaaa  ggaaatagtc atcagtactt tagtttagtg  115560
gggaggacag gttttaaata aataactaca tgaataatta aatagaatta aaaattatga  115620
caaatgctat aaaggaaaag tataagatgg attgagacgc tagtgattta gattgtggag  115680
tgaagaaagg aaggcctctt agaggaagtg acttaagtgg agacttgaaa gcacaaaata  115740
gggaaaagct gttcatgtgc aaggccctga aagggagtc  tctcagcccc caattcactt  115800
tttttttga  aacattttc  ctttgttggc tcaatgttac gctttgtcaa tagagggcac  115860
ttggggaaca atgcagtgat agtggaagga aggcacttcc ttcatgggtt ctggttctct  115920
tctcatactc agcgtgggag ccaatggatc agtgtacaga agccctagca gcgctcacct  115980
cagtggtcct caggacccgc cccagctgcc cctcatgtgt cccacctgca gctgcctcca  116040
```

```
aggcagcttt ggctgcacca ccctgcaact gtctctagaa tcaacagaaa aaatatacag   116100
gacactccat taaatttgaa tttcagctaa acaacaattt tttattttt ttattttat     116160 ttttagtata agtgtgtccc atgcaacatt tggcattgta ttttctttt tttgagacag    116220 ggtcttgctc tgttgcccag gctggagtgc agtggcatga tcatggctca ctgcagcctc   116280
aactccccgg ggtcaaatca tcctgctacc tcagcctccc aagtagctgg aactacatgt   116340
gcatgccacc atgcctggct aatttattta ttttaatttt ttatgttgta gagatggagt   116400
ctcactatgt tgcccaggtt ggtctctcaa actcctaggt tcaagcaatc ctaccacctt   116460
ggcctcccag agcgctgaga ttataggtgt gagctactac acccagccaa accaaattct   116520
aaaagaccct aattaactga tgagtgatag ccaggaagag tccaaaacat tacctcctaa   116580
gtatttaatt tatgtttgca atgtaactaa agactttgcc ttaaatagta gttaacctac   116640
ctgtatttga aaatctcttc aaagaccact tatgtactct ggaattcaga aaggtgcaaa   116700
atccctactt tttaaccctc gtattatttg tattgcaaca aatcaggtga aaagcactg    116760 aagccataga aatcagaact tctggccggg cgcggtggct catgcctgta atcccagcac   116820
tttgggaggc cgaggcgggc ggatcacgag gtcaggagat cgagaccatc ctggctaaca   116880
cggtgaaacc ccgtctctac taaaaataca gaaaattagc cgggcgtggt agcgggcgcc   116940
tgtagtccca gctactcggg aggctgaggc aggagaatgg cgtgaacccg ggaggcggag   117000
cttgcagtga gccgagatcg cgccactgca ctccagcctg ggcgacagag cgagactccg   117060
tctcaaaaaa aaaaaaaaa aaaaagaaa tcagaacttc tttgggtaat tttcaaaggc     117120
atcttgagat taatggaagt actcacttaa gggcacttga ctacttttg agaaacctat    117180 ctaaagatgt ttcatctttt tcaagtagca gtttcctgca agtataggaa ggaaagttgt    117240
ggactactct gttccttcca aagcaaagtc catttcttga gctgccatca tcagtactag    117300
aagcttcatc tgttatgcaa aatttatatg ccatttattt ctgtattttc atcttttgat    117360
cccttaccaa attgtctcat ataaaaaaca acttggctgg gggcagtggc tcacacctat    117420
aatcccagca tgttgggagg gtgaggcagg attgcttgaa cccaggagtt tgaaaccagc    117480
ttgggccttt tttagagacc ctgtctcgaa aaaataaaa aataaaacaa caacaacaac    117540
aacaacaaca aaactcagac caaaactgag cataagatag aatgcacaaa atcaaatttt    117600
ctttttttct caacttttac tttagattgg gggaacatgt gcagctttct tacctgggta    117660
tattgcacga tgctgaggtt tggggtatga atggttccat cacccaggta ctgagcatag    117720
tacctaatgg ttagtctctc aaccttcccc ccagtagttc ccagtttcta ttgttgccat    117780
cattatttcc atgagtaccc aatgtttcac tcccacttat aagtgagaac atgtagtgtt    117840
tggttttctg ttcccacatt aattcacttc agatagtgac ctccagcttc atccatgttg    117900
ctgcaaagga catgatttca ttcttttta tggctgcata gtattccatg gtatatatat     117960
gtaaggaaaa aggctgcatg gcagtcaaga gtaggccaag gtaaacatct ggtgcagcgt   118020
gacacagcag gattggagtg cgtgtgtaca atcctgtgca ttatataatc acagttatgt   118080
aaccatgtta taagtgagct catcaactgg ctctgaggtg caaaaatgta tcactgacac    118140
tgtgagaggg gcacataata aagccctgc ctccggaccc ccagtgttc tttcaactac      118200 ctgccacccg tccaccaact cccctcggac tccagcttag gttggaaccg gacaattggt    118260
gtagttagca ggattctgaa gtgagtgagt cctcagcacc tgatgatccc tggttggcca    118320
tgtggcccca acatggggttg cggtacttgg tggcagctgt gctgtccaga tgggccctgg    118380
tggaaacatg ggcagaggta gacaggtccc ccatgagcat ggagaaggcc ctgaagcacc   118440
```

```
tggaagcata caacaccgag aaggagggtg cctttgccag cagagttgga tgggcatttt  118500
tgactatgct atggaaagtg catgcccagt ccctgcggga tacagcacag gtaaggaacc  118560
tccaggtgct agctgagtgc ctggaggccc aaatacaaag cttggaatga gaatgggtaa  118620
ctgccgtaag tgcaggcttg agcctgcctt cctggccaga gactcccatt ccatctgata  118680
ccgaggagga agaacccctg ctgcaggctc accctgtggt ctgccagaaa atagagcatg  118740
aacagccact tgggccccaa gggtgggccc agggaccccc taccgtggtg gagcacactt  118800
catatagtgc ctacaccccc actgagttgt gggagttagg taagtagcgg aagcccctac  118860
ctgcctggat gctccgcttc tgggacaaag gagctgacag tatttccggt tccactgctg  118920
agacggaaaa gttggcttct gtcacagctc acccctccct ccatcagcgg ttgcaggtga  118980
gcaggcagtt ggcacaaggg aaaggtgacc atatcctgac tgaatggctg atggcagcca  119040
tgtggacagg gtggaatgat gccagagaat tatcaaaaac tgtgagtaaa tggcaatcat  119100
atgcagagct ggtggaggta attcggaaga tgggtatgtg gcaggctatg tttgatttga  119160
atacccaagg gccagatgat gaacgcttta cctcccacat gagggacctt gtgttgggct  119220
ctgcatcccc gagtggtttt ggctctctgg tcgttgtcct tctccataca ttgggcataa  119280
ggtgactacc atacataagg tgatactgcc atggcagccc ttggggaagc agaaagccag  119340
cagtgggagc agggagtctg tgctataaag aaggggaagg tatccctccc atagggagcc  119400
acaggacaaa aagtggcccc agcaggtgac ccccatgcag atgtgaattg atctgatatt  119460
ggctggggtt gcttgagaga aaattgacag gcaacccaat gaagtgctgt taactttgtg  119520
gaagcaattg tccccggagc agcaattccg gaaaatgccc aaggcagggc aggatgatgc  119580
tgctcaaccc agtcctgctg gacactccag ctcaaggatt acttgcagat gggtgggaga  119640
ataaagcctc ttgtgtttga ttagggaact ggccaaggtg cccggcttgg caggacacca  119700
gagatcagag gccacatgtg gaattggcaa tccactggta ccccaccaat gtacagcagg  119760
tgttggtgct ggtaggtact gatgcagatt atagcctcgt ctatgggaaa cgggataagt  119820
ttttaggcaa ggctgcatac acagatggtt atagaggcca gtcagtgaaa gtaaaacctg  119880
tatctttgca cctcggcatt ggctgcttgg cttcccattt atacactgtg tatatctctc  119940
ccatactgga atacattctg gggatggata ttttgcagtc ttaacttaca caccacagcc  120000
agagaattca gactccgcgt acatgtagga aagctggtac tatggggaca tatgcatcac  120060
ctgcccaggt tctgccacaa ccccgatggg ttacctccgc ttgtcaatac cacttgccag  120120
gagggcatac ggagataact gagactatta agaagctaga ggatggccgg gctcggtggc  120180
tcatgcctgt aatcccagca ctttgggagg ccaaggcagg cagatcacga ggtcaggaga  120240
ttaagaccat cctggctaac acggtgaaac cccgtctcta ctaaaaatac aaaaaattag  120300
ccaggagtgg tggcacgcgc cgcagtccca gctactcggg aggctgaggc aggtaaatgg  120360
cgtgaaccta ggaggcagag catgcagtga gccaagatcg cgctactgca ctccagcctg  120420
ggcgacagag cgagactgtc tcaaaaaaaa aaaaaaaaa aaaaaaaag gtagaggagg  120480
tgcagatagt gcatggcaca cacagcccct acaattctct ggtatggcca gtcaaaaggc  120540
ccgttgggac tttgtagatg acagtggact atcaagaact aaataaagta acagcccctt  120600
tacatgcagc agtcctgtct atcacggatt tgatggacca cctgacgatg gaattgggac  120660
agtaccatta tgcagtggat ttggctaatg catcccttc agatgatatc gctccagaga  120720
gccaggaaca gtttggcttc acatgggaag ggcgacaatg gactttcaca gtgttgccac  120780
```

```
agggctacgt gcatagtccc accatatgtc atggtctcgt tgctacggat ttagccacct    120840
ggaaatttcc aaaggggatc cgcctattcc attacattga tgatattatg ttaacctctg    120900
attctcctgc agatttagaa gctgtggtgc ccctcttgca acaacatttg gcagcatgag    120960
gttgggctgt caatgaatcc aaggtgcaag ggcctgggtt gtctgccaaa ttcttgggag    121020
ttatctggtc gggtaagaca aaagtcatac cagaggccat cgtagacaaa attcagacat    121080
atcccagccc accatggtga ggcagctgca gacctttgtg ggcctgctgg ggtattggcg    121140
ggcgttcatg ccccatttgg ctaaaatgac aaaaccgttg tactggttga caaaaaagag    121200
ggctacctgg gattgggatg ataaagctaa ggcagccttt ctggcagcca tgtgggctat    121260
tcaataagca caggccctac aagtgattga ctaggggcac catttaaact ctttctgcct    121320
tggcctccta aagtgtggga gttataggcc tgagccactg cgcctggctt gagaatctaa    121380
ggctagtatt aatttcaatc cttttccatt tggtaacttt attttttactt atttatttt    121440 tttgagacgg agtctcgctc cgtcgcccag gctggagtgc agtggcgaga tctctgctca    121500
ctgtaagctc cgcctcccgg gttcacgcca ttctcctgcc tcagcctccc gagtagctgg    121560
gactacaggc atcagccacc acgcccggct aatttttttgt atttttagta gagacggggt    121620
ttcaccatgt tggcgaggat ggtctcgatc tcctgacctc gtgatccacc cgcctcggcc    121680
tcccaaagtg ctgggattac aggtgtgagg accgcgcccg gcctccattt ggtaactttt    121740
agaatattgt ctggtgtcgg ccaggcacgg tggctcacgc ctgtaatccc agcactttgg    121800
gaggccgagg cgggtggatc acgaggtcag gagatccaga ccatcctggc taacacggtg    121860
aaatcccgtc tctatgaaaa atacaaaaaa ttagccaggt gtgctggccg cgcctgtag    121920 tcccagctac tggggaggct gaggaggaga atggcgtgaa cccggggggc agagcttgca    121980
gtgagccgag atcgcgccac tgcattccag cctgggagag agagcaacac tctgcctcaa    122040 aaaaaaaaa aaaataaat aaataaataa aataaataaa ataaaacgaa taaaataaat    122100
aaaataaaat aaattctagg ccggaaatgg tgactcatga ctgtaatcca ggcccttggg    122160
gaggctgagg caggcgaatc acctgaggtc aagagttcga gaccagcctg gccaatatgg    122220
tgaaaaccgg tctctatgaa aaatacaaaa attagctcgg cgtggtggca ggcctataac    122280
ccccatactt taggaggcca aggcaggaag agtttaaatg gctcccctag tcaatcactt    122340
gtagggccta tgcttattga atagcccaca tggctgccag aaaggctgcc ttagctttat    122400
catcccaatc ccaggtagcc ccctttttg tcaaccagta caacggttt gtcattttag    122460 ccaaatgggg catgaatgcc tcccaatacc aatactacag ctgtagtccc aactactcag    122520
gaggctgggg caggagaatt acttgaaccc aggaggtgga ggttacagtg aaccgagatc    122580
gcgccactgc acttcagcct gggcaacaga gcaagagcaa gactctgtct caaaaaaata    122640
cagtacattc tacccactct atttttctcag ttctttttcct gggatacctg ttagttggtt    122700
attaaacctc ctgtattgag ccaagttaat ttttccctt cactttgat ttctgttcta    122760 aaactgtttc ttgtctttta atattctgaa ttcattcata ttttaaattt ccttttctgg    122820
tattttacta ctatcctgct aattgttttt tgtttgtttt ttgagacagg gtcttgctct    122880
atcacccagg ctggagcaca gtagcacgat cttagctcac tgcaacctcc gcctcctggg    122940
ttcaagggat tctcatgcct cagcctcctg aatagttggg attacaggca cgtgccacca    123000
cacctggcta atttttgtat ttttagtaga cacaggattt ccccacgttg gtcaggctgg    123060
tcttggactc ctggcctcaa gtgggtgatc cacccgcctc agccttccaa agtgctgaga    123120
ttacaggagt gagccacagt gccctgccat attttattta tttatttatt tatttatttt    123180
```

```
ttgagacaga gtctcactct gttgcccagg ctagaatgca atgggatgat ctctgctctt 123240
ggcaccctca gcctcctgag ttaaagtgat tcttgtgtag ctgggattac aggaatgtgc 123300
caccatgccc agataatttt tgtattttta gtagagacgg agttttgcca tgttcaccag 123360
gttggtctcg atcttctgac gtcaggtgat ctacctgcct cgctctccca aaatgctggg 123420
attacaggtt tgagccaccg cagccaggcc ctaatttcat tttttgtagg catgaggtct 123480
tgctatgttg cccaggctgg tttcaaactc ctgggctcaa gcaatcctcc caccttggcc 123540
tcccaaattg ctgggattac aggcctgagt cactgtgtct ggcttcctaa ttttcttttg 123600
tttgttggtt tgttttttga cacagtctcg ctttgcccag gctggagtgc agtagtgcca 123660
tcttggctca ctacaaccac tgcctcctag gttcaagcga ttctcctgcc tcagcctctt 123720
gagtagctgg gattacaggc ttgtgccacc acgcccagtg aattttctgt tgtttgttgg 123780
agacagagtt tccctcttgt tacccaggct ggagtgcagt ggtgcgatct tggctccctg 123840
caacatccgc ctcccaggtt caagtgattc tcctgcctca gcctcctgag tagttgggat 123900
tacagacatg caccaccatg cttggctaat ttttttttt ttttttttga cacagagtct 123960
cgctctgttg cccaggctgg agtgcagtgg cgctatcttg gctcattgca acctctgtct 124020
cccaggttca agcaattctc ccacctcagc cgcctgagca gctgggattt tttgtatttt 124080
tagtagagat gggggggggg ggtctcacca tgttgggcag gctggtctcg aactcctgac 124140
ctcaggtgac ccacccgcct cggcctccca aagtgctagg attacaggcg tgagccactg 124200
tgccctgcct agttttgtat ttttagtaga cagggtttt caccatgttg gccaggttgg 124260
tctcgaactc ccgacctcag gtgttccgcc tgcctcggcc tcccaaagtg ctgggattgc 124320
aggcgtgagc caccgagcct ggccatcatt tcttgaatac aacatcttat ctggggacat 124380
tccagctcct ggaaattttc tgattgagag ttgcttttg tttagagcta cctttcacaa 124440
tcaaagtttt cctcaaattt ctagtggtat tttcccatcc ctatgtaaaa gtgaagcact 124500
aaaaacctgt ctggaagatt tgtgcacatg ggcaggcctt attgactggc tgcagaggga 124560
atggtggcca gttggcgttt tcggtgggtg ctcttaaatg tcagtaactg ttgtctctca 124620
agagtcactt agttttacca cagaaggatc ctccaacatc ctgcctggtg ggtatgtctg 124680
gctgttggca ttctagagct gaacaaggat aaatagctaa ggatctcatt tatccagtat 124740
acaaaattgt gcttaatctc tatttctga acagcatcac ctagtaaagt ttgcttttc 124800 cttttttaaag ttgaatttac tatctcagta acttcaccct ccaactttag gagccacagt 124860
gtaattaatt actggcaatc ttgggaatat cttatctctg aagctagtgc tgcaaacagc 124920
catttgagtg agcagaaatt tcaaataact gtaagacact caagaaatgc taccattggc 124980
tgggcgcagt ggctcactcc tgtaatccca gcacttaggg aggctgaggc aggtggatca 125040
tctgaggtca ggagtttgag atcagcctgt tcaacatggc aaaaccctat ctctactaaa 125100
gatacaaaaa ttcagctggg taaggtggca catgcctata gtcctagcta ctcgggaggc 125160
tgaggcagga gaatcacttg aacccaggag gcagaggctg cagtgagctg agagtgtgcc 125220
accgcactcc agcctgggcg acagagactt cgtctcaaaa aaaaaaaaa aaacaaaaac 125280 aaaaacgggt tttatacac gaacaataaa gtgaattaag cctgtttttt tttttttt 125340 ttttaaaaag gctggtcgtg gtggctcaca cctgtaatcc cagcactttg ggaggtcaag 125400
acaagtggat cacctgagat cgggagttca agaccagcct ggccaatatt gtgaaacccc 125460
atctgtactg aaaacacaaa agttagccag gcgtggtggc aggagcctgt aatcccagct 125520
```

```
actcaggagg ctgaggcaag agaatggctt gaacctagga gggggaggtt gcagggagcc   125580
gagatcacac cattgcactc cagcgtgggg gacaatagtg agacatcatc tcaaaaaaaa   125640
aaaatggttt acaaaaacct gctaccattg acacctgttg ttttcctgtt tggttaatac   125700
atatgaatac atataataca tatgaatttc ctgtttggtt aattcatatg aatatgaatt   125760
atggtcttca aatgaaggta gaaaaaccta ttcaattgag acacactcac acattttatt   125820
aaggctctta aattgaaact catcattttg gatgtacatt caaattctaa acacaacagt   125880
caaaatgcag tgactgtaat gaaatgtaat aacctcctat aaagaaacga ttggggacta   125940 tcattttgt gatttaacaa cagagaaaat ccaggaagaa tgaattgagt tccttctagg   126000
agttgtttat ccctgctcat gcttaagatt gacgatttcg tgaaataaag aacattattt   126060
gagagaaaaa aactgatttt ttttaaagaa atcatcactc tcatttgaaa ggtttgcttt   126120
cttatttcct gtaagtacat ttcgttttc taattcaact gtaacctcag gaccactgta   126180
cagcacttag taaacctgtc tttgtacatg caatctagtt cttaccaact gccttctcaa   126240
atggaataga actataacac acaaataaaa ggaagatgta caagcacagg gacaaaacag   126300
gaggaaaata aagactagaa tgtgaatctc attttcaaca agtatcagca aggaaaatga   126360
gaccctggtt tcataattaa ttaaatctgc agaatgccaa ttccatttgg tgttaaacag   126420
taacccaata taaaccactg attctggaat aagattaaaa aaaaaatacc tgagtgaata   126480
taacaatatg gatagaccaa aaagaaaaaa atctcacac acaataatca ctgcaagaag   126540
atcccacagg ttatagaaaa cataaggaa ctttaatatc caaacattca gggtaaagaa   126600
tactggatta atcacccatt aagtgtaaat cacttcaggt tctttacagt accagaaagt   126660
aaaatctaaa ttttgcatat tgcagagaat gaaaccattt taaaaacttt aatttcctta   126720
cctgatacta ataccagtat gattttaga cggaaaaact aagagtaaga tttaaaccaa   126780
agatagaggt gttcctgaaa tgtgaatttg ttcagtagta accttttcat catgagtact   126840
gataccactt tcttctcaga aagtagtcaa tgtacatttt aagatttgtg caataagcca   126900
atatgctgga taataaaaac tgttattact ggagatagtc aaaatgaaag aaaactattt   126960
aaattattta tgcccaaata atttaccctg cagtccatga gatgcacagg aaataatttt   127020
ttttaataag agaacaatga gggtcctaaa gtagaaacat aagccagaag aaatctaaaa   127080
atagcttcct gatattttat tttaaaatat ttcatttaag ctgcttttgg ttgcatgccc   127140
tgatctgtag aagttaacaa ggaaataaaa tttccaagta tttaaaaaat ttactcatct   127200
tccataaagc gactttaat gtatcaacac ttaaaaatac acagtgactt aatgaaatat   127260
cagcacaact gcatagaatt gagctccaga gaattataca ctcgagctgt ctttcctggg   127320
ctctggttta taagggtatt ggcttagaga ccagcttgga gtcatttgcc ctacccggg   127380 aaatgcaggc caggaaactt aagattttgc gggccttttc tgtttctagg taaaatgcag   127440
ggagctccct gaaggtcttg aaaaccatca accattcaaa tatgtatact gggacctttc   127500
ctcttgagta aaggaagaag gaggtttgtg atcttcactg aaaacaaagt gaaacttccc   127560
acacaagtct tctaagagac tctgaaatat actagaaatt tcaaaactag aacaatgcca   127620
tcaaagatta aacctcttaa tgcttggagc caccccaaaa taataaaatc gggaactcca   127680
ggaaaacagg taccaaacga atcaaaataa tgattgcact gaggattctc ttatctgaag   127740
gctgtttaaa gaggtaggat tttaaggttt tttttttgtt tatcttttgg cctctgaaca   127800
tttaaaagat gctttgccca gctggtcctt caggcaaaat ttggaggtca caatgaactc   127860
caagcctgac acaaagatat tctacagttt cacagctatc atttgtacat attaagttga   127920
```

```
ttcactctttt ttgagcaaat ctacctagaa aacggcaaat taatatattc ctttacatac 127980
aactttgtgt ctcaaaattc ttgaaaaaca agagcagatg actttgtatt caaagactac 128040
caaagtatgt atttgatttt cacatgcaaa caacttaaaa ccttataaat ctcatgtcaa 128100
ctctgcatga tgccttgaag gaaatgacat acaaagtttg ctaactgtgc aaaatattaa 128160
attgctaaaa cattttacat aatgaaataa tacatgtaaa tgttgaagtt gacacatgaa 128220
attaacatgg cataagaact tatcacattt cagatatttt ctttagtaac aagttttgt 128280
ttttatagtt cctggtacac agcaaagttt atcacgaaag ataaaaatcc ttttaaacaa 128340
atccaacagg aaattcttga ggcaccttct catataaaac acaagatgaa tgcaattatc 128400
aatccatctg agaaaagttt tcaatctaaa tgaacatcat ttttccatt taagtatatt 128460
ttacagaact ttaataaggc aagacaaatt tgtgaaaaaa gatgtagata caaaaatgat 128520
gtaaactaat aatttatatt aaaaaacccc aaagggataa cagtggagat gggacagctc 128580
aaacaatgcc ttttttaac ctaaaacaga attgtgcaca agctgaagat gacaaacaac 128640
ttctagactc tgcacagttt tggttttttt ttttaacatc tttatattac atgttttaaa 128700
tcatatcagg aatgcaaact agaactgcac actacttcag tggaaaaaag ttcaatattg 128760
tgcaattttc tgcctcttaa tagttaaaaa gtggcagcaa tccctgcatt tgtgtttgaa 128820
acaaggatct gagaaacttt atcaaaaaag gtaatgaagg caaaaattgg cagacatcca 128880
gcatcttgtt tctttttaaa acaatgtgga tgataagtaa tttcatgatt aaaaatgaat 128940
cttttaaata aatacattgt atctgacatt tgcactgact gatttgataa atctttaagt 129000
aaacaacggc tttactacac tccctgtagc ctcaagccac tggctttaga ttctggagtc 129060
cttattcact gggtttcata ccctgccact cgatacccag aaggctgatt gggcaacatg 129120
ctgccatttt gcccttgagg cggttgcact ccataatttg gtcccatcca tggtcagaaa 129180
gactgtgtct gactggtgga gaatgtgaaa gaagcagagg ggagaggaaa tccactgatt 129240
aaaataaagt attggcaaga acaaacaaca agaacaaata tgggaaatgg gaaacatact 129300
tttcttaat cccaaataga ataatttatg ctagggaaaa tgaaatcttt tactaaagtt 129360
tttttctctt aaaaacaagc atccctgtat gtttaatttg gacagtttaa ttttgttaga 129420
aattaaagct aagaaaatac cctgaactta tcaacattca tctcctttga atatagaaaa 129480
acctaaccc attcttggaa aagaaagcta tccatctcat ctctatgcct tggttgaaca 129540
tatttgctga ggaaaccact acctgaaaga gtcaggtagg ttccctacaa cgaaaaagga 129600
acattatact actcaaagaa gaaatcaaaa caattattag catatgaaag ctcataaaaa 129660
ttcataacat tacaagattt tcttttcttt tcttttttt ttttttttaa gacaggtttt 129720
cattgtgtca cccaggctgg agtacagtgg tatgatctca gctcactgca acctacgtct 129780
ccccaggctc aagcgattct cctacctcag tctcccgaac atctgggatt ataggcacgc 129840
aaccaccatg cctggctaat tttttttgta ccttttgtag agatgagatt tcgccatgtt 129900
gcccaggctg atcttaaact cctggactca agtgatccgc ctgccttggc cttccaaagt 129960
gctaggatta taggcatgag ccaccatgcc caaccacaaa atcctttttt tttttttgaga 130020
cagagtcttg ctctgctgcc caggctggag tgcagtggtg tagtctcagc tcactgcaac 130080
ctccgcctcc caggttcaag tgattctcct gcctcggcct cccaaatagc tggaactact 130140
ggtgtgcacc actacacctg gctaatttt gtatttttag cagaggtggg gtttcgccat 130200
gttggccagg ctggtcgcaa actcctggcc tcaagtgatc cacccacttc agcctcccaa 130260
```

```
aatgctggga ttacaggcag gaactaccac gcccagccca ctaaattcct ttttaacctc   130320
tcaagtattt ttatttccag tgtgttttc agaaatgtaa gtaaaatagt gtaattcagg   130380
gtgtataagg aagcttgcaa tgtaacaagg catattgaaa aaacccttg tacagaaaaa   130440 agcataatga atacaacaac tagcatcaaa ctcagtgtat ataagaatgg ctaagtgacc   130500
attagtcatg tgaaaagctt aacaactatt aagctcttat tttcttacta aaaacaatt   130560 ttaagttctt tcaaggctat agttacgctt tacataagag gccctattac ccactaattc   130620
ttaaaatttc ttcctactta aaatttcttt agacattttc aaaggttagt aaaggaagac   130680
ataagatatg cttacttaaa tccttgctgg ttccatgcct ggccatacat tccatatgca   130740
ggaacttgcc aaccattagg catatactgg ccaatttgtt gtgcatttcc ataccactgg   130800
ccccactggc cataaggttg gggatatcca atttgattct gctattaaat aaaatttagt   130860
attacttgaa gttaactata tatatacaat cctaatatgc tgataccaca aattcttagc   130920
caaaacacac agggccatca ttacaattaa aatgacagga taaacaagag ttgactgcta   130980
aaaaaaaaaa aaaaaaaaaa aaaaacaaaa aacaacaaca aaacaagtga ggttatactg   131040
ctgtaactct acgtgatact ctgaatggca tagttttgg aaggcatcag ttgatacct    131100 agtaataaat gttaaactta gtagaatgtt taagtgtttg gtatactatc tacatgattg   131160
tttcctttag atagggaaga tgtgattaat tatttctata ttcagcttac ttaagacact   131220
tatatagttt aggatttgct tactcccatc tctgtgctcc atttacagtt tcctcataga   131280
aatctttgtg gaatcaagtt tgaaccacta agctgcctg gaaaaaaag gcagcaaaat     131340 ctggaagaaa aatgccaagg ccataactat atttacagct ttatttttgt ttcagttgag   131400
tcaagcatgc ttgtgagttc tccaaatggt atgtgaataa atctaccaag tattaaaaaa   131460
agatgtaata ccctttagg tttctcggag cattttaaaa tccactgtgt gagcatgagt    131520
caattgaggc ggtcacattc atcatgtcac cactgcaatc catgaaacac cattctggaa   131580
ctataataca tgtaggaaga gcccttatat actatcattt tagctagaaa cttattaaca   131640
aggattatca acaatcttca ccttaaaata acattattag cccaacaatt acttctcaaa   131700
gttaagaacc ctctcacctg ttgcacggga tttatcatat caagagtttc tttgccccaa   131760
tagcatttca caacatgacc ttcaatggta gtaccattaa cagaaacaat tgcatgtgct   131820
gcactttcat gggaattgaa cctattgaaa acaatattaa gaatcaccaa tacaaattct   131880
tttaaatatt tatgaataaa acctatttt aaaaatcaag gtgagtctga ggtaaaacag    131940
tttgcgtaac atggcatatt ttcttttgcta ttttttttcaa agatcttgta gttctggggc  132000
aacttgtgtt aacaaagaat gtgtgtttca ctggccttgt gttagggagg gagctataaa   132060
atcacagagg caaatacgct ggatgctaga gaaatttcaa tttttttttt ttgagatggt   132120
gtctggctct gttgcccatg ctggagtgca gtgattgtga tcttggctca ctgcaacctc   132180
cacctcctgg gttcaagtga ttctcctgcc tcagcctccc gagtagctgt gattacaggc   132240
atgcaccgcc atgccggcta attttttatat ttttgtatttt ttagtagaga cggggtttca   132300
caatgttggc caggctggtc tcaaactcat gacggtgatc cacccgtctc ggcctcccaa   132360
agtgctggga atacaggcgt gagccaccgc acccggccaa aatttcaact tttttataac   132420
caaggtaaat ttttaagaaa acgaggtaaa tgttcaaaaa atattttgga ggaaaaagtt   132480 tttattttt attatttc tggttttcca gttacattac caagaaaaat gtttttttaa      132540
aaaaccatcc ctaccgaaca aatgaatatc ctttatctgg aaagactcga atttccatta   132600
tttgtccaaa tggtgaaaaa gtctgacgca ttagttgttc tgttagacaa aaaaccaaaa   132660
```

```
caaacaaatc acactaagtt atataaaaat cctacaaata ttaagctttg cactttaaaa   132720
attaatgcca cacagggaag gctcccatac ctgttagccc agaagtaaca cctccacagt   132780
atacagtaca gttgcttgga ctagactgat ttacaacctc atcatatgat agctgtttgg   132840
tatttgctgg tgagagaaaa ggtttatgtc tttaattcat taaataaaat gtgcagaaag   132900
agaaaagtag cattcactac actactgtaa aggtaacatt aaccttgatc aaaatgctta   132960
tattacacat attatacttc agttcagaat taaacctccc ccacgaatgt ctaaaaaatt   133020
acccagtatt ttctatttaa taggagactt gacattagaa ataatattat ttataattac   133080
aaaaatgaaa actaagtaca tttttgaata gtagtcttga tttgcttctc atctatttct   133140
gcaataagtc tccgggaaca gctctaacat ttaaaatcta gcgtatttt ctccaaaatt   133200
ccacatttcc ttttcttctc aatacacct acactcatat gtactctttg gagcgggagg   133260
ctttcgggtt gcccagttag ttctgatttg tcttccacca agccactggc cacccatctg   133320
ttgaatggcg ttttcagcat cctgttccgt acaacattag aaacaataaa gaagtcacta   133380
ttagttgatg ttaaacaact cttagcagta gagaaaactt ggtgcttttc acaaatgttt   133440
aagtgaaaat gctctatgaa atacacaaca tatgatagct ttcctaaaat gcaatggtgc   133500
tttttatatt tttaaatttt attttattta tttttttcaga tagagtctcg ctctgtcacc   133560
caggatggag tgcagtggtg tgatcttggg tcactgcaac ctccgccaac tgggttcaag   133620
cgattctcct gcctcagcct cctgagtagc ggggattaca ggcatctgcc accatgcctg   133680
gctaattttt gtatttgtag tagagatggg gtttcgccat attggccagg ctggtctcga   133740
acttcttctt ctttttttt tcttttttaa gtctcgctct gtggcccagg ctggagtgta   133800
atggcgtgat ctcggctcac tgcaagctct gcctcccagg ttcacgccat tctcctgcct   133860
cagcctccca agtagctggg actacgggca cctgccacca cgcctggctc attttttgta   133920
tttttagtag agacacggtt tcgccatgtt agccaggatg gtctcgatct cctgacctcg   133980
tgatcctccc aactcggcct ctcaaagtgc tgggattaca ggcgtgagcc actgtgcccg   134040
gccctggtct caaacttctg acctcaagtg atctgtccac ctcagcttcc caaagtgcta   134100
ggattacagg catgagccac catgctcaac ccaatggtgc ttttgtattg ttttttctctt   134160
atttgaatat taaattttgg gaacattaat catctgaaaa ggtcgtgagc ccgacagccc   134220
taatgaggta gatatcataa agttcatgca actcagacta ctatagaaga aaatcttaaa   134280
caatctaaca agcttgttaa caatatttgg tttctcattc atccaacaaa taaatattga   134340
acagttatgt tccaggcatg cggttaagag ctagggacac actggtaaac aagcatacat   134400
ggtctcttac attcttttgt ggggaacaaa taaagcaatt acatattgtg gtaagaccta   134460
tgacagaaac aaaaggctga gatagagaat atgggcacaa ggatctacta cagacaggat   134520
gaataagaaa ggtctctctg aaatgacatt taaactaagc ctgacagcaa taggagatag   134580
ccaagtcaaa acaatgagga agaaagcccc agtagagaga aaagtattgc aaagtgtgtt   134640
aaggcacaaa agtttggtat gcatctgaaa gcagcatgtg aaagactagt ttcagtggaa   134700
tccagcgagc aaaaaagaat gtcagagaat gaaactgaaa gatttttaagc aaggaatcat   134760
catgacctat gttttaagaa ggccattctt ttttttcgaga tggagtcttg ctctgtctcc   134820
caggctggag tgcagtggcg cgttcttggc tcactgcaag ctccgcctcc tgggttcctg   134880
ccattctcct gtacaggtgc cagccaccaa gcccggctaa ttttttttttg tattttttag   134940
tagagacagg gtttcttttt tagtagagac agggtttcac cgtgttagac aggatggtct   135000
```

```
ccatctcctg acctcgtgat ccgcctgcct tggcttccca aagtgctggg attacaggcg   135060
tgagccaccg cacccggcaa gaaggccatt cttagcgcta agaggagaat ggcttaggat   135120
aatgggtagt aaggggataa agatactttg tgaaacttgt gcaatattct agattttttaa  135180 aaagtgttgg tggccaggag cattgcagta gcagtgaatg taacttaaac tcaaggccaa   135240
aataatgggg gctggagggg acaccacaag caaaaggaga gaaagataa ctcttaggtt    135300 cctctagaga aattggaaag acagcattta ttgaaatgcg gagaaagact aggaaagaaa   135360
aggggaacag gtctgaggaa gaaacaaaaa gctccattaa gaaaaaactt tgagatgcct   135420
gtgagacata taaatgaaga ccatttgtta ataaatgtgg aacgcagaga agtgagactga  135480 agatacaaaa ttcatgcaga ctagagaaag agcctaggac agagccctga aaaacagcaa   135540
aacttgaaaa atgggtaaag gaataatcac tagctaaggt gactagggag gagtagccag   135600
tgatgaagga agaaagccac aaaagtgtat ggtccaggga gccaagaaaa cagaggttaa    135660
gaggtgacct tgaaaataga gtagcattgg tacaaagtga gagtaaaacc agcttagagt    135720
agactaaaaa gtaaatggag tgtaactttt gtgtgcacac atcaaaggta agcttaatct    135780
actactgaag gaacaggcaa attcaaggcc tttcttgaaa tatgaaaacg aaatgcttta    135840 aaaaaaatt aaataggtc ttattctgtc atccaggcat gatcacagct tactgtagcc     135900
ttgaactcct tgggctcaag tgatactccc acctcagcct cctagtagct aggactataa    135960
gcatgcacca acaaggttgg ctgttttttt tatttttta atttctttac tatggtagga    136020
acagccttta ctggttgcaa caggcaatgg gagggattcg gggtccacag actaggtcgc    136080
caggcttttt tttttttttt tttttaatgg agacagggtc ttgctgttgc ccaggctggt    136140
ttctaactcc tgggctcaag cagtcctcct cctgccttgg cctcccaaag ttctgttatt    136200
acaggaatga gccactgtgc ctggcaggaa atgcacattc ttaaaaagaa acaaatatta    136260
tcaccccaac cagtccgaac tccatgagac gcttaactaa tgttatgtgt tgaattgtgt    136320
ccctcaaaac gatatgaagt cctataccct ggtatctgtg aaatatggcc ttatttggaa    136380
acagggtctt tgccgaagta attaagatga ggttatactg gattaaggtg ggccccaaat    136440
ccaatgactc aagtcctcat aagaagtaaa gatcagactg gcacggtgg ctcacactta    136500 taatcccagc acttgggagg ccgaggcagg tggatcatga gcccaggagt cgagaccag    136560 cctggacaac atgacaaaat cctgtctcta caaaaaatag aaaaattagc tgggcatggt   136620
gttgcaacac ctgtagtccc agctacttag gaggttgtga tggaaagatc acctaagcct    136680
gggaggtcaa ggctgcagtg agttgtgatt gtgccaccac actccagcct gggtgacaga    136740
gtgaggtcct gtctcgaaaa aaaaagatga tgattatatg gatacacaaa gagagaagat   136800
ggtcatgtga agatgaaggc agagattgga gttatacagc tacaagccaa tgaatgccaa    136860
gaattaccag caaccaccag aagcttggaa gaagcaacaa aggattcttc tacagagcct    136920 tcaaagagc atggacatgc tgacaccttg attgtgaatt tcacgcctcc aaaacattga    136980
gaaaataaat ttttgttgct ctaagccatc cagtttatga tactttgata cagctcctca    137040
ggaaaaaaat aaaactactc actcaaaaaa gtggaaaaaa aacagagatg tatctatgtt   137100
ggtggttgtg aatgggagat aaagtagaag catatgcaaa caactcttga gaattatagc   137160
caagaaatgg ggatacagtt agggaaggga tgtgaggata acagtggtt ttgattaaga     137220 gatactagat ggccaggaac ggtgcctcat gcctataacc ccaccacttt gggaggccaa   137280
ggcgggcgga ctggtggaag ccaggagttc gaggccagac tggcaacaa agtgagattg    137340 ttcctacaaa aaaatatata tatatatttt tgagacggag tctcactctg ttgcccaggc    137400
```

```
tggagtgcag tggcataatc tcagctcact gcaacctttg cctcccaggt tcaagcgatt   137460
ctcctgcctc agcctcctga gtagccgtga ttacaggcgt gtgccaccat gcctggctaa   137520
tttttctatt tttagtagag acggggtttc accatgttgg tcaggctggt ctcgaacttc   137580
tgacctcatg atctgcttgc ctcggccacc caaagtgctg ggattacaag tgtgagccac   137640
catgcctggc ctttttttaa aaaaaaatta ggtgggcatg gtggtgtaca cctgtggtcc   137700
cagctactct ggaggctgag gcaggaggat ggattgaggc caggagttcg aggctgcagt   137760
gagctatgat cacaccactg cactccagcc tgagtgacag agtgagaccc tctctccaaa   137820
aaaaaaagag agatcctagg ttgatgaaaa tgatccagta gagaaggaat agagtgatga   137880
cacagaatag cagtaataac aagaacagca cattatgatt ccatttatag gaaatgttga   137940
gaacagggaa atctcagag acagaaagta gattgacaat tgttcagggc tggcaggagg   138000
ggcatgaaag gaggatagtg actgctaatg agtcatgtag cttcttttg gggtggtaaa   138060 aatattctaa aatttatttt ggtaatagtt gcacaattct gtgaattacc tagaaaccac   138120
tgaattgtat actttaaaaa aaaaatttt tttttgaga cagggtctct gtcgtccagg   138180
ctggagtgca gtggtgcaat ctcagctcac tggatcctca acttcctggg ctcaggtgat   138240
tcccccacct ctgcctctca gtaactggg actacaggtg tgtgccacca tgcctggctc   138300 atttttttgta gagaaggggt tttgccattt tgcccaggct gctctcaaat tcctaggctc   138360
aagtaatctg cctgccttag tctcccaaag tgctgggatt acaggtgtga gccactgtgc   138420
ccggccacac tgtatacttg aattatatct caataaagct gctgttaaaa caaaacaaa   138480 acaaaacaaa caaacaaaaa aaaacaatg aagcagtggc agcataggct caaagtcctt   138540
gaaaaggcaa gagagatggg gacacaatca taagtgattt tgcctttgac aggaaggacc   138600
tttcctgtac tataatagga agaatgggaa ggtggatgaa tttatgtaa gtttggtggt   138660 tgaaagatga gaaacacatg tttgccaaga cagtactctg tactcaccta aagtgtgtga   138720
ccattaaatt agaagcaaaa ccacctgaac tcagtttttt tccaggaaca ttcagttatt   138780
ttggggtagg cagagaagct aagctcaatc agtattgtgg tcttcctagc atgtagaaca   138840
taggaagaga ggctgggggt aattgcaatc agggctgtag cactgcgtaa cagagccaag   138900
cacgtatcac aaattttaca taagttgaaa tttatagatt taaatttata gaagatttta   138960
tagaagatta tattatttac tgccgggcgc agtggctcac gcctgtaatc ccagcactct   139020
gggaggccga ggcaggtgga tcacaaggtc aggagtttga gaccagcctg gccaacatag   139080
tgaaatcctg tctctactaa aaatacaaaa aattagccgt gcatggtggc ggcacctgta   139140
atcccagcta cttgggaggc tgaggcagaa gaattgcttg aacccaggag atggaggttg   139200
cagtgagccg aaattgcgcc attgcgctcc agcctgggca acagagcgaa actccgtctc   139260
aaaaaaaaaa ttatattatt tactcaaagt tacatctgtt ttataatggt tgtcagaatt   139320
tgtatacatc tctggctaac tccagaggcc atacacaggt tatcaagaga catcctttgc   139380
tatttgactc tagttcatac taaatacaca ttcaacagtg atttttatat agcagaaccc   139440
tacagtccac aatctcgaaa atgtgaaaaa tgagttccta gcccatcaaa ccgccaattt   139500
atttccctaa cttgcactaa aacatcctaa aacctatgaa tcaatcctct aaggaactca   139560
aattaatcac ggctatcaat ccattataga aggtattttt ctacctttct aaaacattat   139620
gctatgctta atagtaaagt tttgagaacc aaataaattc tcttaatttt tatttctca   139680 tcttacagga aaaaaaaat ctttggtaga tgggacatgt acatgattga gcttgtattg   139740
```

```
ttttcacctc tcaatgtact ttacaatttt caactttttt tttcttgaga cagggcctca 139800
ctttgtcacc caggctggag tacagtggct tgatcatgac tcactgcagc tttggcctcc 139860
tggatttaag tgatcctccc gcctcagccc tgcaagtagc tgggactaca ggcatgtgtc 139920
gccatgcctg gctaattttt tgtagagatg gggttttgcc atgttgtcca ggttggtctt 139980
gaactcctga cctcaagtga tccgcccacc ttggcatccc aaagtgctgg gattacaggt 140040
gtgagccact gggctcggct gaattttcgg aattcccgga aaaaaaaaaa ttaaaaaaaa 140100
agtaaaataa aaatatata tattttgtag agatagggtc ccactatatt gccagtattt 140160
atctcaaact tctcagcctc ccaaagtgct gaggttatag cataaaccca ctgtgcccgg 140220
gtaatatttta attttttaaa aagttcctat ccatcacagt attttattt atttatttat 140280
tttttgagac agggtctcac tctgtcgccc aggctgtgct gtggcatgat ctcggctcac 140340
tgcaacctgt gcctcctggg ttcaagtgat cctcctgcct cagcttcccg agtagctggg 140400
actacaggcg cctgccacca cgcccggata attttttgtat ttttagtaga acagggttt 140460
caccaggttg acctggctgt tctcaaagtc ctgacctcag gtgatccacc cgcctcagcc 140520
tcccaaagtg ttgggattac aggtgtgagc cactgcgtcc ggcctcctca cagtattta 140580
ttagctactt ttaaactacc atgggaatat aaactaggga gataatgaat taaatccata 140640
aatgagattt tcaacatcta cctttggctg ataatttaaa caactttact ttctacattc 140700
tgaaaacatc ttatcagtac tctgcatgcc tcaggtgcca ataaatgtta aacagacaaa 140760
acagaagaaa tcttctagtg agggtttatt ttaatcatca gtaaaataaa cagcagacga 140820
aaaaaagatt agtaattaaa acggagtgtt tccattcttt actctttaag cattatccat 140880
gcacttctca ctgagctcac ccatttgttg aaaaggaga caaagccata tcccttagac 140940
tttcctgttg ccatgtcttt taccactcgg gcatctctga aatcagaaac aatcagaagt 141000
ttaggtttgc aaactatcct ctggatatca aataagaatt tcacacacaa ctcattctca 141060
tgtttcacct tcattaaagt gaacctttaa tgcaaattca cctttattc tacaaaattt 141120
atcatgtatt aggaaatgag gcttaatttt atagacatgc aaatcaataa cttaagtata 141180
tatgtatatt tatattgtac agaaattgcc tctctcttca aaaacttttt taaactttta 141240
aatattaagc atggtgaaag cagctactca catgaactac ttaaccactt ataaagttca 141300
caggacatta gatgaatggc tttctttaac catgcaattt ataacttatt tgacactata 141360
ttctacctaa tcattaaaaa aaaatagaaa actggaaacc aaaagaatga aaaagttgta 141420
tattccctaa actaattaaa ctatttaatt ttttcagatc aatttatacc ccccttttg 141480
tctaaattt gagaacttga cattttcaga aatgttaaat cattgaagaa aaatactaga 141540
cacacacaag ttttaagcta gacaagaaaa gattttacac tgaattttat aatagcattc 141600
atataaaatt gattggaact acaagatata aaagcaaaat tttaaaaagt cagaaagtaa 141660
aaaagcacgc caacatttat ccactgtgaa ccgtagcttg tagttagcca gggcaattct 141720
gtccattctt cagagacact ctgcaaaata accagagccc tattatttga gattgagtaa 141780
aaacccagcc atgatagcta aaactccata cctcaaaaaa ttggactcaa attgtgcttc 141840
acaggcaatc tgcttttaag ttagtcaggt atgtcacaat gcttgctctc tcaggacaca 141900
tgaacaaaac aggcactttt ataacaaaaa cccaagtcag aaagccatgc aatgtaattt 141960
tctattaaag tatacataag catatttag atcaatctga gtgatttatt aagtgttcag 142020
ggtcaaaatg acaagacgt ggtggtgaaa agggaaaatt aatgtaagtc aatgttcaat 142080
atgcaaaaat acttaataaa ttatctgtat ggtacgcatg catttaatct ggtagctgac 142140
```

```
tctcttctac gctgtaattt gttagtctac cctaaactca aggaatagga agagtttata  142200
ggctgtatat aagggaaaat accatatttt ttatactaca tgcttttaca gaccactgtt  142260
tattacacat ctataaatca agcactgata tttgcactt ttagagaata tcatgagaac   142320
ccttcaacat acagttatca acttatctcc tttaacaaca acaaaaaatc aggaaaatat  142380
gctactgact gccaaatgat tcctttaaat gcaggaaagc taattcctta tatagcctaa  142440
aactcaaaca ttatacatta tctcaattga aaatcataaa acttaaaggt cttaccaaga   142500 aaaaaaagt atacaccaat aatcatggga ccataagaaa atctacagac taaaaatatg   142560
acacagaaat atatttaaga gaaaaaaata taacccacga tttgtaaatc atgaaattgc   142620
taaaatctga aggtcactta acttaaactc accaactgtt aaacaatctt tgcctaattc   142680
caaactaaaa ttcccgtgtt ttcaaaaaaa ctacctcaat taaaatcaaa gcatttaata   142740
aaatagctac ttaatctgtt cacaatgtta gaaaattttt tcttcttaaa gtttcagaaa   142800
atgttagtct tgaaaatat tcaactcatt tatttctctc tgaaaagatt ctctgaagca    142860
gcagcaaaga tctagatcag gcttctttat cctttatgg ttctatgact actctgacaa    142920
taggataaaa tttacaaaga ttttccacac caaaatgaaa acacaaaatt gtgcatagag   142980
atttagagcc cttgagaggc caaaggctaa gactgtctaa gtccagatat tcgaaagcaa   143040
gctaattatt attgaaactc taagatatta ttaagaagga caatcaagaa atgaaagctg   143100
tacttatttt cctgatcagg tctcacaaag aaaaatgtca tctgaaagaa gtccatttat   143160
aagccctaat tctgtgacca cctttaaagt tggtaattcc ttggtcacat cccctaatca   143220
aggaacgata actcttcaaa cgaaagctcc taaaattcac caatactact ggcatttact   143280
ttccagtctc ctcatctcat ctctgctgtt ggtctgttca aaccaaacca cagctagcac   143340 ttcctttta ctattcttct aggtggaaaa ataacagagc aagcagaaac cctgaagaag    143400
ttttctaagc taattactct acagaaagta ctgtaaacaa cttgttattc ttactctaat   143460
atggcatgct tttcaaaatt ttaaagttct tctatgatga atgctatctc aagtaaggta   143520
tttattcata agggcctaaa atgtatgact aataacaagt gcaagcaagg cagtgcttca   143580
taaaatatta ttaaggcact attattgtta gcagttttt taaaagggtg taaatatcta   143640
gaaaataata ttcaataact gcttttaag ttgaattgtt aaggtttctt tttgttaaaa    143700
tatattaaca caaaatgcat ggtatcatag aagtacccaa cagatctaaa ttccttagtt   143760
acagcacaat tttactaaag attgtcacca agctagcttg ataccttatat aagaaagtaa  143820 aacatgtaca atggcaaatt tgtctcttaa gagctatgct aattgaaaaa ggattttaag   143880
ataattgaaa accaaaggtt tattcatcaa tgggaaaaca atcttttgct gttaacttct   143940
tgaatgatct ctaaacaatg taatacatta tattcaagtt ataaaattaa tgtacaaaat   144000
tcacaacaga attattttca agttatgtct acatataatt gtttctaatt aaaaggattt   144060
tatttatctt ctgttactta cgatattctt ccaaatggtg caaagcagc ttttatatct    144120 tcagttgtaa tttctgggct gagatcacca acaaagacat ggaaatgatc ttataagggg   144180
aaggaagggg aagtgaaaag aaaaatagaa ctttagaatt taaaaagtac taaaatctat   144240
ccaataaagt attcttaaaa tgattatggc ttatgataaa gtataaataa aacactatcc   144300
tatatctata caaatcctac caattttaaa caatgaatca aggtaacaat ataggaaaaa   144360
ttctcctgaa acgactgtga tacatctaac tgtaaagtga catttatatt tctatttaca   144420
gtcaattatt acactggtct aagaaaataa actaataaca tacaagtttc agttctgcaa   144480
```

```
aaaaatttaa tgacttagtt accattctaa taataattat ttacttttat tcagtttacc    144540
actatattaa ggctttacaa attaaaataa aatagtggta ctgtgaatta tgtagactag    144600
atttgcctca gttaacacaa tttactgaag ctagctacat gatatatact tggtttaacc    144660
atattttgtg aagaacaatc aaagaaatac cttgcattgc aacagtttga tgttaaagta    144720
tttgacagtt ttctcaaaag ccaacagttt tggttgccca gacattacac cattcagttt    144780
atgtgaatcc atgtgcaagt gaactaagac tgaaggcaac agaatgaaaa cagtaatccc    144840
ttcactttat atcagaacca ttaaaaaagc attggagaga aataaccaac ccatatctga    144900
agtttttaaa aaagacaatt atcaaaaaaa gaaacacttt aaaaatgcaa aattgttgga    144960
ccaacacttt aaaatggaca catacatcaa tttgacaaag catatttgga aagaaaagtt    145020
acccatattt gacaggcctt aaacaacatt ttggattgct ctttgggaaa caaaatttga    145080
ggagcaactc aagcatttgg aagatctggg tatgaagccc aaatggtgac ctcaagaaag    145140
gagggtattt tgccccttag ttggtgaaag tagttctaag gcatcagctg ctaccaaacg    145200
ggtcagaaag cttgaactag caccaaagta gcggacaagt tatacttggt caacactgag    145260
aagggagaaa agtattgcta gagagacaaa tagaaataat atctcctccc gcccccctcc    145320
cccaaatatc aaacaaaaaa acttcaggtg gttagtgaat accctttcaa gagatttcat    145380
tttatgttta agaagataca attaccttgt gaacgctgtg tgctgacaac ggtactacct    145440
gatgacaaag attagatttg ttcttaaatt tattaacaca aacacattca atcatatctt    145500
aggataacga tcaaaacatt actgcaaaca tgtatgatgt ttataggctt tacaataaaa    145560
ctactgggta caataaaaac aaatgttcaa agagcataaa atatacttac tgcttgtatc    145620
tttcttttga ctgctagggg ttgttgccca attcactttg acttcctaaa aaaaaaaaat    145680
ttctacattt atacttcaca aaaataaagc ccaaaatcac atttgtatct ataaacacat    145740
aggaagatat ctgtttaaga tgaaacactg aaggagatac cagctctggt caagtttcaa    145800
cacttaatct tctgacctac atttaggcaa ataatgttga caaatcctaa tctttatgtg    145860
tctgttatca ttcaattaac cttccctacc taaagtaccc atattatttt ttttcctttc    145920
attcttttcc attagcatcc aagcttgagt aattcagcaa atattttgtt atttaccatg    145980
tacaatccac catggaaaat actaacatag gctgctggct gacgtctgta atctcagcac    146040
tttcggaggc caagacaggc ggatcacctg aggtcaggag ttcaagacca gcctggccat    146100
cagagtgaaa ccctgtctct acaaaaatac aaaaattagc tgggcatgat ggtgggtgcc    146160
tgtcatccca gctacccagg aggctgaagc agaagaattg cttgaaccca tgaggcgagg    146220
gttgcagtga gccaagatgg tgccactgca ctccagcctg ggtgacaaag caagattcca    146280
tctcaaaaaa aaaaaacaaa aaaacctggg gacggtggct cacgcctgta atcgcagcac    146340
tttgggaggc cgagacgggc agatcggatc atgaggtcag gcgactgaga ccatcctggc    146400
caacacggtg aaaccctgtt tctactaaaa atacaaaaaa ttagtcaggc gtggtggcgg    146460
gcgcctgtag tcccagctac tccagaggct gaggcaggag aatggcatga acccggaagg    146520
cagagcttgc agtgagctga gatcgcgccg ctgcactcca gcctgggcaa cagagaaaga    146580
cccaactcaa aaaaaaaaaa aagaaaaga aaatactaac ataaacacaa gcctctgccc    146640
tctaaaagct ttatcctacc ttttttaatat tatatgtcaa taactgacct tttgctataa    146700 agtgttttaat gtttcagcca ggcgcggtgg ctcacatcta taatcccaac actttgcgaa    146760
gccgaggcag gcagatcacc tgaggtcagg agtttgagac cagtctggct aacatggtga    146820
aacctcattt ctactaaaaa tacgaaaaat tagctgggtg tggtggtgcg ttcctgtaat    146880
```

```
cccagctact agggaggctg aggcaggaga atcacttgaa cccaggaggc agaggttgca 146940
gtgagccaag actgtgccat tgcactccag attgggcaac aagggcaaaa tttcatctca 147000
aaaaaaaaaa aaaagtgttt aatgtttcta aaaggaaac aaaatcatat ataacttaaa 147060 tttttttcagt gcaagtcacc ttctttaatt acgacagctt accttaccca ttatcttccg 147120
tccattcata gcagctaatg ctgcagctgc atgacgatgc tcatgaaact ccacaaaaca 147180
atagggatca tttccagctg tctgtgggag aagaaacaca aaagccaatt ttaagcttta 147240
ttcacccatt accttaaaat tatgtaaaaa aaaaaatctt aaaccaagtt ttatacatct 147300
aagttatcag gccatggaga atgaatggtc tattccacaa gtaaatttta gatttaaaaa 147360
agtaggctgg gtgaggtggc tcacacctgt aatcccagca ctttgggagg ccaaggcagg 147420
tggatcatga ggtcagcagt ttgagaccaa cttggccaac gtggtgaaac cctgtctcta 147480
ttaaaaaaaa atacaaaaat taaccaggca tggtggcagg ctcctgtaat cccacctact 147540
cgggaggctg aggcaggaga attgcttgaa cccgggaggt ggaggttgca gtaagctgag 147600
actgcgccac tgcactccag cctgggcgac agagcaagac tccgtctcaa aaacaaacaa 147660
acaaaaaagt aaacagccag ctcctgtagt cccagctact ttaggaggct gaggtgggag 147720
gaatgcttga gcccaggagt ttgaatccag cctgggcaac acagcaagat cctgtctcta 147780
aaataattaa aaagtaaaaa aaaaaaagca aacacttaaa atcacactgc ttttatacat 147840
agctattttc ttcaacaggt tatactatag tactataatt taatattaat gactaggtat 147900
cctaactgga tatatagcta cacatacccc atcatcatat aaccatttgt tcaagctaca 147960
cagattaagt ttgactgaac tcctaagttc tgaagtctca cttcggcttt ttatgatttt 148020
tctatcccct ccctgttata agttacttt tactgctaca aatgtacatt gctccttgct 148080
gctactagct tgctgagtag cagaaaatct tagccaacct tcttaaacct gttttaaaat 148140
ataggtaaat aggctctgaa aactgaagag attctctggt aagtaaaatt ttagaataag 148200
ttttagaatg tgaactttct gacatcaatt ttttgcttgc tcagaagcct ttaaaaatt 148260 atcttcccgc caggcgcagt ggctcatgcc tgtaatccca gcacttcgag aggccgaggc 148320
aggcggatca tgaggtcagg agatcgacac catcctggct agcacggtga aacccgtct 148380 ctactaaaaa tacaaaaaat tagccgggcc tggtggcggg cgcctgtagt cccagctact 148440
caggaggcta aggcaggaga atggcgtgaa cccaggagac ggagcttgca gtgtgcagtg 148500
agccgagatt gcaccactgc actccagcct gggcgacaga gcgagactct gtctcaaaaa 148560
aaaaaaaaaa aagaaaaaag aaaaagaaa aaaaattatc ttcccagcca ggcatgatgg 148620
ctcacacctg taatcccagc actttgggag gccaaggtgg gctgatcacc tgaggtcagg 148680
agtttgagac cagcctgacc aacatggtga accctgtctc tactaaaaaa tacaaaatta 148740
gccgggcgtg gtggtgcatg cctgtaatcc cagctactcg ggaggctgag gcaggagaat 148800
cgcttgaacc ctgaggcgga aggttgtggt gagccgagat tgcgccattg cactccagcc 148860
tgggcaacaa gagtgaaact ctgtctcaaa aaaaaaaaaa aaaaaaaaa aaaaaaaaaa 148920 attatcttcc cttggccggg cacagtagct catgcctgta atctcagcac tctgggagga 148980
tgaggcaggt ggatcacctg aggtcaggag ttcgagacta gcctggccaa aatggtgaaa 149040
cctcatctct actaaaaata caaaaatcag ctgggtgtgg tggcgtgtgc ttgtaatccc 149100
atctactcgg gaggctgagg caggagattc gcttgaactc aggaggggga cgttgcagtg 149160
agccaagatg gtgccactgg attccagtct gggcgcacag cgagactctg tctcaaaaaa 149220
```

```
aaaaacaaaa cttcccttttt ctgctggtgt tccaggtagg tgaggctatg tgataaatag   149280
aacctggatg tttaattata aattcaagta gcagaaaaaa attccaattt ttacacctac   149340
agtgcaaaat atcaaatgac attataggcc attttaaaat tctttccata gcctcctaaa   149400
cagatttgtt aaaataaaaa actaattcaa aagactagaa agctactaaa atagaggaat   149460
atacaatttt atttcaagta cagttaatta attttttttt agagatgtgg tcttgttatg   149520
ttgcccaggc tggtctcaaa ttcctgggct caagtgatcc tccagcctct gcctcccaaa   149580
gtgttgggat tacaggcatc agtcactgtg cacatcaaca attaatagtt tgagagtcac   149640
tggcaatgac ttgtaaaaat tttaaagcaa cgaggccaag acaaagttta atatattggg   149700
actatatttt gtctaaaaaa attagagaat aaaaatgtta tataactcaa actaataaaa   149760
cacaatggga attctattac caagatcaat gctgacaggc aacactgaaa tgaagttaga   149820
aaaagtcact tgcggctggc tgtggtggct cacgcctgta atcccagcac tttgggaagc   149880
tggggtgggc ggatcatgac atcaggagat caagaccacc tggccaacat ggtgaaaccc   149940
tgtctctact gaaaatacga aaactagcca ggtgtggtgg cgcatgcctg taatcccagc   150000
tacttaggag gctgaggcag gagaatagct tgaacctggg aggcagagtt gcagtgagc    150060 tgagatcatg ccattgcact ccagcctggg caacagagtg agactctgtc taaaaaaaaa   150120
aaaagaaaaa gtcacttgca tttaagagta aataaatgaa aaagaatatg ctttacttaa   150180
tttatatgca gaaaaaacta acttttaaa taagaatcga agcatatata catattatca   150240
gtccagggag cataaaattt ataaatgtga acattagtct cagaatgtga acagactgga   150300
atttagattt gaataataaa aatctaagct tttgagcgat cagaatccac aaatgataaa   150360
aagtggcaaa ggctaacctg gttttttctg tagccaaggc aatcattaac gttttgtcta   150420
atgatctttc cccagggaaa catatgacca gccagagaga gagtagcagc aggcaaacca   150480
acagagaaga tttatattcg gataaatcaa ttagggttta cagccttgct ttgcctcatt   150540
tcctcataca tgaaatgaaa ataacacctt ctttatgttt ctattgagca tttatgacaa   150600
tgtattaaag taactgacag gcagcaaatt ttccataaat gctaccattg ggataagtaa   150660
ggagatctag attaaggaaa gactggtttt aaatttctct tcatctttcc ccatcttcc    150720 ctcctgtctt tctctatggg tacatggatt ttttctcctt tatccaaagg cataccgata   150780
ttaaatgtga tagaataaaa gaacataact ctttgttgat ttcatctata taatatgcag   150840
atgattttgc agcatcagaa caaaggtctg acaacatttt aagatctaag acaacaaatc   150900
aaagccaatt ggataaatat atatttttga gacagtctcc ctctgtcgcc caggctggag   150960
tgcaatggtg caatctcggc tcactgcaac cttcgcctcc tgggttcaaa caattctact   151020
gccttagcct cctgagtagc tgggattaca ggcgcttgcc accatgtccg ctaattttg    151080 gtatttttag tagagacggg gtttcgccat gttggtcagg ctagtctcga actcctgacc   151140
tcatgatctg cctgcctcgg cctcccaaag tgctgggatt acaggtgtga gccactgtgc   151200
ccggctaaat aattactttt aaaaatatta agtaaaaaaa agttgaactg gaatacaaca   151260
ggaaagaagg taacagatac acatacacac atacatgatt gtcttttctg gagaaaagaa   151320
aactgaaagt ttatagcagg ctgggtgcaa tggctatacc aagaccctgt ctttcaagac   151380
aaacaaacaa acaaacaaac aaacgaaaag tttacagaaa agagagacca tgggacaaaa   151440
ggatttctct ttaacatagc ctttcccatt aaaaaattta ggccaggtac agtggctcat   151500
acctgtaatc ccagtacttt gggaggccaa gacaggtgga tcacctgagg tcgggagttc   151560
taaaccagcc tgaccaacat ggagaaaccc catctctact aagaatacaa aattagccag   151620
```

```
gtgtagtggc gcatgcctgt aatcccagct acttgggagg ctgagccaga agaattgctt 151680
gaacccggga ggcggaggtt gcagcgagcc gagatcgcac cattgtattc cagcctgggc 151740
aacaagagca aaactccgtc tcaaaaaaaa atttaaagtc ttttccccccc aaccaggaga 151800 caaagactcc agggaaatgg ggtaaatgtt ccctaaatgt cttttttatac ctattatgat 151860 tcagggttaa caccaattag atgaatgagt gtgtgtgtgt gtgtgtgtgt gtgtgtgtat 151920
gtgtgtgtgt ttaatacatt gtctcataaa taggaattgc ctaaatacaa gaaaaacttg 151980
aatgatgacc tttaaaaata aagttaaaaa tactttcact gtaccaaatg cctattattt 152040
ttaaacctgt tttccaattt aattgtaaga gctgaatttta ttagccaacc agttgacacc 152100
acatataaac atttctgatg cctcaatgca cctgaaagag cccatatata tgttcccatc 152160
tgatctagaa ataactagtt ctattgtcat cttccatcat gtaataaaac aaattaaatt 152220
cagctgtcaa aacaggttca ttacaaattc actaaaatcc ctattaactt agaatatggt 152280
aaactaagac tatatttaga ctacagtaaa ctaataattt atactatatt tagaccatgg 152340
taaactaaga attccttcca agcaatggct ttaagtaatg tgtaaaaaaa aaagaataa 152400 agttaactaa gtaaaatacc cttacatcca taatcatttt gcagttttta caaggtccaa 152460
tctggctaaa gagttgcaga attagagctt ctgtcacatc tctggaaagg ttaccgacgt 152520
atctgaaaca caaagagaaa caatttacct tttttttttt ttgagacaga gtttcactct 152580
tgttgcccag gatagagtgc aatggcacga tctcggctca ccacaacctc cgcctccagg 152640
gttcaagtga ttcccctgcc tcagcctccc cgagtagctg ggattacagg catgcgtgac 152700
cacacccagc taattttgta ttttttagtag agacggggtt tctccatgtt ggtcaggctg 152760
gtctccaact cctgacctca ggtgacccgc ctgcttcagc ctcccaaagt gctgaaatta 152820
caggtgtgag ccactgcacc cggttttttt ttttaagaga aatagtctgg ctatattgct 152880
caggctgctc tcaaactcct ggcctcaagc aaacctactg ccttggtccc ctgagtaacg 152940
gactagagga accaccacac ccagctcaat ttacctcaat ttatttttt ttcagacaag 153000 gtcttctggg ttgcccagac tagagtgtag tggcgcaatc ttggctcact acaatctcca 153060
cctcctgggc acaagggatt ctcccacttc agcctcccaa gtagctggga ccacaggcgt 153120
gtgccatcat atctggctaa ttttttttaca gtttctgtag agaaggcgtt tcaccatgtt 153180
gctgagctgg tctcaaactc ctgggttcaa gcgatctgcc tgccttggcc tcccaaagtg 153240
taatcttaaa gattacaggc atgaggcatt gtgcccagcc cttgatttac cattttaat 153300 ttgcttattc tccatcggtt tctaaagttg ttcattaaaa attaaacttg agaaataggc 153360
agatctttgc cttaaactat aatatttggg agtaacttt aaaagtttgc caacacttca 153420
aaatctcttt gaaaacagat gtaaagtatg ttatttgaaa atatattagc taggtgtggt 153480
ggctcacgcc tgtaatccca gcactttggg aagccaaggt gggaagatca cctgaggcca 153540
ggagttgaga ccagcctggt aaacatggtg aaaccctgtc tctactaaaa acacaaaaat 153600
tagccaggca tggtggtgca catctgtaaa cccagctact gggaggctg aggcaggaga 153660 atcacttgaa cccaggaggc agaggctggg ttagctgagg ttgcaccact gcactccagc 153720
ctgggcaaca gagtgagact atgtctcaaa aagaaaata tattcaccct tgctagtgaa 153780
ggggaagcta gtatgtgctt gtctgttta gtcatcgttt tgcaaactga ttgcttgttt 153840 ctacgttttcc aggcttacct taggaagaca agctttaaaa acactcaaat gaatcatcat 153900
tagttatata aaatatctta tacaataatg gctgggcgag gtggctcaca cctgtaatcc 153960
```

```
cagcactttg ggaggctgag gagagaggat cacttgaggc aggagtttga taccagcctg 154020
gccaacacag tgaaacccct tctctactaa aaacacaaaa attagccggg cgtggtggcg 154080
cctgcctgta atcccagcta ctgggggacg gctgaggcat gagaattgct tgaacccagg 154140
aggcagaggt tgcaacgagc cccgatcacg ccactgcact ccagcctggg tgacggagca 154200
agactgtctt taaaaagaaa aaaaaggct gggtgcggtg gctcatgcct gtaatcccag 154260
cactttggga ggccgaggtg ggcggatcac gaggtcagga gatcaagacc atcctggcta 154320
acacgatgaa acctcgtctc taataaaaat ataaaaatt agctgggcgt ggtggtgggc 154380
gcctgtagtc ccggctactc gggaggctga ggcaggagaa cggcgtgaac ctgggagacg 154440
gaacttgcag tgagccgaga tggtgccact gcactccagc ttgggcaaca gagcgagact 154500
ccatctcaat taaaaaaaaa aatgtatacc atcaaaccta aaaggcattg caattatttc 154560
tacttctatg gtattactac tactaagaac attgacgttc ccccaagttt tttttttttt 154620
tttttttttt ttttgtggac aaagtctctc tctgtcgccc aggctggagt gcagtggtgc 154680
gatctcggct cattgcaacc tccacctccc aggttcaagt gattctcctg cctcagccac 154740
ccacgtagct ggggctacag gcgcccgcca ccacgcccag ctaatttttt tatattttg 154800 gtagagacgg ggtttcacca tattggccag ctggtaccc ccaattttta aattaacatt 154860 atttcccttaa tttgttcaat ttaggtagac tttggttatg caatgaacac attttgaaa 154920 agttataggt aaattatcag ttgttttgaa tgcttacagt gggatgagaa accttccatt 154980
taacattact gatcagtaga agaggggtga aagggagtag aaacatcaca gattatgagt 155040
tggttatcaa tataaaaata taaatcgtgc attacaagac cataagactg tgatgatctt 155100
catttaaagg gtttagatta ggggcagtgg ctcacatctg taatcccagc acttttggag 155160
gccaaggtgg aaagatcact ttagccaagg agttcaagat cagcccagtc aatacagcga 155220
gacccccgtc tctacaaaaa ataaaaataa agataaaaaa ttagcggaca tggtggcact 155280
atgtcccatg gcatggtccc agctacttcg gacgctgagg tgggaagatc acttgaaccc 155340
aggagttaag aggctgcagt gagctatgat tatgccactg cactccatcc caggtgacag 155400
agcaaaactc tatctctaaa aagaaaataa aggttttact atttattcat ttatttagag 155460
acggagtctt gctctgtcgc ccaggctgga gtgcagtggc gtgatctcgg ctcactgcaa 155520
gctccgcctc ctgagttcac gccattctcc tgcctcagcc tcccgagtag ctgggactac 155580
aggcacccgc caccacgccc ggctagtttt ttgtattttt agtagagatg gggtttcacc 155640
atgttagcca ggatggtctc gatctcctga cctcgtgatc tgcttgcctc ggcctcccaa 155700
agtgtttgga ttacaggcgt gagccactgc gcccggccaa taagggtttt ataaataagt 155760
ttttaaatga gattttgaga tgagattacc tctagtcatt ttacagagtt agaggtttat 155820
cagttctgga atcagggaat gcagtctccc cagaatggta gtttctcatt tgtctctcag 155880
gtacccttca gaaaatttga tacaaggtat ggactttctc cccagaaaag taaatattca 155940
tacatgctca caaagtgtgg aatcaatttc ttctttccat ctaccattca acaaacacat 156000
attgagtgct taacacgaag cctttggaaa aggttaagat ggcaaaggaa gaaatgctga 156060
gtcttaataa caaatgacat ttaacgatca ggtaaaataa tggtactcaa aagagaaagt 156120
aacagcaaca tttacccaac agcaatttac cagtattggg agttattact acaccaagtc 156180
tttattctga aaaagagaca gaattaagca tttatcctat taagtaggaa ctcccactaa 156240
atagtgtaat ctaatagctc tagtttagaa aagttctcct ttacaggaga atgctagtta 156300
ataaatgtag aaagatagta ttaaattaac aatgtgtaaa ccctaatgaa ataactgttt 156360
```

```
caggcaagga tctttaatta atgcttaaac tactacatga acagttggtg tggaaatagt   156420
cacaaggtgt caaagttatc acatagatta cttaataaat tgcaaaggga aaaccttacc   156480
ttaaaaatga gagctttggc tgttaccact atgacccagt gataaaattt tcaattattt   156540
tatagatggg caacgaccaa tgagatactg catatatata atatgaatta cacagtatca   156600
cctatgaaat atttacataa aaaagtctaa cctaaatcta accaagctga aaattagatt   156660
taagtttata ggatatcagg caaataaaac aattccatga atccagatgt gggacacttt   156720
ataagacaac tcagtctctt caaaaaatta ttgtcctaaa acaaaaacaa cagatgactg   156780
ttcttgaata aaagggagtg gtggcacaag cccgcagccc cagctacttg agaggctgag   156840
gtgggtggat cccttgaacc caggagtttg agtccagcct gggaacatag caagacctca   156900
tttctaagat ataaataaat aaaagaaaca gaaagctggg cacagtggct caagcctgaa   156960
atcctagcac tttgggaggc cgaggtaggc agttcacttg agaccaggag ttagagacca   157020
gcctggccaa catggtgaaa cctcatctct actacaataa atacaaaaat cagccaggtg   157080
tggtggcgca tgcctgtaat cccagctacc tgggaagggg aggcacaaga atcacttgaa   157140
cttgggaggt ggacattgca gtgagctcat attacaccac agtactccag ccagggtgac   157200
agagcaagac actgccctcc ctgccccccc accaaaaaaa aaggacataa aaaacactga   157260
caaccaaata caatcaataa tgtttaaatg gatcccggat gaggggaaaa tagttttttc   157320
ttacagaatt aataaatgta gaaagaatga gagaaataga aaatcaccat taaaacacca   157380
cagtaataat ttctaaagga agatccaccc atggaagctc acattagttg atgaaacctt   157440
aaaaggggaa acagggtatc tgaatagcct caaagtacct ccactaaaat atttattaaa   157500
aattggtttt gggacaggtg cggtggctca cgcctgtaat cctagcactt tgggagaccg   157560
aggcggatca caggtcagga gatcaagacc atcctggcca acatagtgaa accccgtctc   157620
tactaaaaaa tacaaaaaat tagctgggct tggtggcgtg tgcctgtagt ttcagctact   157680
agggaggccg aggcaggaga atcgcttgaa cccaggaggc agaggttgca gtgagccgag   157740
atcatgccac tgtactccag cctggcaaca gagcgagact ctgtcttaaa aaagaaaaa   157800 aaaaagttttt gaccaatgaa ctagtggttt tacatgacta tgaattcttt ggatatacct   157860
ccctccagga agtgtaactt aatcttcctc ttcctgagtg tgagctagcc tcggtgactt   157920
acttctaacc aacagagtaa gttaagaaaa agaagtcac ggtgattttg gagaacagga   157980
gaaacagtac ccttccaaag tgtcggtagg gtgtggtggc tcacacctgt aaacccagtg   158040
ctttgggagg ccgaggtgag agattcactt gaggccagta gtttgagacc agctagggca   158100
acatagtgat atgcaccgtc tctacaaaaa ataagaaaaa attagctggg tgtggtggtg   158160
tgcacctgta gttccagcta cttgggaagc tgaagtgaac aatgattgtg ccactgaact   158220
ccagtctggg caccagagtg agaccttacc tctaaaaaaa aaaaaagtg ttaaggtcag   158280 aaagacctct cacagaatga aggagaataa agagacgatg acgaaatgca atgtggtatt   158340
ttcctgaatt ggatcctaga atataaaaag gatatcagtg gaaaaattgg aataaagcct   158400
atagtgttaa tttcttaatt ttgataatta taccacggtt atataagatg gtaacattaa   158460
gggatgctag atgaaggtta tcatgccatt cttccgcaaa accctccccc gcaaaaaaca   158520
aaactctgta ctatctctgc atctcttgtg tgtctactct cacctgactc ttgtgcctat   158580
aagaaatttt caggattagc tgggagcggt ggctcacgcc tgtaatccca gcactttggg   158640
aggctgaggt gggggatcac ttgagctcag gagttcgaga tcagcctggc caatatgttg   158700
```

```
aaacttgcct ctactaaaaa cacaaaaaat tagccaagtg tgatggtggg cgagagaatc 158760
acctgaaccc gggaagtgga ggttgcagtg agccgagatc tcaccacggc agtccagcct 158820
gagtgacaga gactcagtct caaaaaaaaa aaaaaaaaa aaaaaaagg cagaatttga 158880 taaggtctct gaaaatttga gtaaaaacga tgaatagttt tttacctaat aataaattcc 158940
ataagaggtt ttcatttta ttcttagttg gtatctacca tctagaacag gggtccccaa 159000
ctccccccta ggccatggac cattatgcgt ccatggcctg ttaggaactg gccacacag 159060 caggaggtga gcagcagggg agggagcatt actgcttgag ctctgcctcc tgtaagatca 159120
gcagcatttg tgaactgggc atgcaaggga tctaggttgt gtgttcctta tgagaattta 159180
tctaatgcct gatgctctga ggtggaacag tttcatcctg aaaccatccc gcccatggaa 159240
aaattgtctt ccacaaaact ggtctcggtg ccaaaaggc tggggactgc tagtctagaa 159300
cactgcctgg aacattgcaa tatcattgca gtgatattta ttgctctata aatatctgtt 159360
aaagagttaa atgtactgtc tcagaatgac ttctgaacat ttgcaatttg ctagaaaatt 159420
ctctcatttt gcttaagtta ccctagaggg aaaagattag ttatgtcttt tgctaatgaa 159480
gaaactgtgt aaacaccagg cacggtggct cacacctata atcccacttt gggaggctaa 159540
ggtgggaaga tcgcttgagc ccaggagttg gagaccagcc tgggcaacac agtgagatcg 159600
cttctctaca aatattttta aaattagcc agacatggtg gcacatgcct atagtcccag 159660
ctattcagga ggctgaggtg ggaagatccc ttgagcctga gaggtcgagg ctacagtgag 159720
ctgtgatcac accactgcgc cagagcctgg acaacaggat gagaccctat ctcaattaaa 159780
ataaataaat aaataaattg tgtagaatag taagtgcttg tgtatatact atacatcagc 159840
atcctaacct tattattatt taacaaatgt atacccatca caaagaataa tctgttacaa 159900
gagatggctg aaactgcctt actagttggg acctccttca ctaggtaaac cagcttgaac 159960
aaatgtattc aatactatgc ctgtagacat cttaagggat atcgatcctc aagacttttc 160020 attttttactt atattttgca acaaactata acattttaga taactgatat tacacatttt 160080
aaaataaatc catttattgt tgacatcatt ctcacatgcc acatctaagc cactggtaat 160140
tcctgttgct ctatttcaa aacatatcca taattcaact acttcccatc actttcacca 160200
gcactaacta caattacagg cactgctttc tctgatacct ggattggctt cctgactagg 160260
ctacttgctt ttgccagttt taaggttaag ataggctata ccactactct gcgtgaaacc 160320
cacttacagc ttccattcct actcagataa gatagccctc ataaggatcc gtatgatctg 160380
gcattttcta tctcccctaa cattcctatt tatcattctg acctcatttc ctactcctct 160440
actacattta ctctcttcag gctaaccaac cagcatgacc tgcccccaag ggccccttgc 160500
actagctctt tctagggtgc tcctccttca gatagaagca tggctctccc tcatctcctt 160560
cacttttttc ctcaaatgtc acttatcaaa ggatgacctt cctttattat tctctataaa 160620
tatccacccc ttcctcctta ccatgcatac cctgcattat gtttctccat agcacttatt 160680
accatctaac ataattactt atgtaaattc gtaaaaggcc tattatatgt actaccatat 160740
ccccagttcc cagaagacgg acagccatgt agtatgctct caatattact gagtgaatgt 160800
aatgttctta gcatattctt aattactagc agttatttgg aaacataagt attatctaat 160860
aaatatctca ttttggccaa ccttgccttc aatctaatct ttaaaatagg tctgattgtc 160920
gcctgtaatc ccagcacttt gggaggctga ggcaggcgga tcgcgaggtc aggagatcga 160980
gaccatcctg gctaacacgg tgaaactgtg tctctactac aaatacaaaa aattagccag 161040
gcgtggtggc gggtgcctgc agtcccagct actccggagg ctgaggcagg agaatggcgt 161100
```

```
gaacctggaa ggcagagctt gcagtgagcc aagattgggc cactgcattc cagcctgggt    161160
gacagagcga gactctgtct caaaaaaaaa aaaaaaaaa aaaagatagg tctgattctc     161220
aatacaagag attttatttc atacaaatta caaggccaat actatttgga gagtggagta    161280
gacaacaaga atgaaagatg agcatggagc agaagaaagg caaggccctc attagtatat    161340
agcaattaat tgggctccgt cttgctctgt catccaggct ggagtgcagt ggcgtgatct    161400
cggctcactg caacctccac ctcccgggcg attctccttc ctgagcctcc ggagtcccga    161460
gtagctgagg ctactggcat gtgtcaccac acctagctaa tttttgtatt tttagtagag    161520
atggggtttc accatgttgc ccaggttggt ctcaaacttc tgacctcagg tgatccactc    161580
acctcggctt cccaaagtgc tgggattaca ggtgtgagcc accatgcctg gccagctgca    161640
ggcttttaaa gatggtctat aatttacaga tctgcatctt agcaaatggg aaagccgcac    161700
aataacagta tagttatctc aaaagagaac actcatgcat ttgagagtaa accacacaaa    161760
ggatattaag gtgtctggat ttgagggaat taactttcat caactaacac cagcaatgtt    161820
tttctagtct agtgtgtagc ttttagttca caagttgaat attttttaaag taaccaaggc    161880 caattcagac tcactataca cgtattttta ttttttttact gtggaaaatt tcaaatttat    161940
atatggagaa gagtagtata catcacccat atgctcacta caaatgtttg aacttattaa    162000
ctgtaccttg aatactcctc aaaataatct tgcagtataa actttcggga agtttgtctc    162060
agaatatgat tccaaagtat tggtgacaag aaatcaaata ctggtattct ctaacttaac    162120
atggagatgc cgaacactca gatgtagcaa atgaaggaat ttccagtgag ccatttaggt    162180
atgtgggtga taaaaattca gactctattt tatcctcaag aaagagtaaa atcttaattc    162240
actgcttgaa attctaccag attttttttt tttttttttt tttttttgag atggagcctc    162300
cctcctgttg cacaggctgg agtgcaatgg cgcaacctcg gctcactgca acctccacct    162360
cccgggttca gcgattctc cttcctcagc ctcccgagta gctgggatta caggcatgcg    162420
ccaccatgct cagttaattt ttgtatttgt agtagagaca gggtttcgcc atgttggcca    162480
ggctggtctt gaactcctgc cctcaagtga tccaccctcc tcagcccccc aaagtgttag    162540
gattataggc gtgagccact gtgcccagcc aattatacca gtttcttaaa caatgtatt     162600 gattacttac catggaccac actaagaaca tatattgaga ggctgtgttt ttaatgtgct    162660
aagaactctg ctaagaacat atattaaaag cctctgactt ccagggtcat taaagcaaaa    162720
atcttacatt aaaattaaaa acactattag gaaaacttag ggattagtac cctcatgttt    162780
ggtcaaggtt tgcctgacta gaaaaatggg agtttgggtt gagggaggta gaaacaagag    162840
aagactttta cagtatgact actttgagga agagtttctt ggatggggtg tattagtgag    162900
ggatacaagg caaaataagt aataaatgta atagttaaaa gttgaggaca ggccaggcgc    162960
agtggctcac acctgtaatc ccagcactct gggaggccga ggtgtgcgga tcacctgagg    163020
tcaggagttc gagaccagct tggccgacat ggtgaaaccc catctctact aaaaatacaa    163080
aaattagccg ggcatggtgg tgcccgcatg tagtgccagc tacttgggag ggtgaggcag    163140
gagaatcatt taaacccagg aggtggaggt tgcagtgagc cgaaatcgca tcactgcact    163200
ctagccttgc agcctgggtg acaaagtgag actccatctc aaaaaattaa aaagtaaaaa    163260
caaaattaaa aagttaaaaa gttaagtggt cagatacttc tgcagtttct aaaattaaac    163320
attttcaaac taatactgag aatattaagt ttacattata aaacacgagc agtgccttaa    163380
cccaaaatgc tgatgactgt catagctaag aggcaagagg gaagagattc caccaacacc    163440
```

```
gtgaggctag tagttttttta gggagtattc atctacagat acaatctttc ctaaaacaaa   163500
ggtcatgcac taattgctac gtcctactga aaagatactt tctgagcctc aggaatagag   163560
aaaagaaatt tcaaggttac taacagatta actgacaatc tattaagaaa acaagtgtaa   163620
ccacatttcc aatatagaca agaaatagca acttaaaagt ggaaaaattt tggaggtaaa   163680
aaaacaatta catcgtactt cagagcaact ttattagaga gctgcaaaga gaaacctaaa   163740
attgcatttt taatgcatgg agctctcaaa ctgccagtat tccaagaata taaacaaaaa   163800
gctatgtcat ccaagaaaaa caaaaagcta tgtcaagaac tcattgagct tttcttcttc   163860
cgagaaatgc caacaaaggc aggatcaact catccgataa tacctcgaaa acaaagaac   163920 gcagttgggg aagccacacg acaaagaaaa tatccacgct ccggtaattt aacgctatct   163980
ctaaaaattc tctgtaaata tgttagggca tttacagccc gctcgttcaa caccatgtca   164040
atcacaacag tagtaaacga ctataaaaat aatattaaat ccatttcccc tcaattgata   164100
tattccttct gggtgagatt tccaaatcct tggggtgtct ggttaggctt tttggtcggt   164160
gggtgctaca gaaggaaagc cagaggttaa agaaaaatgc ttggcttttt tccaattggc   164220
aactgcaaga ataaagttta ctgcactgaa aatgagtaca agcaccctcg aggaggaaaa   164280
aaaatcttat caccgagaag aaaatgaaag gaagaatttc agtaggaaat caaagtaaa   164340 attaaaggga gacggctgta aagataagaa gaggttaatc aaaaagggg agaagcggga   164400 aaaggaaaga aagcatagga caaaggaag gttcgacgag ttctaaaaag aggtctgaat   164460 taaagtctt tctccaggtc taagaccaca gagggcccgt ggcgagagca aaggtcatgc   164520
aatggtgttg ctaaagtgaa gggattaatt gagagggttg agcccgtct cccttcacct   164580 cgtcctcaca gattgggtct tggttgtaag catccaggtg catgctaagg aaacaaaaac   164640
cacgatatcg cggtgtccac ggagaacaat aggctgggag cggcgcaggg ccgaggcctt   164700
ccctccggga cgaccaccat cccgcctccc tcatcgctgc cccagactca cagagtcttg   164760
ggcatctcgt cctccatggc tgctgctgtc gcggcggcgc ctccaggtcc agctccctgc   164820
ccttcactac ctcccaaatc gtttaagcgg ttatggctac aggatagtgg ggtttctcgg   164880
ctgaccagag gttactccgc ctcctcctcc ggcggcaatt acactaaacc gcccggccca   164940
gcgggaacaa tgaaaccccca atacaagatg gcgggcgagcc gggagcctag gagcagccag   165000
caaagttacc cggggccgcgc aggcgcagaa taatcttgca ctctcaacct ccgggccgcc   165060
cggctacacc ttaatccata ggttcacttg ttgcgcagcc gctcttccac ccgacgcgag   165120
ggacgcctca gactgcgcag gcgcaagtat taactacttc acgatttgcg tgaacttttt   165180
tgtcttctgg ctgcggattc gagtgtttcg accgcgaatt atgagggagt ggaaaccttc   165240
agggacagta aaaagcctaa atctttcctc ttttggaaag atatataaag actcttcaag   165300
ctatctggtt tttagcgagc gagaagcaaa acgcctatgc gccgcccggg aatcgaaccc   165360
gggtcgcaag aatgggaatc ttgcatgata ccactacacc agcggcgctg ttgacatgcc   165420
cagccgccac agtattttag gaggaaatag aagcagacgt tctctcatgt gaaaagaatt   165480
gtcatgtatt atttattcat ttaaaagtaa agtttattg acagtctgta atcttctgtt   165540
ttccaataac ataaataatt tatcttttct catcccaaac ataggaatgg atgtttcaac   165600
tttctctgta cagaaaaaaa atttcaattt aaaatgtta cttaagaaat aagaaaaaag   165660
aaaaaaagtt ttacttaaaa aagtaaggat tttattaaga atttgcgtcg ttggtgctag   165720
ccagattttt cagcgcgggg aggatatttc cagatgccag atttttattt atatttgcat   165780
ttcttccgtg tattgattgc acattgaaaa gcatttaaga aatagctgtt taggccgggg   165840
```

```
gcagtggctc acgcctgtta ttccagcact ttggatggct gaggcgggcg gatcacctga 165900
gatcaggagt tcgagaccag cctgaccaac atggcgaaac cctgtctcta ctaaaaatac 165960
aaaaattagc tggatgtggt ggtgggggcc cgtaatccca actactcagg aggctgaggc 166020
aggagaatcc ttgaatctgg gaggtggaga ttgcagtgag ccgagatctt gccattgcac 166080
tccagcctgg gcaacagaac gaggatccgt ctcaaaaaac aaacaaagaa acaaacaaaa 166140
aaccccagct atttaatgca aattggtcac aagaatctta aaagtaaaca agtcaaaaga 166200
tacataaact tcagtccaac tttaggaggc agagaaatta gagctctgaa atgtgattca 166260
gtatactctg tatgcatttc acattgctta ttatatatat atgtcactaa agtaatccta 166320
tgtctaggaa tctatcctac agaaataaaa caattaattt ataaagattt atgtgccaag 166380
atacaactgc agcattgttt acagtagaaa aaaatggagt aacctgaata tccatcaatg 166440
ccacttatgg taatttattc aatttacacc aaatacatgt ggaacttttt cttttctttt 166500
ctttcttttt tttttttgag acagtctcgc tctatctccc aggctggagt gcagtgacac 166560
aatcttggct cactgcaacc tctgcctccc aggttcaagc gattctcctg cctcagcctc 166620
cctagtagct gggattacag acgtgcgcca ccacctaaat tagcctaact aattttttgta 166680
ttttagtaga cagggtttt tgccatgttg gccaggctgg tcttgaactc ctgacctcag 166740
gtgatctgcc tgccttagcc tcccaaagtg ctgagataac agacgtgagc cgctgccccc 166800
agatggaaca ttcattttat ggactatttt gcagttattg aaaagctatt aatcagatct 166860
gtagtgttga actggaaaat atctatgatg taagtttatt taagttgtag aaatattttt 166920
taaacatagg agaatttaca catcgaaaaa cgtgatgtcg gctgagcggg gcggctcacg 166980
cctgtaatcc cagtctttgg gagaccgagg caggcagatc actagagctc aggagttcaa 167040
gaccagcgtg gccaacatgg agaaacccg tctctactttt aaaatacaaa aattagccag 167100
atgtggcggc acatgtctgt aatcccggct actcgggagg ctgaggtagg aggagaatca 167160
cttgaacccg ggagtcggag gttgcagtga gcccctgggc cacagagcaa gactcctcaa 167220
aaacaaaaca aaacaccaaa aaaacaaaaa cgtgatgtcc tctttaaagt agttcttca 167280
gactgtatac attctggatt tttcattttt ggaattgtct ttagagtctc tgacacattc 167340
ttcagattat tttcaaagat atcaagtact agtcttttga tggtgaataa acaaatgtt 167400
aatggggatg gtgtttttaaa aacacctttt tgggacatcc atataaagtg ttttttcagtt 167460
taatggtttt tagtttattc acagaggtgt gtgtgcaaca atcaccacaa tcaattttat 167520
aacatttct tcacctcaaa aaggaaaccc gtagcaatta gcagacactc cctgtccctc 167580
atcccattcc atgtcccagc cactagtctt tctgccccta tagatttgcc tattctagac 167640
atttcatata aatggaagca tgtaatatat ggtttcttgt aactgactta tttcacttaa 167700
cattatgctt ttcagggtca tctatgttgt aacgtgtatc ggtacttcat tccttttat 167760
tcccaaataa aactccatta tatggatatt gcacaagtac tttttttaaa gtagttttta 167820
agttacaaaa gtacaacgtg cttagtgtta caaatgaaat gaaatggata cataaggaaa 167880
atattaaaaaa tgtatcttct tcctcctttt gaggtaagta atattaatag attcatctgt 167940
aatattccac attttactct atacagatgc acatgtatac acttgggatt tttagggttt 168000
ttttttttgt ttttgtttt tttttacag agtgtcaccc agagtgacag tgtcttggct 168060
cactgtgaac tctgtctcct gggctcaagc gtttcttgtg cctcagcctc cagagtagtt 168120
ggggattacag gtgtgagcca ccacacctgg ctagtttttt ttttttgagac agagtttcgc 168180
```

```
tcttgttgcc caggctggag tgcaatggca tgatctcggc tcactgccac ctccacctcc  168240
cgggttcaag cgattctcct gcctcagcct cccgagtagg tgggattaca ggcatgtgcc  168300
accatgcccg gctaatttta tattttagt agagatgggg tttctccgtg ttggtcaggc  168360
tggtcttgaa ttcctgacct cagatgatct gcctgcctcg gctcccaaa gtgctgggat  168420
tacaggcgtg agccaccatg cccggcctaa ttttttttta ttttagtag agacaggatt  168480
tcaccatgat ggccaggctg gtctcaaact cctgacttca aatgatccac cgcctgatc  168540
tcagctcact gcaacctctg cctcccaggt tcaagcgatt ttcctgcctc agcccgccta  168600
gtagctgaga ttacaggcgt gggccagcat gccccgctaa tttttgcatt ttttagtaga  168660
gatggggtgt caccatgttg gactgtctgg tctcaaactc ctaacctcaa gtgatccgcc  168720
caccttggcc tcccaaaatg ctgggattac aggtgtgagc cactgcgccg gcttttttt  168780
tttttttttt tttttgagac agggtctcgc tctgttgccc aggctggagt gcagtggcaa  168840
tgatgtcagc tcactgcagc ctctgcctcc aggctcaggt gttcctgcta ccttagcctc  168900
ctgagtagct gggactacag gcacgtgcca ccatgcctgg ctaatttttt ttttttttg  168960
agatagagtt tcactcttgt tgcccaggct ggagtgcaat ggctcgatct cagctcactg  169020
caacctccac ctcccgggtt caagcaattc tcctgcctca gcctcctgag ttgctgggat  169080
tacaagcgcc tgccaccaca cccggccaat ttttgtattt ttagtagaga tggggtttca  169140
ccatattggc caggctggtc tcgaattcct gacctcaggt catccgcctg cctcggcctc  169200
ccaaagtgct gggattacag gcatgagcca ccatgcccgg cccacgccca gctaattttt  169260
gtattctttg tagagacgga ggtctcactt tgttgcccag attggtctca aattgctggg  169320
ctcaagtgat gcaccagcct cggcctccca aaatgctgga attacaggtg tgagccactg  169380
cgcccagtcc tggcctaata gttttttaat agttgcaaaa tcgtccataa aatgaaagtt  169440
ccccaatgta ttgaatggta aattgaataa attaccataa ctggcattga tggatattca  169500
ggttactact tttcaaaaac ctattgtatt acaaataatg ttgcagttgt atcctggtac  169560
atgtaccttt tttttttttt tttttttttt tggaggttgg ggggcagagt ctcactctgt  169620
gcccagactg gaatgcagta ccacaatcac tgctcacctc agcctctacc tcccaggctc  169680
aggtgatcct cctgcctcag cctcctgagt agctgggact acaggtgcac accaccatgc  169740
caggctaatt ttttgtatt tttcgtaga acgggtttt cgccattttg ctcaggctgg  169800
tctcgaaccc tgggctcaaa tcgtccgcct gccctagcct cccaaagtgc tgggattaca  169860
ggtgtgagcc actgagccca gcctcttct ccaagtttaa cttatttgg tatccaacct  169920
attttcttct catctatatt gttcttcatg ttcatgtact agttattttt gtttgtttgt  169980
ttgggtgaag tattgtaatt acagaaatga gacttttttt tttaaatga aaggcctcac  170040
atatttatta ctgaacccag ccaaccaatg cgttcataac agattcggag aggaaaacac  170100
gtcgaactct ccagatagg gtgacatttt cagcttgata tggtaacgtg atcgtgacct  170160
tcagacagca taaatatgtg tgccatctca tgtacaattc cttatagacc cagcttggtt  170220
cttctccaat gtctcctttt ggagttgtac ctgattttat ttccagtttt catccgaatc  170280
cactggggaa tgggacgatt ttgcttttgt ttcttgggca ggaatcactt aatcctgaaa  170340
gtcttgtgag aagacatggt gagggtggag tcaagaacac accacgatgg cagagaaagg  170400
aaaagaggca tgagatcatt ttatacccat catgcaacca caagcttttc tcaactgata  170460
atactaggac attagttata gacccatttt tttttttttt gagacggagt ctcactctgt  170520
cgcccaggtt ggagtgcagt ggcgtaatct tggctcactg cagcctctgc ctcctgggtt  170580
```

```
caagcaattg tcctgtctca gcgttcctga gtagctggga ttacaggtgt gcgctaccac  170640
gcctggctga ttttatatt tttagtagta gagacagggt ttcaccatgt tgaccagcct  170700
ggtctcaaat tcctgacctc aggtgatctg cctgcttcag cctcccaaag tgctgggatt  170760
acaggtgtga gccactgcgc caagctccaa cattcttttt ttgtaatttt ttttttttt  170820
gagatcagcc tgtcaggttg gagtgcagtg gtgcaatctc agctcactgc aaccttggcc  170880
tcccaagttc aagtgattct cctgcctcaa cctcccaagt aggtgggatt acaggcatgc  170940
atcaccacgc ccagctaatt tttgtattct tagtagaggc agagttttgc cacgttggcc  171000
aggctggtct tgaactcctg acctcagata ttctgcctgc cttggtctcc cagagtgctg  171060
ggattacagg cgtgagccac cgtgcctggc ttccttttaa tgcatgcata atgttctatt  171120
gtatggtatt tgggagaa aaaagagtt ttcctctacc cttccgaggt tttggttgtg  171180
atagacccct gtaacaaaag acagattaac aagaagaaaa caaacaggac caggcatggt  171240
ggctcatgcc tgtaatccca cactttggg agcccaggag ttccagacca gcctgggcaa  171300
tatggcaaaa aaccatctct acaaaaaatg taaaaattag ctgggcatgg tagtggatgc  171360
ctgtggtccc aggtactcta ctctggtggc tgaggtgggt ggatcgcttg agcccaggag  171420
cgagaggttg cagtgagccg tgatagtgcc attgcacttc agcctgggtg acagagcgaa  171480
gccatctcaa aataaataaa agaaagaaag aaaaaaagaa aaacagaaat ttaaaaacat  171540
gtacgtcacg tattcaaaag agagaccagg gaaatgagca atctccaag aggtagcttt  171600
gaattcagga ttatacagca tcttcaaaaa agaacagtat atgtttagag aagtgttaag  171660
agaaccgggc acagtgactc acgcctgtaa ttccagcact ttgggaggcc gaggtgggcg  171720
gatcacctga ggtcgggagt tcgagaccag cctaaccaac acggagaaac cccatctcta  171780
ctaaaaatac aaaattagct gggtgtggtg gcgcttccct ataatcccag ctactcagga  171840
ggctgaggca ggagaattgc ttgaacccga gaggcggacg ttgccgtgag actgcgccat  171900
tgcactccag cctgggcaac aagagcgaaa cttcgtctca aaaaaaaaaa aaaaagaaa  171960
gaaagaaaaa aaaagagaag tgttaagaga aggaaatga ttttgagtct ctaggggtgg  172020
caaattatgg gaaggcaaat acgcgataga aaaaggctca ttaatgaagt ttgtcatgta  172080
gattcctggc tgataaaggt ttgtcaaaag acaaaattac aactaattta gtttaaagag  172140
cataattggc ttttagttgc gattgtagaa ttgtgcaaca cctcatttta taaaatcgaa  172200
tgagtgttcc tatgagttga gtggaggagg ttggcttca gaagggctg aagaaagcag  172260
aaacagaaaa gtgcattggt tgtttcgagg ttactttcct tgaaaagttt aaagcagagg  172320
gtatttcctt atcatgtcac ttcaaactgg tctgtcggga atttggctat tatttttctt  172380
tctcctgatt tcttagaaag tcagatcgac aacttagttt tgaccttgtg atgtggaaca  172440
tgagtgactt gagtgactcc attttggttt agtctgttgg gcctagtcta gtgcaggagc  172500
tcagtccaaa ccaatggctt cctatgaatt ttatttaaca ggcgtaaaat tgtctttagt  172560
gattaacctt tgtccttcca ggcagtgtgg gaagagggat acctttgcct tttaaaattt  172620
atgtcctgct ttacttcaga cattacacta aataggagtg ttgagtataa aaatgaattc  172680
acaattaaag ttgttaaatt atttgtatat aactttaaaa ggagtttttt tgaagctttg  172740
taattacatt gaaagtatat ttgttttcctt gaaaacaatt ttttgaaaag tgaataataa  172800
tataatacag ctttcaaatt actttatgct gttactttat ttctattgta ttcacatgtg  172860
aaagtatgtg atcagttgtt gctgtatcag agatattaga gattctttat tagttgggca  172920
```

```
ttctttatga ccttttctat aaaagagtaa ggacattaaa atgtaagatg catgataaaa  172980
atataagtag cgaggctcat tgtagttagc ctaaattaag taatgtttaa ggtaggtgtt  173040
catggccagg cgcggtggct cacacctgta atcccagcac tttgtgaggc cgaggcgggt  173100
ggatcatgag gtcaggagat cgagaccatc ctggctgaca cactgaaacc tcgtctctac  173160
taaaaataca caaaattagc caggcacggt ggcgggtgcc tgtagtccca gctacaggct  173220
gaggcagaag aattgcttga acccgggacg tagagtttgc agtgagctga gatcgcacca  173280
ctgcactcca gactgggcaa cagagcgaga ctccgtctca aaaaaaaaaa aaaaagtaa  173340 gtgttcagag taatactttt ctacattata ctgagagaaa ttataaatta taaagtatat  173400
caaattatat tattttacta attttacttt tatgtaataa aatgcaatat atttaaaaat  173460
tgttaaaaaa ataaaattta tgtcctgctt ttaggcaaat ggggaaggcg gagaactttc  173520
cacccacgta tctacatcgt atctacatct tctcaattgt cttcggcttg aaataatcct  173580
taggctaaag aggcgtattt tggggtggca cattctggtg tccttacagg tacactactt  173640
ttattcatgt ctgttactac tattacaccc ccttcacctt gggccacccc atcctcagtc  173700
tccctcattt ttctttacag ttagcaccat ttacccattc acggagaacc ttacagttct  173760
cgcaacaggg tgatcactca gtaagtactg ttgtcccttt ggtctgtttc tggcagcgat  173820
tagctgtgcg cattctttga gaggagcgac ggagggaaca aagagggta ctagtgaaga  173880 actaaggtgc ttcacccaaa tagatagggaa aggaggagga gagctgaggc gagcctcagc  173940
ttctgccttt tttttttttt tttttttttt gagacggagt ctggctctgt ctcccaggct  174000
ggagtgcagt ggcgcaatct cggctcactg caagctccgc ctcccgggtt cacgccattc  174060
tcctgcctca gcctcccgag tagctgggac tacaggcgcc cgccactatg ccgagctaaa  174120 ttttttgtatt tttagtagag acggggtttc accgtgttag ccaggatggt ctcgatctcc  174180
tgacctcatg atccacccac ctcggcctcc caaagtgctg ggattacagg cttgagccac  174240
cgcgcccggc cagcttctgc cttcgatgtc ttctgaagga gggtgggctt cgaggcggca  174300
ggatgtgctt agggcactga gtggcccaga gtggggagct cctgcagggt tgagaggacc  174360
ggcggggcga ggtcggggcg gggctcgcag gacctgggcg gggctcgcag gggctgggcg  174420
gcctgggggc ggggctgggc ggagcgcgca gccgcgcagc ggtgggagga ctgcggggct  174480
cttgaggcca gctgcagagc ttgtggaggc catgggcgc gtcgtcgcgg agctcgtctc  174540
ctcgctgctg gggttgtggc tgttgctgtg cagctgcgga tgccccgagg gcgccgagct  174600
gcgtgctccg ccagataaaa tcggtaggcg agaaggggc ggcgcgggaa ggtgctggag  174660
cgcgccccgc gccgggcggc cgctgcgcag tgcgcccaga tcccacagcc gcgacgcagt  174720
ccagcggtgc aggccgagcc agctgcgcag gtcgcgcttt cccccattca cacttccaggg  174780 cggctttcag ctctggtcgg aataggactg tgcattccca ggcgtggaga ggtgcccact  174840
tgaggaatgg gcgtggacgg ggacaggggc gggcgggcag gcaggcgcct agcgtacctg  174900
tagcccctgt ctcttaggtg tggggctccg gggaggccta ggtttctcta tcttcccgtt  174960
gaacactgac cgtgaagact ccagtgttct ggcttgacct ggggcgcccg gccagattaa  175020
caggctcacg caggcacagc acaggggagga gtgcaaacaa gttgaccctg cctgcttccc  175080
ttgggaggct gaaccgcctt cccccagctc cgctttgctg aggtcggcct gctctcagag  175140
gcccttggct tgcacagttt ctccgcctag gactaacaca gctgcagaaa gaatctgttc  175200
tctttccact gtcaagagct ccagtgtcag gagccttggc tctttgcttc ctgtctccct  175260 cccgccccccc tttaaagttg tgttcttcgg tatcattaac ctatctacat tgaatctaga  175320
```

```
cacaacaaag ctaggcataa atggccgtca ctttattaaa aatgcgtgct ggaaaggtcc    175380
acctctaatg tgcccgtgag ttgggcatct ggaagggtgt gcaggcccct tggttcctcc    175440
ataaagacct gtgagaatct ttgggcatct ggaaaaaaaa tcgagttaat gtcaatatgt    175500
taattaatct actgcttttg tctgggaaca gtgtctgtcc agattcaggg agttagacct    175560
tcgctgcagg tgtcactctt cccccaccaa attgttggta atagctttga gtaacaacct    175620
ctgctattga tggtctttca aaacaaaac aactcacaga gctggtaaaa ggggaaaata     175680
taatcttctg ttttttcc tcatagcgat tattggagcc ggaattggtg gcacttcagc      175740
agcctattac ctgcggcaga aatttgggaa agatgtgaag atagacctgt ttgaaagaga    175800
agaggtcggg ggccgcctgg ctaccatgat ggtgcagggg caagaatacg aggcaggagg    175860
ttctgtcatc catcctttaa atctgcacat gaaacgtttt gtcaaagacc tgggtatgta    175920
attttggtct tggagctcac cagattactg tgtgacatcc ccggatattt ttatcagatg    175980
gagaactgaa atttctgcct tgttaattgc cttacagaga cgttggtaaa actgttttcc    176040
tcactttctt gttagttggt actgcctgag ttaggagcag ttctgctgta atgggacact    176100
agttgtctgt atcttcagtt atctggaatt acagccatgg ggtgggggtg gaatggctg     176160 ccattgtctt ttttttctt ttgaggagtt tcgctcttgt cgctcaggct ggagtgcaat     176220
ggtgcgatct tggctcactg caacctctgc ctcccgggtt caagcgattc tcctgcctta    176280
gcctcctgag tagctgggat tacaggtgcc tgccaccacg cccagctaat ttttgtattt    176340
tcagtagtga cggggtttca ccatgttggc cagctggtct tgaactcctg acctcaggtg    176400
atccgcctgc cttggccttc caaagtgctg ggattacagg ggtgagccac cgtgcccggc    176460
ctgtgttgtc tgttcttaaa attctgggtt tgtgttaaag aatcagagaa ggtttggaga    176520
tagtcatctc attgtgatca ttttgcagct gagtaaatga acccagaga cttgaattgt     176580 ctggctcaaa gtcactcaca tatgccatg gccagggtca gtggctcatg cctgtaatcc     176640
cagcactttg ggaggccgag gcagaggatc acttgagccc aggagttaga aaccagtctg    176700
ggcaacatag tgagatcctg tctttactaa aaataaaaaa gttagcctgg tgtgatggca    176760
caaacctgta gtcccagctt cttgggaggc agaggcagga ggatcccttg agcctgggag    176820
atagaagctg cagtgagcct tgcatgccac tgcactccag cctgggcaac aaagtgagac    176880
cctatcaaaa caaaccacca ccaacaaaac aaactccgtc acacagctgt ggatgcagac    176940
acgtgcctag aacttgggat gtgcaactgc tgccctgaca gcagaggagc tggataggtc    177000
atggggaaag tctgacaggc ctctggaggc cctttcggca gggagtattt tgtaactttg    177060
gcctccttcc agttatctga aatatccagt tttgcaaaat aggattctca caggaatgga    177120
agtgcctcag ctgccttcca catcctctgt agatgctgcc tctgcttccg tttcctccac    177180
gagggcgaag gtatacccag aacaaattat gccacgaaga tgcatgtctg acatctttgt    177240
ttttaaattg aattcagttg gtactctggc ttttttcctt tgactatcca gttttttag     177300 acttttagtc taaaaatagc caggtaaaaa tatatctact tttgatatat taatatttac    177360
atgatcatct gacccatcgc ctagcaaatc tgcttttgga cagtgtagtg aaagtatagt    177420
gtttcacact gttccaaaga tagagctcct ttatgtgtct cctgagaact gagggaagcc    177480
ccaaattcac tcagattacg ttctttcatt tgatcagcat agacaccact gacttagctg    177540
tgctttatgt ttttgcaggt ctctctgctg ttcaggcctc tggtggccta ctggggatat    177600
ataatggaga gactctggta tttgaggaga gcaactggtt cataattaac gtgattaaat    177660
```

```
tagtttggcg ctatggattt caattcctcc gtatgcacat gtgggtagag gacgtgttag    177720
acaagttcat gaggtaattt tttttccttc catttaacct aagatctttt aatttaggtt    177780
aaattaaact tgatgaactt taggaattat gatttcttgt aagcattttc tacctcacag    177840
caaggcctgt ttataacatt gttaggcaaa atgtttttgta gaaactatgc agactatttg    177900
cttggatatt gaaaggttgg tttatttttg cttctgaagt gtattttgca aatgcttctt    177960
tagtgttgcc agatactgtt agatgccttg aattc                               177995

<210> SEQ ID NO 52
<211> LENGTH: 20
<212> TYPE: DNA
<213> ORGANISM: Homo sapiens

<400> SEQUENCE: 52
gtgatctgag cattttccca                                                    20
```